United States Patent
Allen et al.

(10) Patent No.: US 8,946,230 B2
(45) Date of Patent: Feb. 3, 2015

(54) ARYL- AND HETEROARYL-NITROGEN-HETEROCYCLIC COMPOUNDS AS PDE10 INHIBITORS

(75) Inventors: Jennifer R. Allen, Newbury Park, CA (US); Kristin L. Andrews, Thousand Oaks, CA (US); Michael J. Frohn, Thousand Oaks, CA (US); Paul E. Harrington, Camarillo, CA (US); Alexander J. Pickrell, Westlake Village, CA (US); Robert M. Rzasa, Ventura, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/103,858

(22) Filed: May 9, 2011

(65) Prior Publication Data
US 2011/0306590 A1  Dec. 15, 2011

Related U.S. Application Data

(60) Provisional application No. 61/334,527, filed on May 13, 2010.

(51) Int. Cl.
| | | |
|---|---|---|
| A61K 31/497 | (2006.01) | |
| A61K 31/506 | (2006.01) | |
| A61K 31/4709 | (2006.01) | |
| C07D 471/04 | (2006.01) | |
| C07D 401/14 | (2006.01) | |
| C07D 403/14 | (2006.01) | |
| C07D 405/14 | (2006.01) | |

(52) U.S. Cl.
CPC ............ *C07D 471/04* (2013.01); *C07D 401/14* (2013.01); *C07D 403/14* (2013.01); *C07D 405/14* (2013.01)
USPC ...... 514/255.05; 514/256; 514/314; 544/333; 544/405; 546/152

(58) Field of Classification Search
USPC .................................. 544/333, 405; 546/152
See application file for complete search history.

(56) References Cited

U.S. PATENT DOCUMENTS

| | | | |
|---|---|---|---|
| 4,107,288 A | 8/1978 | Oppenheim et al. | |
| 5,145,684 A | 9/1992 | Liversidge et al. | |
| 2006/0019975 A1 | 1/2006 | Humphrey et al. | |
| 2011/0306587 A1 | 12/2011 | Allen et al. | |
| 2011/0306588 A1 | 12/2011 | Allen et al. | |
| 2011/0306591 A1 | 12/2011 | Allen et al. | |

FOREIGN PATENT DOCUMENTS

| | | | |
|---|---|---|---|
| CA | 2567003 A1 | 11/2006 | |
| EP | 0 039 051 A2 | 4/1981 | |
| FR | 2 870 541 A1 | 5/2004 | |
| WO | WO 2004/035549 A1 | 4/2004 | |
| WO | WO 2005/012485 A2 | 2/2005 | |
| WO | WO 2007/100880 A1 | 9/2007 | |
| WO | WO 2008/070014 | * 6/2008 | |
| WO | WO 2009/051705 A1 | 4/2009 | |

OTHER PUBLICATIONS

Berge, et al "Pharmaceutical Salts", *JPharmaSci*, 66:1 (1977).
Bundgaard, et al., "A Novel Solution-Stable, Water-Soluble Prodrug Type for Drugs Containing a Hydroxyl or an NH-Acidic Group", *JMedChem*, 32:12, 2503-2507, (1989).
Celen, et al., "Preclinical Evaluation of $^{18}$F-JNJ41510417 as a Radioligand for PET Imaging of Phosphodiesterase-10A in the Brain," J Nuclear Med., 51(10):1584-1591, (2010).
Fujishige, et al., "Cloning and Characterization of a Novel Human Phosphodiesterase That Hydrolyzes Both cAMP and cGMP ((PDE10A)", *Jour Biol Chem*, 274:26, 18438-18445, (1999).
Giedd, et al., "MRI Assessment of Children With Obsessive-Compulsive Disorder or Tics Associated with Streptococcal Infection", *AmJPsych*, 157:281-283, (2000).
Loughney, et al., "Isolation and characterization of PDE10A, a novel human 3', 5'—cyclic nucleotide phosphodiesterase", *Gene*, 234: 109-117, (1999).
Obeso, et al, "The origin of motor fluctuations in Parkinson's disease", Neurology, 62(Suppl 1): S17-S30 (2004).
Saxena, et al., "Neuroimaging and frontal-subcortical circuitry in obsessive-compulsive disorder", BrJPsychSuppl, 173(Suppl. 35):26-37, (1998).
Solderling, et al., "Isolation and characterization of a dual-substrate phosphodiesterase gene family: PDE10", *Proc. Natl. Acad. Sci*, 96: 7071-7076, (1999).
Svensson, et al., "The Design and Bioactivation of Presystemically Stable Prodrugs", *Drug Metabolism Rev.*, 19(2), 165-194 (1988).
Vora, et al., "Synthesis and Biological Evaluation of Potent Benzimidazolone Deriatives", *Der Pharma Chemica*, 2(5): 178-183 (2010).

(Continued)

*Primary Examiner* — Brian McDowell
(74) *Attorney, Agent, or Firm* — Elsa D. Lemoine

(57) ABSTRACT

Aryl- and heteroaryl-nitrogen heterocyclic compounds of formula (I):

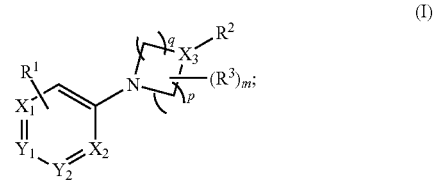

or a pharmaceutically acceptable salt thereof, wherein m, p, q, $R^1$, $R^2$, $R^3$, $X_1$, $X_2$, $X_3$, $Y_1$ and $Y_2$ are defined herein; and compositions containing them, and processes for preparing such compounds. Provided herein also are methods of treating disorders or diseases treatable by inhibition of PDE10, such as obesity, non-insulin dependent diabetes, schizophrenia, Huntington's Disease, bipolar disorder, obsessive-compulsive disorder, and the like.

24 Claims, No Drawings

(56) References Cited

OTHER PUBLICATIONS

Database Registry [online] Chemical Abstract Service, XP002643184, Dec. 16, 2009, Accession No. 1197572-10-3.
Database Registry [online] Chemical Abstract Service, XP002643185, Feb. 25, 2009, Accession No. 1111454-29-5.
Database Registry [online] Chemical Abstract Service, XP002643186, Jul. 2, 2007, Accession No. 940776-69-2.
Database Registry [online] Chemical Abstract Service, XP002643187, Apr. 24, 2007, Accession No. 932152-49-3.
Database Registry [online] Chemical Abstract Service, XP002643188, Apr. 22, 2007, Accession No. 931669-43-1.
Database Registry [online] Chemical Abstract Service, XP002643189, Jun. 4, 2007, Accession No. 941111-06-4.
Database Registry [online] Chemical Abstract Service, XP002643190, Oct. 9, 2007, Accession No. 949850-47-9.
Database Registry [online] Chemical Abstract Service, XP002643191, Mar. 16, 2010, Accession No. 1210468-38-4.
Database Registry [online] Chemical Abstract Service, XP002643192, May 14, 2010, Accession No. 1223495-41-7.
Database Registry [online] Chemical Abstract Service, XP002643193, Sep. 13, 2010, Accession No. 1240745-97-4.
Database Registry [online] Chemical Abstract Service, XP002643194, Sep. 15, 2010, Accession No. 1241349-40-5.
Database Registry [online] Chemical Abstract Service, XP002643195, Nov. 10, 2010, Accession No. 1252357-97-3.

\* cited by examiner

ARYL- AND HETEROARYL-NITROGEN-HETEROCYCLIC COMPOUNDS AS PDE10 INHIBITORS

CROSS-REFERENCE TO RELATED APPLICATIONS

This application claims the benefit of U.S. Provisional Application No. 61/334,527, filed May 13, 2010, which is hereby incorporated by reference.

FIELD OF THE INVENTION

Provided herein are certain aryl- and heteroaryl-nitrogen-heterocyclic compounds that are PDE10 inhibitors, pharmaceutical compositions containing such compounds, and processes for preparing such compounds. Provided herein also are methods of treating disorders or diseases treatable by inhibition of PDE10, such as obesity, non-insulin dependent diabetes, schizophrenia, Huntington's Disease, bipolar disorder, obsessive-compulsive disorder, and the like.

BACKGROUND

Neurotransmitters and hormones, as well as other types of extracellular signals such as light and odors, create intracellular signals by altering the amounts of cyclic nucleotide monophosphates (cAMP and cGMP) within cells. These intracellular messengers alter the functions of many intracellular proteins. Cyclic AMP regulates the activity of cAMP-dependent protein kinase (PKA). PKA phosphorylates and regulates the function of many types of proteins, including ion channels, enzymes, and transcription factors. Downstream mediators of cGMP signaling also include kinases and ion channels. In addition to actions mediated by kinases, cAMP and cGMP bind directly to some cell proteins and directly regulate their activities.

Cyclic nucleotides are produced from the actions of adenylyl cyclase and guanylyl cyclase, which convert ATP to cAMP and GTP to cGMP. Extracellular signals, often through the actions of G protein-coupled receptors, regulate the activities of the cyclases. Alternatively, the amount of cAMP and cGMP may be altered by regulating the activities of the enzymes that degrade cyclic nucleotides. Cell homeostasis is maintained by the rapid degradation of cyclic nucleotides after stimulus-induced increases. The enzymes that degrade cyclic nucleotides are called 3',5'-cyclic nucleotide-specific phosphodiesterases (PDEs).

Eleven PDE gene families (PDE1-PDE11) have been identified based on their distinct amino acid sequences, catalytic and regulatory characteristics, and sensitivity to small molecule inhibitors. These families are coded for by 21 genes; and further multiple splice variants are transcribed from many of these genes. Expression patterns of each of the gene families are distinct. PDEs differ with respect to their affinity for cAMP and cGMP. Activities of different PDEs are regulated by different signals. For example, PDE1 is stimulated by $Ca^{2+}$/calmodulin. PDE2 activity is stimulated by cGMP. PDE3 is inhibited by cGMP. PDE4 is cAMP specific and is specifically inhibited by rolipram. PDE5 is cGMP-specific. PDE6 is expressed in retina.

PDE10 sequences were identified by using bioinformatics and sequence information from other PDE gene families (Fujishige et al., *J. Biol. Chem.* 274:18438-18445, 1999; Loughney et al., *Gene* 234:109-117, 1999; Soderling et al., *Proc. Natl. Acad. Sci. USA* 96:7071-7076, 1999). The PDE10 gene family is distinguished based on its amino acid sequence, functional properties and tissue distribution. The human PDE10 gene is large, over 200 kilobases, with up to 24 exons coding for each of the splice variants. The amino acid sequence is characterized by two GAF domains (which bind cGMP), a catalytic region, and alternatively spliced N and C termini. Numerous splice variants are possible because at least three alternative exons encode N termini and two exons encode C-termini. PDE10A1 is a 779 amino acid protein that hydrolyzes both cAMP and cGMP. The $K_m$ values for cAMP and cGMP are 0.05 and 3.0 micromolar, respectively. In addition to human variants, several variants with high homology have been isolated from both rat and mouse tissues and sequence banks.

PDE10 RNA transcripts were initially detected in human testis and brain. Subsequent immunohistochemical analysis revealed that the highest levels of PDE10 are expressed in the basal ganglia. Specifically, striatal neurons in the olfactory tubercle, caudate nucleus and nucleus accumbens are enriched in PDE10. Western blots did not reveal the expression of PDE10 in other brain tissues, although immunoprecipitation of the PDE10 complex was possible in hippocampal and cortical tissues. This suggests that the expression level of PDE10 in these other tissues is 100-fold less than in striatal neurons. Expression in hippocampus is limited to the cell bodies, whereas PDE10 is expressed in terminals, dendrites and axons of striatal neurons.

The tissue distribution of PDE10 indicates that PDE10 inhibitors can be used to raise levels of cAMP and/or cGMP within cells that express the PDE10 enzyme, for example, in neurons that comprise the basal ganglia and therefore would be useful in treating a variety of neuropsychiatric conditions involving the basal ganglia such as obesity, non-insulin dependent diabetes, schizophrenia, bipolar disorder, obsessive compulsive disorder, and the like.

Noninvasive, nuclear imaging techniques can be used to obtain basic and diagnostic information about the physiology and biochemistry of a variety of living subjects including experimental animals, normal humans and patients. These techniques rely on the use of sophisticated imaging instrumentation that is capable of detecting radiation emitted from radiotracers administered to such living subjects. The information obtained can be reconstructed to provide planar and tomographic images that reveal distribution of the radiotracer as a function of time. Use of appropriately designed radiotracers can result in images which contain information on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the subject or the effects that various diseases or drugs have on the physiology or biochemistry of the subject. Currently, radiotracers are available for obtaining useful information concerning such things as cardiac function, myocardial blood flow, lung perfusion, liver function, brain blood flow, regional brain glucose and oxygen metabolism.

Compounds of the invention can be labeled with either positron or gamma emitting radionuclides. For imaging, the most commonly used positron emitting (PET) radionuclides are $^{11}C$, $^{18}F$, $^{15}O$, $^{13}N$, $^{76}Br$, $^{77}Br$, $^{123}I$, or $^{125}I$, wherein $^{11}C$, $^{18}F$, $^{123}I$, or $^{125}I$ are preferred, all of which are accelerator produced. In the two decades, one of the most active areas of nuclear medicine research has been the development of receptor imaging radiotracers. These tracers bind with high affinity and specificity to selective receptors and neuroreceptors. For example, Johnson and Johnson has synthesized and evaluated $^{18}$F-JNJ41510417 as a selective and high-affinity radioligand for in vivo brain imaging of PDE10A using PET (*The Journal Of Nuclear Medicine*; Vol. 51; No. 10; October 2010).

SUMMARY OF THE INVENTION

The present invention comprises a new class of aryl- and heteroaryl-nitrogen-heterocyclic compounds useful in the treatment of diseases, such as PDE10-mediated diseases and other maladies, such as schizophrenia, bipolar disorder, or obsessive-compulsive disorder. Accordingly, the invention also comprises pharmaceutical compositions comprising the compounds, methods for the treatment of PDE10-mediated diseases and other maladies, such as schizophrenia, bipolar disorder, or obsessive-compulsive disorder, using the compounds and compositions of the invention, and intermediates and processes useful for the preparation of the compounds of the invention.

The present invention further comprises a new class of aryl- and heteroaryl-nitrogen-heterocyclic compounds radiolabeled with a positron emitting radionuclide which are independently $^{11}$C, $^{18}$F, $^{15}$O, $^{13}$N, [76]Br, [77]Br, $^{123}$I, or $^{125}$I, a radiopharmaceutical composition comprising the radiolabelled compound, a method for the diagnostic imaging of PDE10 receptors in a mammal, including human, or tissues bearing PDE10 receptors in a mammal, including human brain, which comprises administering to a mammal in need of such diagnostic imaging an effective amount of the radiolabeled compound, and a method for the detection or quantification of PDE10 receptors in mammalian tissue, including human tissue, which comprises contacting such mammalian tissue in which such detection or quantification is desired with an effective amount of the radiolabeled compound.

The compounds of the invention are represented by the following general structure:

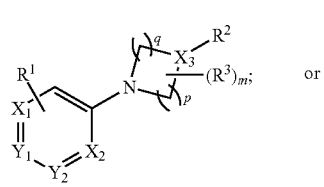
(I)

or

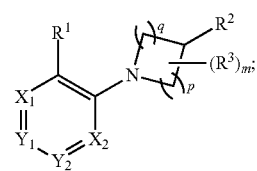
(Ia)

or a pharmaceutically acceptable salt thereof, wherein m, p, q, $R^1$, $R^2$, $R^3$, $X_1$, $X_2$, $X_3$, $Y_1$ and $Y_2$ are defined below.

Other compounds of the invention are represented by the following general structure:

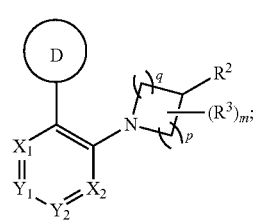
(II) or (IIa)

or a pharmaceutically acceptable salt thereof, wherein m, p, q, Ring D, $R^2$, $R^3$, $X_1$, $X_2$, $Y_1$ and $Y_2$ are defined below.

DETAILED DESCRIPTION OF THE INVENTION

One aspect of the current invention relates to compounds having the general structure of formula (I):

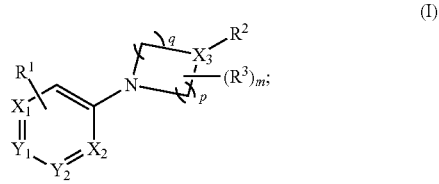
(I)

or a pharmaceutically-acceptable salt thereof, wherein:
each of $X_1$, $X_2$, $X_3$, $Y_1$ and $Y_2$ is independently N or $CR^4$;
wherein no more than two of $X_1$, $X_2$, $Y_1$ and $Y_2$ are N;
$R^1$ is halo, $C_{1-8}$alk, $C_{1-4}$haloalk, —$OR^a$, —$OR^c$, —$N(R^a)C(=O)R^b$, —$C(=O)R^a$, —$C(=O)R^c$, —$C(=O)$—O—$R^b$, —$NR^aR^c$, —$N(R^c)C(=O)R^b$, —$N(R^a)C(=O)R^c$, —$C(=O)NR^aR^b$, —$C(=O)NR^a(C_{0-4}alk)R^c$, or $C_{0-4}$alk-$L^1$; wherein said $C_{1-8}$alk group is substituted by 0, 1, 2 or 3 groups which are independently halo, $C_{1-3}$haloalk, —OH, —$OC_{1-4}$alk, —$NH_2$, —$NHC_{1-4}$alk, —$OC(=O)C_{1-4}$alk, or —$N(C_{1-4}alk)C_{1-4}$alk;
$R^2$ is unsaturated 9- or 10-membered bicyclo-heterocyclic ring; wherein each $R^2$ is substituted by 0, 1, 2 or 3 $R^5$ groups;
$R^3$ is halo, OH, $OC_{1-4}$alk, $C_{1-4}$alk, $C_{1-4}$haloalk, or oxo;
$R^4$ is independently H, halo, OH, $OC_{1-4}$alk, $C_{1-4}$alk or $C_{1-4}$haloalk;
$R^5$ is independently halo, CN, OH, $OC_{1-4}$alk, $C_{1-4}$alk, $C_{1-4}$haloalk, or a carbon-linked or nitrogen-linked saturated, partially-saturated or unsaturated 3-, 4-, 5-, 6-, or 7-membered monocyclic ring, wherein each said ring contains 0, 1, 2, 3, or 4 N atoms and 0, 1, or 2 atoms which are independently O or S;
m is 0, 1, 2, 3, or 4;
each of p and q is independently 0, 1, 2, 3, 4, 5, or 6; wherein the sum of p and q is 2 to 6;
the ring containing p and q contains 0, 1, or 2 double bonds;
$R^a$ is independently H or $R^b$;
$R^b$ is independently phenyl, benzyl, or $C_{1-6}$alk, wherein said phenyl, benzyl, and $C_{1-6}$alk are being substituted by 0, 1, 2 or 3 substituents which are independently halo, $C_{1-4}$alk, $C_{1-3}$haloalk, —OH, —$OC_{1-4}$alk, —$NH_2$, —$NHC_{1-4}$alk, —$OC(=O)C_{1-4}$alk, or —$N(C_{1-4}alk)C_{1-4}$alk;
$R^c$ is $C_{0-4}$alk-$L^2$; and
each of $L^1$ and $L^2$ is independently a carbon-linked or nitrogen-linked saturated, partially-saturated or unsaturated 3-, 4-, 5-, 6-, or 7-membered monocyclic ring or a saturated, partially-saturated or unsaturated 8-, 9-, 10-, 11-, or 12-membered bicyclic ring, wherein each said ring contains 0, 1, 2, 3, or 4 N atoms and 0, 1, or 2 atoms which are independently O or S; wherein each $L^1$ and $L^2$ is independently substituted by 0, 1, 2 or 3 $R^6$ groups which are independently F, Cl, Br, $C_{1-6}$alk, $C_{1-4}$haloalk, —$OR^a$, —$OC_{1-4}$haloalk, CN, —$C(=O)R^b$, —$C(=O)OR^a$, —$C(=O)NR^aR^a$, —$C(=NR^a)NR^aR^a$, —$OC(=O)R^b$, —$OC(=O)NR^aR^a$, —$OC_{1-6}alkNR^aR^a$, —$OC_{1-6}alkOR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{1-6}alkNR^aR^a$, —$NR^aC_{1-6}alkOR^a$, —$C_{1-6}alkNR^aR^a$, —$C_{1-6}alkOR^a$, —$C_{1-6}alkN(R^a)C(=O)R^b$, —$C_{1-6}alkOC(=O)R^b$, —$C_{1-6}alkC(=O)NR^aR^a$, —$C_{1-6}alkC(=O)OR^a$ or oxo;

with the proviso that when R² is

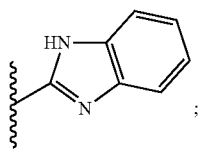 [SMILES: *c1nc2ccccc2[nH]1 ; ";"]

then at least one of X₁, X₂, Y₁ and Y₂ must be N.

In another embodiment of the compounds of formula (I), or a pharmaceutically acceptable salt thereof, the group:

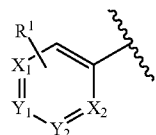 is:

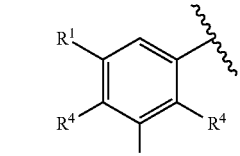,

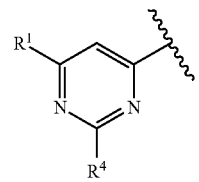, 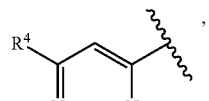,

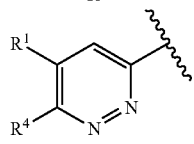, 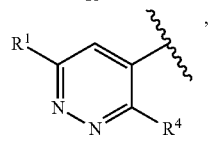,

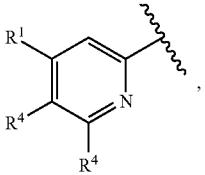, 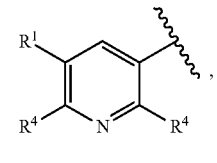,

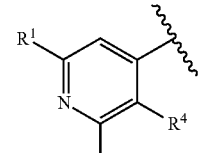, 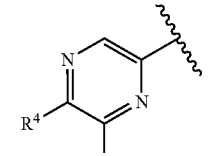,

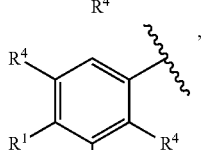, 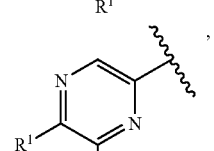,

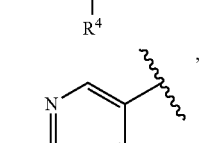, 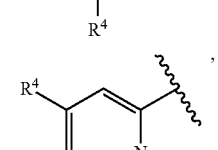,

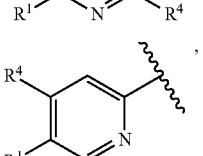, 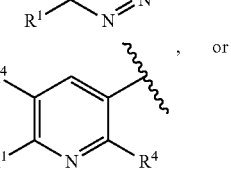 or

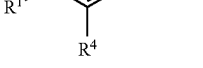, 

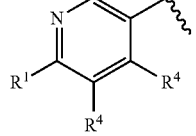

In another embodiment of the compounds of formula (I), or a pharmaceutically acceptable salt thereof, the group

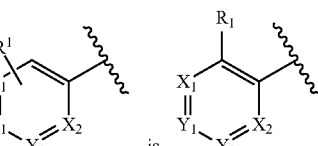 is 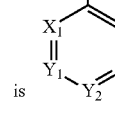.

In another embodiment of the compounds of formula (I), or a pharmaceutically acceptable salt thereof, the group:

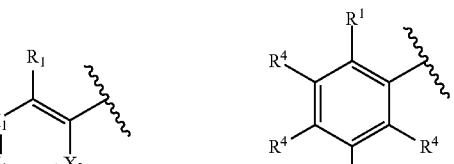 is: 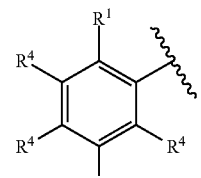,

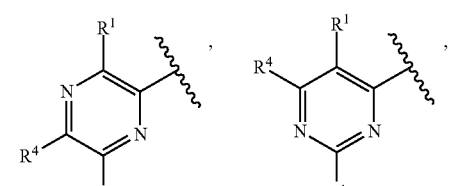, 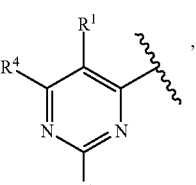,

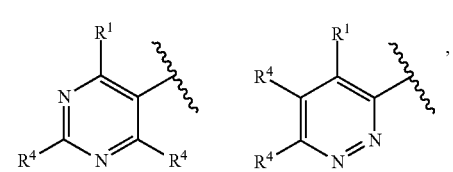, 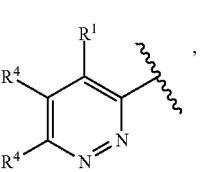,

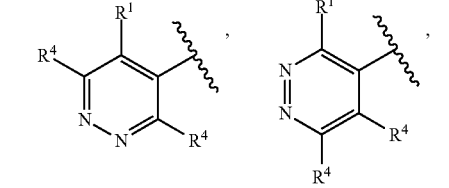, 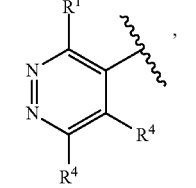,

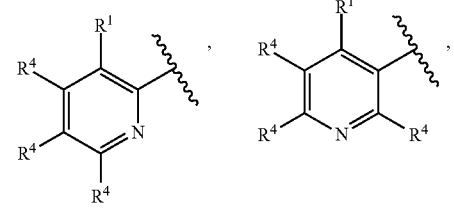, 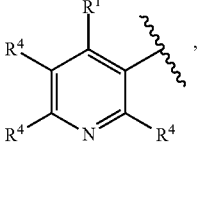,

-continued

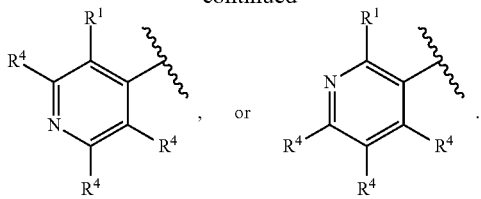

In another embodiment of the compounds of formula (I), or a pharmaceutically acceptable salt thereof, the group

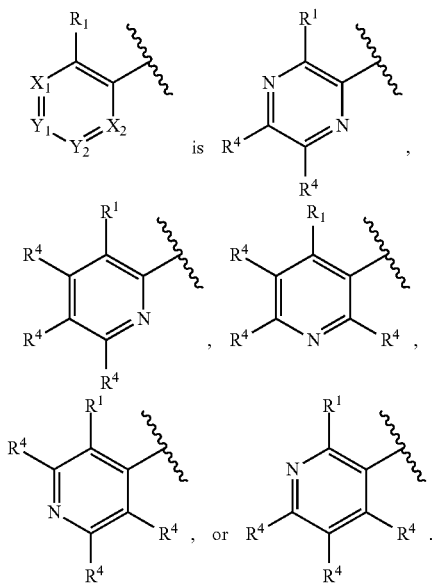

In another embodiment of the compounds of formula (I) or (II), or a pharmaceutically acceptable salt thereof, m is 1 or 2.

In another embodiment of the compounds of formula (I), or a pharmaceutically acceptable salt thereof, the group

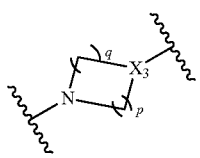

is azetidinyl, pyrrolidinyl, piperidinyl, azepanyl, or piperazinyl.

In another embodiment of the compounds of formula (I), or a pharmaceutically acceptable salt thereof, the group

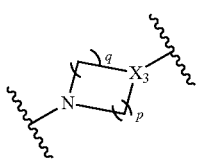

is azetidinyl.

In another embodiment of the compounds of formula (I) or (II), or a pharmaceutically acceptable salt thereof, p is 0, 1, or 2.

In another embodiment of the compounds of formula (I) or (II), or a pharmaceutically acceptable salt thereof, q is 0, 1, or 2.

In another embodiment of the compounds of formula (I), or a pharmaceutically acceptable salt thereof, $R^1$ is Cl, Br, —$OR^a$, —$OR^c$, —C(=O)$R^c$, —$NR^aR^c$, —C(=O)$NR^aR^b$, —C(=O)$NR^a(C_{0-4}alk)R^c$, or $C_{0-4}$alk-$L^1$.

In another embodiment of the compounds of formula (I), or a pharmaceutically acceptable salt thereof, $R^1$ is Cl, Br, or $C_{0-4}$alk-$L^1$.

In another embodiment of the compounds of formula (I), or a pharmaceutically acceptable salt thereof, $R^1$ is Cl.

In another embodiment of the compounds of formula (I) or (II), or a pharmaceutically acceptable salt thereof, wherein $R^1$ or ring D is a carbon-linked or nitrogen-linked unsaturated 4-, 5-, 6-, or 7-membered monocyclic ring, wherein each said ring contains 0, 1, 2, or 3 N atoms and 0, 1, or 2 O atoms, and wherein each said ring is substituted by 0, 1, or 2 $R^6$ groups which are independently F, Cl, Br, or $C_{1-6}$alk.

In another embodiment of the compounds of formula (I) or (II), or a pharmaceutically acceptable salt thereof, $R^1$ or ring D is a carbon-linked saturated or partially-saturated 5- to 6-membered monocyclic ring, wherein each said ring contains 0, 1, 2, or 3 N atoms and 0, 1, or 2 O atoms, and wherein each said ring is substituted by 0, 1, 2 or 3 $R^6$ groups which are independently F, Cl, Br, or $C_{1-6}$alk.

In another embodiment of the compounds of formula (I) or (II), or a pharmaceutically acceptable salt thereof, $R^1$ or ring D is a carbon-linked or nitrogen-linked saturated, partially-saturated or unsaturated 8-, 9-, 10-, 11-, or 12-membered bicyclic ring, wherein each said ring contains 0, 1, 2, or 3 N atoms and 0, 1, or 2 O atoms, and wherein each said ring is substituted by 0, 1, 2 or 3 $R^6$ groups which are independently F, Cl, Br, $C_{1-6}$alk, $C_{1-4}$haloalk, —$OR^a$, —$OC_{1-4}$haloalk, CN, —C(=O)$R^b$, —C(=O)$OR^a$, —$NR^aR^a$, —$SR^a$, or oxo.

In another embodiment of the compounds of formula (I) or (II), or a pharmaceutically acceptable salt thereof, $R^1$ or ring D is a nitrogen-linked saturated, partially-saturated or unsaturated 4-, 5-, 6-, or 7-membered monocyclic ring wherein each said ring contains 0, 1, 2, 3, or 4 N atoms and 0, 1, or 2 atoms which are independently O or S; substituted by 0, 1, 2 or 3 $R^6$ groups which are independently F, Cl, Br, $C_{1-6}$alk, $C_{1-4}$haloalk, —$OR^a$, —$OC_{1-4}$haloalk, CN, —C(=O)$R^b$, —C(=O)$OR^a$, —$NR^aR^a$, $SR^a$, or oxo.

In another embodiment of the compounds of formula (I) or (II), or a pharmaceutically acceptable salt thereof, $R^1$ or ring D is cyclohexyl, cyclopentyl, cyclopentenyl, cyclohexenyl, cycloheptyl, azetidinyl, phenyl, 2-pyridyl, 3-pyridyl, pyrazolyl, morpholinyl, pyrimidyl, piperazinyl, piperidinyl, dihydropyranyl, tetrahydropyranyl, tetrahydrofuranyl, tetrahydropyridinyl, tetrahydrothiopyranyl, oxaspiro[3.5]nonyl, azepanyl, oxepanyl, or quinolinyl, all of which are substituted by 0, 1, 2 or 3 $R^6$ groups which are independently F, Cl, Br, $C_{1-6}$alk, $C_{1-4}$haloalk, —$OR^a$, CN, —C(=O)$R^b$, —C(=O)$OR^a$, —$SR^a$, or oxo.

In another embodiment of the compounds of formula (I) or (II), or a pharmaceutically acceptable salt thereof, $R^1$ or ring D is a carbon-linked or nitrogen-linked unsaturated 4-, 5-, 6-, or 7-membered monocyclic ring, wherein each said ring contains 0, 1, 2, or 3 N atoms and 0, 1, or 2 O atoms, and wherein each said ring is substituted by 0, 1, or 2 $R^6$ groups which are independently F, Cl, Br, or $C_{1-6}$alk.

In another embodiment of the compounds of formula (I) or (II), or a pharmaceutically acceptable salt thereof, $R^1$ or ring D is a carbon-linked or nitrogen-linked saturated or partially-saturated 5- to 6-membered monocyclic ring, wherein each said ring contains 0, 1, 2, or 3 N atoms and 0, 1, or 2 O atoms, and wherein each said ring is substituted by 0, 1, 2 or 3 $R^6$ groups which are independently F, Cl, Br, or $C_{1-6}$alk.

In another embodiment of the compounds of formula (I) or (II), or a pharmaceutically acceptable salt thereof, $R^1$ or ring D is $C_{1-6}$alk substituted by 0, 1, 2 or 3 groups which are independently halo, $C_{1-3}$haloalk, —OH, —$OC_{1-4}$alk, —$NH_2$, —$NHC_{1-4}$alk, —OC(=O)$C_{1-4}$alk, or —N($C_{1-4}$alk)$C_{1-4}$alk.

In another embodiment of the compounds of formula (I), or a pharmaceutically acceptable salt thereof, $R^a$ is H or $C_{1-6}$alk substituted by 0 or 1 —OH, —$OC_{1-4}$alk, —OC(=O)$C_{1-4}$alk, or —N($C_{1-4}$alk)$C_{1-4}$alk.

In another embodiment of the compounds of formula (I), or a pharmaceutically acceptable salt thereof, $R^c$ is a $C_{0-4}$alk-saturated, partially-saturated or unsaturated 3-, 4-, 5-, or 6-membered monocyclic ring containing 0 or 1 N atom and 0 or 1 atom which are independently O or S, which is substituted by 0 or 1 $R^6$ groups which are independently F, Cl, $C_{1-6}$alk, $C_{1-4}$haloalk, or —$OR^a$.

In another embodiment of the compounds of formula (I), or a pharmaceutically acceptable salt thereof, $R^c$ is a $C_{0-4}$alk-saturated, partially-saturated or unsaturated 3-, 4-, 5-, or 6-membered monocyclic ring which is cyclohexyl, cyclopentyl, cyclopentenyl, cyclohexenyl, cycloheptyl, azetidinyl, phenyl, pyridyl, pyrazolyl, morpholinyl, pyrimidyl, piperazinyl, piperidinyl, dihydropyranyl, tetrahydropyranyl, tetrahydrofuranyl, tetrahydropyridinyl, and tetrahydrothiopyranyl, all of which are substituted by 0, 1, 2 or 3 $R^6$ groups which are independently F, Cl, Br, $C_{1-6}$alk, $C_{1-4}$haloalk, —$OR^a$, CN, —C(=O)$R^b$, —C(=O)$OR^a$, —$SR^a$, or oxo.

In another embodiment of the compounds of formula (I), or a pharmaceutically acceptable salt thereof, $R^1$ is: Cl, Br,

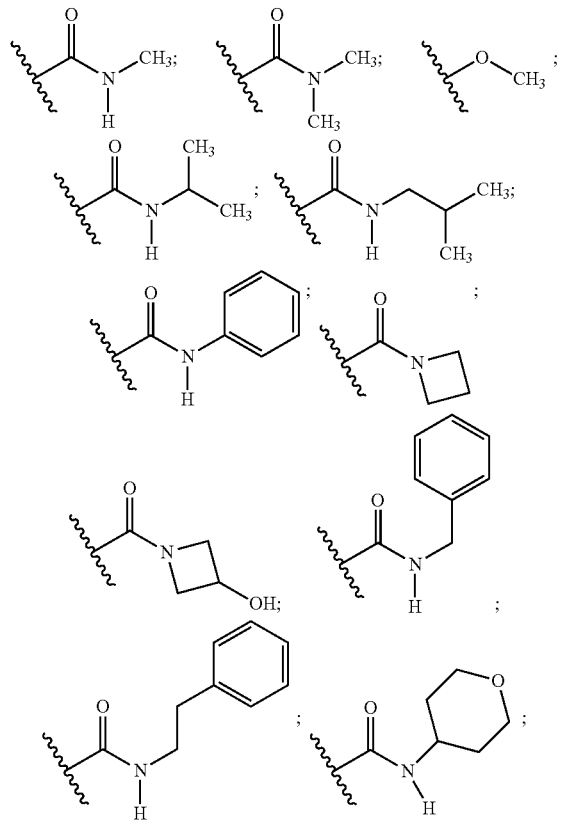

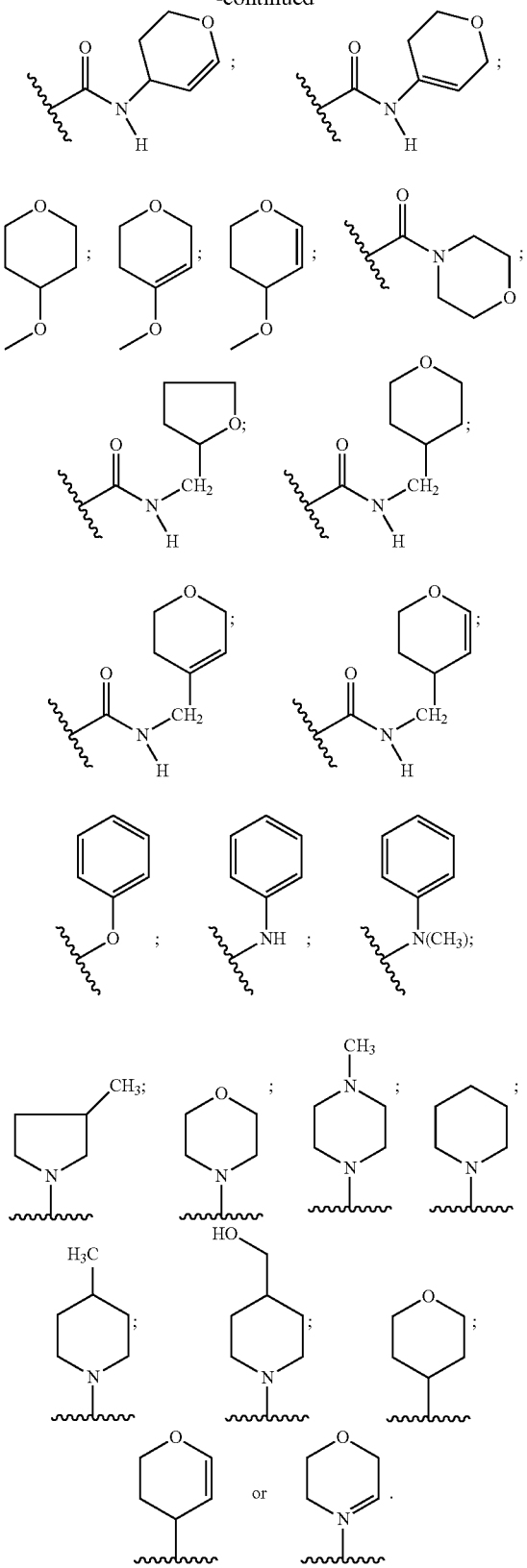

In another embodiment of the compounds of formula (I) or (II), or a pharmaceutically acceptable salt thereof, $R^1$ or ring D is:

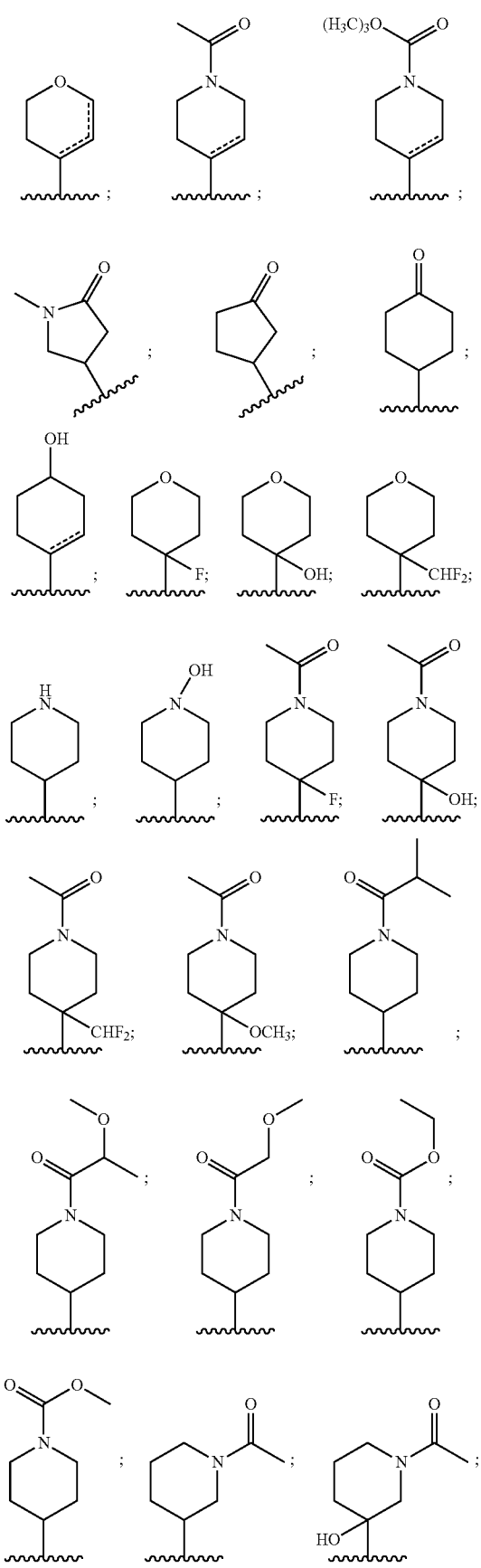
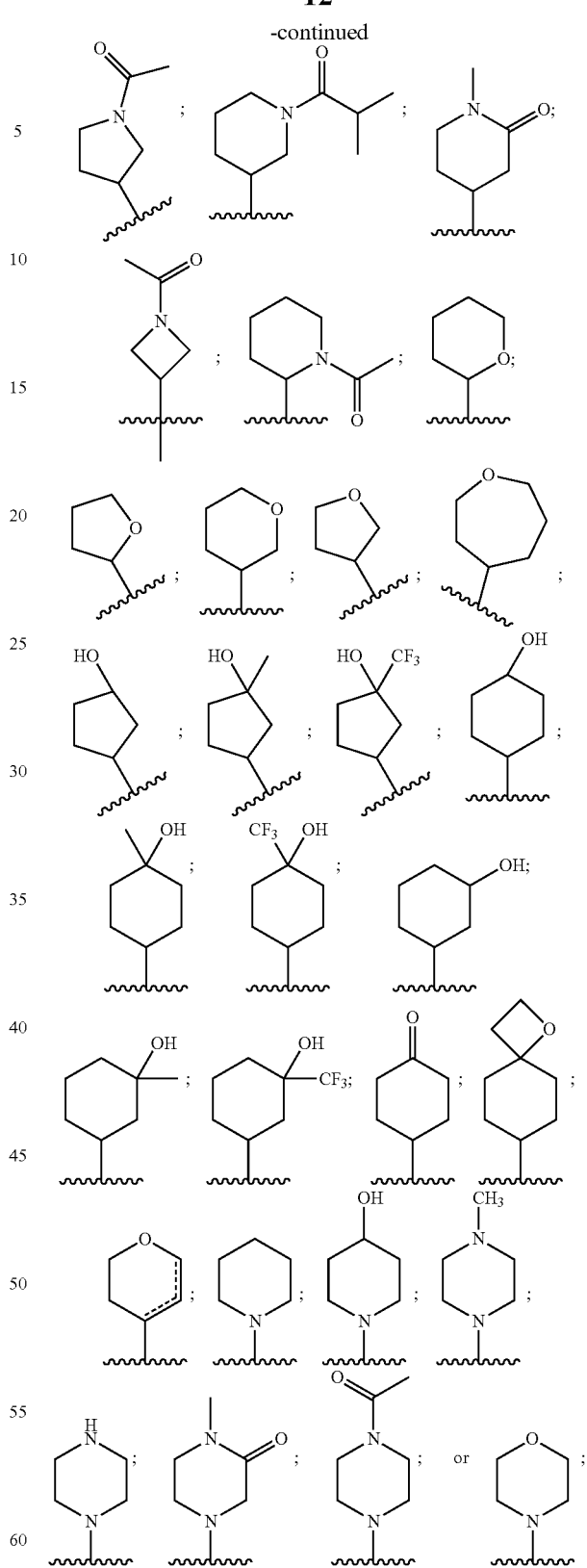
wherein the dotted bond is an optional double bond.
In another embodiment of the compounds of formula (I) or (II), or a pharmaceutically acceptable salt thereof, $R^1$ or ring D is:

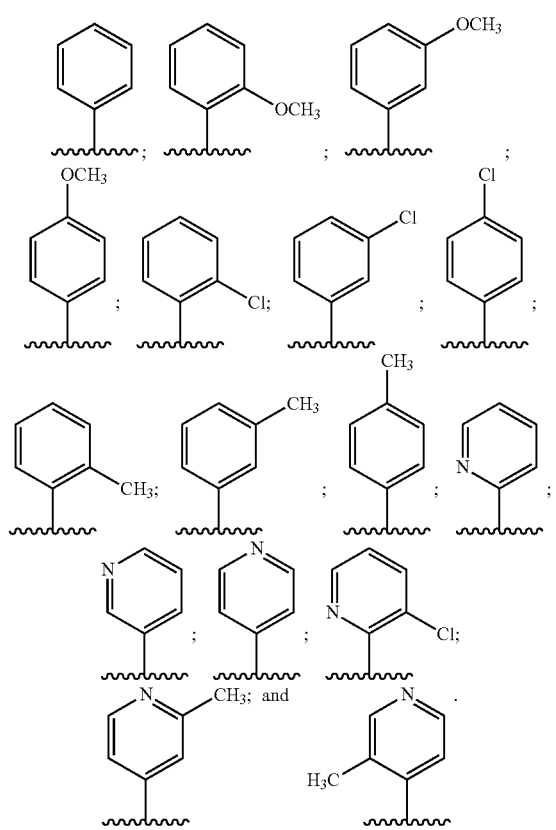

In another embodiment of the compounds of formula (I) or (II), or a pharmaceutically acceptable salt thereof, $R^4$ is independently H, F, Cl, $OC_{1-4}$alk, $C_{1-4}$alk or $C_{1-4}$haloalk.

In another embodiment of the compounds of formula (I) or (II), or a pharmaceutically acceptable salt thereof, $R^4$ is Cl.

In another embodiment of the compounds of formula (I) or (II), or a pharmaceutically acceptable salt thereof, $R^3$ is independently F, $OC_{1-4}$alk, $C_{1-4}$alk or $C_{1-4}$haloalk.

In another embodiment of the compounds of formula (I) or (II), or a pharmaceutically acceptable salt thereof, m is 1 and $R^3$ is oxo.

In another embodiment of the compounds of formula (I) or (II), or a pharmaceutically acceptable salt thereof, $R^2$ is

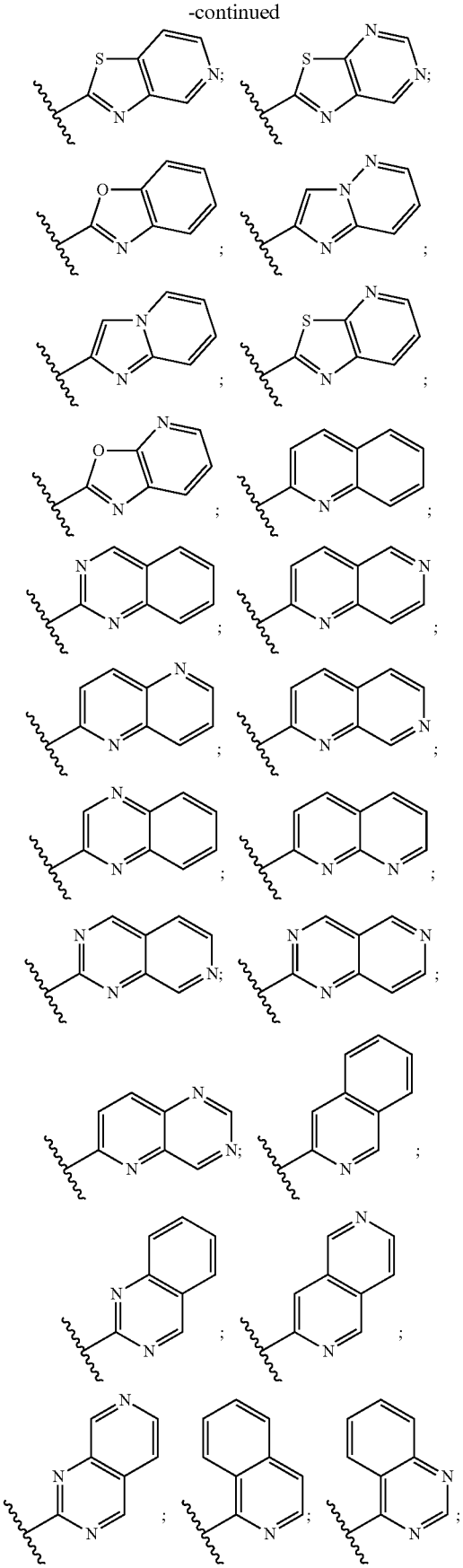

-continued

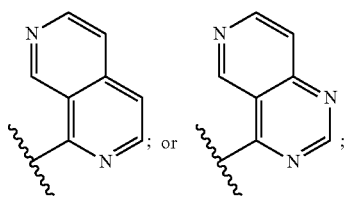

wherein each R² is substituted by 0, 1 or 2 R⁵ groups.

In another embodiment of the compounds of formula (I) or (II), or a pharmaceutically acceptable salt thereof, R² is

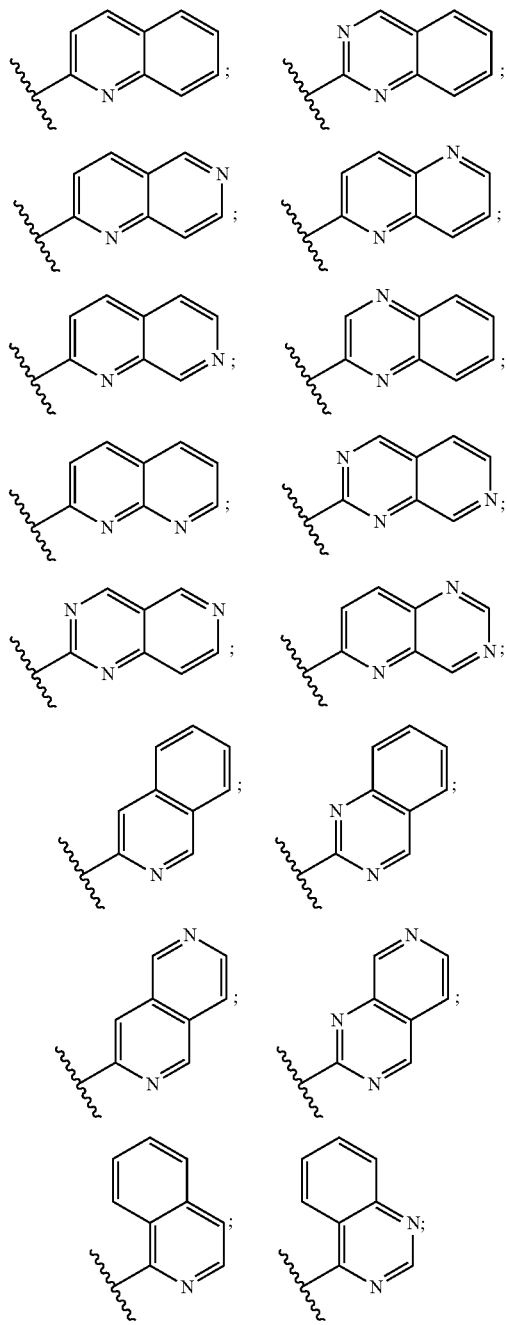

-continued

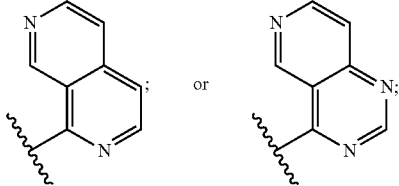

wherein each R² is substituted by 0, 1 or 2 R⁵ groups.

In another embodiment of the compounds of formula (I) or (II), or a pharmaceutically acceptable salt thereof, R² is

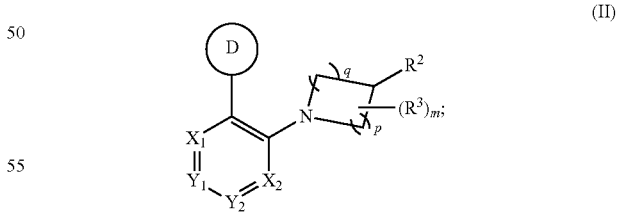

wherein each R² is substituted by 0, 1 or 2 R⁵ groups.

In another embodiment of the compounds of formula (I) or (II), or a pharmaceutically acceptable salt thereof, each $X_1$ and $X_2$ is N; each p and q is 2; and the ring containing p and q contains 1 double bond.

In another embodiment of the compounds of formula (I) or (II), or a pharmaceutically acceptable salt thereof, each $X_1$ and $X_2$ is N; $X_3$ is CH; each p and q is 2; m is 1; and R³ is oxo.

In another embodiment of the compounds of formula (I) or (II), or a pharmaceutically acceptable salt thereof, each $X_1$, $X_2$, and $X_3$ is N; and each p and q is 2.

In another embodiment of the compounds of formula (I) or (II), or a pharmaceutically acceptable salt thereof, each $X_1$, $X_2$, and $X_3$ is N; and each p and q is 2; m is 1; and R³ is oxo.

In another embodiment of the compounds of formula (I) or (II), or a pharmaceutically acceptable salt thereof, R⁵ is independently F, Br, Cl, CN, $C_{1-4}$alk, $C_{1-4}$haloalk, $OC_{1-4}$alk, or 3- to 6-membered-saturated or -partially saturated carbocyclic ring.

In another embodiment of the compounds of formula (I) or (II), or a pharmaceutically acceptable salt thereof, R⁵ is F, Br Cl, CN, methyl, methoxy, —CH₂CH₃, —CF₂CH₃, or cyclopropyl.

Another aspect of the current invention relates to compounds having the general structure of formula (II):

(II)

$$\text{structure}$$

or any pharmaceutically-acceptable salt thereof, wherein:
ring D is -L¹;
each of $X_1$, $X_2$, $Y_1$ and $Y_2$ is independently N or CR⁴; wherein no more than two of $X_1$, $X_2$, $Y_1$ and $Y_2$ are N;
R² is unsaturated 9- or 10-membered bicyclo-heterocyclic ring; wherein each R² is substituted by 0, 1, 2 or 3 R⁵ groups;
R³ is halo, OH, $OC_{1-4}$alk, $C_{1-4}$alk, $C_{1-4}$haloalk, or oxo;
R⁴ is independently H, halo, OH, $OC_{1-4}$alk, $C_{1-4}$alk, or $C_{1-4}$haloalk;

$R^5$ is independently halo, CN, OH, $OC_{1-4}$alk, $C_{1-4}$alk, $C_{1-4}$haloalk, or a carbon-linked or nitrogen-linked saturated, partially-saturated or unsaturated 3-, 4-, 5-, 6-, or 7-membered monocyclic ring, wherein each said ring contains 0, 1, 2, 3, or 4 N atoms and 0, 1, or 2 atoms which are independently O or S;

m is 0, 1, 2, 3, or 4;

each of p and q is independently 0, 1, 2, 3, 4, 5, or 6; wherein the sum of p and q is 2 to 6;

$R^a$ is independently H or $R^b$;

$R^b$ is independently phenyl, benzyl, or $C_{1-6}$alk, wherein said phenyl, benzyl, and $C_{1-6}$alk are being substituted by 0, 1, 2 or 3 substituents which are independently halo, $C_{1-4}$alk, $C_{1-3}$haloalk, —OH, —$OC_{1-4}$alk, —$NH_2$, —$NHC_{1-4}$alk, —OC(=O)$C_{1-4}$alk, or —N($C_{1-4}$alk)$C_{1-4}$alk; and each of $L^1$ and $L^2$ is independently a carbon-linked or nitrogen-linked saturated, partially-saturated or unsaturated 3-, 4-, 5-, 6-, or 7-membered monocyclic ring or a saturated, partially-saturated or unsaturated 8-, 9-, 10-, 11-, or 12-membered bicyclic ring, wherein each said ring contains 0, 1, 2, 3, or 4 N atoms and 0, 1, or 2 atoms which are independently O or S; wherein each $L^1$ and $L^2$ is independently substituted by 0, 1, 2 or 3 $R^6$ groups which are independently F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{1-6}$alk$NR^aR^a$, —$OC_{1-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{1-6}$alk$NR^aR^a$, —$NR^aC_{1-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$ or oxo;

with the proviso that when $R^2$ is

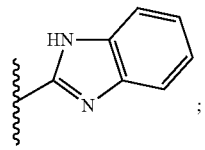 [SMILES: *c1nc2ccccc2[nH]1 ; ";"]

then at least one of $X_1$, $X_2$, $Y_1$ and $Y_2$ must be N.

In another embodiment of the compounds of formula (II), or a pharmaceutically acceptable salt thereof, $R^2$ is of formula:

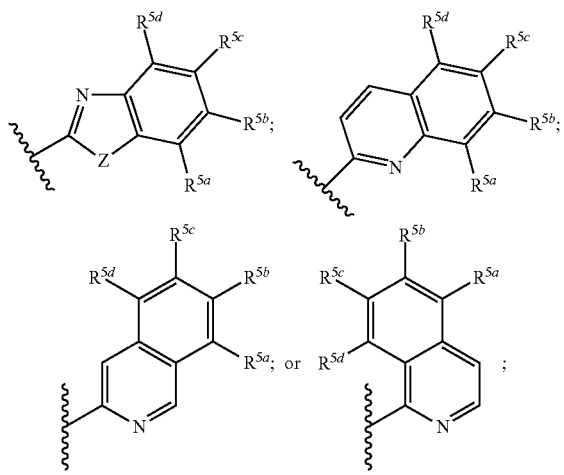

wherein each of $R^{5a}$, $R^{5b}$, $R^{5c}$, and $R^{5d}$ is $R^5$; Z is S, O, or $NR^7$; and $R^7$ is H or $C_{1-6}$alk. Preferably, Z is NH and $R^5$ is halo.

In another embodiment of the compounds of formula (II), or a pharmaceutically acceptable salt thereof, ring D is a carbon-linked saturated, partially-saturated or unsaturated 4-, 5-, 6-, or 7-membered monocyclic ring, wherein each said ring contains 0, 1, 2, 3, or 4 N atoms and 0, 1, or 2 atoms which are independently O or S; independently substituted by 0, 1, 2 or 3 $R^6$ groups which are independently F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{1-6}$alk$NR^aR^a$, —$OC_{1-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{1-6}$alk$NR^aR^a$, —$NR^aC_{1-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$ or oxo.

In another embodiment of the compounds of formula (II), or a pharmaceutically acceptable salt thereof, ring D is a carbon-linked-saturated, partially-saturated or unsaturated 8-, 9-, 10-, 11-, or 12-membered bicyclic ring, wherein each said ring contains 0, 1, 2, 3, or 4 N atoms and 0, 1, or 2 atoms which are independently O or S; independently substituted by 0, 1, 2 or 3 $R^6$ groups which are independently F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{1-6}$alk$NR^aR^a$, —$OC_{1-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{1-6}$alk$NR^aR^a$, —$NR^aC_{1-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$ or oxo.

In another embodiment of the compounds of formula (II), or a pharmaceutically acceptable salt thereof, ring D is a nitrogen-linked saturated, partially-saturated or unsaturated 4-, 5-, 6-, or 7-membered monocyclic ring, wherein each said ring contains 0, 1, 2, 3, or 4 N atoms and 0, 1, or 2 atoms which are independently O or S; independently substituted by 0, 1, 2 or 3 $R^6$ groups which are independently F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{1-6}$alk$NR^aR^a$, —$OC_{1-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{1-6}$alk$NR^aR^a$, —$NR^aC_{1-6}$alk$OR^a$, —$C_{1-6}$alk$NR^aR^a$, —$C_{1-6}$alk$OR^a$, —$C_{1-6}$alkN($R^a$)C(=O)$R^b$, —$C_{1-6}$alkOC(=O)$R^b$, —$C_{1-6}$alkC(=O)$NR^aR^a$, —$C_{1-6}$alkC(=O)$OR^a$ or oxo.

In another embodiment of the compounds of formula (II), or a pharmaceutically acceptable salt thereof, ring D is a nitrogen-linked-saturated, partially-saturated or unsaturated 8-, 9-, 10-, 11-, or 12-membered bicyclic ring, wherein each said ring contains 0, 1, 2, 3, or 4 N atoms and 0, 1, or 2 atoms which are independently O or S; independently substituted by 0, 1, 2 or 3 $R^6$ groups which are independently F, Cl, Br, $C_{1-6}$alk, $C_{1-4}$haloalk, —$OR^a$, —$OC_{1-4}$haloalk, CN, —C(=O)$R^b$, —C(=O)$OR^a$, —C(=O)$NR^aR^a$, —C(=$NR^a$)$NR^aR^a$, —OC(=O)$R^b$, —OC(=O)$NR^aR^a$, —$OC_{1-6}$alk$NR^aR^a$, —$OC_{1-6}$alk$OR^a$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)$NR^aR^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{1-6}$alkNR$^a$R$^a$, —NR$^a$C$_{1-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$ or oxo.

In another embodiment of the compounds of formula (II), or a pharmaceutically acceptable salt thereof, ring D is cyclohexyl, cyclopentyl, cyclopentenyl, cyclohexenyl, or cycloheptyl.

In another embodiment of the compounds of formula (II), or a pharmaceutically acceptable salt thereof, ring D is azetidinyl, phenyl, 2-pyridyl, 3-pyridyl, pyrazolyl, morpholinyl, pyrimidyl, piperazinyl, piperidinyl, dihydropyranyl, tetrahydropyranyl, tetrahydrofuranyl, tetrahydropyridinyl, or tetrahydrothiopyranyl.

In another embodiment of the compounds of formula (II), or a pharmaceutically acceptable salt thereof, ring D is cyclohexyl, cyclopentyl, cyclopentenyl, cyclohexenyl, cycloheptyl, azetidinyl, phenyl, 2-pyridyl, 3-pyridyl, pyrazolyl, morpholinyl, pyrimidyl, piperazinyl, piperidinyl, dihydropyranyl, tetrahydropyranyl, tetrahydrofuranyl, tetrahydropyridinyl, tetrahydrothiopyranyl, oxaspiro[3.5]nonyl, azepanyl, oxepanyl, or quinolinyl, all of which are substituted by 0, 1, 2 or 3 R$^6$ groups which are independently F, Cl, Br, or C$_{1-6}$alk.

In another embodiment of the compounds of formula (II), or a pharmaceutically acceptable salt thereof, ring D is

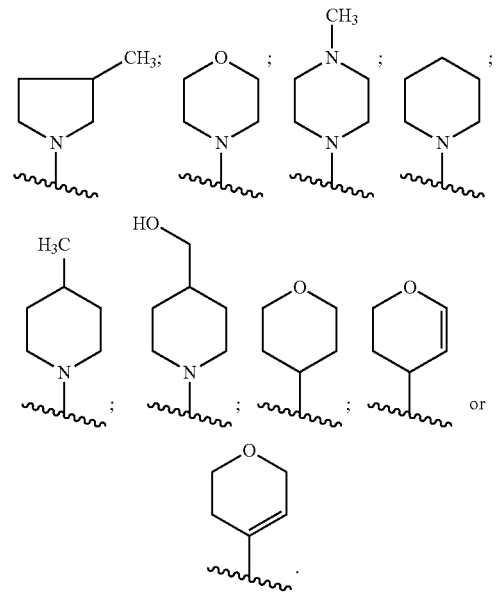

In another embodiment of the compounds of formula (II), or a pharmaceutically acceptable salt thereof, ring D is

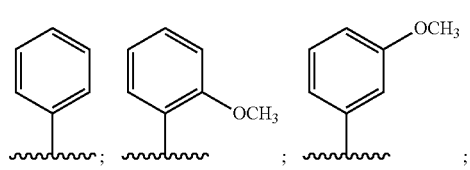

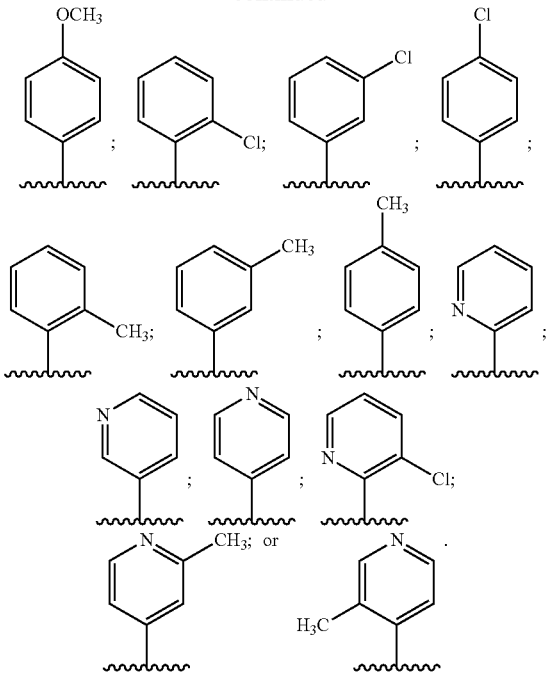

Another aspect of the invention relates to a compound of formula (II) having the formula:

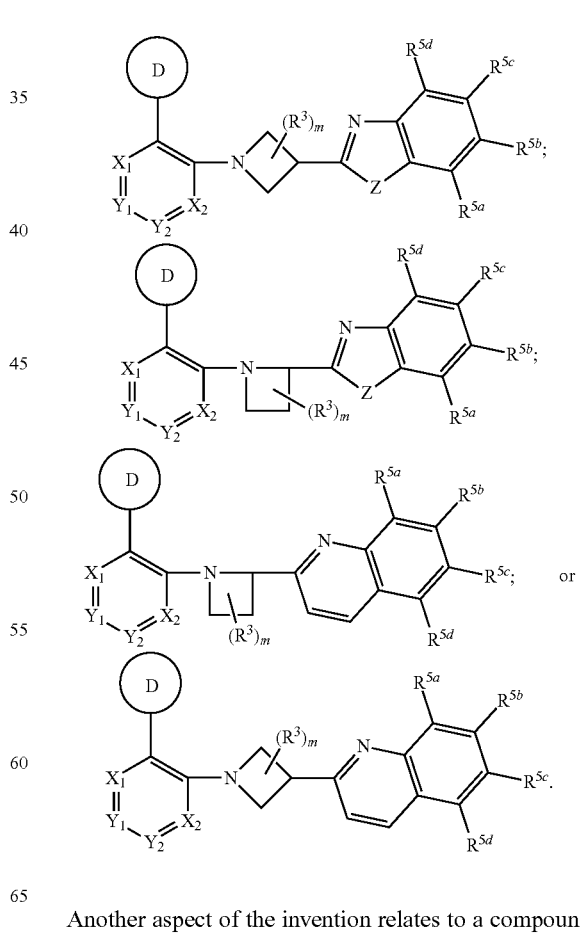

Another aspect of the invention relates to a compound of formula (II) having the formula:

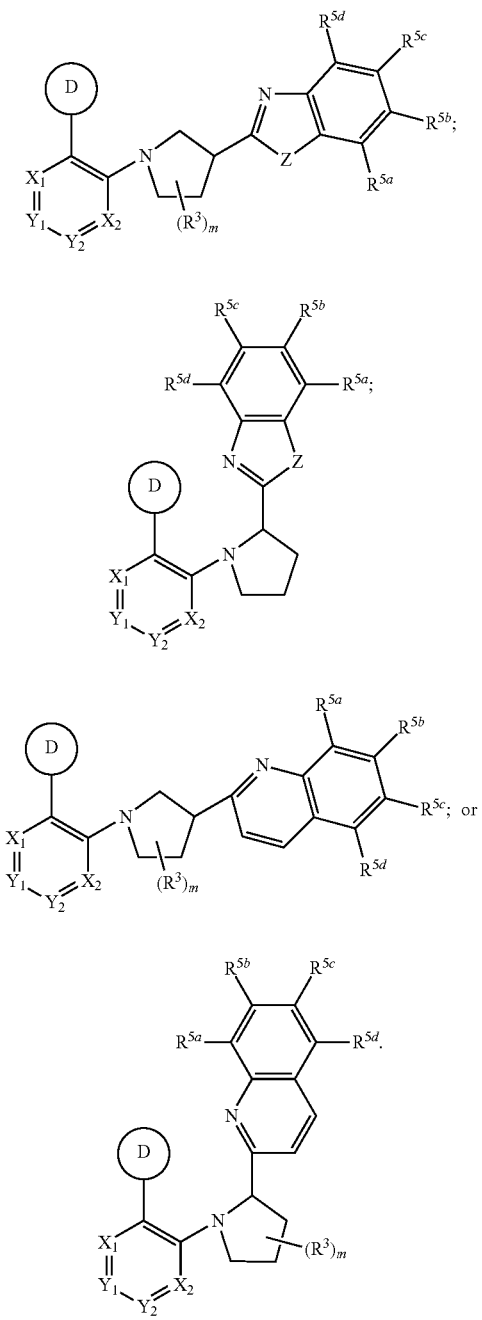
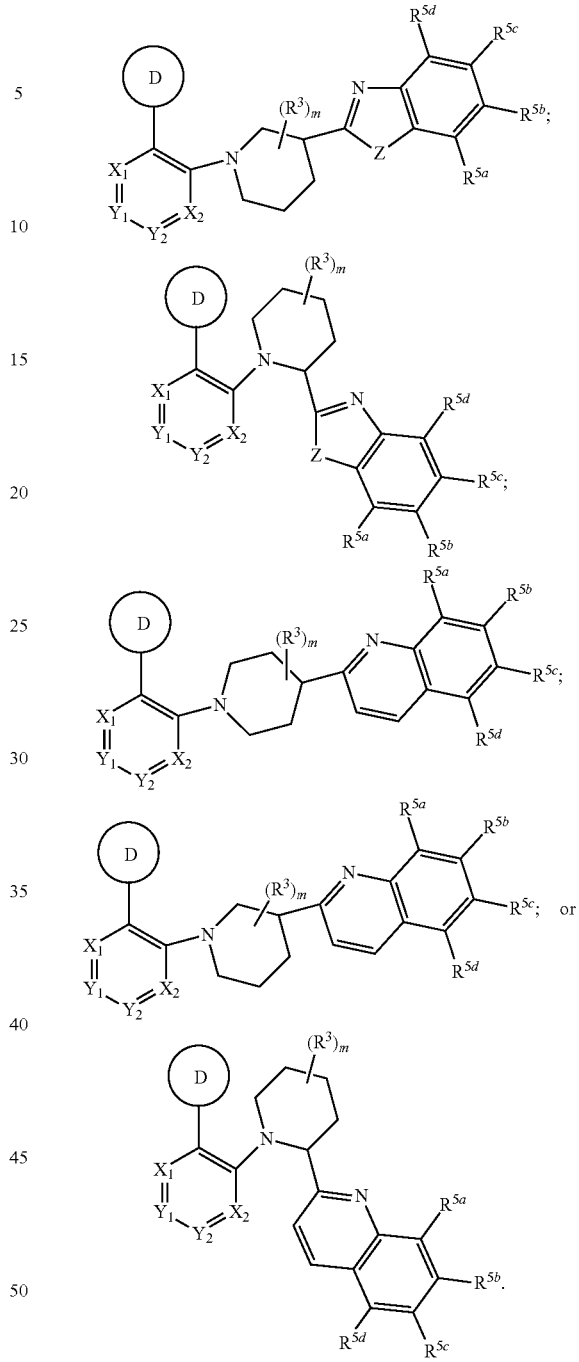

Another aspect of the invention relates to a compound of formula (II) having the formula:

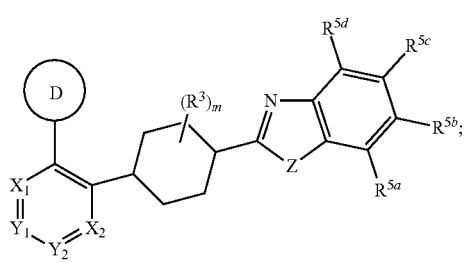

Another aspect of the invention relates to a method of treating conditions that may be treated with PDE10 inhibitors comprising the step of administering any of the above compounds.

Another aspect of the invention relates to a method of treating conditions that may be treated with PDE10 inhibitors comprising the step of administering any of the above compounds; wherein said condition is psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Another aspect of the invention relates to a method of treating conditions that may be treated with PDE10 inhibitors comprising the step of administering any of the above compounds; wherein said condition is schizophrenia, Huntington's Disease, bipolar disorder, and obsessive-compulsive disorder.

Another aspect of the invention relates to a pharmaceutical composition comprising any of the above compounds and a pharmaceutically-acceptable diluent or carrier.

Another aspect of the invention relates to a method of treating a disorder treatable by inhibition of PDE10 in a patient which method comprises administering to the patient a pharmaceutical composition comprising an effective amount of any of the above compounds.

Another aspect of the invention relates to the use of any of the above compounds as a medicament.

Another aspect of the invention relates to the use of any of the above compounds in the manufacture of a medicament for the treatment of schizophrenia, bipolar disorder, or obsessive-compulsive disorder.

Another aspect of the invention relates to compounds or a pharmaceutically-acceptable salt thereof, which is:

2-[1-(3-phenyl-pyrazin-2-yl)-piperidin-4-yl]-1H-benzoimidazole-5-carbonitrile;
2-[1-(3-morpholin-4-yl-pyrazin-2-yl)-piperidin-4-yl]-1H-benzoimidazole-5-carbonitrile;
5-methyl-2-(1-(3-(tetrahydro-2H-pyran-4-yloxy)pyrazin-2-yl)azetidin-3-yl)-1H-benzo[d]imidazole;
4-(4-(3-(5-chloro-1H-benzo[d]imidazol-2-yl)azetidin-1-yl)pyrimidin-2-yl)morpholine;
2-[1-(3,5-dichloro-pyridin-4-yl)-azetidin-3-yl]-5-methyl-1H-benzoimidazole;
2-[1-(3-chloro-5-phenyl-pyridin-4-yl)-azetidin-3-yl]-5-methyl-1H-benzoimidazole;
{2-[3-(5-chloro-1H-benzoimidazol-2-yl)-azetidin-1-yl]-pyridin-3-yl}-(3-hydroxy-azetidin-1-yl)-methanone;
3-[3-(5-chloro-1H-benzoimidazol-2-yl)-azetidin-1-yl]-pyrazine-2-carboxylic acid methylamide;
5-chloro-2-(1-(4-(tetrahydro-2H-pyran-4-yloxy)pyridin-2-yl)azetidin-3-yl)-1H-benzo[d]imidazole;
5-chloro-2-(1-(6-(tetrahydro-2H-pyran-4-yl)pyrimidin-4-yl)azetidin-3-yl)-1H-benzo[d]imidazole;
4-(5-chloro-4-(3-(5-chloro-1H-benzo[d]imidazol-2-yl)azetidin-1-yl)pyrimidin-2-yl)morpholine;
5-chloro-2-(1-(3-(tetrahydro-2H-pyran-4-yl)pyrazin-2-yl)azetidin-3-yl)-1H-benzo[d]imidazole;
5-chloro-2-(1-(4-(tetrahydro-2H-pyran-4-yl)pyridin-2-yl)azetidin-3-yl)-1H-benzo[d]imidazole;
5-chloro-2-(1-(3-(tetrahydro-2H-pyran-4-yloxy)pyrazin-2-yl)azetidin-3-yl)-1H-benzo[d]imidazole;
2-[1-(3-chloro-pyridin-2-yl)-pyrrolidin-3-yl]-1H-benzoimidazole-5-carbonitrile;
2-[1-(3-Morpholin-4-yl-pyrazin-2-yl)-pyrrolidin-3-yl]-1H-benzoimidazole-5-carbonitrile;
5-cyclopropyl-2-[1-(3-phenyl-pyrazin-2-yl)-piperidin-4-yl]-1H-benzoimidazole;
2-[1-(3-phenyl-pyrazin-2-yl)-azetidin-3-yl]-1H-benzoimidazole-5-carbonitrile;
2-[1-(3-phenyl-pyrazin-2-yl)-pyrrolidin-3-yl]-1H-benzoimidazole-5-carbonitrile;
azetidin-1-yl-{2-[3-(5-chloro-1H-benzoimidazol-2-yl)-azetidin-1-yl]-pyridin-3-yl}-methanone;
{2-[3-(5-chloro-1H-benzoimidazol-2-yl)-azetidin-1-yl]-pyridin-3-yl}-morpholin-4-yl-methanone;
2-[3-(5-chloro-1H-benzoimidazol-2-yl)-azetidin-1-yl]-N-phenyl-nicotinamide;
N-benzyl-2-[3-(5-chloro-1H-benzoimidazol-2-yl)-azetidin-1-yl]-nicotinamide;
2-[3-(5-chloro-1H-benzoimidazol-2-yl)-azetidin-1-yl]-N-phenethyl-nicotinamide;
2-[3-(5-chloro-1H-benzoimidazol-2-yl)-azetidin-1-yl]-N-isopropyl-nicotinamide;
2-[3-(5-chloro-1H-benzoimidazol-2-yl)-azetidin-1-yl]-N-isobutyl-nicotinamide;
2-[3-(5-chloro-1H-benzoimidazol-2-yl)-azetidin-1-yl]-N-(tetrahydro-pyran-4-ylmethyl)-nicotinamide;
5-chloro-2-[1-(3-o-tolyl-pyrazin-2-yl)-azetidin-3-yl]-1H-benzoimidazole;
5-chloro-2-[1-(3-m-tolyl-pyrazin-2-yl)-azetidin-3-yl]-1H-benzoimidazole;
5-chloro-2-[1-(3-p-tolyl-pyrazin-2-yl)-azetidin-3-yl]-1H-benzoimidazole;
5-chloro-2-{1-[3-(2-methoxy-phenyl)-pyrazin-2-yl]-azetidin-3-yl}-1H-benzoimidazole;
5-chloro-2-{1-[3-(3-methoxy-phenyl)-pyrazin-2-yl]-azetidin-3-yl}-1H-benzoimidazole;
5-chloro-2-{1-[3-(4-methoxy-phenyl)-pyrazin-2-yl]-azetidin-3-yl}-1H-benzoimidazole;
5-chloro-2-{1-[3-(2-chloro-phenyl)-pyrazin-2-yl]-azetidin-3-yl}-1H-benzoimidazole;
5-chloro-2-{1-[3-(3-chloro-phenyl)-pyrazin-2-yl]-azetidin-3-yl}-1H-benzoimidazole;
5-chloro-2-{1-[3-(4-chloro-phenyl)-pyrazin-2-yl]-azetidin-3-yl}-1H-benzoimidazole;
5-chloro-2-[1-(3-pyridin-3-yl-pyrazin-2-yl)-azetidin-3-yl]-1H-benzoimidazole;
5-chloro-2-[1-(3-pyridin-4-yl-pyrazin-2-yl)-azetidin-3-yl]-1H-benzoimidazole;
3-[3-(5-chloro-1H-benzoimidazol-2-yl)-azetidin-1-yl]-pyrazine-2-carboxylic acid dimethylamide;
3-[3-(5-chloro-1H-benzoimidazol-2-yl)-azetidin-1-yl]-pyrazine-2-carboxylic acid (tetrahydro-pyran-4-yl)-amide;
3-[3-(5-chloro-1H-benzoimidazol-2-yl)-azetidin-1-yl]-pyrazine-2-carboxylic acid (tetrahydro-furan-2-ylmethyl)-amide;
3-[3-(5-chloro-1H-benzoimidazol-2-yl)-azetidin-1-yl]-pyrazine-2-carboxylic acid (tetrahydro-furan-2-ylmethyl)-amide;
5-methyl-2-(1-(3-phenylpyrazin-2-yl)azetidin-3-yl)-1H-benzo[d]imidazole;
3-(3-(5-chloro-1H-benzo[d]imidazol-2-yl)azetidin-1-yl)-N-phenylpyrazin-2-amine;
3-(3-(5-chloro-1H-benzo[d]imidazol-2-yl)azetidin-1-yl)-N-methyl-N-phenylpyrazin-2-amine;
5-chloro-2-(1-(3-phenoxypyrazin-2-yl)azetidin-3-yl)-1H-benzo[d]imidazole;
5-chloro-2-(1-(3-(4-methylpiperazin-1-yl)pyrazin-2-yl)azetidin-3-yl)-1H-benzo[d]imidazole;
5-chloro-2-(1-(3-(piperidin-1-yl)pyrazin-2-yl)azetidin-3-yl)-1H-benzo[d]imidazole;
5-chloro-2-(1-(3-methoxypyrazin-2-yl)azetidin-3-yl)-1H-benzo[d]imidazole;
4-(3-(3-(5-methyl-1H-benzo[d]imidazol-2-yl)azetidin-1-yl)pyrazin-2-yl)morpholine;
2-(1-(3-chloropyridin-2-yl)azetidin-3-yl)-5-methyl-1H-benzo[d]imidazole;
2-(1-(3-chloropyrazin-2-yl)azetidin-3-yl)-5-methyl-1H-benzo[d]imidazole;
5-chloro-2-(1-(3-(tetrahydro-2H-pyran-4-yloxy)pyridin-2-yl)azetidin-3-yl)-1H-benzo[d]imidazole;

4-(3-(3-(5-chloro-1H-benzo[d]imidazol-2-yl)azetidin-1-yl)pyrazin-2-yl)morpholine;

5-chloro-2-(1-(3-(3,6-dihydro-2H-pyran-4-yl)pyrazin-2-yl)azetidin-3-yl)-1H-benzo[d]imidazole;

2-(1-(3-bromopyridin-2-yl)azetidin-3-yl)-5-chloro-1H-benzo[d]imidazole;

5-chloro-2-(1-(3-chloropyrazin-2-yl)azetidin-3-yl)-1H-benzo[d]imidazole;

5-chloro-2-(1-(3-chloropyridin-2-yl)azetidin-3-yl)-1H-benzo[d]imidazole;

5-chloro-2-(1-(2,5-dichloropyrimidin-4-yl)azetidin-3-yl)-1H-benzo[d]imidazole;

5-chloro-2-(1-(3-(tetrahydro-2H-pyran-4-yl)pyridin-2-yl)azetidin-3-yl)-1H-benzo[d]imidazole;

2-[1-(3-Piperidin-1-yl-pyrazin-2-yl)-azetidin-3-yl]-quinoline;

2-[1-(3-m-Tolyl-pyrazin-2-yl)-azetidin-3-yl]-quinoline;

2-{1-[3-(3-Methoxy-phenyl)-pyridin-2-yl]-azetidin-3-yl}-quinoline;

2'-(3-Quinolin-2-yl-azetidin-1-yl)-3,4,5,6-tetrahydro-2H-[1,3']bipyridinyl;

2-{1-[3-(4-Methyl-piperidin-1-yl)-pyrazin-2-yl]-azetidin-3-yl}-quinoline;

{1-[3-(3-Quinolin-2-yl-azetidin-1-yl)-pyrazin-2-yl]-piperidin-4-yl}-methanol;

2-{1-[3-(3-Methyl-pyrrolidin-1-yl)-pyrazin-2-yl]-azetidin-3-yl}-quinoline; or

2-{1-[3-(3-Methoxy-phenyl)-pyrazin-2-yl]-azetidin-3-yl}-quinoline.

Another aspect of the current invention relates to compounds having the general structure of formula (Ia):

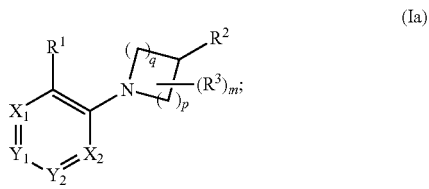

(Ia)

or a pharmaceutically-acceptable salt thereof, wherein:

Each of $X_1$, $X_2$, $Y_1$ and $Y_2$ is independently N or $CR^4$; wherein no more than two of $X_1$, $X_2$, $Y_1$ and $Y_2$ are N;

$R^1$ is F, Cl, Br, I, $C_{1-8}$alk, $C_{1-4}$haloalk, —$OR^a$, —$OR^c$, —$N(R^a)C(=O)R^b$, —$C(=O)R^a$, —$C(=O)R^c$, —$C(=O)$—$O$—$R^b$, —$NR^aR^c$, —$N(R^c)C(=O)R^b$, —$N(R^a)C(=O)R^c$, —$C(=O)NR^aR^b$, —$C(=O)NR^a(C_{0-4}$alk)$R^c$, or $C_{0-4}$alk-$L^1$; wherein said $C_{1-8}$alk group is substituted by 0, 1, 2 or 3 groups selected from halo, $C_{1-3}$haloalk, —OH, —$OC_{1-4}$alk, —$NH_2$, —$NHC_{1-4}$alk, —$OC(=O)C_{1-4}$alk, or —$N(C_{1-4}$alk$)C_{1-4}$alk;

$R^2$ is unsaturated 9- or 10-membered bicyclo-heterocyclic ring; wherein each $R^2$ is substituted by 0, 1, 2 or 3 $R^5$ groups;

Each of $R^3$ and $R^4$ is independently H, F, Cl, Br, I, OH, $OC_{1-4}$alk, $C_{1-4}$alk or $C_{1-4}$haloalk;

$R^5$ is independently H, F, Cl, Br, I, CN, OH, $OC_{1-4}$alk, $C_{1-4}$alk, $C_{1-4}$haloalk, or a carbon-linked or nitrogen-linked saturated, partially-saturated or unsaturated 3-, 4-, 5-, 6-, or 7-membered monocyclic ring, wherein each said ring contains 0, 1, 2, 3, or 4 N atoms and 0, 1, or 2 atoms selected from O or S;

m is 1, 2, 3, or 4;

each of p and q is independently 0, 1, 2, 3, 4, 5, or 6; wherein the sum of p and q is 2 to 6;

$R^a$ is independently H or $R^b$;

$R^b$ is independently phenyl, benzyl, or $C_{1-6}$alk, wherein said phenyl, benzyl, and $C_{1-6}$alk are being substituted by 0, 1, 2 or 3 substituents selected from halo, $C_{1-4}$alk, $C_{1-3}$haloalk, —OH, —$OC_{1-4}$alk, —$NH_2$, —$NHC_{1-4}$alk, —$OC(=O)C_{1-4}$alk, or —$N(C_{1-4}$alk$)C_{1-4}$alk;

$R^c$ is $C_{0-4}$alk-$L^2$; and

Each of $L^1$ and $L^2$ is independently a carbon-linked or nitrogen-linked saturated, partially-saturated or unsaturated 3-, 4-, 5-, 6-, or 7-membered monocyclic ring or a saturated, partially-saturated or unsaturated 8-, 9-, 10-, 11-, or 12-membered bicyclic ring, wherein each said ring contains 0, 1, 2, 3, or 4 N atoms and 0, 1, or 2 atoms selected from O or S; wherein each $L^1$ and $L^2$ is independently substituted by 0, 1, 2 or 3 $R^6$ groups selected from F, Cl, Br, $C_{1-6}$alk, $C_{1-4}$haloalk, —$OR^a$, —$OC_{1-4}$haloalk, CN, —$C(=O)R^b$, —$C(=O)OR^a$, —$C(=O)NR^aR^a$, —$C(=NR^a)NR^aR^a$, —$OC(=O)R^b$, —$OC(=O)NR^aR^a$, —$OC_{2-6}$alkNR^aR^a$, —$OC_{2-6}$alkOR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkNR^aR^a$, —$NR^aC_{2-6}$alkOR^a$, —$C_{1-6}$alkNR^aR^a$, —$C_{1-6}$alkOR^a$, —$C_{1-6}$alkN(R^a)C(=O)R^b$, —$C_{1-6}$alkOC(=O)R^b$, —$C_{1-6}$alkC(=O)NR^aR^a$, —$C_{1-6}$alkC(=O)OR^a$ or oxo;

with the proviso that when $R^2$ is

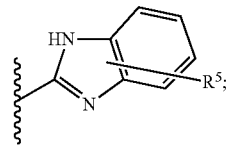

then at least one of $X_1$, $X_2$, $Y_1$ and $Y_2$ must be N.

In another embodiment of compounds having the general structure of formula (Ia), the group:

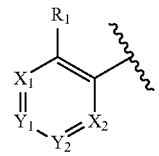

is selected from the group consisting of:

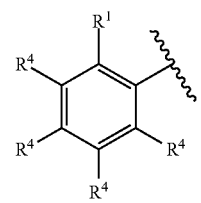

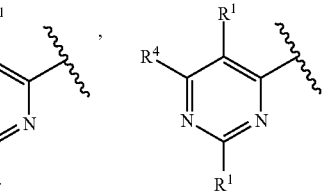

-continued

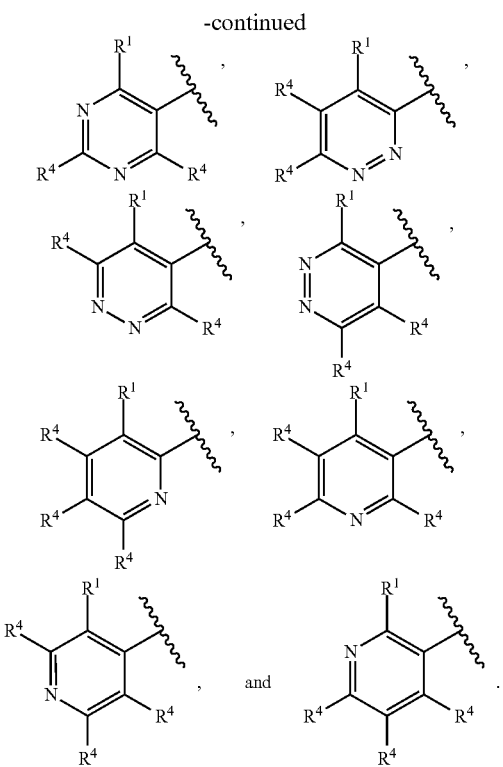

In another embodiment of compounds having the general structure of formula (Ia), the group

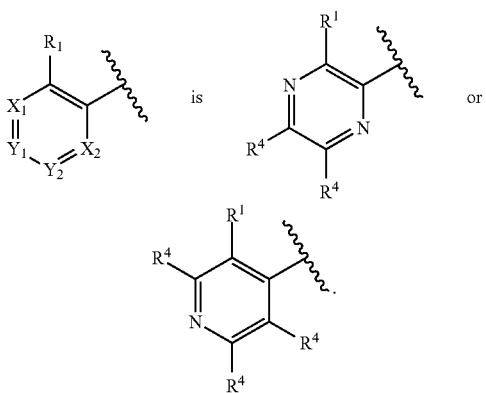

In another embodiment of compounds having the general structure of formula (Ia), m is 1 or 2.

In another embodiment of compounds having the general structure of formula (Ia), p is 0, 1, or 2.

In another embodiment of compounds having the general structure of formula (Ia), q is 0, 1, or 2.

In another embodiment of compounds having the general structure of formula (Ia), the group

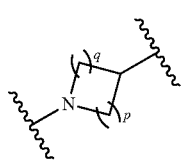

is azetidinyl, pyrrolidinyl, piperidinyl, or azepanyl.

In another embodiment of compounds having the general structure of formula (Ia), $R^1$ is Cl, Br, —$OR^a$, —$OR^c$, —$C(=O)R^c$, —$NR^aR^c$, —$C(=O)NR^aR^b$, —$C(=O)NR^a$ ($C_{0-4}$alk)$R^c$, or $C_{0-4}$alk-$L^1$.

In another embodiment of compounds having the general structure of formula (Ia), $R^1$ is a saturated, partially-saturated or unsaturated 4-, 5-, 6-, or 7-membered monocyclic ring, wherein each said ring contains 0, 1, 2, or 3 N atoms and 0, 1, or 2 O atoms, and wherein each said ring is substituted by 0, 1, 2 or 3 $R^6$ groups selected from F, Cl, Br, $C_{1-6}$alk, $C_{1-4}$haloalk, —$OR^a$, —$OC_{1-4}$haloalk, CN, —$C(=O)R^b$, —$C(=O)OR^a$, —$NR^aR^a$, —$SR^a$, or oxo.

In another embodiment of compounds having the general structure of formula (Ia), $R^1$ is a saturated or partially-saturated 5- to 6-membered monocyclic ring, wherein each said ring contains 0, 1, 2, or 3 N atoms and 0, 1, or 2 O atoms, and wherein each said ring is substituted by 0, 1, 2 or 3 $R^6$ groups selected from F, Cl, Br, $C_{1-6}$alk, $C_{1-4}$haloalk, —$OR^a$, —$OC_{1-4}$haloalk, CN, —$C(=O)R^b$, —$C(=O)OR^a$, —$NR^aR^a$, —$SR^a$, or oxo.

In another embodiment of compounds having the general structure of formula (Ia), $R^1$ is a saturated, partially-saturated or unsaturated 8-, 9-, 10-, 11-, or 12-membered bicyclic ring, wherein each said ring contains 0, 1, 2, or 3 N atoms and 0, 1, or 2 O atoms, and wherein each said ring is substituted by 0, 1, 2 or 3 $R^6$ groups selected from F, Cl, Br, $C_{1-6}$alk, $C_{1-4}$haloalk, —$OR^a$, —$OC_{1-4}$haloalk, CN, —$C(=O)R^b$, —$C(=O)OR^a$, —$NR^aR^a$, —$SR^a$, or oxo.

In another embodiment of compounds having the general structure of formula (Ia), $R^1$ is a nitrogen-linked saturated, partially-saturated or unsaturated 4-, 5-, 6-, or 7-membered monocyclic ring wherein each said ring contains 0, 1, 2, 3, or 4 N atoms and 0, 1, or 2 atoms selected from O or S; substituted by 0, 1, 2 or 3 $R^6$ groups selected from F, Cl, Br, $C_{1-6}$alk, $C_{1-4}$haloalk, —$OR^a$, —$OC_{1-4}$haloalk, CN, —$C(=O)R^b$, —$C(=O)OR^a$, —$NR^aR^a$, $SR^a$, or oxo.

In another embodiment of compounds having the general structure of formula (Ia), $R^1$ is cyclohexyl, cyclopentyl, cyclopentenyl, cyclohexenyl, cycloheptyl, azetidinyl, phenyl, 2-pyridyl, 3-pyridyl, pyrazolyl, morpholinyl, pyrimidyl, piperazinyl, piperidinyl, dihydropyranyl, tetrahydropyranyl, tetrahydrofuranyl, tetrahydropyridinyl, tetrahydrothiopyranyl, oxaspiro[3.5]nonyl, azepanyl, oxepanyl, or quinolinyl, all of which are substituted by 0, 1, 2 or 3 $R^6$ groups selected from F, Cl, Br, $C_{1-6}$alk, $C_{1-4}$haloalk, —$OR^a$, CN, —$C(=O)R^b$, —$C(=O)OR^a$, —$SR^a$, or oxo.

In another embodiment of compounds having the general structure of formula (Ia), $R^1$ is $C_{1-6}$alk substituted by 0, 1, 2 or 3 groups selected from halo, $C_{1-3}$haloalk, —OH, —$OC_{1-4}$alk, —$NH_2$, —$NHC_{1-4}$alk, —$OC(=O)C_{1-4}$alk, or —$N(C_{1-4}$alk)$C_{1-4}$alk.

In another embodiment of compounds having the general structure of formula (Ia), $R^a$ is H or $C_{1-6}$alk substituted by 0 or 1 —OH, —$OC_{1-4}$alk, —$OC(=O)C_{1-4}$alk, or —$N(C_{1-4}$alk)$C_{1-4}$alk.

In another embodiment of compounds having the general structure of formula (Ia), $R^c$ is a $C_{0-4}$alk-saturated, partially-saturated or unsaturated 3-, 4-, 5-, or 6-membered monocyclic ring containing 0 or 1 N atom and 0 or 1 atom selected from O or S, which is substituted by 0 or 1 $R^6$ groups selected from F, Cl, $C_{1-6}$alk, $C_{1-4}$haloalk, or —$OR^a$.

In another embodiment of compounds having the general structure of formula (Ia), $R^c$ is a $C_{0-4}$alk-saturated, partially-saturated or unsaturated 3-, 4-, 5-, or 6-membered monocyclic ring selected from the group consisting of cyclohexyl, cyclopentyl, cyclopentenyl, cyclohexenyl, cycloheptyl, azetidinyl, phenyl, pyridyl, pyrazolyl, morpholinyl, pyrimidyl, piperazinyl, piperidinyl, dihydropyranyl, tetrahydropyranyl, tetrahydrofuranyl, tetrahydropyridinyl, and tetrahydrothiopyranyl, all of which are substituted by 0, 1, 2 or 3 $R^6$ groups selected from F, Cl, Br, $C_{1-6}$alk, $C_{1-4}$haloalk, —$OR^a$, CN, —C(=O)$R^b$, —C(=O)$OR^a$, —$SR^a$, or oxo.

In another embodiment of compounds having the general structure of formula (Ia), $R^1$ is selected from the group consisting of: Cl, Br,

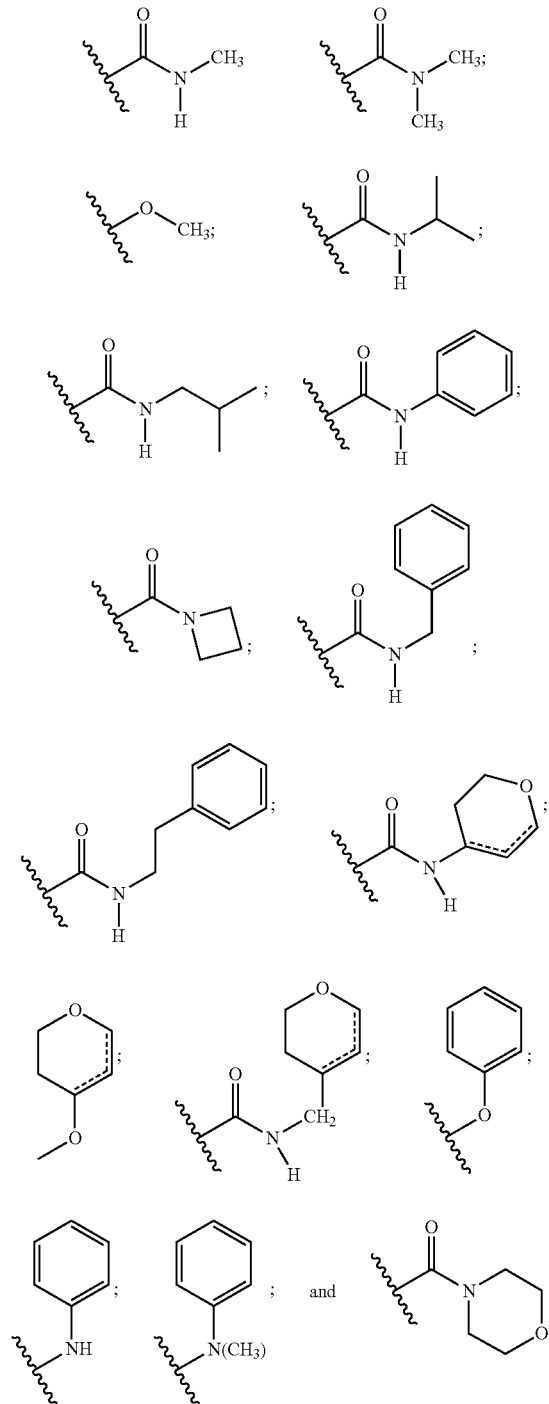

In another embodiment of compounds having the general structure of formula (Ia), $R^1$ is selected from the group consisting of:

-continued

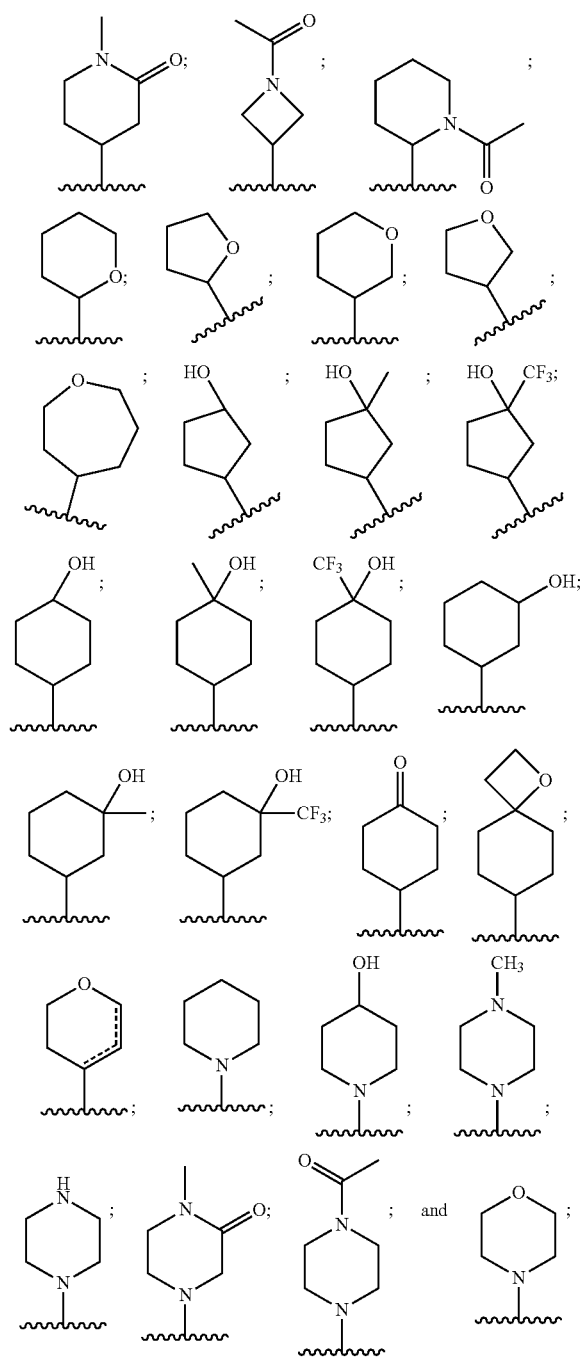

wherein the dotted bond is an optional double bond.

In another embodiment of compounds having the general structure of formula (Ia), $R^1$ is selected from the group consisting of:

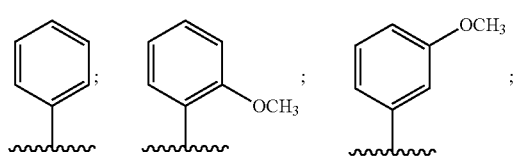

-continued

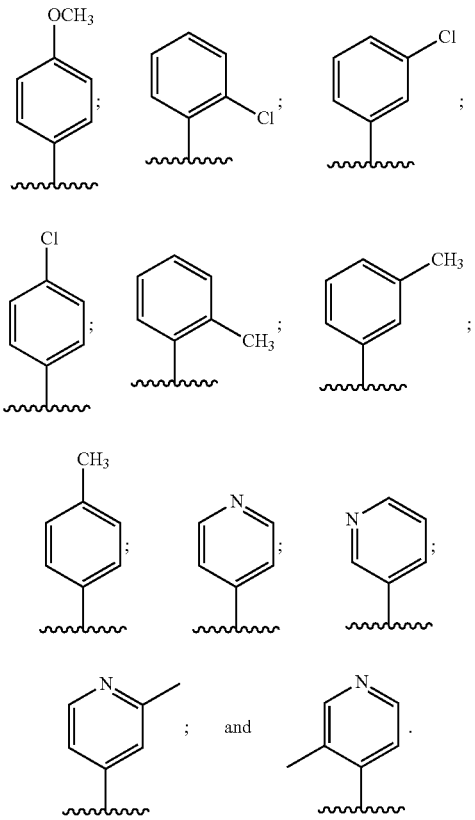

In another embodiment of compounds having the general structure of formula (Ia), $R^4$ is independently H, F, Cl, $OC_{1-4}$alk, $C_{1-4}$alk or $C_{1-4}$haloalk.

In another embodiment of compounds having the general structure of formula (Ia), $R^3$ is independently H, F, $OC_{1-4}$alk, $C_{1-4}$alk or $C_{1-4}$haloalk.

In another embodiment of compounds having the general structure of formula (Ia), $R^3$ is H.

In another embodiment of compounds having the general structure of formula (Ia), $R^2$ is

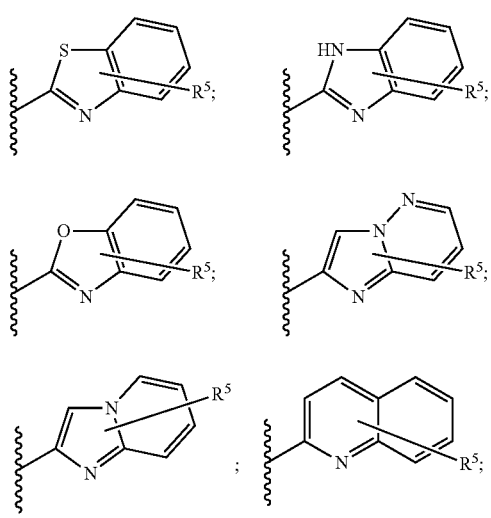

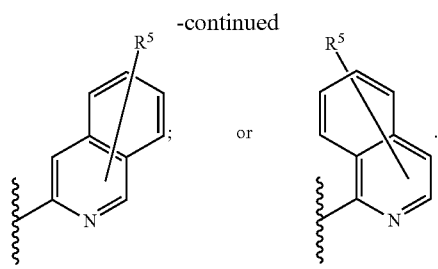

In another embodiment of compounds having the general structure of formula (Ia), $R^5$ is independently H, F, Cl, CN, $C_{1-4}$alk, $C_{1-4}$haloalk, or 3- to 8-membered-saturated or -partially saturated carbocyclic ring In another embodiment, $R^2$ and $R^3$ are H.

In another embodiment of compounds having the general structure of formula (Ia), $R^5$ is H, methyl, —$CH_2CH_3$ or —$CF_2CH_3$.

Another aspect of the current invention relates to compounds having the general structure of formula (IIa):

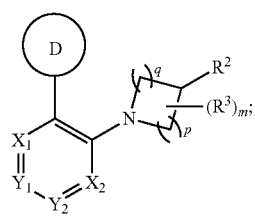

(IIa)

or any pharmaceutically-acceptable salt thereof, wherein:
Ring D is -$L^1$;
Each of $X_1$, $X_2$, $Y_1$ and $Y_2$ is independently N or $CR^4$; wherein no more than two of $X_1$, $X_2$, $Y_1$ and $Y_2$ are N;
$R^2$ is unsaturated 9- or 10-membered bicyclo-heterocyclic ring; wherein each $R^2$ is substituted by 0, 1, 2 or 3 $R^5$ groups;
Each of $R^3$ and $R^4$ is independently H, F, Cl, Br, I, OH, $OC_{1-4}$alk, $C_{1-4}$alk or $C_{1-4}$haloalk;
$R^5$ is independently H, F, Cl, Br, I, CN, OH, $OC_{1-4}$alk, $C_{1-4}$alk, $C_{1-4}$haloalk, or a carbon-linked or nitrogen-linked saturated, partially-saturated or unsaturated 3-, 4-, 5-, 6-, or 7-membered monocyclic ring, wherein each said ring contains 0, 1, 2, 3, or 4 N atoms and 0, 1, or 2 atoms selected from O or S;
m is 1, 2, 3, or 4;
each of p and q is independently 0, 1, 2, 3, 4, 5, or 6; wherein the sum of p and q is 2 to 6;
$R^a$ is independently H or $R^b$;
$R^b$ is independently phenyl, benzyl, or $C_{1-6}$alk, wherein said phenyl, benzyl, and $C_{1-6}$alk are being substituted by 0, 1, 2 or 3 substituents selected from halo, $C_{1-4}$alk, $C_{1-3}$haloalk, —OH, —$OC_{1-4}$alk, —$NH_2$, —$NHC_{1-4}$alk, —$OC(=O)$ $C_{1-4}$alk, or —$N(C_{1-4}alk)C_{1-4}$alk; and
Each of $L^1$ and $L^2$ is independently a carbon-linked or nitrogen-linked saturated, partially-saturated or unsaturated 3-, 4-, 5-, 6-, or 7-membered monocyclic ring or a saturated, partially-saturated or unsaturated 8-, 9-, 10-, 11-, or 12-membered bicyclic ring, wherein each said ring contains 0, 1, 2, 3, or 4 N atoms and 0, 1, or 2 atoms selected from O or S; wherein each $L^1$ and $L^2$ is independently substituted by 0, 1, 2 or 3 $R^6$ groups selected from F, Cl, Br, $C_{1-6}$alk, $C_{1-4}$haloalk, —$OR^a$, —$OC_{1-4}$haloalk, CN, —$C(=O)R^b$, —$C(=O)OR^a$, —$C(=O)NR^aR^a$, —$C(=NR^a)NR^aR^a$, —$OC(=O)R^b$, —$OC(=O)NR^aR^a$, —$OC_{2-6}alkNR^aR^a$, —$OC_{2-6}alkOR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}alkNR^aR^a$, —$NR^aC_{2-6}alkOR^a$, —$C_{1-6}alkNR^aR^a$, —$C_{1-6}alkN(R^a)C(=O)R^b$, —$C_{1-6}alkOC(=O)R^b$, —$C_{1-6}alkC(=O)NR^aR^a$, —$C_{1-6}alkC(=O)OR^a$ or oxo;

with the proviso that when $R^2$ is

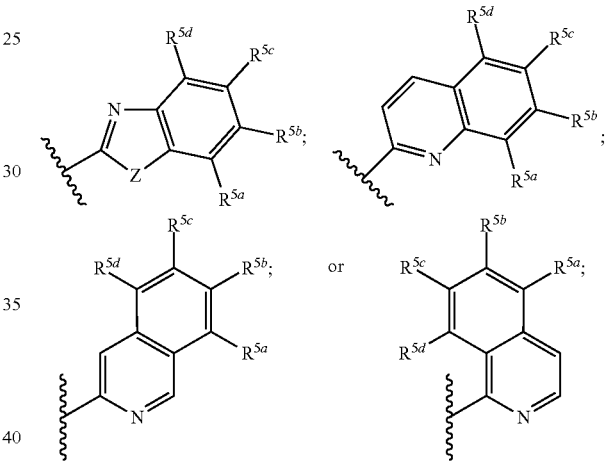

then at least one of $X_1$, $X_2$, $Y_1$ and $Y_2$ must be N.
In another embodiment of compounds of formula (IIa): $R^2$ is of formula:

wherein each of $R^{5a}$, $R^{5b}$, $R^{5c}$, and $R^{5d}$ is $R^5$; Z is S, O, or $NR^7$; and $R^7$ is H or $C_{1-6}$alk.

In another embodiment of compounds of formula (IIa), ring D is a carbon-linked saturated, partially-saturated or unsaturated 4-, 5-, 6-, or 7-membered monocyclic ring, wherein each said ring contains 0, 1, 2, 3, or 4 N atoms and 0, 1, or 2 atoms selected from O or S; independently substituted by 0, 1, 2 or 3 $R^6$ groups selected from F, Cl, Br, $C_{1-6}$alk, —$OR^a$, —$OC_{1-4}$haloalk, CN, —$C(=O)R^b$, —$C(=O)OR^a$, —$C(=O)NR^aR^a$, —$C(=NR^a)NR^aR^a$, —$OC(=O)R^b$, —$OC(=O)NR^aR^a$, —$OC_{2-6}alkNR^aR^a$, —$OC_{2-6}alkOR^a$, —$SR^a$, —$S(=O)R^b$, —$S(=O)_2R^b$, —$S(=O)_2NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}alkNR^aR^a$, —$NR^aC_{2-6}alkOR^a$, —$C_{1-6}alkNR^aR^a$, —$C_{1-6}alkOR^a$, —$C_{1-6}alkN(R^a)C(=O)R^b$, —$C_{1-6}alkOC(=O)R^b$, —$C_{1-6}alkC(=O)NR^aR^a$, —$C_{1-6}alkC(=O)OR^a$ or oxo.

In another embodiment of compounds of formula (IIa), ring D is a carbon-linked-saturated, partially-saturated or unsaturated 8-, 9-, 10-, 11-, or 12-membered bicyclic ring, wherein each said ring contains 0, 1, 2, 3, or 4 N atoms and 0, 1, or 2 atoms selected from O or S; independently substituted by 0, 1, 2 or 3 $R^6$ groups selected from F, Cl, Br, $C_{1-6}$alk, $C_{1-4}$haloalk, —$OR^a$, —$OC_{1-4}$haloalk, CN, —$C(=O)R^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$ or oxo.

In another embodiment of compounds of formula (IIa), ring D is a nitrogen-linked saturated, partially-saturated or unsaturated 4-, 5-, 6-, or 7-membered monocyclic ring, wherein each said ring contains 0, 1, 2, 3, or 4 N atoms and 0, 1, or 2 atoms selected from O or S; independently substituted by 0, 1, 2 or 3 R$^6$ groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$ or oxo, In another embodiment, of compounds of formula (IIa) ring D is a nitrogen-linked-saturated, partially-saturated or unsaturated 8-, 9-, 10-, 11-, or 12-membered bicyclic ring, wherein each said ring contains 0, 1, 2, 3, or 4 N atoms and 0, 1, or 2 atoms selected from O or S; independently substituted by 0, 1, 2 or 3 R$^6$ groups selected from F, Cl, Br, C$_{1-6}$alk, C$_{1-4}$haloalk, —OR$^a$, —OC$_{1-4}$haloalk, CN, —C(=O)R$^b$, —C(=O)OR$^a$, —C(=O)NR$^a$R$^a$, —C(=NR$^a$)NR$^a$R$^a$, —OC(=O)R$^b$, —OC(=O)NR$^a$R$^a$, —OC$_{2-6}$alkNR$^a$R$^a$, —OC$_{2-6}$alkOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkNR$^a$R$^a$, —NR$^a$C$_{2-6}$alkOR$^a$, —C$_{1-6}$alkNR$^a$R$^a$, —C$_{1-6}$alkOR$^a$, —C$_{1-6}$alkN(R$^a$)C(=O)R$^b$, —C$_{1-6}$alkOC(=O)R$^b$, —C$_{1-6}$alkC(=O)NR$^a$R$^a$, —C$_{1-6}$alkC(=O)OR$^a$ or oxo.

In another embodiment of compounds of formula (IIa), ring D is cyclohexyl, cyclopentyl, cyclopentenyl, cyclohexenyl, or cycloheptyl.

In another embodiment of compounds of formula (IIa), ring D is azetidinyl, phenyl, 2-pyridyl, 3-pyridyl, pyrazolyl, morpholinyl, pyrimidyl, piperazinyl, piperidinyl, dihydropyranyl, tetrahydropyranyl, tetrahydrofuranyl, tetrahydropyridinyl, or tetrahydrothiopyranyl.

In another embodiment of compounds of formula (IIa), ring D is oxaspiro[3.5]nonyl, azepanyl, oxepanyl, or quinolinyl.

In another embodiment of compounds of formula (IIa), ring D is cyclohexyl, cyclopentyl, cyclopentenyl, cyclohexenyl, cycloheptyl, azetidinyl, phenyl, 2-pyridyl, 3-pyridyl, pyrazolyl, morpholinyl, pyrimidyl, piperazinyl, piperidinyl, dihydropyranyl, tetrahydropyranyl, tetrahydrofuranyl, tetrahydropyridinyl, tetrahydrothiopyranyl, oxaspiro[3.5]nonyl, azepanyl, oxepanyl, or quinolinyl, all of which are substituted by 0, 1, 2 or 3 R$^6$ groups selected from F, Cl, Br, C$_{1-6}$alk, C$_{1-4}$haloalk, —OR$^a$, CN, —C(=O)R$^b$, —C(=O)OR$^a$, —NR$^a$R$^a$, —SR$^a$, or oxo.

Another aspect of the invention relates to compounds of formula (IIa) having the formula:

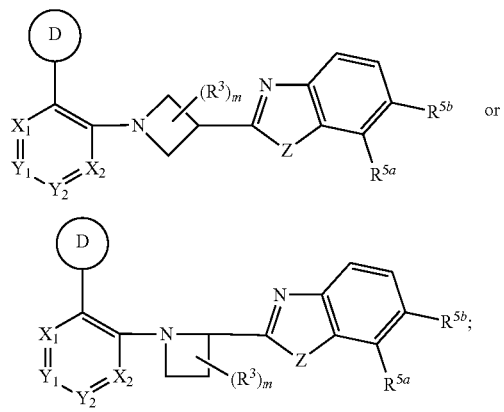

Another aspect of the invention relates to compounds of formula (IIa) having the formula:

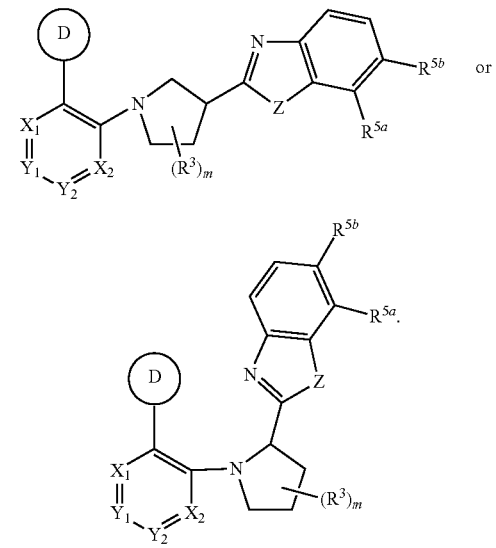

Another aspect of the invention relates to compounds of formula (IIa) having the formula:

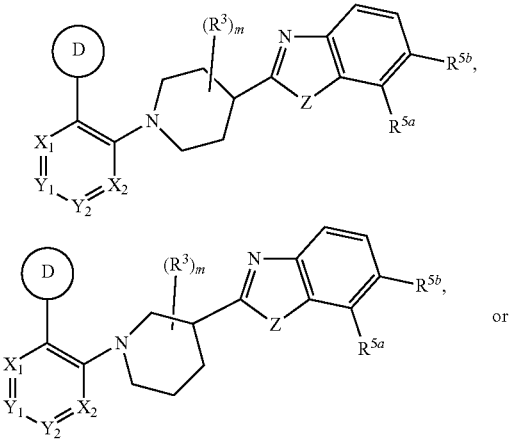

-continued

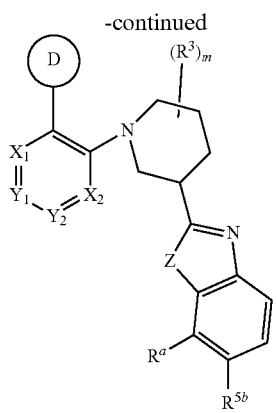

Another aspect of the invention relates to a method of treating conditions that may be treated with PDE10 inhibitors comprising the step of administering any of the above compounds of formula (IIa).

Another aspect of the invention relates to a method of treating conditions that may be treated with PDE10 inhibitors comprising the step of administering any of the above compounds of formula (IIa); wherein said condition is selected from the group consisting of psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Another aspect of the invention relates to a method of treating conditions that may be treated with PDE10 inhibitors comprising the step of administering any of the above compounds of formula (IIa); wherein said condition is selected from the group consisting of schizophrenia, bipolar disorder, and obsessive-compulsive disorder.

Another aspect of the invention relates to a pharmaceutical composition comprising any of the above compounds of formula (IIa) and a pharmaceutically-acceptable diluent or carrier.

Another aspect of the invention relates to a method of treating a disorder treatable by inhibition of PDE10 in a patient which method comprises administering to the patient a pharmaceutical composition comprising an effective amount of any of the above compounds.

Another aspect of the invention relates to the use of any of the above compounds as a medicament.

Another aspect of the invention relates to the use of any of the above compounds in the manufacture of a medicament for the treatment of schizophrenia, bipolar disorder, or obsessive-compulsive disorder.

Another aspect of the invention relates to compounds or a pharmaceutically-acceptable salt thereof, selected from the group consisting of:

2-[1-(3-phenyl-pyrazin-2-yl)-piperidin-4-yl]-1H-benzoimidazole-5-carbonitrile;
2-[1-(3-morpholin-4-yl-pyrazin-2-yl)-piperidin-4-yl]-1H-benzoimidazole-5-carbonitrile;
5-methyl-2-(1-(3-(tetrahydro-2H-pyran-4-yloxy)pyrazin-2-yl)azetidin-3-yl)-1H-benzo[d]imidazole;
4-(4-(3-(5-chloro-1H-benzo[d]imidazol-2-yl)azetidin-1-yl)pyrimidin-2-yl)morpholine;
2-[1-(3,5-dichloro-pyridin-4-yl)-azetidin-3-yl]-5-methyl-1H-benzoimidazole;
2-[1-(3-chloro-5-phenyl-pyridin-4-yl)-azetidin-3-yl]-5-methyl-1H-benzoimidazole;
{2-[3-(5-chloro-1H-benzoimidazol-2-yl)-azetidin-1-yl]-pyridin-3-yl}-(3-hydroxy-azetidin-1-yl)-methanone;
3-[3-(5-chloro-1H-benzoimidazol-2-yl)-azetidin-1-yl]-pyrazine-2-carboxylic acid methylamide;
5-chloro-2-(1-(4-(tetrahydro-2H-pyran-4-yloxy)pyridin-2-yl)azetidin-3-yl)-1H-benzo[d]imidazole;
5-chloro-2-(1-(6-(tetrahydro-2H-pyran-4-yl)pyrimidin-4-yl)azetidin-3-yl)-1H-benzo[d]imidazole;
4-(5-chloro-4-(3-(5-chloro-1H-benzo[d]imidazol-2-yl)azetidin-1-yl)pyrimidin-2-yl)morpholine;
5-chloro-2-(1-(3-(tetrahydro-2H-pyran-4-yl)pyrazin-2-yl)azetidin-3-yl)-1H-benzo[d]imidazole;
5-chloro-2-(1-(4-(tetrahydro-2H-pyran-4-yl)pyridin-2-yl)azetidin-3-yl)-1H-benzo[d]imidazole;
5-chloro-2-(1-(3-(tetrahydro-2H-pyran-4-yloxy)pyrazin-2-yl)azetidin-3-yl)-1H-benzo[d]imidazole;
2-[1-(3-chloro-pyridin-2-yl)-pyrrolidin-3-yl]-1H-benzoimidazole-5-carbonitrile;
2-[1-(3-Morpholin-4-yl-pyrazin-2-yl)-pyrrolidin-3-yl]-1H-benzoimidazole-5-carbonitrile;
5-cyclopropyl-2-[1-(3-phenyl-pyrazin-2-yl)-piperidin-4-yl]-1H-benzoimidazole;
2-[1-(3-phenyl-pyrazin-2-yl)-azetidin-3-yl]-1H-benzoimidazole-5-carbonitrile;
2-[1-(3-phenyl-pyrazin-2-yl)-pyrrolidin-3-yl]-1H-benzoimidazole-5-carbonitrile;
azetidin-1-yl-{2-[3-(5-chloro-1H-benzoimidazol-2-yl)-azetidin-1-yl]-pyridin-3-yl}-methanone;
{2-[3-(5-chloro-1H-benzoimidazol-2-yl)-azetidin-1-yl]-pyridin-3-yl}-morpholin-4-yl-methanone;
2-[3-(5-chloro-1H-benzoimidazol-2-yl)-azetidin-1-yl]-N-phenyl-nicotinamide;
N-benzyl-2-[3-(5-chloro-1H-benzoimidazol-2-yl)-azetidin-1-yl]-nicotinamide;
2-[3-(5-chloro-1H-benzoimidazol-2-yl)-azetidin-1-yl]-N-phenethyl-nicotinamide;
2-[3-(5-chloro-1H-benzoimidazol-2-yl)-azetidin-1-yl]-N-isopropyl-nicotinamide;
2-[3-(5-chloro-1H-benzoimidazol-2-yl)-azetidin-1-yl]-N-isobutyl-nicotinamide;
2-[3-(5-chloro-1H-benzoimidazol-2-yl)-azetidin-1-yl]-N-(tetrahydro-pyran-4-ylmethyl)-nicotinamide;
5-chloro-2-[1-(3-o-tolyl-pyrazin-2-yl)-azetidin-3-yl]-1H-benzoimidazole;
5-chloro-2-[1-(3-m-tolyl-pyrazin-2-yl)-azetidin-3-yl]-1H-benzoimidazole;
5-chloro-2-[1-(3-p-tolyl-pyrazin-2-yl)-azetidin-3-yl]-1H-benzoimidazole;
5-chloro-2-{1-[3-(2-methoxy-phenyl)-pyrazin-2-yl]-azetidin-3-yl}-1H-benzoimidazole;
5-chloro-2-{1-[3-(3-methoxy-phenyl)-pyrazin-2-yl]-azetidin-3-yl}-1H-benzoimidazole;
5-chloro-2-{1-[3-(4-methoxy-phenyl)-pyrazin-2-yl]-azetidin-3-yl}-1H-benzoimidazole;
5-chloro-2-{1-[3-(2-chloro-phenyl)-pyrazin-2-yl]-azetidin-3-yl}-1H-benzoimidazole;
5-chloro-2-{1-[3-(3-chloro-phenyl)-pyrazin-2-yl]-azetidin-3-yl}-1H-benzoimidazole;
5-chloro-2-{1-[3-(4-chloro-phenyl)-pyrazin-2-yl]-azetidin-3-yl}-1H-benzoimidazole;
5-chloro-2-[1-(3-pyridin-3-yl-pyrazin-2-yl)-azetidin-3-yl]-1H-benzoimidazole;
5-chloro-2-[1-(3-pyridin-4-yl-pyrazin-2-yl)-azetidin-3-yl]-1H-benzoimidazole;

3-[3-(5-chloro-1H-benzoimidazol-2-yl)-azetidin-1-yl]-pyrazine-2-carboxylic acid dimethylamide;
3-[3-(5-chloro-1H-benzoimidazol-2-yl)-azetidin-1-yl]-pyrazine-2-carboxylic acid (tetrahydro-pyran-4-yl)-amide;
3-[3-(5-chloro-1H-benzoimidazol-2-yl)-azetidin-1-yl]-pyrazine-2-carboxylic acid (tetrahydro-furan-2-ylmethyl)-amide;
3-[3-(5-chloro-1H-benzoimidazol-2-yl)-azetidin-1-yl]-pyrazine-2-carboxylic acid (tetrahydro-furan-2-ylmethyl)-amide;
5-methyl-2-(1-(3-phenylpyrazin-2-yl)azetidin-3-yl)-1H-benzo[d]imidazole;
3-(3-(5-chloro-1H-benzo[d]imidazol-2-yl)azetidin-1-yl)-N-phenylpyrazin-2-amine;
3-(3-(5-chloro-1H-benzo[d]imidazol-2-yl)azetidin-1-yl)-N-methyl-N-phenylpyrazin-2-amine;
5-chloro-2-(1-(3-phenoxypyrazin-2-yl)azetidin-3-yl)-1H-benzo[d]imidazole;
5-chloro-2-(1-(3-(4-methylpiperazin-1-yl)pyrazin-2-yl)azetidin-3-yl)-1H-benzo[d]imidazole;
5-chloro-2-(1-(3-(piperidin-1-yl)pyrazin-2-yl)azetidin-3-yl)-1H-benzo[d]imidazole;
5-chloro-2-(1-(3-methoxypyrazin-2-yl)azetidin-3-yl)-1H-benzo[d]imidazole;
4-(3-(3-(5-methyl-1H-benzo[d]imidazol-2-yl)azetidin-1-yl)pyrazin-2-yl)morpholine;
2-(1-(3-chloropyridin-2-yl)azetidin-3-yl)-5-methyl-1H-benzo[d]imidazole;
2-(1-(3-chloropyrazin-2-yl)azetidin-3-yl)-5-methyl-1H-benzo[d]imidazole;
5-chloro-2-(1-(3-(tetrahydro-2H-pyran-4-yloxy)pyridin-2-yl)azetidin-3-yl)-1H-benzo[d]imidazole;
4-(3-(3-(5-chloro-1H-benzo[d]imidazol-2-yl)azetidin-1-yl)pyrazin-2-yl)morpholine;
5-chloro-2-(1-(3-(3,6-dihydro-2H-pyran-4-yl)pyrazin-2-yl)azetidin-3-yl)-1H-benzo[d]imidazole;
2-(1-(3-bromopyridin-2-yl)azetidin-3-yl)-5-chloro-1H-benzo[d]imidazole;
5-chloro-2-(1-(3-chloropyrazin-2-yl)azetidin-3-yl)-1H-benzo[d]imidazole;
5-chloro-2-(1-(3-chloropyridin-2-yl)azetidin-3-yl)-1H-benzo[d]imidazole;
5-chloro-2-(1-(2,5-dichloropyrimidin-4-yl)azetidin-3-yl)-1H-benzo[d]imidazole; and
5-chloro-2-(1-(3-(tetrahydro-2H-pyran-4-yl)pyridin-2-yl)azetidin-3-yl)-1H-benzo[d]imidazole.

Yet another aspect of the current invention relates to the compounds of the invention, or a pharmaceutically-acceptable salt thereof, radiolabeled with a positron emitting radionuclide which are independently $^{11}C$, $^{18}F$, $^{15}O$, $^{13}N$, $^{76}Br$, $^{77}Br$, $^{123}I$, or $^{125}I$.

Yet another aspect of the current invention relates to a radiopharmaceutical composition comprising the radiolabeled compounds of the invention, or a pharmaceutically-acceptable salt thereof and at least one pharmaceutically acceptable carrier or excipient.

Yet another aspect of the current invention relates to a method for the diagnostic imaging of PDE10 receptors in a mammal, including human, or tissues bearing PDE10 receptors in a mammal, including human brain, which comprises administering to a mammal in need of such diagnostic imaging an effective amount of the radiolabeled compounds of the invention.

Yet another aspect of the current invention relates to a method for the detection or quantification of PDE10 receptors in mammalian tissue, including human tissue, which comprises contacting such mammalian tissue in which such detection or quantification is desired with an effective amount of the radiolabeled compounds of the invention.

Yet another aspect of the current invention relates to a method of preparation of a compound of the invention, or its pharmaceutically acceptable salt thereof, including the key intermediates thereof.

The present invention includes all pharmaceutically acceptable isotopically-labelled compounds of the present invention wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2H$ and $^3H$, carbon, such as $^{11}C$, $^{13}C$ and $^{14}C$, chlorine, such as $^{38}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the present invention, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$, $^{13}N$, $^{76}Br$, $^{77}Br$, $^{123}I$, or $^{125}I$ can be useful in Positron Emission Topography (PET) studies for examining substrate receptor occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

The compounds of this invention may have in general several asymmetric centers and are typically depicted in the form of racemic mixtures. This invention is intended to encompass racemic mixtures, partially racemic mixtures and separate enantiomers and diasteromers Specific embodiments of the present invention include the compounds exemplified in the Examples below and their pharmaceutically acceptable salts, complexes, solvates, polymorphs, stereoisomers, metabolites, prodrugs, and other derivatives thereof, Unless otherwise specified, the following definitions apply to terms found in the specification and The term "$C_{\alpha-\beta}alk$" means an alkyl group comprising a minimum of $\alpha$ and a maximum of $\beta$ carbon atoms in a branched, cyclical or linear relationship or any combination of the three, wherein $\alpha$ and $\beta$ represent integers. The alkyl groups described in this section may also contain one or two double or triple bonds. A designation of $C_0alk$ indicates a direct bond. Examples of $C_{1-6}alkyl$ include, but are not limited to the following:

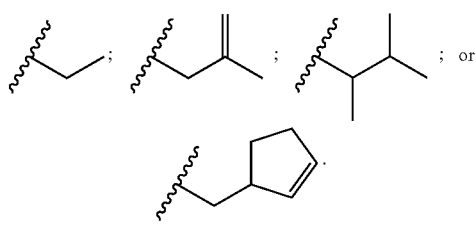

The term "benzo group", alone or in combination, means the divalent radical C$_4$H$_4$=, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

The term "halo" or "halogen" means a halogen atoms which are independently F, Cl, Br or I.

The term "C$_{\alpha-\beta}$haloalk" means an alk group, as described above, wherein one or more hydrogen atom of the alk group is replaced by F, Cl, Br or I.

The term "carbon-linked" means a substituent is linked to another group through a carbon atom. Examples of "carbon-linked" substituents include, but are not limited to the following:

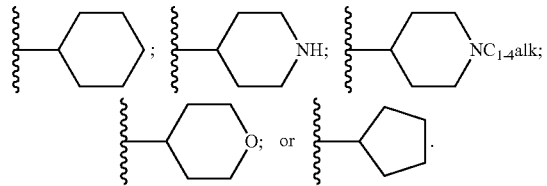

The term "nitrogen-linked" means a substituent is linked to another group through a nitrogen atom. Examples of "nitrogen-linked" substituents include, but are not limited to the following:

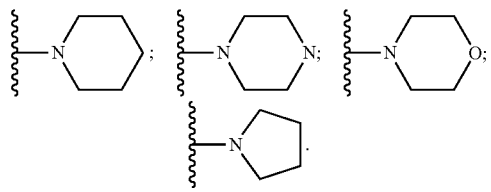

The group N(R$^a$)R$^a$ and the like include substituents where the two R$^a$ groups together form a ring, optionally including a N, O or S atom, and include groups such as:

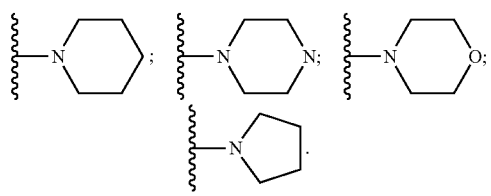

The group N(C$_{\alpha-\beta}$alk) C$_{\alpha-\beta}$alk, wherein α and β are as defined above, include substituents where the two C$_{\alpha-\beta}$alk groups together form a ring, optionally including a N, O or S atom, and include groups such as:

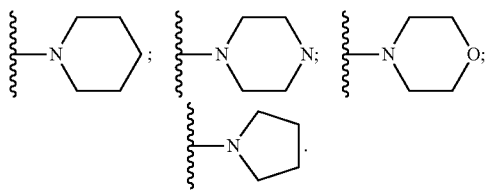

The term "carbocyclyl" means a ring comprising by itself or in combination with other terms, represents, unless otherwise stated, cyclic version of "C$_{\alpha-\beta}$alk". Thus, the term "carbocyclyl" is meant to be included in the terms "C$_{\alpha-\beta}$alk". Examples of carbocycle include cyclopentyl, cyclohexyl, or partially unsaturated ring such as 1-cyclohexenyl, 3-cyclohexenyl, cycloheptyl, cyclobutylene, cyclohexylene and the like. Unless otherwise stated, carbocycle can include fully saturated ring such as phenyl or naphthyl.

The term "heteroatom" means N, O or S.

The term "heterocyclyl" means a ring comprising at least one carbon atom and at least one other atom which are independently N, O or S. "Heterocyclyl" includes aromatic heterocyclic ring which is commonly known as heteroaryl. Thus, the term "heteroaryl" is meant to be included in the terms "heterocyclyl". Examples of heterocycles that may be found in the claims include, but are not limited to, the following:

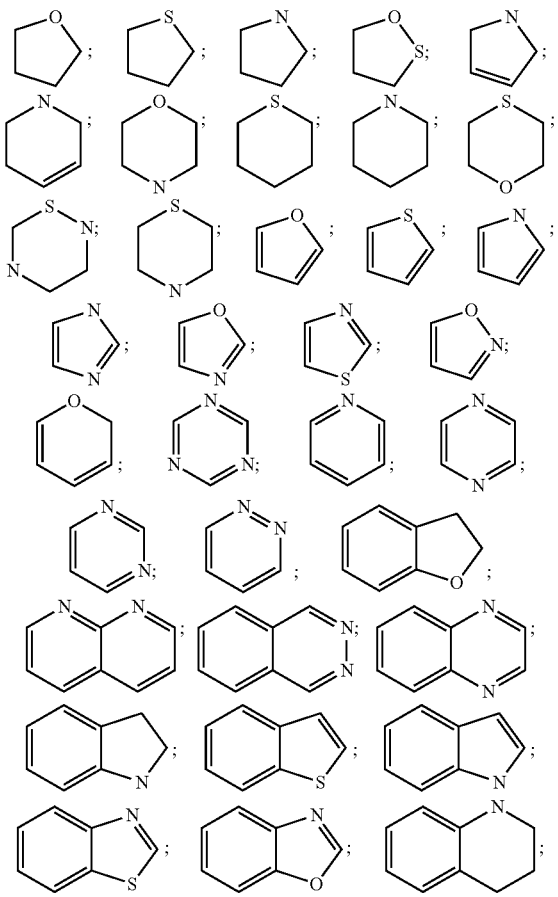

-continued

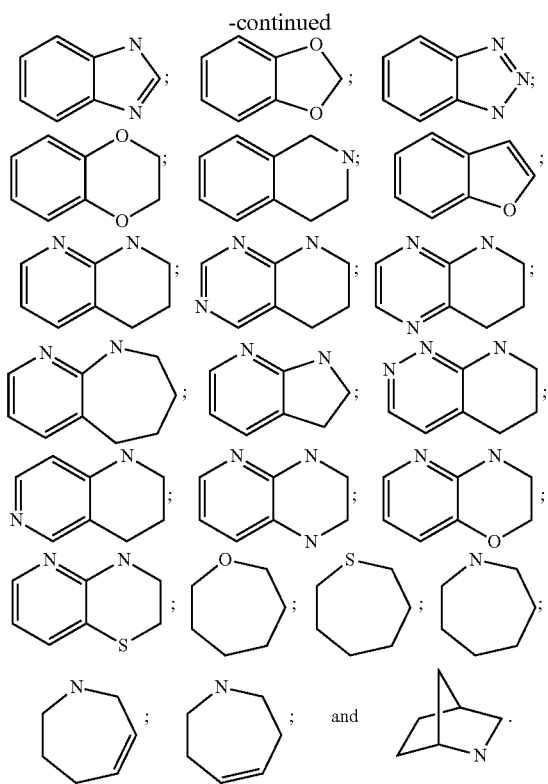

The term "pharmaceutically acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," and Berge et al., J. Pharm. Sci. 66:1 (1977).

The term "saturated, partially-saturated or unsaturated" includes substituents saturated with hydrogens, substituents completely unsaturated with hydrogens and substituents partially saturated with hydrogens.

Representative examples of "saturated, partially-saturated or unsaturated" five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyndazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

The term "monocyclic" means a group having a single saturated, partially-saturated, or unsaturated ring system. Typically a monocyclic ring system can have from 3- to 8 atoms in the ring system. The term includes, but is not limited to, cyclopropyl, cyclopropyl, cyclobutyl, cyclopentyl, cyclohexyl, cycloheptyl, phenyl, and the like.

The term "bicyclic" means a group having two interconnected saturated, partially-saturated, or unsaturated rings that include stable bridged, fused, or spiro rings. The bicyclic ring may be attached at any carbon or heteroatom which affords a stable group. Typically a bicyclic ring system can have from 6- to 14 atoms in the ring system. The term includes, but is not limited to, benzimidazole, naphthyl, bicyclo[3.1.0]hexane, bicyclo[4.1.0]heptane, spiro[2.4]heptane, spiro[2.5]octane, bicyclo[4.4.0]decane, bicyclo[4.3.0]nonane, bicyclo[3.3.1] nonane, bicyclo[3.2.1]octane, spiro[4.5]decane, spiro[3.5] nonane, norbornane, bicyclo[2.1.0]pentane, bicyclo[3.3.0] octane, bicyclo[2.2.2]octane, bicyclo[3.3.3]undecane, and the like.

The term "tricyclic" means a group having three interconnected saturated, partially-saturated, or unsaturated rings that include stable bridged, fused, or spiro rings. Typically a tricyclic ring system can have from 11 to 18 ring atoms in the ring system. The term includes, but is not limited to, adamantyl, tricyclo[5.2.1.0.sup.2,6]decane, and the like.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b) pyridinyl, pyrano(3,4-b)pyrrolyl, benzofuryl, isobenzofuryl, benzo[b]thienyl, benzo[c]thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b) pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule or group is replaced with a group or atom. Typical substitutents include: halogen, $C_{1-8}$alkyl, hydroxyl, $C_{1-8}$alkoxy, $-NR^xR^x$, nitro, cyano, halo or perhalo$C_{1-8}$alkyl, $C_{2-8}$alkenyl, $C_{2-8}$alkynyl, $-SR^x$, $-S(=O)_2R^x$, $-C(=O)$ $OR^x$, $-C(=O)R^x$, wherein each $R^x$ is independently hydrogen or $C_1$-$C_8$ alkyl. It is noted that when the substituent is $-NR^xR^x$, the $R^x$ groups may be joined together with the nitrogen atom to form a ring.

A group or atom that replaces a hydrogen atom is also called a substituent.

Any particular molecule or group can have one or more substituent depending on the number of hydrogen atoms that can be replaced.

The symbol "-" represents a covalent bond and can also be used in a radical group to indicate the point of attachment to another group. In chemical structures, the symbol is commonly used to represent a methyl group in a molecule.

The term "leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

The term "protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene) benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

The term "silyl protecting groups" means silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted aromatic heterocyclyl groups (Y'=O, S, NR), and the like, which are illustrated in the following examples:

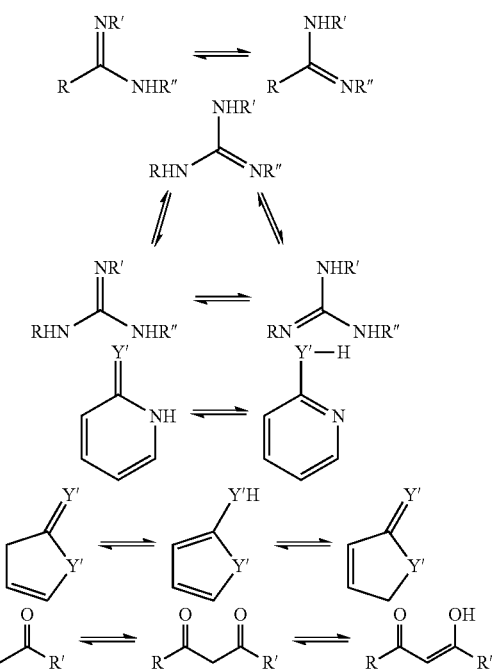

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The term "therapeutically effective amount" means an amount of a compound that ameliorates, attenuates or eliminates one or more symptom of a particular disease or condition, or prevents or delays the onset of one of more symptom of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of Formula I, or a salt of a compound of Formula I, or a formulation containing a compound of Formula I, or a particular excipient, are suitable for administration to a patient.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

Utility and Methods of Use

Provided herein are methods for treating a disorder or disease by inhibiting PDE10 enzyme. The methods, in general, comprises the step of administering a therapeutically effective amount of a compounds of the present invention, or an individual stereoisomer, a mixture of stereoisomers, or a pharmaceutically acceptable salt or solvate thereof, to a patient in need thereof to treat the disorder or disease.

In certain embodiments, this invention provides a use of a compound as described herein in the manufacture of a medicament for treating a disorder or disease treatable by inhibition of PDE10.

The compounds of the present invention inhibit PDE10 enzyme activity, and hence raise the levels of cAMP or cGMP within cells that express PDE10. Accordingly, inhibition of PDE10 enzyme activity would be useful in the treatment of diseases caused by deficient amounts of cAMP or cGMP in cells. PDE10 inhibitors would also be of benefit in cases wherein raising the amount of cAMP or cGMP above normal levels results in a therapeutic effect. Inhibitors of PDE10 may be used to treat disorders of the peripheral and central nervous system, cardiovascular diseases, cancer, gastro-enterological diseases, endocrinological diseases and urological diseases.

Indications that may be treated with PDE10 inhibitors, either alone or in combination with other drugs, include, but are not limited to, those diseases thought to be mediated in part by the basal ganglia, prefrontal cortex, and hippocampus. These indications include psychoses, Parkinson's disease, dementias, obsessive compulsive disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Psychoses are disorders that affect an individual's perception of reality. Psychoses are characterized by delusions and hallucinations. The compounds of the present invention are suitable for use in treating patients suffering from all forms of psychoses, including, but not limited to, schizophrenia, late-onset schizophrenia, schizoaffective disorders, prodromal schizophrenia, and bipolar disorders. Treatment can be for the positive symptoms of schizophrenia as well as for the cognitive deficits and negative symptoms. Other indications for PDE10 inhibitors include psychoses resulting from drug abuse (including amphetamines and PCP), encephalitis, alcoholism, epilepsy, Lupus, sarcoidosis, brain tumors, multiple sclerosis, dementia with Lewy bodies, or hypoglycemia. Other psychiatric disorders, like posttraumatic stress disorder (PTSD), and schizoid personality can also be treated with PDE10 inhibitors.

Obsessive-compulsive disorder (OCD) has been linked to deficits in the frontal-striatal neuronal pathways (Saxena et al., Br. J. Psychiatry Suppl, 35:26-37, 1998). Neurons in these pathways project to striatal neurons that express PDE10. PDE10 inhibitors cause cAMP to be elevated in these neurons; elevations in cAMP result in an increase in CREB phosphorylation and thereby improve the functional state of these neurons. The compounds of the present invention are therefore suitable for use in the indication of OCD. OCD may result, in some cases, from streptococcal infections that cause autoimmune reactions in the basal ganglia (Giedd et al., Am J Psychiatry. 157:281-283, 2000). Because PDE10 inhibitors may serve a neuroprotective role, administration of PDE10 inhibitors may prevent the damage to the basal ganglia after repeated streptococcal infections and thereby prevent the development of OCD.

In the brain, the level of cAMP or cGMP within neurons is believed to be related to the quality of memory, especially long term memory. Without wishing to be bound to any particular mechanism, it is proposed that, since PDE10 degrades cAMP or cGMP, the level of this enzyme affects memory in animals, for example, in humans. A compound that inhibits cAMP phosphodiesterase (PDE) can thereby increase intracellular levels of cAMP, which in turn activate a protein kinase that phosphorylates a transcription factor (cAMP response binding protein). The phosphorylated transcription factor then binds to a DNA promoter sequence to activate genes that are important in long term memory. The more active such genes are, the better is long-term memory. Thus, by inhibiting a phosphodiesterase, long term memory can be enhanced.

Dementias are diseases that include memory loss and additional intellectual impairment separate from memory. The compounds of the present invention are suitable for use in treating patients suffering from memory impairment in all forms of dementia. Dementias are classified according to their cause and include: neurodegenerative dementias (e.g., Alzheimer's, Parkinson's disease, Huntington's disease, Pick's disease), vascular (e.g., infarcts, hemorrhage, cardiac disorders), mixed vascular and Alzheimer's, bacterial meningitis, Creutzfeld-Jacob Disease, multiple sclerosis, traumatic (e.g., subdural hematoma or traumatic brain injury), infectious (e.g., HIV), genetic (down syndrome), toxic (e.g., heavy metals, alcohol, some medications), metabolic (e.g., vitamin B12 or folate deficiency), CNS hypoxia, Cushing's disease, psychiatric (e.g., depression and schizophrenia), and hydrocephalus.

The condition of memory impairment is manifested by impairment of the ability to learn new information and/or the inability to recall previously learned information. The present invention includes methods for dealing with memory loss separate from dementia, including mild cognitive impairment (MCI) and age-related cognitive decline. The present invention includes methods of treatment for memory impairment as a result of disease. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. The compounds of the present invention are suitable for use in the treatment of memory impairment due to, for example, Alzheimer's disease, multiple sclerosis, amylolaterosclerosis (ALS), multiple systems atrophy (MSA), schizophrenia, Parkinson's disease, Huntington's disease, Pick's disease, Creutzfeld-Jakob disease, depression, aging, head trauma, stroke, spinal cord injury, CNS hypoxia, cerebral senility, diabetes associated cognitive impairment, memory deficits from early exposure of anesthetic agents, multiinfarct dementia and other neurological conditions including acute neuronal diseases, as well as HIV and cardiovascular diseases.

The compounds of the present invention are also suitable for use in the treatment of a class of disorders known as polyglutamine-repeat diseases. These diseases share a common pathogenic mutation. The expansion of a CAG repeat, which encodes the amino acid glutamine, within the genome leads to production of a mutant protein having an expanded polyglutamine region. For example, Huntington's disease has been linked to a mutation of the protein huntingtin. In individuals who do not have Huntington's disease, huntingtin has a polyglutamine region containing about 8 to 31 glutamine residues. For individuals who have Huntington's disease, huntingtin has a polyglutamine region with over 37 glutamine residues. Aside from Huntington's disease (HD), other known polyglutamine-repeat diseases and the associated proteins include dentatorubral-pallidoluysian atrophy, DRPLA (atrophin-1); spinocerebellar ataxia type-1 (ataxin-1); spinocerebellar ataxia type-2 (ataxin-2); spinocerebellar ataxia type-3 (also called Machado-Joseph disease or MJD) (ataxin-3); spinocerebellar ataxia type-6 (alpha 1a-voltage dependent calcium channel); spinocerebellar ataxia type-7 (ataxin-7); and spinal and bulbar muscular atrophy (SBMA, also know as Kennedy disease).

The basal ganglia are important for regulating the function of motor neurons; disorders of the basal ganglia result in movement disorders. Most prominent among the movement disorders related to basal ganglia function is Parkinson's disease (Obeso et al., Neurology. 62(1 Suppl 1):S17-30, 2004). Other movement disorders related to dysfunction of the basal ganglia include tardive dyskinesia, progressive supranuclear palsy and cerebral palsy, corticobasal degeneration, multiple system atrophy, Wilson disease, dystonia, tics, and chorea. The compounds of the invention are also suitable for use to treat movement disorders related to dysfunction of basal ganglia neurons.

PDE10 inhibitors are useful in raising cAMP or cGMP levels and prevent neurons from undergoing apoptosis. PDE10 inhibitors may be anti-inflammatory by raising cAMP in glial cells. The combination of anti-apoptotic and anti-inflammatory properties, as well as positive effects on synaptic plasticity and neurogenesis, make these compounds useful to treat neurodegeneration resulting from any disease or injury, including stroke, spinal cord injury, Alzheimer's disease, multiple sclerosis, amylolaterosclerosis (ALS), and multiple systems atrophy (MSA).

Autoimmune diseases or infectious diseases that affect the basal ganglia may result in disorders of the basal ganglia including ADHD, OCD, tics, Tourette's disease, Sydenham chorea. In addition, any insult to the brain can potentially damage the basal ganglia including strokes, metabolic abnormalities, liver disease, multiple sclerosis, infections, tumors, drug overdoses or side effects, and head trauma. Accordingly, the compounds of the invention can be used to stop disease progression or restore damaged circuits in the brain by a combination of effects including increased synaptic plasticity, neurogenesis, anti-inflammatory, nerve cell regeneration and decreased apoptosis.

The growth of some cancer cells is inhibited by cAMP and cGMP. Upon transformation, cells may become cancerous by expressing PDE10 and reducing the amount of cAMP or cGMP within cells. In these types of cancer cells, inhibition of PDE10 activity inhibits cell growth by raising cAMP. In some cases, PDE10 may be expressed in the transformed, cancerous cell but not in the parent cell line. In transformed renal carcinoma cells, PDE10 is expressed and PDE10 inhibitors reduce the growth rate of the cells in culture. Similarly, breast cancer cells are inhibited by administration of PDE10 inhibitors. Many other types of cancer cells may also be sensitive to growth arrest by inhibition of PDE10. Therefore, compounds disclosed in this invention can be used to stop the growth of cancer cells that express PDE10.

The compounds of the invention are also suitable for use in the treatment of diabetes and related disorders such as obesity, by focusing on regulation of the cAMP signaling system. By inhibiting PDE-10, especially PDE-10A, intracellular levels of cAMP are increased, thereby increasing the release of insulin-containing secretory granules and, therefore, increasing insulin secretion. See, for example, WO 2005/012485. The compounds of Formula (I) can also be used to treat diseases disclosed in US Patent application publication No. 2006/019975.

Testing

The PDE10 inhibitory activities of the compounds of the present invention can be tested, for example, using the in vitro and in vivo assays described in the Biological Examples below.

Administration and Pharmaceutical Compositions

In general, the compounds of this invention can be administered in a therapeutically effective amount by any of the accepted modes of administration for agents that serve similar utilities. The actual amount of a compound of this invention, i.e., the active ingredient, depends upon numerous factors, such as the severity of the disease to be treated, the age and relative health of the subject, the potency of the compound used, the route and form of administration, and other factors.

Therapeutically effective amounts of compounds of formula (I) may range from approximately 0.1-1000 mg per day; preferably 0.5 to 250 mg/day, more preferably 3.5 mg to 70 mg per day.

In general, compounds of this invention can be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors, such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area, i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compounds of the present invention in combination with at least one pharmaceutically acceptable excipient. Acceptable excipients are non-toxic, aid administration, and do not adversely affect the therapeutic benefit of the compounds of the present invention. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients include glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, Gennaro, A. R. (Mack Publishing Company, 18th ed., 1995).

The level of the compound in a formulation can vary within the full range employed by those skilled in the art. Typically, the formulation contains, on a weight percent (wt %) basis, from about 0.01-99.99 wt % of a compounds of the present invention based on the total formulation, with the balance being one or more suitable pharmaceutical excipients. Preferably, the compound is present at a level of about 1-80 wt %.

The compounds can be administered as the sole active agent or in combination with other pharmaceutical agents such as other agents used in the treatment of psychoses, especially schizophrenia and bipolar disorder, obsessive-compulsive disorder, Parkinson's disease, Alzheimer's disease, cognitive impairment and/or memory loss, e.g., nicotinic α-7 agonists, PDE4 inhibitors, other PDE10 inhibitors, calcium channel blockers, muscarinic m1 and m2 modulators, adenosine receptor modulators, ampakines, NMDA-R modulators, mGluR modulators, dopamine modulators, serotonin modulators, canabinoid modulators, and cholinesterase inhibitors (e.g., donepezil, rivastigimine, and galanthanamine). In such combinations, each active ingredient can be administered either in accordance with their usual dosage range or a dose below their usual dosage range, and can be administered either simultaneously or sequentially.

Drugs suitable in combination with the compounds of the present invention include, but are not limited to, other suitable schizophrenia drugs such as Clozaril, Zyprexa, Risperidone, and Seroquel; bipolar disorder drugs, including, but not limited to, Lithium, Zyprexa, and Depakote; Parkinson's disease drugs, including, but not limited to, Levodopa, Parlodel, Permax, Mirapex, Tasmar, Contan, Kemadin, Artane, and Cogentin; agents used in the treatment of Alzheimer's disease, including, but not limited to, Reminyl, Cognex, Aricept, Exelon, Akatinol, Neotropin, Eldepryl, Estrogen and Cliquinol; agents used in the treatment of dementia, including, but not limited to, Thioridazine, haloperidol, Risperidone, Cognex, Aricept, and Exelon; agents used in the treatment of epilepsy, including, but not limited to, Dilantin, Luminol, Tegretol, Depakote, Depakene, Zarontin, Neurontin, Barbita, Solfeton, and Felbatol; agents used in the treatment of multiple sclerosis, including, but not limited to, Detrol, Ditropan XL, OxyContin, Betaseron, Avonex, Azothioprine, Methotrexate, and Copaxone; agents used in the treatment of Huntington's disease, including, but not limited to, Amitriptyline, Imipramine, Despiramine, Nortriptyline, Paroxetine, Fluoxetine, Setraline, Terabenazine, haloperidol, Chloropromazine, Thioridazine, Sulpride, Quetiapine, Clozapine, and Risperidone; agents useful in the treatment of diabetes, including, but not limited to, PPAR ligands (e.g. agonists, antagonists, such as Rosiglitazone, Troglitazone and Pioglitazone), insulin secretagogues (e.g., sulfonylurea drugs, such as Glyburide, Glimepiride, Chlorpropamide, Tolbutamide, and Glipizide, and non-sulfonyl secretagogues), α-glucosidase inhibitors (such as Acarbose, Miglitol, and Voglibose), insulin sensitizers (such as the PPAR-γ agonists, e.g., the glitazones; biguanides, PTP-1B inhibitors, DPP-IV inhibitors, and 11beta-HSD inhibitors), hepatic glucose output lowering compounds (such as glucagon antagonists and metaformin, e.g., Glucophage and Glucophage XR), insulin and insulin derivatives (both long and short acting forms and formulations of insulin); and anti-obesity drugs, including, but not limited to, β-3 agonists, CB-1 agonists, neuropeptide Y5 inhibitors, Ciliary Neurotrophic Factor and derivatives (e.g., Axokine), appetite suppressants (e.g., Sibutramine), and lipase inhibitors (e.g., Orlistat).

Experimental

In the following schemes, the compounds of the invention, along with their definitions, are as described above.

Unless otherwise noted, all materials were obtained from commercial suppliers and used without further purification.

All parts are by weight and temperatures are in degrees centigrade unless otherwise indicated. All microwave assisted reactions were conducted with a Smith Synthesizer™ from Biotage™. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography. Unless otherwise stated, reactions were run at room temperature.

The following abbreviations are commonly used:
Ac the group $CH_3$—(CO)—
AcOH or HOAc acetic acid
$Ac_2O$ acetic anhydride
BINAP 2,2'-bis(diphenylphosphino)-1,1'-binaphthalene
BnO benzyloxy
$Boc_2O$ di-tert-butyl dicarbonate
BTEACl benzyltriethylammonium chloride
Bz Benzyl group
Cbz carboxylic acid benzyl ester
CDI 1,1'-carbonyldiimidazole
d day
DCM dichloromethane
DIAD $(CH_3)_2CHOOCN=NCOOCH(CH_3)_2$
DIEA N,N-diisopropylethylamine
Diox dioxane
DIPEA diisopropylethyl amine
DMA dimethylamine
DMAP 4-(dimethylamino)pyridine
DME dimethoxyethane
DMF N,N-dimethylformamide
DMSO dimethyl sulfoxide
DPPA diphenyl phosphoryl azide
EDCI N-(3-Dimethylaminopropyl)-N'-ethylcarbodiimide hydrochloride
ESIMS electrospray ionization mass spectrometry
$Et_2O$ diethyl ether
EtOAc ethyl acetate
EtOH ethyl alcohol
$Et_3N$ triethyl amine
g Grams
h hour or hours
HATU O-(7-Azobenzotriazol-1-yl)-1,1,3,3-tetramethyluronium hexafluorophosphate
HBTU 2-(1H-Benzotriazole-1-yl)-1,1,3,3-tetramethylaminium hexafluorophosphate
HCl Hydrochloric acid
HPLC high pressure liquid chromatography
IPA isopropyl alcohol
$iPr_2NEt$ diisopropylethylamine
iPrOH Isopropyl alcohol
ISCO in-situ chemical oxidation
LCMS liquid chromatography mass spectrometry
LDA Lithium diisopropyl amide
LiHMDS Lithium bis(trimethylsilyl)amide
Me Methyl
MeCN Acetonitrile
MeI Iodomethane
MeOH methyl alcohol
MeOD deuterated methyl alcohol
mg Milligrams
min minutes
mL milliliters
$Mo(CO)_6$ molybdenum hexacarbonyl
MTBE methyl tert-butyl ether
NBS N-bromosuccinimide
NMP 1-methyl-2-pyrrolidinone
NMR nuclear magnetic resonance
NOESY nuclear Overhauser effect spectroscopy
$Pd(dppf)Cl_2$ [1,1'-Bis(diphenylphosphino)ferrocene]dichloropalladium(II), complex with dichloromethane
PMBCl 1-(chloromethyl)-4-methoxybenzene
PTSA p-toluenesulfonic acid
Py pyridine
RT room temperature
sat. saturated
Tbu tert-butyl group
TFA trifluoroacetic acid
THF tetrahydrofuran
TLC thin layer chromatography
TMSCl trimethylsilyl chloride
Tol toluene
TsCl 4-toluenesulfonyl chloride $(CH_3C_6H_4SO_2Cl)$ Preparations 1-8 that follow describe the routes through which key intermediates of the compounds of the present invention can be prepared. The preparation of exemplified compounds below include any tautomers thereof, if any. For example: the following depicted compounds:

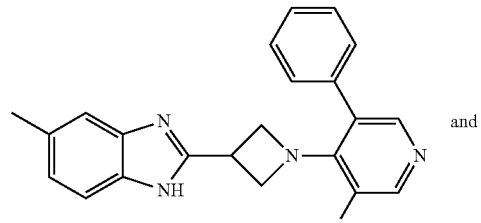

and

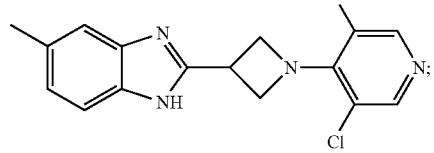

include the tautomer compounds below:

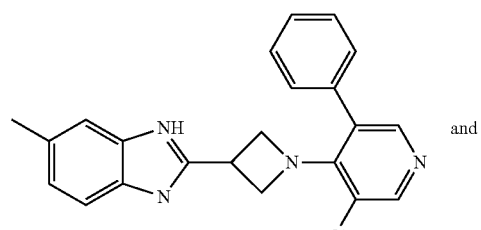

and

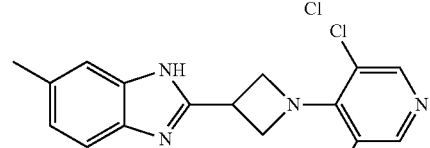

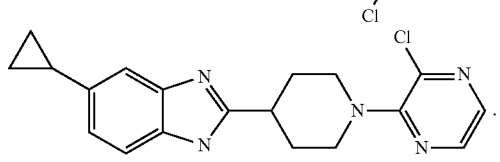

PREPARATION 1: 2-[1-(3-CHLORO-PYRAZIN-2-YL)-PIPERIDIN-4-YL]-5-CYCLOPROPYL-1H-BENZOIMIDAZOLE

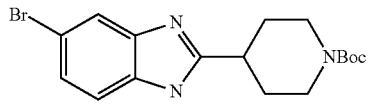

STEP 1. 5-BROMO-2-PIPERIDIN-4-YL-1H-BENZOIMIDAZOLE

To the mixture of piperidine-1,4-dicarboxylic acid mono-tert-butyl ester (2 g, 8.7 mmol) in DMF (15 mL) and pyridine (15 mL) was added CDI (1.55 g, 9.57 mmol) at 45° C. and the mixture was stirred for another 2 h at this temperature. Then 4-Bromo-benzene-1,2-diamine (1.63 g, 8.7 mmol) was added and the mixture was stirred at RT overnight. Solvents were removed in vacuo and the residue was dissolved in HOAc (10 mL) and heated for 1 h at 100° C. Then the reaction mixture was concentrated and the residue was partitioned between DCM and aqueous of $Na_2CO_3$. The organic layer was dried over $Na_2SO_4$ and concentrated to give the crude product which was purified by column chromatography (ethyl acetate:petroleum ether=1:2) to give the compound 5-Bromo-2-piperidin-4-yl-1H-benzoimidazole (1.47 g, 55%) as yellow solid.

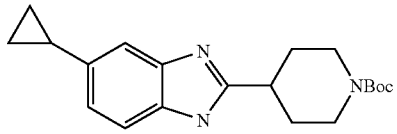 [SMILES: CC(C)(C)OC(=O)N1CCC(c2nc3cc(C4CC4)ccc3[nH]2)CC1]

STEP 2. 5-CYCLOPROPYL-2-PIPERIDIN-4-YL-1H-BENZOIMIDAZOLE

The mixture of 5-bromo-2-piperidin-4-yl-1H-benzoimidazole (200 mg, 0.53 mol), cyclopropanylboronic acid (58.4 mg, 0.687 mmol), $K_3PO_4$ (391 mg, 1.85 mmol), Pd $(OAc)_2$ (6.8 mg, 0.005 mmol) and tricyclohexylphosphine (14.9 mg, 0.053 mmol) in toluene (10 mL) and $H_2O$ (3 mL) was stirred at 90° C. under $N_2$ for 12 h. Then it was poured into $H_2O$ and extracted with ethyl acetate. The organic layer was dried over $Na_2SO_4$ and concentrated to give the crude product which was purified by column chromatography (ethyl acetate:petroleum ether=1:2) to give the compound 5-Cyclopropyl-2-piperidin-4-yl-1H-benzoimidazole (58 mg, 30%) as white solid.

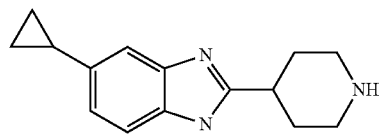 [SMILES: c1cc2[nH]c(C3CCNCC3)nc2cc1C1CC1]

STEP 3. 5-CYCLOPROPYL-2-PIPERIDIN-4-YL-1H-BENZOIMIDAZOLE

The mixture of 5-cyclopropyl-2-piperidin-4-yl-1H-benzoimidazole (100 mg, 0.29 mmol) in a HCl/MeOH (50 mL) was stirred at 60° C. for 1 h. Then it was concentrated to give the crude product (98 mg, 85%) which was used in the next step without further purification.

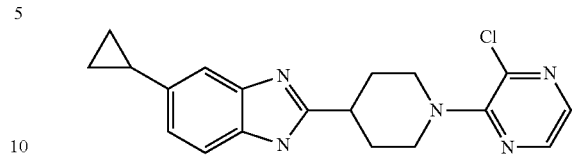

STEP 4. 2-[1-(3-CHLORO-PYRAZIN-2-YL)-PIPERIDIN-4-YL]-5-CYCLOPROPYL-1H-BENZOIMIDAZOLE

The mixture of 5-cyclopropyl-2-piperidin-4-yl-1H-benzoimidazole (98 mg, 0.41 mmol), 2,3-dichloro-pyrazine (74 mg, 0.5 mmol) and $K_2CO_3$ (115 mg, 0.83 mmol) in $CH_3CN$ (15 mL) was heated to 80° C. for 10 h. Then it was concentrated and partitioned between DCM and $H_2O$, the organic layer was dried over $Na_2SO_4$, and concentrated to give the desired compound 2-[1-(3-chloro-pyrazin-2-yl)-piperidin-4-yl]-5-cyclopropyl-1H-benzo imidazole (88 mg, 65%).

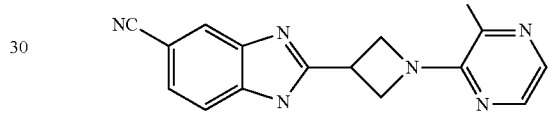

PREPARATION 2: 2-[1-(3-CHLORO-PYRAZIN-2-YL)-AZETIDIN-3-YL]-1H-BENZOIMIDAZOLE-5-CARBONITRILE

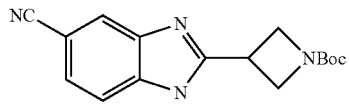

STEP 1. 3-(5-CYANO-1H-BENZOIMIDAZOL-2-YL)-AZETIDINE-1-CARBOXYLIC ACID TERT-BUTYL ESTER

To the mixture of azetidine-1,3-dicarboxylic acid mono-tert-butyl ester (1.5 g, 6.6 mmol) in DMF (50 mL) and pyridine (50 mL) was added CDI (1.06 g, 6.8 mmol) at 45° C. and the mixture was stirred for another 2 h at this temperature. Then 3,4-diamino-benzonitrile (0.87 g, 6.6 mmol) was added and the mixture was stirred at RT overnight. Solvents were removed in vacuo and the residue was dissolved in HOAc (20 mL) and heated for 1 h at 100° C. Then the reaction mixture was concentrated and the residue was partitioned between DCM and aqueous of $Na_2CO_3$. The organic layer was dried over $Na_2SO_4$ and concentrated to give the crude product which was purified by column chromatography (ethyl acetate:petroleum ether=1:2) to give the compound 3-(5-cyano-1H-benzoimidazol-2-yl)-azetidine-1-carboxylic acid tert-butyl ester (0.8 g, 65%) as pale solid.

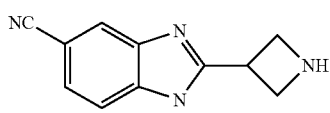 [SMILES: N#Cc1ccc2[nH]c(C3CNC3)nc2c1]

STEP 2. 2-AZETIDIN-3-YL-1H-BENZOIMIDAZOLE-5-CARBONITRILE

A solution of 2-piperidin-4-yl-1H-benzoimidazole-5-carbonitrile (0.8 g, 2.7 mmol) in HCl/MeOH (50 mL) was stirred at 60° C. for 1 h, and then it was concentrated to give the crude product (0.55 g, 100%). The crude product was used in the next step without further purification.

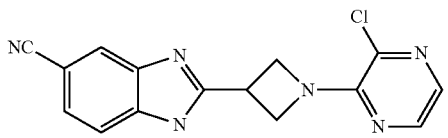 [SMILES: N#Cc1ccc2[nH]c(C3CN(c4nccnc4Cl)C3)nc2c1]

STEP 3. 2-[1-(3-CHLORO-PYRAZIN-2-YL)-AZETIDIN-3-YL]-1H-BENZOIMIDAZOLE-5-CARBONITRILE

The mixture of 2-azetidin-3-yl-1H-benzoimidazole-5-carbonitrile (1.7 g, 8.8 mmol), 2,3-dichloro-pyrazine (1.43 g, 9.7 mmol) and $K_2CO_3$ (2.4 g, 17.6 mmol) in $CH_3CN$ (20 mL) was heated to 80° C. for 10 h, then it was concentrated and partitioned between DCM and $H_2O$. The organic layer was dried over $Na_2SO_4$, and concentrated to give the desired compound (1.4 g, 65%). The crude product was used in the next step without further purification.

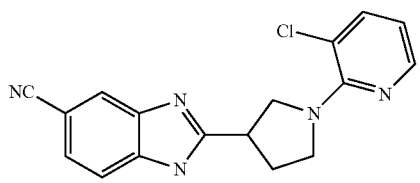 [SMILES: N#Cc1ccc2[nH]c(C3CCN(c4ncccc4Cl)C3)nc2c1]

PREPARATION 3: 2-[1-(3-CHLORO-PYRIDIN-2-YL)-PYRROLIDIN-3-YL]-1H-BENZOIMIDAZOLE-5-CARBONITRILE

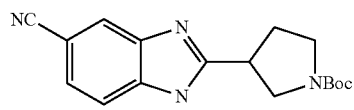 [SMILES: CC(C)(C)OC(=O)N1CCC(c2nc3cc(C#N)ccc3[nH]2)C1]

STEP 1. 3-(5-CYANO-1H-BENZOIMIDAZOL-2-YL)-PYRROLIDINE-1-CARBOXYLIC ACID TERT-BUTYL ESTER

To a mixture of piperidine-1,4-dicarboxylic acid mono-tert-butyl ester (15 g, 69.7 mmol) in DMF (50 mL) and pyridine (50 mL) was added CDI (11.3 g, 69.7 mmol) at 45° C. and the mixture was stirred for another 2 h at this temperature. Then 3,4-diamino-benzonitrile (9.27 g, 69.7 mmol) was added and the mixture was stirred at RT overnight. Solvents were removed in vacuo and the residue was dissolved in HOAc (20 mL) and heated for 1 h at 100° C. Then the reaction mixture was concentrated and the residue was partitioned between DCM and aqueous of $Na_2CO_3$. The organic layer was dried over $Na_2SO_4$ and concentrated to give the crude product which was purified by column chromatography (ethyl acetate:petroleum ether=1:2) to give the compound 2-piperidin-4-yl-1H-benzoimidazole-5-carbonitrile (9 g, 70%) as pale solid.

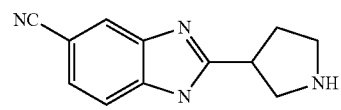 [SMILES: N#Cc1ccc2[nH]c(C3CCNC3)nc2c1]

STEP 2. 2-PYRROLIDIN-3-YL-1H-BENZOIMIDAZOLE-5-CARBONITRILE

The 3-(5-cyano-1H-benzoimidazol-2-yl)-pyrrolidine-1-carboxylic acid tert-butyl ester (9 g, 28.8 mmol) in a solution of 4M HCl in MeOH (50 mL) was stirred at 60° C. for 1 h, then it was concentrated to give the crude product (8 g, 79%). The crude product was used in the next step without further purification.

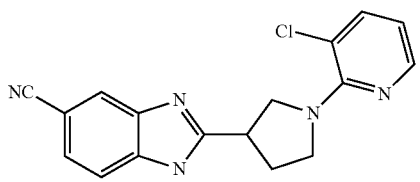 [SMILES: N#Cc1ccc2[nH]c(C3CCN(c4ncccc4Cl)C3)nc2c1]

STEP 3. 2-[1-(3-CHLORO-PYRIDIN-2-YL)-PYRROLIDIN-3-YL]-1H-BENZOIMIDAZOLE-5-CARBONITRILE

The mixture of 2-pyrrolidin-3-yl-1H-benzoimidazole-5-carbonitrile (120 mg, 0.57 mmol), 2-bromo-3-chloro-pyridine (109 mg, 0.57 mmol) in pyridine was heated at 130° C. by microwave for 45 mins. Then it was concentrated to give the crude product and purified by column chromatography and followed by preparative HPLC to afford pure product (25 mg, 18%).

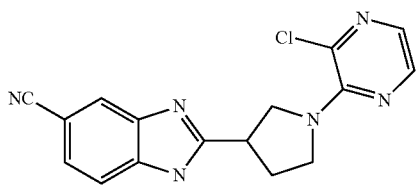

PREPARATION 4: 2-[1-(3-CHLORO-PYRAZIN-2-YL)-PYRROLIDIN-3-YL]-1H-BENZOIMIDAZOLE-5-CARBONITRILE

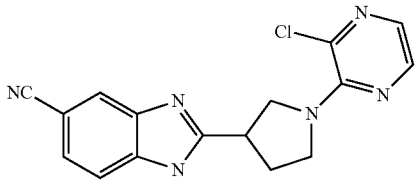 [SMILES: N#Cc1ccc2[nH]c(C3CCN(c4nccnc4Cl)C3)nc2c1]

STEP 1. 2-[1-(3-CHLORO-PYRAZIN-2-YL)-PYRROLIDIN-3-YL]-1H-BENZOIMIDAZOLE-5-CARBONITRILE

The mixture of 2-pyrrolidin-3-yl-1H-benzoimidazole-5-carbonitrile (2 g, 9.43 mmol), 2,3-dichloro-pyrazine (1.43 g, 9.7 mmol) and $K_2CO_3$ (2.4 g, 17.6 mmol) in $CH_3CN$ (20 mL) was heated to 80° C. for 10 h, then it was concentrated and washed with DCM and $H_2O$, the organic layer was dried over $Na_2SO_4$, and concentrated to give the desired compound (1.5 g, 79%). The crude product was used in the next step without further purification.

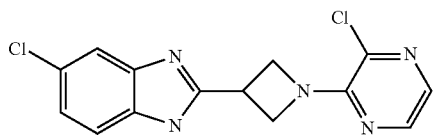

PREPARATION 5: 5-CHLORO-2-[1-(3-CHLORO-PYRAZIN-2-YL)-AZETIDIN-3-YL]-1H-BENZOIMIDAZOLE

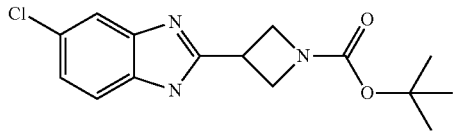 [SMILES: CC(C)(C)OC(=O)N1CC(c2nc3cc(Cl)ccc3[nH]2)C1]

STEP 1. TERT-BUTYL 3-(5-CHLORO-1H-BENZO[D]IMIDAZOL-2-YL)AZETIDINE-1-CARBOXYLATE 2-(1H-benzotriazole-1-yl)-1,1,3,3-tetramethyluronium hexafluorophosphate (2926 mg, 7.71 mmol) was added to a solution of o-phenylenediamine, 4-chloro- (1000 mg, 7.01 mmol), 1-(tert-butoxycarbonyl)azetidine-3-carboxylic acid (1411 mg, 7.01 mmol), and triethylamine (1.075 mL, 7.71 mmol) in DMF (30 mL) under argon at 0° C. The mixture was stirred for 16 h with warming to RT before water (100 mL) was slowly added, at which time a suspension formed. The mixture was filtered and the collected solid was washed with water several times and then air-dried. The solid was dissolved in EtOAc and the mixture was washed with satd. $NaHCO_3$, brine, dried ($MgSO_4$), decolorized with activated charcoal, filtered, and concentrated in vacuo to give product as an off-white solid as a 4:1 ratio of regioisomers. A solution of tert-butyl 3-(2-amino-5-chlorophenylcarbamoyl)azetidine-1-carboxylate (2.28 g, 7.00 mmol) in acetic acid (20 mL) was heated to 100° C. for 1 h. The acetic acid was removed in vacuo and the resulting solid was partitioned between EtOAc and saturated $NaHCO_3$. The layers were separated and the organic layer was dried ($MgSO_4$), filtered, and concentrated in vacuo to give tert-butyl 3-(5-chloro-1H-benzo[d]imidazol-2-yl)azetidine-1-carboxylate as a light brown solid (2.03 g, 94%).

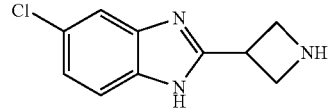 [SMILES: Clc1ccc2[nH]c(C3CNC3)nc2c1]

STEP 2. 2-(AZETIDIN-3-YL)-5-CHLORO-1H-BENZO[D]IMIDAZOLE

Hydrochloric acid, 4.0 m solution in 1,4-dioxane (16.25 mL, 65.0 mmol) was added to a solution of tert-butyl 3-(5-chloro-1H-benzo[d]imidazol-2-yl)azetidine-1-carboxylate (2 g, 6.50 mmol) in dioxane (20 ml) under argon. MeOH (20 mL) was added to the resulting suspension to make a solution and the mixture was stirred for 2 h at RT, at which time it turned back to a suspension. The mixture was filtered and the collected solid was washed with dioxane and air dried to give product as a white solid (840 mg). The filtrate was then concentrated and then dissolved in a minimum of MeOH. $Et_2O$ was added slowly and the resulting suspension was filtered and dried to give an additional 560 mg product as a light grey solid.

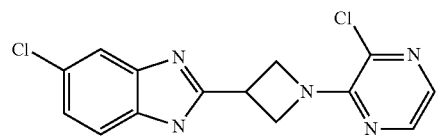 [SMILES: Clc1ccc2[nH]c(C3CN(c4nccnc4Cl)C3)nc2c1]

STEP 3. 5-CHLORO-2-[1-(3-CHLORO-PYRAZIN-2-YL)-AZETIDIN-3-YL]-1H-BENZOIMIDAZOLE

A mixture of 2-azetidin-3-yl-5-chloro-1H-benzoimidazole (as prepared by Preparation 2) (1.0 g, 4.83 mmol) and 2,3-dichloro-pyrazine (0.71 g, 10.4 mmol) was dissolved in DMF (20 mL) and heated for 2 h at 100° C. The mixture was diluted with water (10 mL), and extracted with EtOAc (2×20 mL). The combined organic extracts were washed with water (50 mL) and brine (50 mL), dried over $Na_2SO_4$, and filtered. The filtrate was evaporated in vacuo to afford the product as a yellow solid.

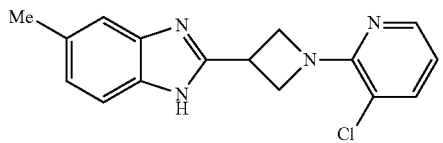

PREPARATION 6: 2-(1-(3-CHLOROPYRIDIN-2-YL)AZETIDIN-3-YL)-5-METHYL-1H-BENZO[D]IMIDAZOLE

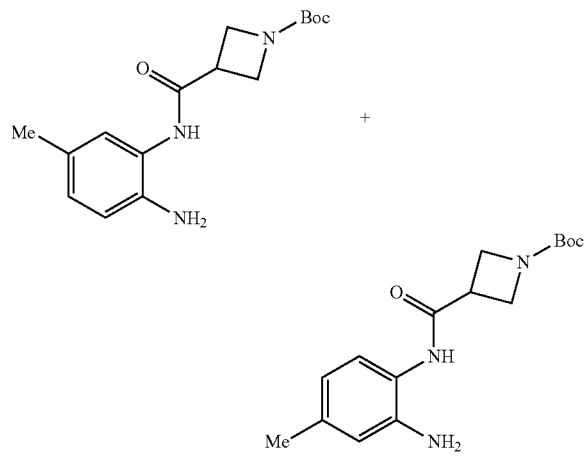

STEP 1. TERT-BUTYL 3-(2-AMINO-5-METHYLPHENYLCARBAMOYL)AZETIDINE-1-CARBOXYLATE AND TERT-BUTYL 3-(2-AMINO-4-METHYLPHENYLCARBAMOYL)AZETIDINE-1-CARBOXYLATE

To a mixture of 4-methylbenzene-1,2-diamine (1.76 g, 14.4 mmol) and 1-(tert-butoxycarbonyl)azetidine-3-carboxylic acid (2.77 g, 13.8 mmol) was added DMF (30 mL) and triethylamine (2.1 mL, 15 mmol). The solution was cooled to 0° C. and 2-(1H-benzo[d][1,2,3]triazol-1-yl)-1,1,3,3-tetramethylisouronium hexafluorophosphate(V) (5.22 g, 13.8 mmol) was added. The reaction mixture was warmed to RT, stirred for 6 h, and poured into water (200 mL). The solid was collected by filtration, washed with water, and dried under high vacuum to give a mixture of tert-butyl 3-(2-amino-4-methylphenylcarbamoyl)azetidine-1-carboxylate and tert-butyl 3-(2-amino-5-methylphenylcarbamoyl)azetidine-1-carboxylate which was used in the next step without further purification.

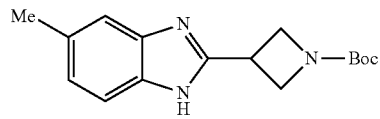 [SMILES: Cc1ccc2[nH]c(C3CN(C(=O)OC(C)(C)C)C3)nc2c1]

STEP 2. TERT-BUTYL 3-(5-METHYL-1H-BENZO[D]IMIDAZOL-2-YL)AZETIDINE-1-CARBOXYLATE

A solution of tert-butyl 3-(2-amino-4-methylphenylcarbamoyl)azetidine-1-carboxylate and tert-butyl 3-(2-amino-5-methylphenylcarbamoyl)azetidine-1-carboxylate (prepared in the previous step) in AcOH (40 mL) was heated to 100° C. for 1.5 h and concentrated. The product tert-butyl 3-(5-methyl-1H-benzo[d]imidazol-2-yl)azetidine-1-carboxylate was used in the next step without further purification.

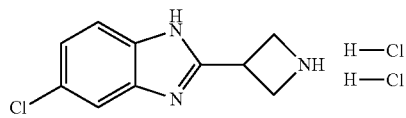

STEP 3. 2-(AZETIDIN-3-YL)-5-METHYL-1H-BENZO[D]IMIDAZOLE DIHYDROCHLORIDE

To tert-butyl 3-(5-methyl-1H-benzo[d]imidazol-2-yl)azetidine-1-carboxylate (prepared in the previous step) was added 4 M HCl in dioxane (30 mL). The reaction mixture was stirred at RT. After 30 min, a solid coated the inside of the flask. The liquid was removed from the flask and the remaining solid was dried under high vacuum. The solid was dissolved in MeOH (20 mL) and diluted with ether (50 mL). The precipitate was collected by filtration and dried under high vacuum to give 2-(azetidin-3-yl)-5-methyl-1H-benzo[d]imidazole dihydrochloride (2.99 g, 11.5 mmol 84% yield over three steps) as a dark red solid.

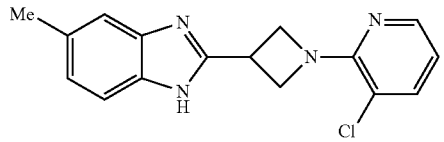

STEP 4. 2-(1-(3-CHLOROPYRIDIN-2-YL)AZETIDIN-3-YL)-5-METHYL-1H-BENZO[D]IMIDAZOLE

To a mixture of cesium carbonate (435 mg, 1.34 mmol) and 2-(azetidin-3-yl)-5-methyl-1H-benzo[d]imidazole dihydrochloride (0.100 g, 0.384 mmol) was added NMP (1 mL) and 3-chloro-2-fluoropyridine (0.105 g, 0.798 mmol). The reaction mixture was degassed and heated to 100° C. for 1 h, then heated to 130° C. for 2 h. The reaction was diluted with EtOAc. The organic phase was washed with water (2×), brine (1×), dried over MgSO$_4$, filtered, and concentrated. Purification by flash column chromatography on silica gel (30% to 90% EtOAc in hexanes) followed by purification by reverse phase HPLC (10% to 50% water/MeCN followed by neutralization of the TFA salt with saturated NaHCO$_3$) gave 2-(1-(3-chloropyridin-2-yl)azetidin-3-yl)-5-methyl-1H-benzo[d]imidazole (0.011 g, 0.037 mmol, 10% yield) as a dark yellow foam.

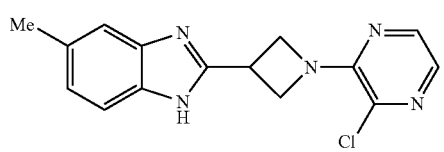

PREPARATION 7: 2-(1-(3-CHLOROPYRAZIN-2-YL)AZETIDIN-3-YL)-5-METHYL-1H-BENZO[D]IMIDAZOLE

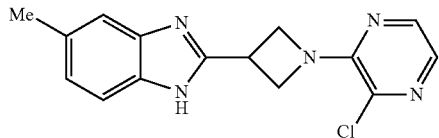 [SMILES: Cc1ccc2[nH]c(C3CN(c4nccnc4Cl)C3)nc2c1]

STEP 1. 2-(1-(3-CHLOROPYRAZIN-2-YL)AZETIDIN-3-YL)-5-METHYL-1H-BENZO[D]IMIDAZOLE

To a mixture of cesium carbonate (4.44 g, 13.6 mmol) and 2-(azetidin-3-yl)-5-methyl-1H-benzo[d]imidazole dihydrochloride (1.05 g, 4.04 mmol) was added NMP (6 mL) and 2,3-dichloropyrazine (1.0 mL, 9.6 mmol). The reaction mixture was degassed and heated to 100° C. for 30 min. The reaction was diluted with EtOAc. The organic phase was washed with water (2×), brine (1×), dried over MgSO$_4$, filtered, and concentrated. Purification by flash column chromatography on silica gel (50% to 100% EtOAc in hexanes) gave 2-(1-(3-chloropyrazin-2-yl)azetidin-3-yl)-5-methyl-1H-benzo[d]imidazole (0.532 g, 1.78 mmol, 44% yield) as an orange solid.

PREPARATION 8: 4-(4-(3-(5-CHLORO-1H-BENZO[D]IMIDAZOL-2-YL)AZETIDIN-1-YL)PYRIMIDIN-2-YL)MORPHOLINE

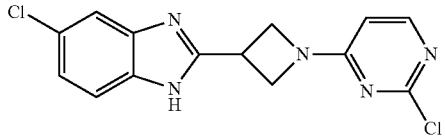 [SMILES: Clc1ccc2[nH]c(C3CN(c4ccnc(Cl)n4)C3)nc2c1]

STEP 1. 5-CHLORO-2-(1-(2-CHLOROPYRIMIDIN-4-YL)AZETIDIN-3-YL)-1H-BENZO[D]IMIDAZOLE

A mixture of triethylamine (0.17 mL, 1.25 mmol), 2,4-dichloropyrimidine (0.053 g, 0.36 mmol), and 2-(azetidin-3-yl)-5-chloro-1H-benzo[d]imidazole dihydrochloride, as prepared in preparation 5, (0.10 g, 0.36 mmol) in dioxane (1.25 mL) was stirred under argon atmosphere for 3 h at RT. Ethyl acetate and water were added, the resulting layers were separated, and the organic layer was dried over anhydrous magnesium sulfate, filtered, and concentrated in vacuo to give an oil. The oil was purified by silica gel chromatography to give 5-chloro-2-(1-(2-chloropyrimidin-4-yl)azetidin-3-yl)-1H-benzo[d]imidazole (0.069 g, 0.22 mmol, 61% yield).

General Synthetic Methodology

The compounds of this invention may be prepared in general by methods known to those skilled in the art for analogous compounds, as illustrated by the general schemes below, and the preparative examples that follow.

GENERAL SCHEME 1

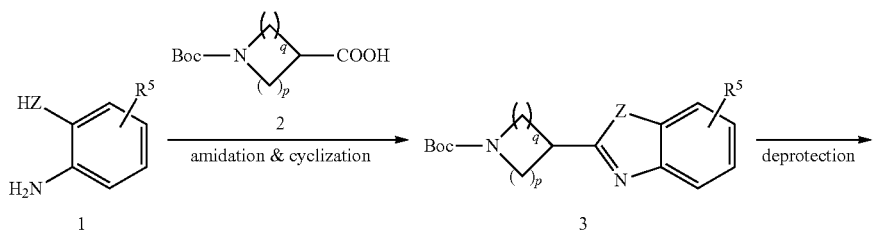

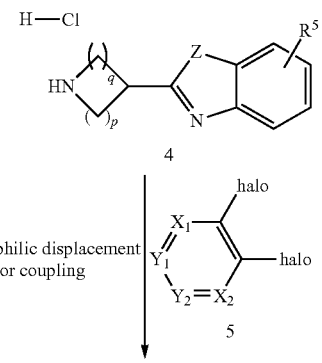

-continued
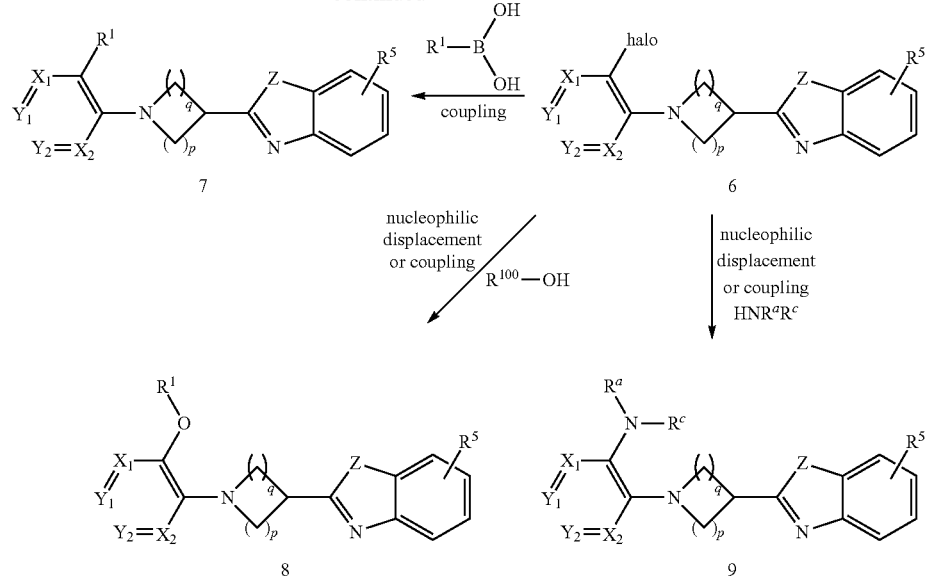
$R^{100}$ is $R^a$ or $R^b$
GENERAL SCHEME 2
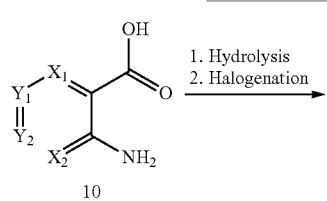
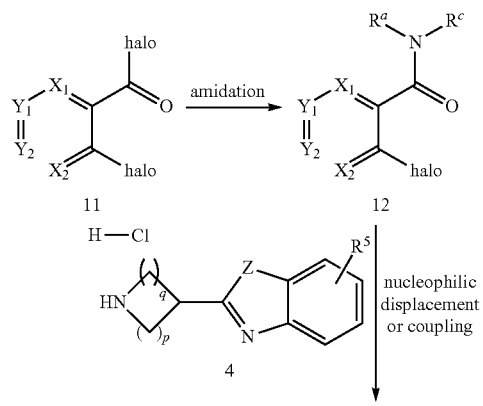
GENERAL SCHEME 3
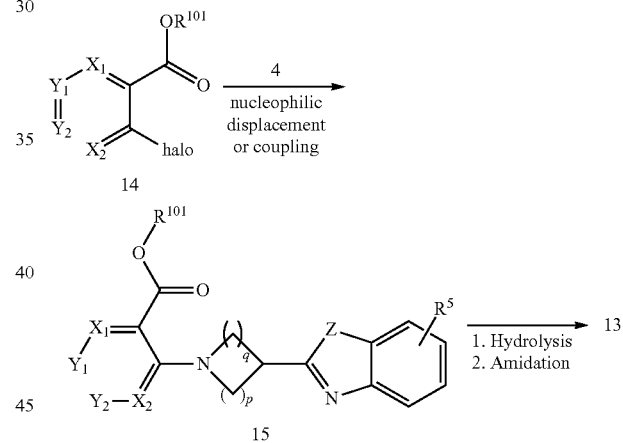
$R^{101}$ is $(C_{1-4})$alkyl
GENERAL SCHEME 4
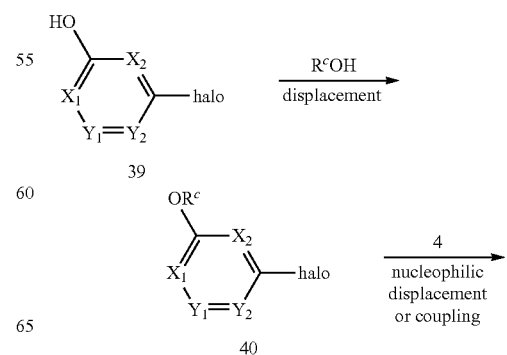

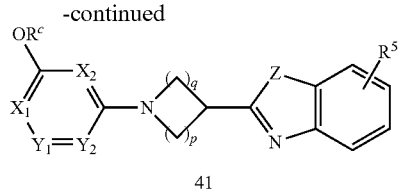
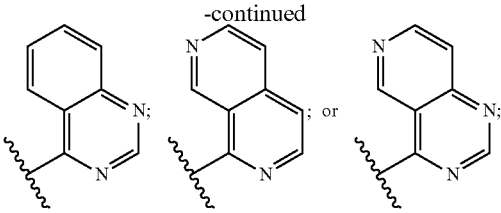

General Schemes 1-4 above show a general method for preparing compounds of formula I wherein the group $R^2$ is a 5,6-bicyclic-rings, such as benzimidazolyl, benzthiazolyl, and benzoxazolyl, wherein $R^2$ is substituted by 0, 1 or 2 $R^5$ groups as defined above.

Although the synthesis of certain compounds are depicted above, it will be appreciated that other compounds of formula I having 6,6-bicyclic-rings $R^2$ group such as

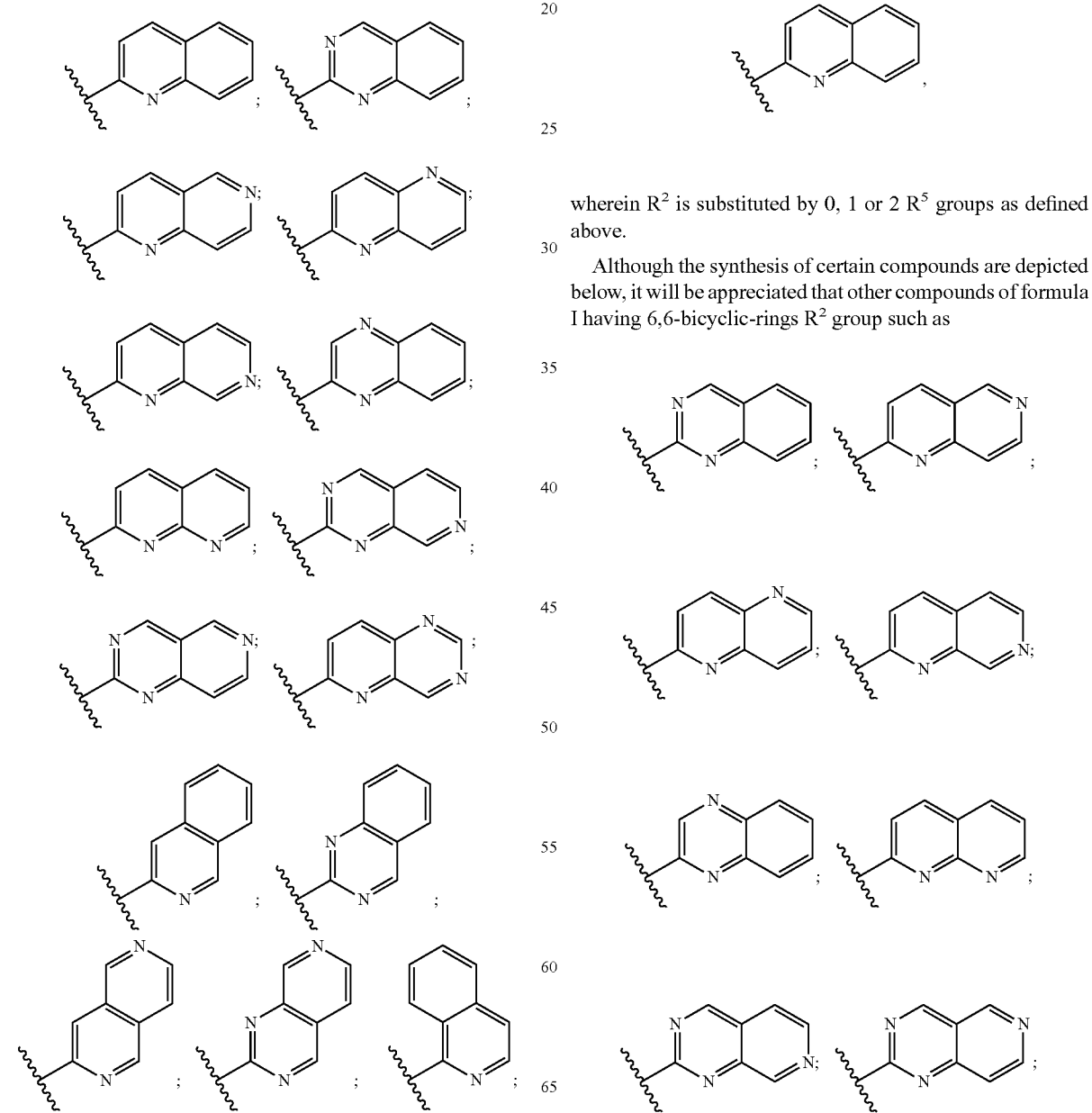

wherein $R^2$ is substituted by 0, 1 or 2 $R^5$ groups as defined above, can be made according to General Schemes 1-4 above.

General Schemes 5-6 below depict methods for preparing compounds of formula I wherein the group $R^2$ is a 6,6-bicyclic-rings, such as wherein $R^2$ is substituted by 0, 1 or 2 $R^5$ groups as defined above.

Although the synthesis of certain compounds are depicted below, it will be appreciated that other compounds of formula I having 6,6-bicyclic-rings $R^2$ group such as -continued
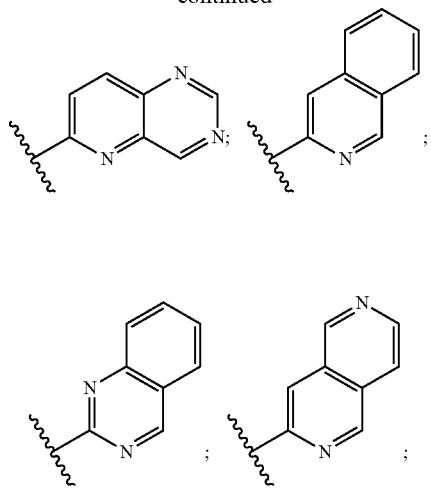
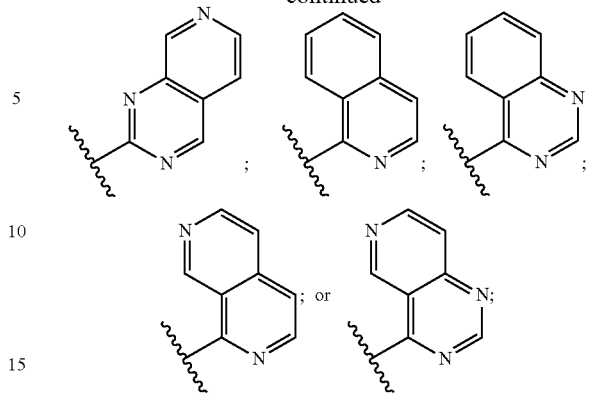
wherein each $R^2$ is substituted by 0, 1 or 2 $R^5$ groups as defined above, can be made according to General Schemes 5-6 below.
GENERAL SCHEME 5
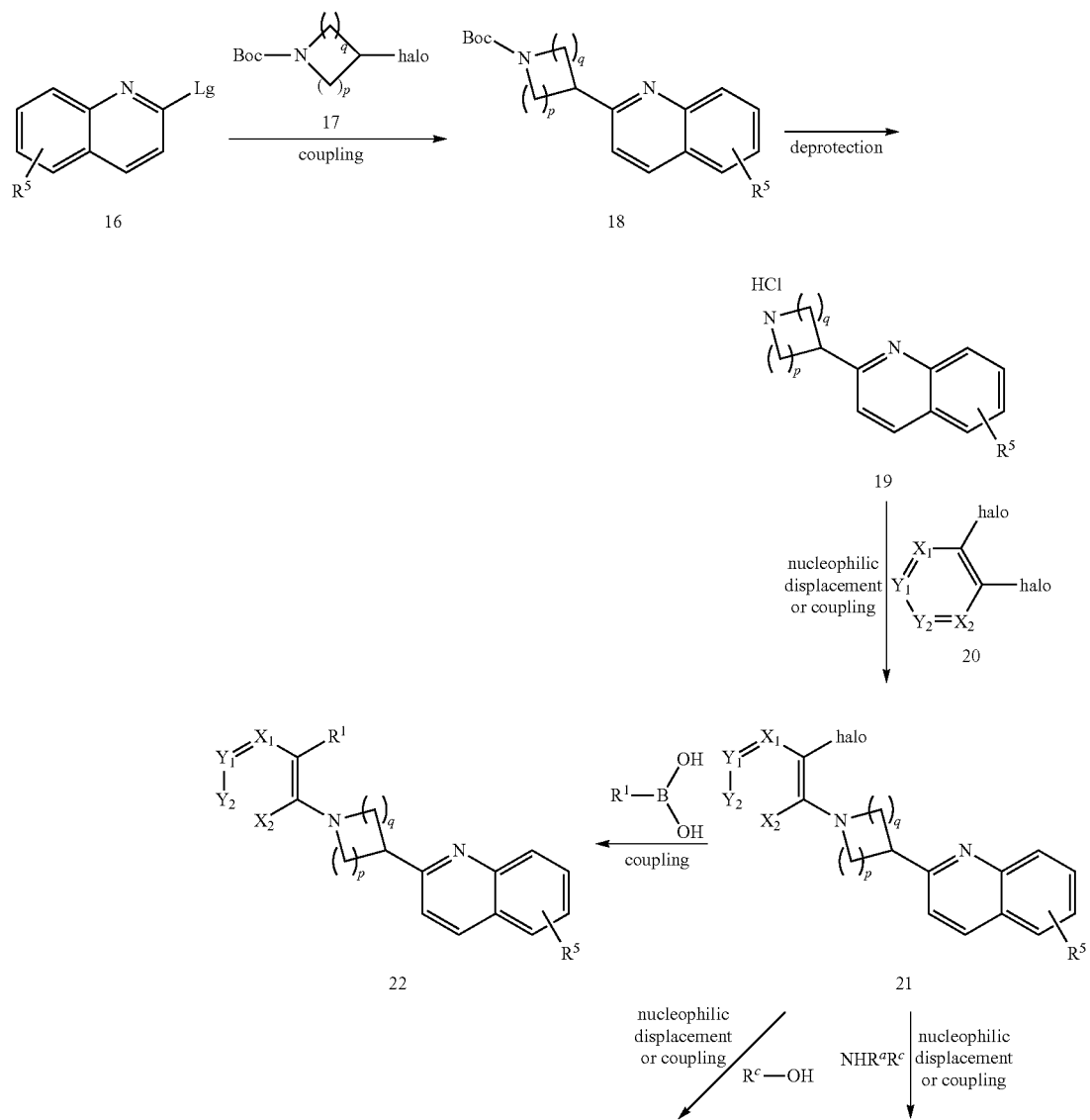

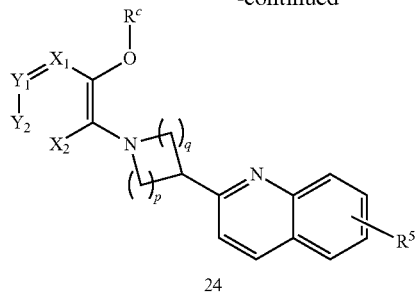
24
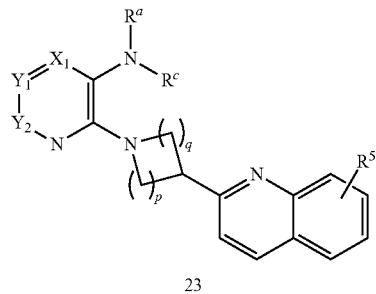
23
Lg is a leaving group such as halo or —OTs.
Alternate Route to Key Intermediate 21 of General Scheme 5
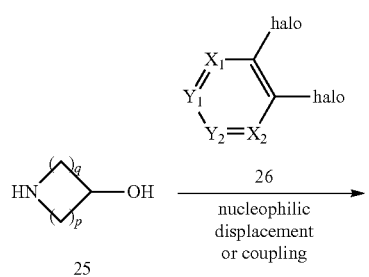
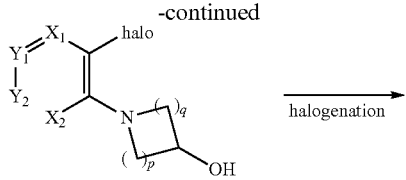
GENERAL SCHEME 6
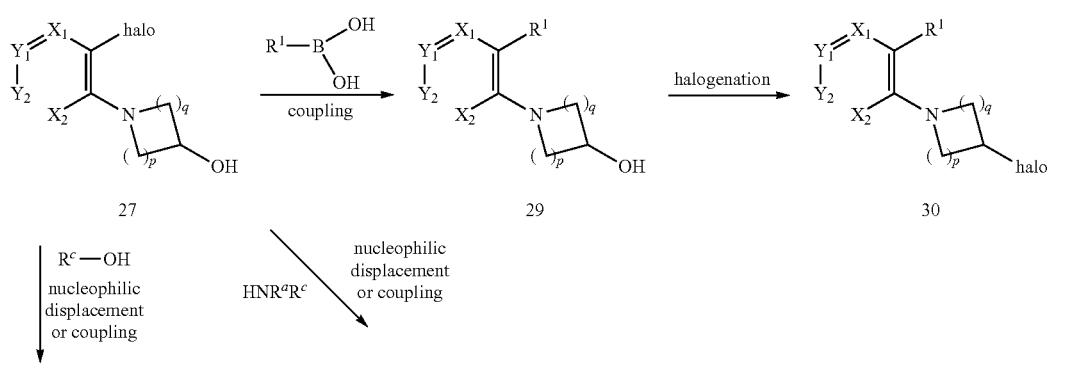

US 8,946,230 B2

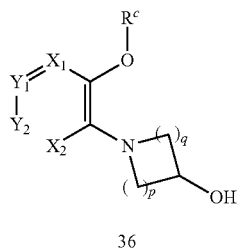

36

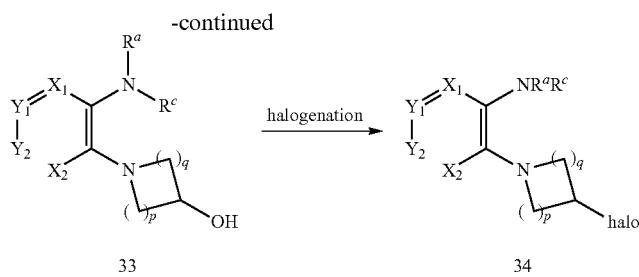

33    halogenation    34 halogenation

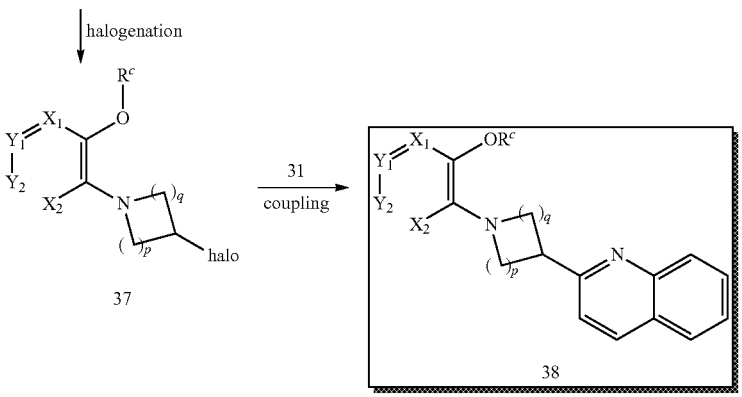

37    31 coupling    38 coupling | 31

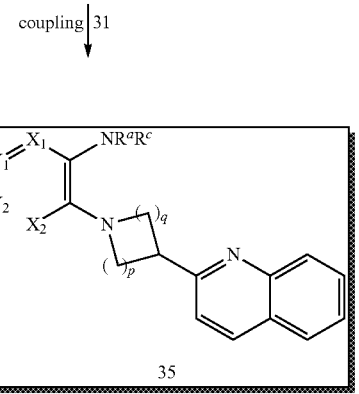

35

It will be appreciated that a compound of the invention can be prepared according to the methods described in Schemes 1-14 and Examples below using appropriate starting materials.

SCHEME 1

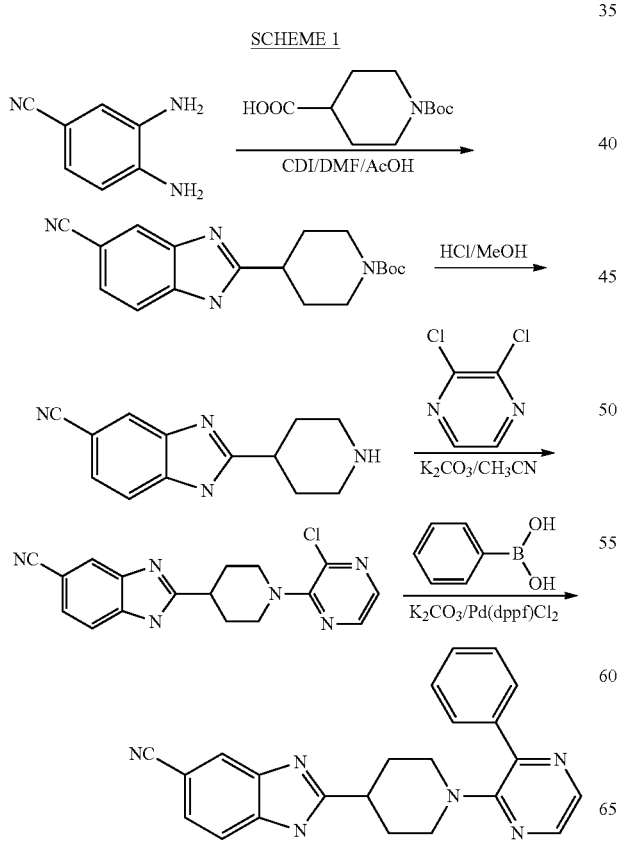

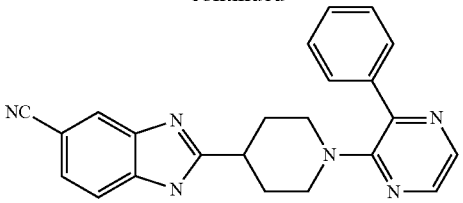

Example 1A

2-[1-(3-PHENYL-PYRAZIN-2-YL)-PIPERIDIN-4-YL]-1H-BENZOIMIDAZOLE-5-CARBONITRILE

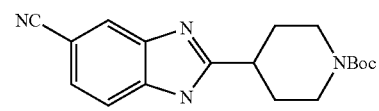 [SMILES: CC(C)(C)OC(=O)N1CCC(c2nc3cc(C#N)ccc3[nH]2)CC1]

STEP 1. TERT-BUTYL 4-(5-CYANO-1H-BENZO [D]IMIDAZOL-2-YL)PIPERIDINE-1-CARBOXYLATE

To the solution of piperidine-1,4-dicarboxylic acid mono-tert-butyl ester (15 g, 65.5 mmol) in DMF (50 mL) and pyridine (50 mL) was added CDI (10.6 g, 65.5 mmol) at 45° C. and the mixture was stirred for another 2 h at this temperature. Then 3,4-diamino-benzonitrile (8.7 g, 65.5 mmol) was added and the mixture was stirred at RT overnight. Solvents were removed in vacuo and the residue was dissolved in HOAc (20 mL) and heated for 1 h at 100° C. Then the reaction mixture was concentrated and the residue was partitioned between DCM and aqueous of $Na_2CO_3$. The organic layer was dried over Na₂SO₄ and concentrated to give the crude product which was purified by column chromatography (ethyl acetate:petroleum ether=1:2) to give the compound tert-butyl 4-(5-cyano-1H-benzo[d]imidazol-2-yl)piperidine-1-carboxylate (8 g, 65%) as pale solid.

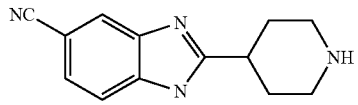 [SMILES: N#Cc1ccc2[nH]c(C3CCNCC3)nc2c1]

STEP 2. 2-PIPERIDIN-4-YL-1H-BENZOIMIDAZOLE-5-CARBONITRILE

A solution of tert-butyl 4-(5-cyano-1H-benzo[d]imidazol-2-yl)piperidine-1-carboxylate (6 g, 26.7 mmol) in HCl saturated MeOH (50 mL) was stirred at 60° C. for 1 h, then it was concentrated to give the crude product (9 g, 88%). The crude product was used for next step without further purification.

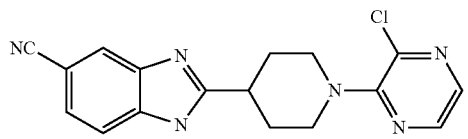 [SMILES: N#Cc1ccc2[nH]c(C3CCN(c4nccnc4Cl)CC3)nc2c1]

STEP 3. 2-[1-(3-CHLORO-PYRAZIN-2-YL)-PIPERIDIN-4-YL]-1H-BENZOIMIDAZOLE-5-CARBONITRILE

The mixture of 2-piperidin-4-yl-1H-benzoimidazole-5-carbonitrile (2 g, 8.8 mmol), 2,3-dichloro-pyrazine (1.43 g, 9.7 mmol) and K₂CO₃ (2.4 g, 17.6 mmol) in CH₃CN (20 mL) was heated to 80° C. for 10 h, then it was concentrated and partitioned between DCM and H₂O. The organic layer was dried over Na₂SO₄ and concentrated to give the desired compound (1.5 g, 65%). The crude product was used for next step without further purification.

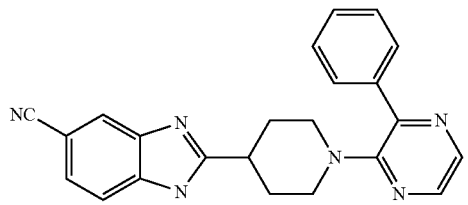 [SMILES: N#Cc1ccc2[nH]c(C3CCN(c4nccnc4-c4ccccc4)CC3)nc2c1]

STEP 4. 2-[1-(3-PHENYL-PYRAZIN-2-YL)-PIPERIDIN-4-YL]-1H-BENZOIMIDAZOLE-5-CARBONITRILE

The mixture of 2-[1-(3-chloro-pyrazin-2-yl)-piperidin-4-yl]-1H-benzoimidazole-5-carbonitrile (160 mg, 0.47 mol), phenylboronic acid (69.3 mg, 0.57 mmol), K₂CO₃ (131 mg, 0.95 mmol) and Pd(dppf)Cl₂ (34 mg, 0.047 mmol) in toluene (10 mL) and H₂O (3 mL) was stirred at 90° C. under N₂ for 12 h. Then it was poured into H₂O and extracted with ethyl acetate. The organic layer was dried over Na₂SO₄ and concentrated to give the crude product which was purified by column (ethyl acetate:petroleum ether=1:2) to give the compound 2-[1-(3-phenyl-pyrazin-2-yl)-piperidin-4-yl]-1H-benzoimidazole-5-carbonitrile (35 mg, yield 19.1%) as white solid. [M+1] 381. IC$_{50}$ (uM) 0.272.

Examples 1B, 1C, and 1D were made according to the above Scheme 1 as follows:

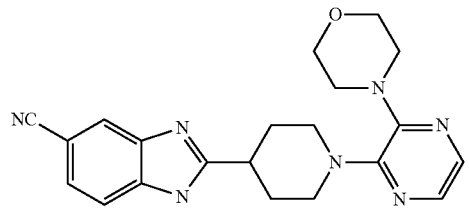 [SMILES: N#Cc1ccc2[nH]c(C3CCN(c4nccnc4N4CCOCC4)CC3)nc2c1]

Example 1B

2-[1-(3-MORPHOLIN-4-YL-PYRAZIN-2-YL)-PIPERIDIN-4-YL]-1H-BENZOIMIDAZOLE-5-CARBONITRILE

A mixture of 2-[1-(3-chloro-pyrazin-2-yl)-piperidin-4-yl]-1H-benzoimidazole-5-carbonitrile (150 mg, 0.68 mmol) and morpholine (3 mL) in pyridine was heated at 130° C. under microwave for 45 min. Then it was concentrated to give the crude product which was purified by column chromatography and followed by preparative HPLC to afford pure product 2-[1-(3-morpholin-4-yl-pyrazin-2-yl)-piperidin-4-yl]-1H-benzoimidazole-5-carbonitrile (30 mg, 16%). [M+1] 390. IC$_{50}$ (uM) 1.996.

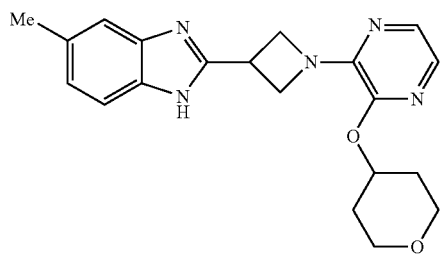 [SMILES: Cc1ccc2[nH]c(C3CN(c4nccnc4OC4CCOCC4)C3)nc2c1]

Example 1C

5-METHYL-2-(1-(3-(TETRAHYDRO-2H-PYRAN-4-YLOXY)PYRAZIN-2-YL)AZETIDIN-3-YL)-1H-BENZO[D]IMIDAZOLE

To a mixture of cesium carbonate (0.223 g, 0.684 mmol) and 2-(1-(3-chloropyrazin-2-yl)azetidin-3-yl)-5-methyl-1H-benzo[d]imidazole (0.103 g, 0.344 mmol) was added NMP (1 mL) and tetrahydro-2H-pyran-4-ol (0.20 mL, 2.1 mmol). The reaction mixture was heated to 100° C. for 1 h, heated to 130° C. for 2 h, and heated to 150° C. for 21 h. The reaction was diluted with EtOAc, and the organic phase was washed with saturated NaHCO₃ (1×), brine (1×), dried over MgSO₄, filtered, and concentrated. Purification by flash column chromatography on silica gel (60% to 100% EtOAc in hexanes) gave 5-methyl-2-(1-(3-(tetrahydro-2H-pyran-4-yloxy)pyrazin-2-yl)azetidin-3-yl)-1H-benzo[d]imidazole (0.061 g, 0.17 mmol, 49% yield) as a pale yellow foam. [M+1] 366. IC$_{50}$ (uM) 0.2388.

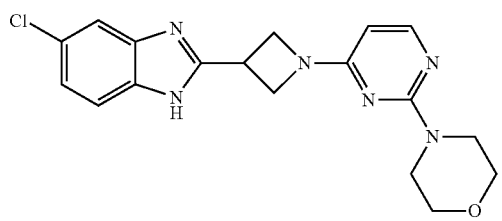 [SMILES: Clc1ccc2[nH]c(C3CN(c4ccnc(N5CCOCC5)n4)C3)nc2c1]

Example 1D

4-(4-(3-(5-CHLORO-1H-BENZO[D]IMIDAZOL-2-YL)AZETIDIN-1-YL)PYRIMIDIN-2-YL)MORPHOLINE

A mixture of morpholine (0.19 mL, 2.19 mmol) and 5-chloro-2-(1-(2-chloropyrimidin-4-yl)azetidin-3-yl)-1H-benzo[d]imidazole, as prepared according to Example 1a, but using 1-(tert-butoxycarbonyl)azetidine-3-carboxylic acid in place of piperidine-1,4-dicarboxylic acid mono-tert-butyl ester, (0.069 g, 0.22 mmol) in DMA (1 mL) under argon was heated to 75° C. for 5 h, then cooled to RT. Ethyl acetate and water were added, the resulting layers were separated, and the organic layer was washed with water (2×), brine, dried over anhydrous magnesium sulfate, filtered, and concentrated in vacuo to give an oil. The oil was purified by silica gel chromatography to give 4-(4-(3-(5-chloro-1H-benzo[d]imidazol-2-yl)azetidin-1-yl)pyrimidin-2-yl)morpholine (0.068 g, 0.18 mmol, 84% yield) as a white solid. [M+1] 371. IC$_{50}$ (uM) 0.645.

SCHEME 2

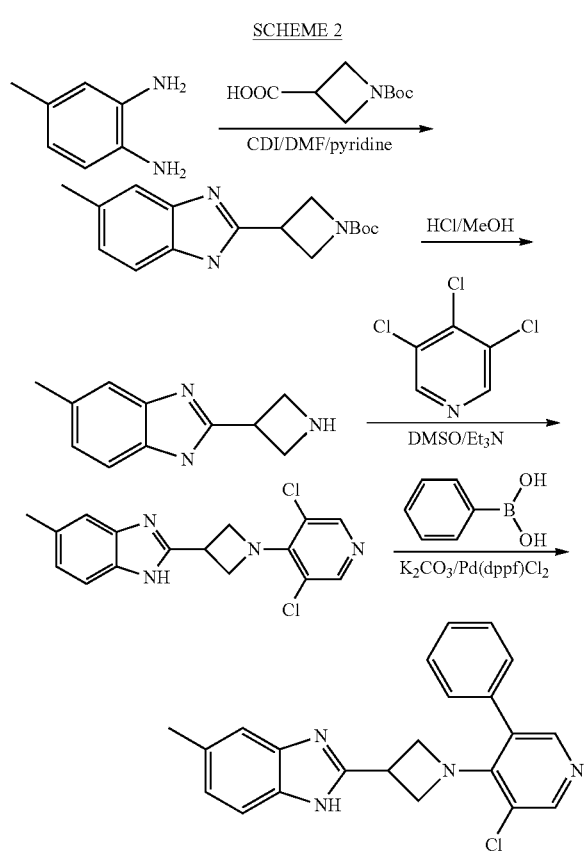

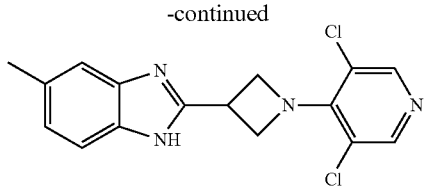

Example 2A

2-[1-(3,5-DICHLORO-PYRIDIN-4-YL)-AZETIDIN-3-YL]-5-METHYL-1H-BENZOIMIDAZOLE

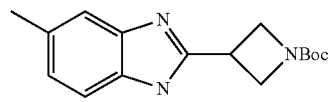 [SMILES: Cc1ccc2[nH]c(C3CN(C(=O)OC(C)(C)C)C3)nc2c1]

STEP 1. 3-(5-METHYL-1H-BENZOIMIDAZOL-2-YL)-AZETIDINE-1-CARBOXYLIC ACID TERT-BUTYL ESTER

To the mixture of 1-(tert-butoxycarbonyl)azetidine-3-carboxylic acid (4.94 g, 24.6 mmol) in DMF (30 mL) and pyridine (30 mL) was added CDI (4.38 g, 27 mmol) at 45° C. and the mixture was stirred for another 2 h at this temperature. Then 4-methyl-benzene-1,2-diamine (3 g, 24.6 mmol) was added and the mixture was stirred at RT overnight. Solvents were removed in vacuo and the residue was dissolved in HOAc (30 mL) and heated for 1 h at 100° C. Then the reaction mixture was concentrated and the residue was partitioned between DCM and aqueous of Na$_2$CO$_3$. The organic layer was dried over Na$_2$SO$_4$ and concentrated to give the crude product which was purified by column chromatography (ethyl acetate:petroleum ether=1:2) to give the compound (4.6 g, yield 61%) as yellow solid.

STEP 2. 2-AZETIDIN-3-YL-5-METHYL-1H-BENZOIMIDAZOLE

The mixture of 3-(5-methyl-1H-benzoimidazol-2-yl)-azetidine-1-carboxylic acid tert-butyl ester (1 g, 3.5 mmol) in a solution of 4M HCl in MeOH (50 mL) was stirred at 60° C. for 1 h, then it was concentrated to give the crude product (0.8 g, yield 100%). The crude product was used in the next step without further purification.

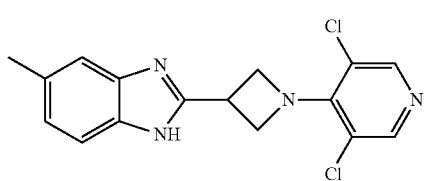 [SMILES: Cc1ccc2[nH]c(C3CN(c4c(Cl)cncc4Cl)C3)nc2c1]

STEP 3. 2-[1-(3,5-DICHLORO-PYRIDIN-4-YL)-AZETIDIN-3-YL]-5-METHYL-1H-BENZOIMIDAZOLE

The mixture of 2-azetidin-3-yl-5-methyl-1H-benzoimidazole (450 mg, 2.4 mmol), 3,4,5-trichloro-pyridine (438 mg, 2.4 mmol) and Et$_3$N (969 mg, 9.6 mmol) in DMSO (20 ml) was heated at 120° C. under microwave for 1.5 h. Then it was diluted with DCM and H$_2$O. The organic layers were concentrated to give the title compound which was purified by column chromatography and followed by preparative HPLC to afford the pure product 2-[1-(3,5-dichloro-pyridin-4-yl)-azetidin-3-yl]-5-methyl-1H-benzoimidazole (800 mg, yield 55%). [M+1] 333. IC$_{50}$ (uM) 0.21.

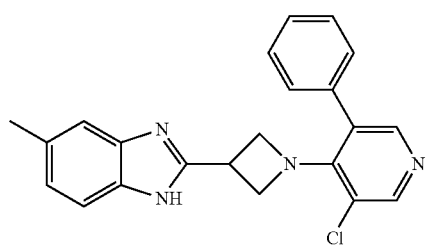 [SMILES: Cc1ccc2[nH]c(C3CN(c4c(Cl)cncc4-c4ccccc4)C3)nc2c1]

Example 2B

2-[1-(3-CHLORO-5-PHENYL-PYRIDIN-4-YL)-AZETIDIN-3-YL]-5-METHYL-1H-BENZOIMIDAZOLE

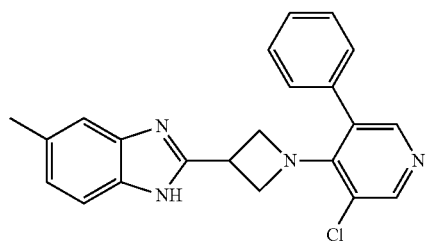 [SMILES: Cc1ccc2[nH]c(C3CN(c4c(Cl)cncc4-c4ccccc4)C3)nc2c1]

STEP 1. 2-[1-(3-CHLORO-5-PHENYL-PYRIDIN-4-YL)-AZETIDIN-3-YL]-5-METHYL-1H-BENZOIMIDAZOLE

The mixture of 2-[1-(3,5-dichloro-pyridin-4-yl)-azetidin-3-yl]-5-methyl-1H-benzoimidazole (200 mg, 0.60 mol), phenylboronic acid (80 mg, 0.66 mmol), K$_2$CO$_3$ (166 mg, 1.2 mmol) and Pd(dppf)Cl$_2$ (44 mg, 0.06 mmol) in toluene (10 mL) and H$_2$O (3 mL) was stirred at 100° C. under N$_2$ for 12 h. The mixture was then poured into H$_2$O and extracted with ethyl acetate. The organic layer was dried over Na$_2$SO$_4$ and concentrated to give the crude product and purified by column chromatography and followed by preparative HPLC to afford pure product 2-[1-(3-chloro-5-phenyl-pyridin-4-yl)-azetidin-3-yl]-5-methyl-1H-benzoimidazole (30 mg, 14%) as white solid. [M+1] 375. IC$_{50}$ (uM) 0.022.

SCHEME 3

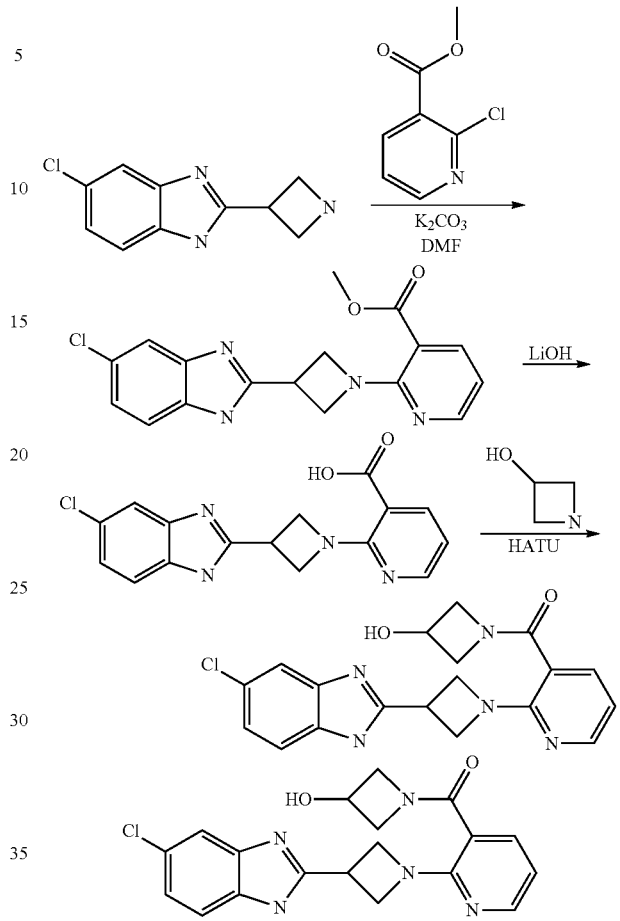

Example 3

{2-[3-(5-CHLORO-1H-BENZOIMIDAZOL-2-YL)-AZETIDIN-1-YL]-PYRIDIN-3-YL}-(3-HYDROXY-AZETIDIN-1-YL)-METHANONE

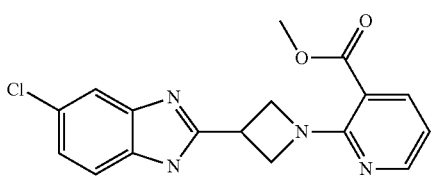 [SMILES: COC(=O)c1cccnc1N1CC(c2nc3cc(Cl)ccc3[nH]2)C1]

STEP 1. 2-[3-(5-CHLORO-1H-BENZOIMIDAZOL-2-YL)-AZETIDIN-1-YL]-NICOTINIC ACID METHYL ESTER

A mixture of 2-azetidin-3-yl-5-chloro-1H-benzoimidazole (as prepared according to Preparation 5 above) (3.2 g, 15.4 mmol) and 2-chloro-nicotinic acid methyl ester (1.78 g, 10.4 mmol) was dissolved in DMF (10 mL) and heated to 100° C. for 2 h. The mixture was diluted with water (10 mL), and extracted with EtOAc (2×20 mL). The combined organic extracts were washed with water (5 mL) and brine (5 mL), dried over Na$_2$SO$_4$, and filtered. The filtrate was evaporated in vacuo to afford the product as yellow solid.

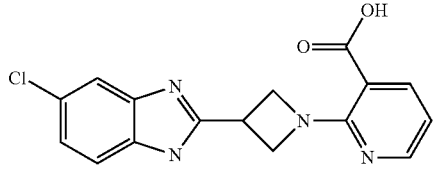 [SMILES: O=C(O)c1cccnc1N1CC(c2nc3cc(Cl)ccc3[nH]2)C1]

STEP 2. 2-[3-(5-CHLORO-1H-BENZOIMIDAZOL-2-YL)-AZETIDIN-1-YL]-NICOTINIC ACID

A solution of methyl 2-[3-(5-chloro-1H-benzoimidazol-2-yl)-azetidin-1-yl]-nicotinic acid methyl ester (1.6 g, 4.6 mmol) and water (10 mL) in MeOH (10 mL) at RT was treated with LiOH (414 mg, 9.87 mmol). The mixture was stirred at RT overnight, and made acidic with a 10% HCl solution. The resulting solution was extracted with EtOAc (2×100 mL). The combined organic layers were washed with brine, dried over anhydrous MgSO$_4$ and concentrated in vacuo. The residue was triturated with hexanes and washed several times with hexanes to give the desired carboxylic acid as a white crystalline solid (1.1 g, yield 71%).

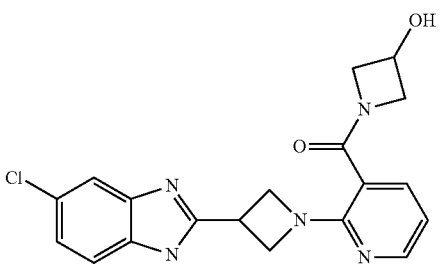 [SMILES: O=C(c1cccnc1N1CC(c2nc3cc(Cl)ccc3[nH]2)C1)N1CC(O)C1]

STEP 3. {2-[3-(5-CHLORO-1H-BENZOIMIDAZOL-2-YL)-AZETIDIN-1-YL]-PYRIDIN-3-YL}-(3-HYDROXY-AZETIDIN-1-YL)-METHANONE

A mixture of 2-[3-(5-chloro-1H-benzoimidazol-2-yl)-azetidin-1-yl]-nicotinic acid (100 mg, 0.30 mmol), azetidin-3-ol (200 mg, 2.73 mmol), HATU (347 mg, 0.9 mmol), and Et$_3$N (101 mg, 1 mmol) in dry DCM (10 mL) was stirred at RT overnight. The mixture was then poured into saturated aqueous Na$_2$CO$_3$. The organic layer was washed with brine, dried over Na$_2$SO$_4$ and concentrated to give the crude compound which was purified by column chromatography and followed by preparative HPLC to afford pure product {2-[3-(5-chloro-1H-benzoimidazol-2-yl)-pyridin-3-yl}-(3-hydroxy-azetidin)-methanone (30 mg, yield 30%). [M+1] 384. IC$_{50}$ (uM) 0.549.

SCHEME 4

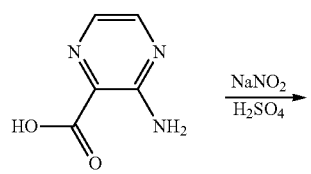

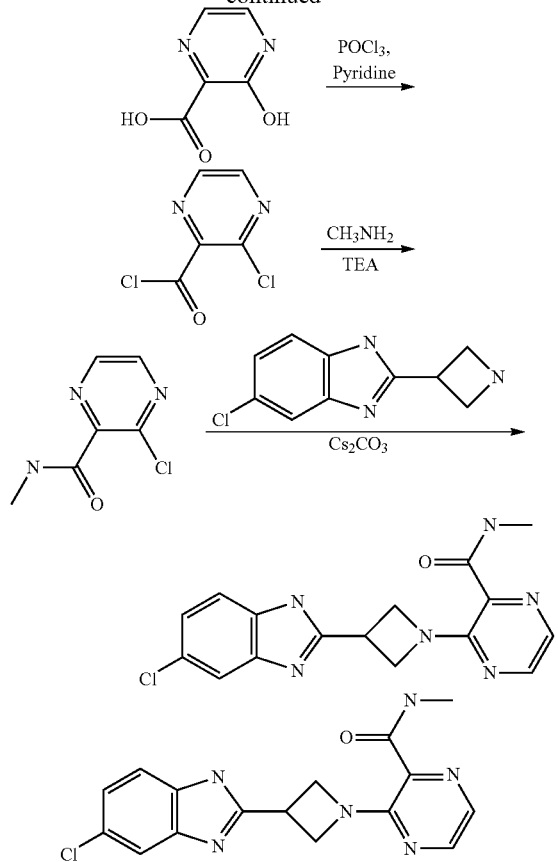

Example 4

3-[3-(5-CHLORO-1H-BENZOIMIDAZOL-2-YL)-AZETIDIN-1-YL]-PYRAZINE-2-CARBOXYLIC ACID METHYLAMIDE

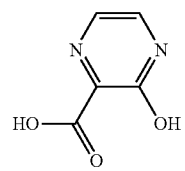

STEP 1. 3-HYDROXY-PYRAZINE-2-CARBOXYLIC ACID

The 3-amino-pyrazine-2-carboxylic acid (6.95 g, 0.05 mmol) was dissolved in a mixture of water (55 mL) and sulfuric acid (55 mL, 3.75M) and heated to 50° C. A solution of sodium nitrite (18.5 mL, 0.06 mmol) was added to the above solution which was cooled to 12° C. The temperature was maintained at 10-16° C. over 30 mins during addition period and then the mixture was heated to boiling over a period of 30 mins. After cooling to RT, the yellow solid was collected by filtration. The solid was dissolved in a dilute sodium bicarbonate solution, the carboxylic acid product precipitated by treatment with hydrochloric acid (10%) and collected by filtration, the crude carboxylic acid product was recrystallized from water to give a yellow-orange crystalline solid (4.1 g, yield 58%).

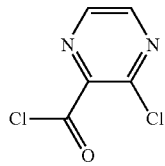

STEP 2. 3-CHLORO-PYRAZINE-2-CARBONYL CHLORIDE

3-Hydroxy-pyrazine-2-carboxylic acid (154 mg, 1.1 mmol) was dissolved in phosphorus oxychloride (2 ml) followed by adding one drop of pyridine. The mixture was heated to reflux for 2 h. After that, the reaction solution was concentrated under reduced pressure to give 3-chloropyrazine-2-carboxylic acid chloride.

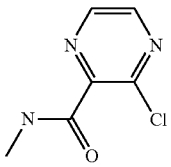

STEP 3. 3-CHLORO-PYRAZINE-2-CARBOXYLIC ACID METHYLAMIDE

To a solution of 3-chloropyrazine-2-carboxylic acid chloride (350 mg, 2.0 mmol) in THF (10 mL) was added methylamine (300 mg, 10 mmol) and triethylamine (303 mg, 3.0 mmol). The reaction mixture was stirred at RT for 3 h. The reaction solution was concentrated under reduced pressure to give the desired compound (200 mg, yield 100%).

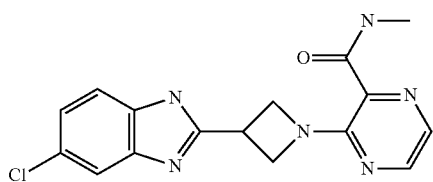 [SMILES: CNC(=O)c1nccnc1N1CC(c2nc3cc(Cl)ccc3[nH]2)C1]

STEP 4. 3-[3-(5-CHLORO-1H-BENZOIMIDAZOL-2-YL)-AZETIDIN-1-YL]-PYRAZINE-2-CARBOXYLIC ACID METHYLAMIDE

A mixture of 3-chloro-pyrazine-2-carboxylic acid methylamide (100 mg, 0.41 mmol) and 2-azetidin-3-yl-5-chloro-1H-benzoimidazole (as prepared by Preparation 5) (71 mg, 0.41 mmol) and $K_2CO_3$ (113 mg, 0.82 mmol) was dissolved in DMF (20 mL) and heated for 2 h at 100° C. The mixture was diluted with water (10 mL), and extracted with EtOAc (2×20 mL). The combined organic extracts were washed with water (5 mL) and brine (5 mL), dried over $Na_2SO_4$, and filtered. The filtrate was evaporated in vacuo and the residue was purified by column chromatography to give the pure product (70 mg, yield 44%). [M+1] 343. $IC_{50}$ (uM) 3.882.

SCHEME 5

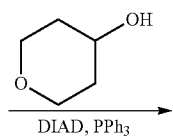
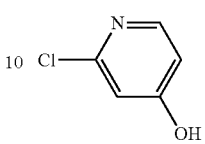
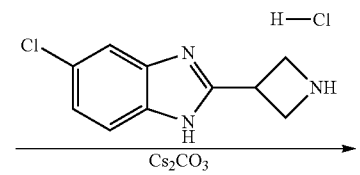
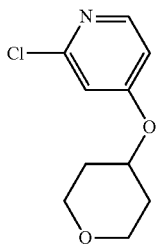 [SMILES: Clc1cc(OC2CCOCC2)ccn1]
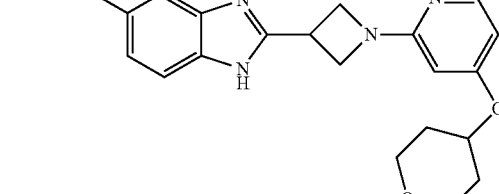
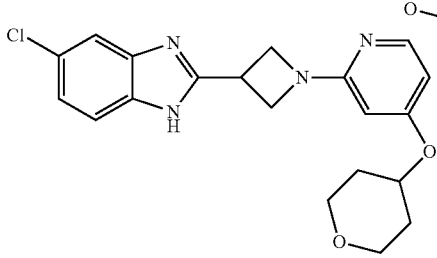

Example 5

5-CHLORO-2-(1-(4-(TETRAHYDRO-2H-PYRAN-4-YLOXY)PYRIDIN-2-YL)AZETIDIN-3-YL)-1H-BENZO[D]IMIDAZOLE

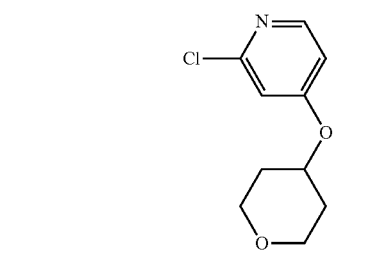

STEP 1. 2-CHLORO-4-(TETRAHYDRO-2H-PYRAN-4-YLOXY)PYRIDINE

Triphenylphosphine (6.88 g, 26.2 mmol) was added to a mixture of tetrahydro-2H-pyran-4-ol (2.68 g, 26.2 mmol) and 2-chloropyridin-4-ol (2.72 g, 21.00 mmol) in THF (70 mL) under argon. Diisopropyl azodicarboxylate (DIAD) (5.28 mL, 26.9 mmol) was added dropwise over 5 mins and then the mixture was heated to 55° C. overnight. The mixture was cooled to RT and the solvent was removed in vacuo to give an oil. The oil was purified by silica gel chromatography to give crude 2-chloro-4-(tetrahydro-2H-pyran-4-yloxy)pyridine as an oil. This material was dissolved in ethyl acetate and then washed with 1N aqueous sodium hydroxide, dried over anhydrous magnesium sulfate, filtered, and concentrated in vacuo to give 2-chloro-4-(tetrahydro-2H-pyran-4-yloxy)pyridine (3.71 g, 17.4 mmol, 83% yield) as a light yellow solid.

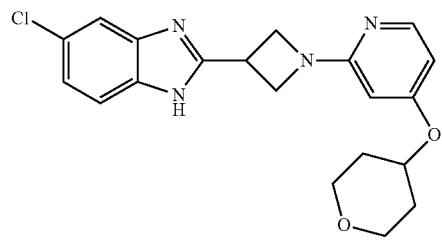 [SMILES: Clc1ccc2[nH]c(C3CN(c4cc(OC5CCOCC5)ccn4)C3)nc2c1]

STEP 2. 5-CHLORO-2-(1-(4-(TETRAHYDRO-2H-PYRAN-4-YLOXY)PYRIDIN-2-YL)AZETIDIN-3-YL)-1H-BENZO[D]IMIDAZOLE

A mixture of 2-chloro-4-(tetrahydro-2H-pyran-4-yloxy)pyridine (0.060 g, 0.27 mmol), 2-(azetidin-3-yl)-5-chloro-1H-benzo[d]imidazole dihydrochloride (as described in Preparation 5) (0.076 g, 0.27 mmol), and cesium carbonate (0.35 g, 1.09 mmol) in NMP (0.5 mL) was heated to 130° C. for 24 h, then cooled to RT. Ethyl acetate and saturated aqueous ammonium chloride were added and the resulting biphasic mixture was separated. The organic layer was washed with water (2×), brine, dried over anhydrous magnesium sulfate, filtered, and concentrated in vacuo to give an oil that was purified by silica gel chromatography to give 5-chloro-2-(1-(4-(tetrahydro-2H-pyran-4-yloxy)pyridin-2-yl)azetidin-3-yl)-1H-benzo[d]imidazole (0.024 g, 0.062 mmol, 23% yield) as a light yellow solid. [M+1] 385. $IC_{50}$ (uM) 1.087.

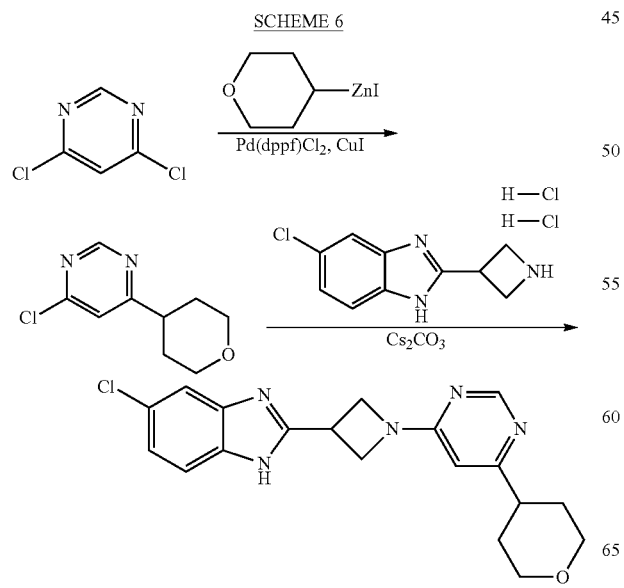

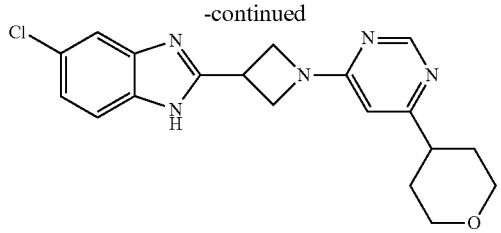

Example 6

5-CHLORO-2-(1-(6-(TETRAHYDRO-2H-PYRAN-4-YL)PYRIMIDIN-4-YL)AZETIDIN-3-YL)-1H-BENZO[D]IMIDAZOLE

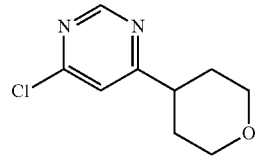 [SMILES: Clc1cc(C2CCOCC2)ncn1]

STEP 1. 4-CHLORO-6-(TETRAHYDRO-2H-PYRAN-4-YL)PYRIMIDINE

Step 1a. Preparation of Zinc Reagent.

To a suspension of zinc dust (0.70 g, 10.75 mmol) in DMA (9 mL) was added 0.32 mL of a 7:5 v/v mixture of TMSCl/1,2-dibromoethane over 5 min. The solution was stirred for an additional 15 min and 4-iodotetrahydro-2H-pyran (1.9 g, 8.96 mmol) was added over 15 min. After the addition, the mixture was stirred for an additional 30 min before being used directly in the next step (see below).

Step 1b. A mixture of copper(I) iodide (0.067 g, 0.35 mmol), Pd(dppf)Cl$_2$ (0.14 g, 0.18 mmol), and 4,6-dichloropyrimidine (0.52 g, 3.50 mmol) in DMA (3 mL) was placed under argon atmosphere using 3 evacuation/backfill cycles. The zinc reagent prepared in Step 1a above (4.5 mL, about 4.5 mmol) was added dropwise via syringe and the mixture was heated to 80° C. for 4 h, then cooled to RT. Ethyl acetate and saturated aqueous ammonium chloride were added, the resulting layers were separated, and the organic layer was washed with water (2×), brine, dried over anhydrous magnesium sulfate, filtered, and concentrated in vacuo to give an oil. The oil was purified by silica gel chromatography to give 4-chloro-6-(tetrahydro-2H-pyran-4-yl)pyrimidine (0.13 g, 0.64 mmol, 14% yield) as a light yellow solid.

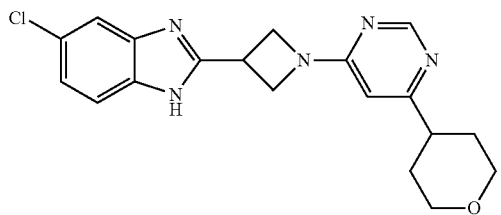

STEP 2. 5-CHLORO-2-(1-(6-(TETRAHYDRO-2H-PYRAN-4-YL)PYRIMIDIN-4-YL)AZETIDIN-3-YL)-1H-BENZO[D]IMIDAZOLE

A mixture of cesium carbonate (0.83 g, 2.56 mmol), 2-(azetidin-3-yl)-5-chloro-1H-benzo[d]imidazole dihydrochloride (as described in Preparation 5) (0.18 gg, 0.64 mmol), and 4-chloro-6-(tetrahydro-2H-pyran-4-yl)pyrimidine (0.13 g, 0.64 mmol) in DMA (1 mL) was heated to 70° C. for 18 h, then cooled to RT. The resulting suspension was partitioned between ethyl acetate and water, the layers were separated, and the organic layer was washed with water twice, brine once, dried over anhydrous magnesium sulfate, filtered, and concentrated in vacuo. The resulting oil was purified by silica gel chromatography to give 5-chloro-2-(1-(6-(tetrahydro-2H-pyran-4-yl)pyrimidin-4-yl)azetidin-3-yl)-1H-benzo[d]imidazole (0.11 g, 0.30 mmol, 47% yield) as a white solid. [M+1] 370. $IC_{50}$ (uM) 1.283.

STEP 1. 5-CHLORO-2-(1-(2,5-DICHLOROPYRIMIDIN-4-YL)AZETIDIN-3-YL)-1H-BENZO[D]IMIDAZOLE 2-(Azetidin-3-yl)-5-chloro-1H-benzo[d]imidazole dihydrochloride, as prepared in preparation 5, (0.16 g, 0.57 mmol) was added to a solution of 2,4,5-trichloropyrimidine (0.11 g, 0.57 mmol) and triethylamine (0.28 mL, 2.00 mmol) in dioxane (2 mL) under argon. The mixture was stirred for 2 h at RT, then dichloromethane and water were added. The resulting layers were separated and the aqueous layer was extracted with dichloromethane. The combined extracts were dried over anhydrous magnesium sulfate, filtered, and concentrated in vacuo to give an oil that was purified by silica gel chromatography to give 5-chloro-2-(1-(2,5-dichloropyrimidin-4-yl)azetidin-3-yl)-1H-benzo[d]imidazole (0.18 g, 0.51 mmol, 89% yield) as a white solid.

SCHEME 7

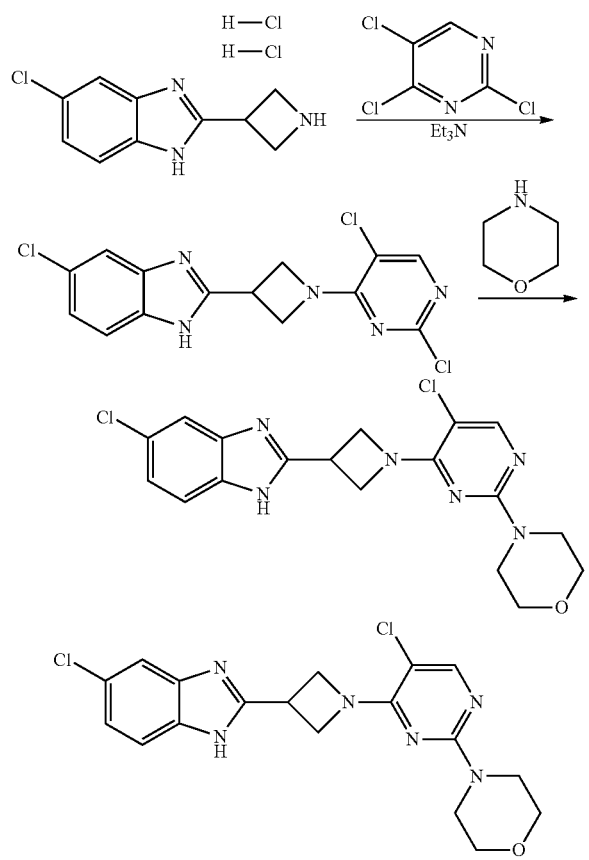

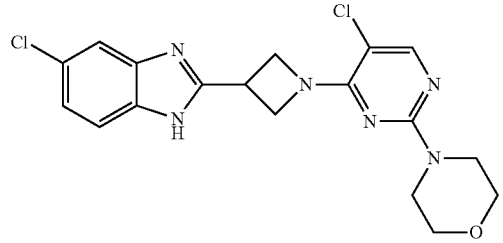

STEP 2. 4-(5-CHLORO-4-(3-(5-CHLORO-1H-BENZO[D]IMIDAZOL-2-YL)AZETIDIN-1-YL)PYRIMIDIN-2-YL)MORPHOLINE

A mixture of morpholine (0.062 mL, 0.711 mmol) and 5-chloro-2-(1-(2,5-dichloropyrimidin-4-yl)azetidin-3-yl)-1H-benzo[d]imidazole (0.063 g, 0.18 mmol) in dioxane (1 mL) was heated to 60° C. under argon and stirred for 6 h. The mixture was cooled to RT, dichloromethane and water were added, and the layers were separated. The organic layer was dried over anhydrous magnesium sulfate, filtered, and concentrated in vacuo to give an oil that was purified by silica gel chromatography to give 4-(5-Chloro-4-(3-(5-chloro-1H-benzo[d]imidazol-2-yl)azetidin-1-yl)pyrimidin-2-yl)morpholine (0.052 g, 0.13 mmol, 72%) as a white solid. [M+1] 405. $IC_{50}$ (uM) 0.1554.

SCHEME 8

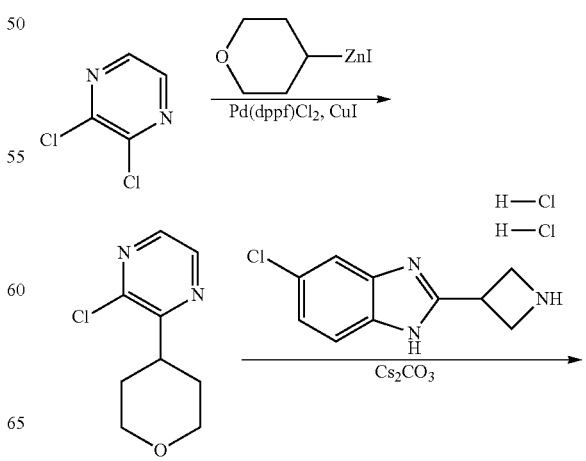

Example 7

4-(5-CHLORO-4-(3-(5-CHLORO-1H-BENZO[D]IMIDAZOL-2-YL)AZETIDIN-1-YL)PYRIMIDIN-2-YL)MORPHOLINE

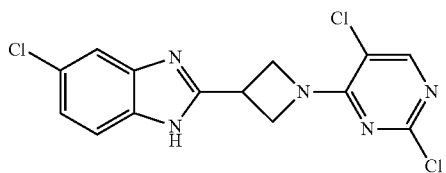 [SMILES: Clc1ccc2[nH]c(C3CN(c4nc(Cl)ncc4Cl)C3)nc2c1]

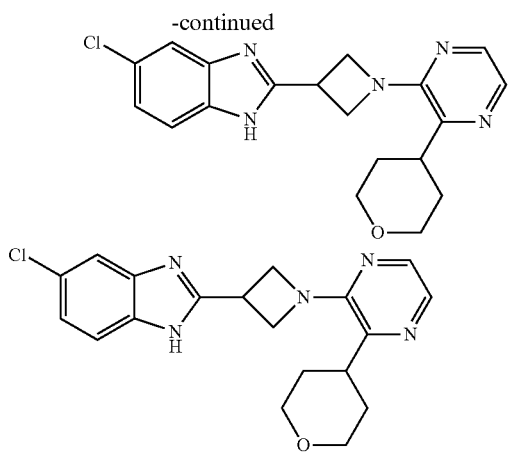

Example 8

5-CHLORO-2-(1-(3-(TETRAHYDRO-2H-PYRAN-4-YL)PYRAZIN-2-YL)AZETIDIN-3-YL)-1H-BENZO[D]IMIDAZOLE

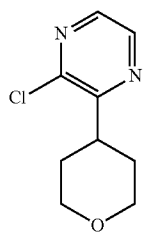 [SMILES: Clc1nccnc1C1CCOCC1]

STEP 1. 2-CHLORO-3-(TETRAHYDRO-2H-PYRAN-4-YL)PYRAZINE

A mixture of copper(I) iodide (0.066 g, 0.35 mmol), Pd(dppf)Cl2 (0.14 g, 0.18 mmol), and 2,3-dichloropyrazine (0.52 g, 3.50 mmol) in DMA (3 mL) was placed under argon atmosphere using 3 evacuation/backfill cycles. A solution of (tetrahydro-2H-pyran-4-yl)zinc(II) iodide (about 3.50 mmol, prepared in example 6, step 1) was added dropwise via syringe and the mixture was heated to 80° C. for 4 h, then cooled to RT. Ethyl acetate and saturated aqueous ammonium chloride were added, the resulting layers were separated, and the organic layer was washed with water (2×), brine, dried over anhydrous magnesium sulfate, filtered, and concentrated in vacuo to give an oil. The oil was purified by silica gel chromatography to give 2-chloro-3-(tetrahydro-2H-pyran-4-yl)pyrazine (0.20 g, 1.03 mmol, 29% yield) as a light yellow solid.

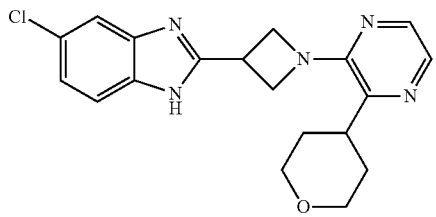 [SMILES: Clc1ccc2[nH]c(C3CN(c4nccnc4C4CCOCC4)C3)nc2c1]

STEP 2. 5-CHLORO-2-(1-(3-(TETRAHYDRO-2H-PYRAN-4-YL)PYRAZIN-2-YL)AZETIDIN-3-YL)-1H-BENZO[D]IMIDAZOLE

A mixture of cesium carbonate (0.82 g, 2.52 mmol), 2-(azetidin-3-yl)-5-chloro-1H-benzo[d]imidazole dihydrochloride (as described in Preparation 5) (0.18 gg, 0.63 mmol), and 2-chloro-3-(tetrahydro-2H-pyran-4-yl)pyrazine (0.13 g, 0.63 mmol) in DMA (1 mL) was heated to 80° C. for 20 h, then cooled to RT. The resulting suspension was partitioned between ethyl acetate and water, the layers were separated, and the organic layer was washed with water (2×), brine, dried over anhydrous magnesium sulfate, filtered, and concentrated in vacuo. The resulting oil was purified by silica gel chromatography to give 5-chloro-2-(1-(3-(tetrahydro-2H-pyran-4-yl)pyrazin-2-yl)azetidin-3-yl)-1H-benzo[d]imidazole as a white solid. [M+1] 370. IC$_{50}$ (uM) 1.157.

SCHEME 9

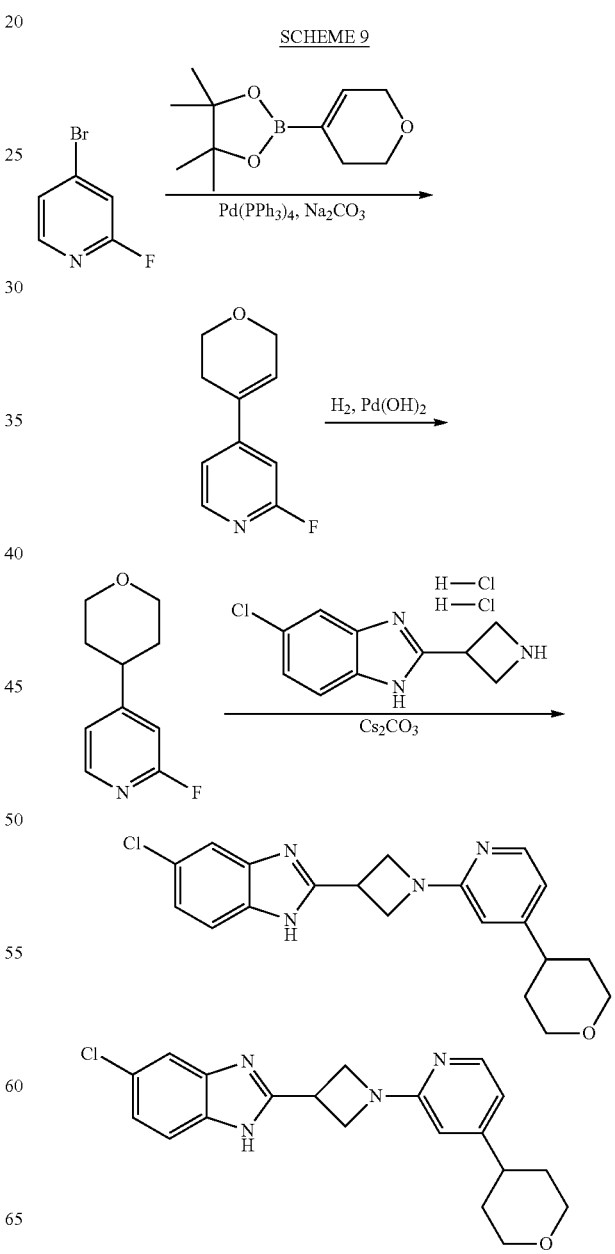

Example 9

5-CHLORO-2-(1-(4-(TETRAHYDRO-2H-PYRAN-4-YL)PYRIDIN-2-YL)AZETIDIN-3-YL)-1H-BENZO[D]IMIDAZOLE

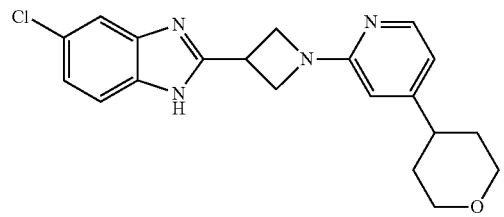 [SMILES: Clc1ccc2[nH]c(C3CN(c4cc(C5CCOCC5)ccn4)C3)nc2c1]

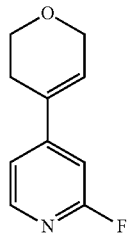

STEP 1. 4-(3,6-DIHYDRO-2H-PYRAN-4-YL)-2-FLUOROPYRIDINE

A mixture of tetrakis(triphenylphosphine)palladium(0) (0.20 g, 0.17 mmol), aqueous sodium carbonate (2N aqueous, 8.52 mL, 17.05 mmol), 2-(3,6-dihydro-2H-pyran-4-yl)-4,4,5,5-tetramethyl-1,3,2-dioxaborolane (1.43 g, 6.82 mmol), and 4-bromo-2-fluoropyridine (1.0 g, 5.68 mmol) in 1,2-dimethoxyethane (25 mL) was placed under argon atmosphere using 3 evacuation/backfill cycles. The mixture was then heated to 80° C. for 16 h then cooled to RT. Ethyl acetate and saturated aqueous ammonium chloride were added and the layers of the resulting biphasic mixture were separated. The organic layer was dried over anhydrous magnesium sulfate, filtered, and concentrated in vacuo to give an oil that was purified by silica gel chromatography to give 4-(3,6-dihydro-2H-pyran-4-yl)-2-fluoropyridine (0.90 g, 5.0 mmol, 89% yield) as a light yellow solid.

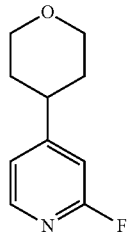

STEP 2. 2-FLUORO-4-(TETRAHYDRO-2H-PYRAN-4-YL)PYRIDINE

A suspension of palladium hydroxide, (20 wt % palladium dry basis on carbon, wet, degussa type e101 ne/w, 150 mg), and 4-(3,6-Dihydro-2H-pyran-4-yl)-2-fluoropyridine (0.90 g, 5.0 mmol) in EtOH (10 mL) was placed under 1 atm hydrogen (balloon) and stirred for 4 h at RT. The mixture was then placed back under argon atmosphere, the palladium was filtered off, and the filtrate was concentrated to give 2-fluoro-4-(tetrahydro-2H-pyran-4-yl)pyridine (0.86 g, 4.76 mmol, 95%) as a yellow oil.

STEP 3. 5-CHLORO-2-(1-(4-(TETRAHYDRO-2H-PYRAN-4-YL)PYRIDIN-2-YL)AZETIDIN-3-YL)-1H-BENZO[D]IMIDAZOLE

A mixture of cesium carbonate (1.08 g, 3.31 mmol), 2-(azetidin-3-yl)-5-chloro-1H-benzo[d]imidazole dihydrochloride (as described in Preparation 5) (0.23 g, 0.83 mmol), and 2-fluoro-4-(tetrahydro-2H-pyran-4-yl)pyridine (0.15 g, 0.83 mmol) in DMA (1 mL) under argon was heated to 110° C. for 18 h. The mixture was then cooled to RT, ethyl acetate and saturated aqueous ammonium chloride were added and the layers were separated. The organic layer was washed with water (2×), brine, and dried over anhydrous magnesium sulfate. The aqueous layer was then extracted with ethyl acetate (2×) and the combined extracts were washed with water (2×), brine, and added to the original organic layer. The combined organic extracts were filtered and concentrated in vacuo to give an oil that was purified by reversed phase HPLC to give an oil. This oil was partitioned between ethyl acetate and saturated aqueous sodium carbonate solution. The biphasic mixture was stirred vigorously for 30 mins, the layers were separated, and the organic layer was dried over anhydrous magnesium sulfate, filtered, and concentrated in vacuo to give 5-chloro-2-(1-(4-(tetrahydro-2H-pyran-4-yl)pyridin-2-yl)azetidin-3-yl)-1H-benzo[d]imidazole (0.16 g, 0.43 mmol, 51% yield) as a white solid. [M+1] 369. $IC_{50}$ (uM) 1.169.

SCHEME 10

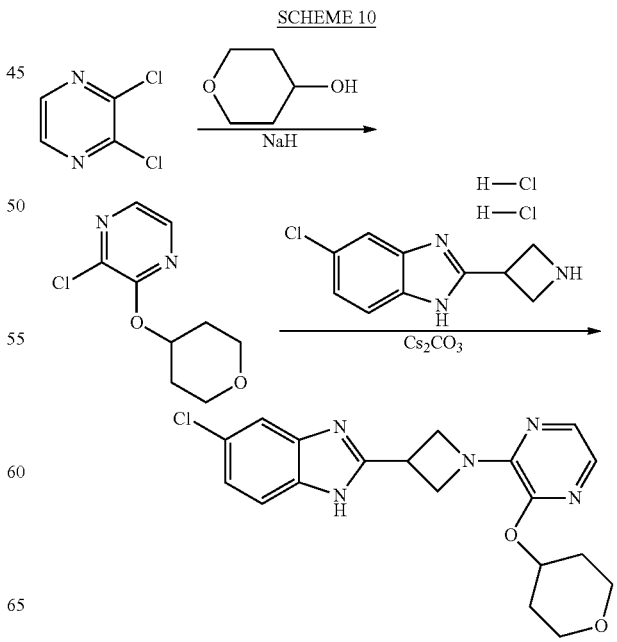

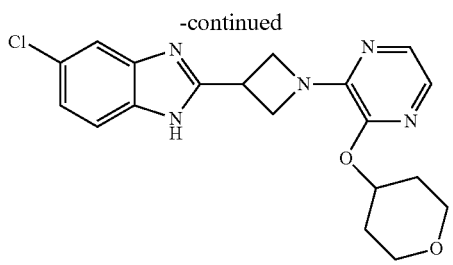

Example 10

5-CHLORO-2-(1-(3-(TETRAHYDRO-2H-PYRAN-4-YLOXY)PYRAZIN-2-YL)AZETIDIN-3-YL)-1H-BENZO[D]IMIDAZOLE

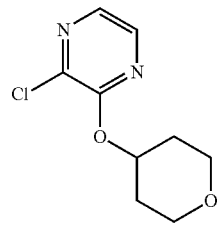 [SMILES: Clc1nccnc1OC1CCOCC1]

STEP 1. 2-CHLORO-3-(TETRAHYDRO-2H-PYRAN-4-YLOXY)PYRAZINE

Sodium hydride (60% dispersion in mineral oil, 0.22 g, 5.39 mmol) was added to a solution of tetrahydro-4H-pyran-4-ol (0.47 mL, 4.90 mmol) in THF (10 mL) and the mixture was stirred for 30 mins, during which time a suspension formed. This mixture was added dropwise to a solution of 2,3-dichloropyrazine (0.73 g, 4.90 mmol) in THF (10 mL) at −78° C. under argon. The cooling bath was removed and the mixture was stirred for 3 h with warming to RT. Ethyl acetate and saturated aqueous ammonium chloride were added, the layers were separated, and the organic layer was dried over anhydrous magnesium sulfate, filtered, and concentrated in vacuo to give an oil that was purified by silica gel chromatography to give 2-chloro-3-(tetrahydro-2H-pyran-4-yloxy)pyrazine (0.75 g, 3.49 mmol, 71% yield) as a white solid.

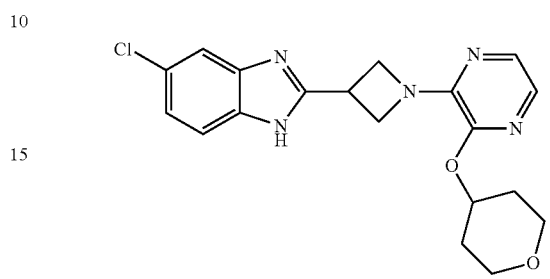

STEP 2. 5-CHLORO-2-(1-(3-(TETRAHYDRO-2H-PYRAN-4-YLOXY)PYRAZIN-2-YL)AZETIDIN-3-YL)-1H-BENZO[D]IMIDAZOLE

A mixture of cesium carbonate (0.63 g, 1.94 mmol), 2-(azetidin-3-yl)-5-chloro-1H-benzo[d]imidazole dihydrochloride (as described in Preparation 5) (0.14 g, 0.49 mmol), and 2-chloro-3-(tetrahydro-2H-pyran-4-yloxy)pyrazine (0.10 g, 0.49 mmol) in DMA (1 mL) was heated to 100° C. for 16 h, then cooled to RT. The resulting suspension was partitioned between ethyl acetate and water, the layers were separated, and the organic layer was washed with water (2×), brine, dried over anhydrous magnesium sulfate, filtered, and concentrated in vacuo. The resulting oil was purified by silica gel chromatography to give 5-chloro-2-(1-(3-(tetrahydro-2H-pyran-4-yloxy)pyrazin-2-yl)azetidin-3-yl)-1H-benzo[d]imidazole (0.16 g, 0.40 mmol, 83% yield) as a white solid. [M+1] 386. IC$_{50}$ (uM) 0.9004.

TABLE 1A

EXAMPLES 11-56 WERE PREPARED ACCORDING TO SCHEMES 1, 3-5, 7, AND 9.

| Example No. | Chemical Structure | Chemical Name | [M + 1] | PDE10 IC$_{50}$ (uM) |
|---|---|---|---|---|
| 11 | 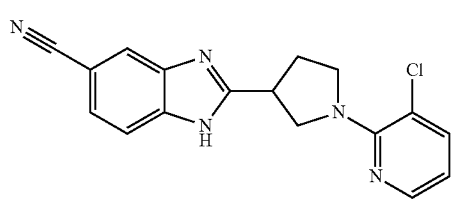 [SMILES: N#Cc1ccc2[nH]c(C3CCN(c4ncccc4Cl)C3)nc2c1] | 2-[1-(3-chloro-pyridin-2-yl)-pyrrolidin-3-yl]-1H-benzoimidazole-5-carbonitrile | 324 | 0.31 |
| 12 | 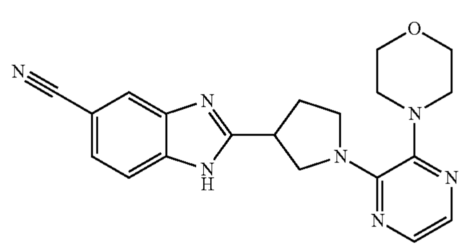 [SMILES: N#Cc1ccc2[nH]c(C3CCN(c4nccnc4N4CCOCC4)C3)nc2c1] | 2-[1-(3-Morpholin-4-yl-pyrazin-2-yl)-pyrrolidin-3-yl]-1H-benzoimidazole-5-carbonitrile | 376 | 0.535 |

TABLE 1A-continued

EXAMPLES 11-56 WERE PREPARED ACCORDING TO SCHEMES 1, 3-5, 7, AND 9.

| Example No. | Chemical Structure | Chemical Name | [M + 1] | PDE10 IC$_{50}$ (uM) |
|---|---|---|---|---|
| 13 | 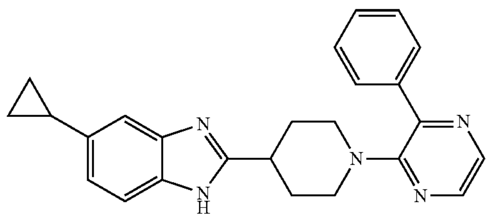 [SMILES: c1ccc(-c2nccnc2N2CCC(c3nc4cc(C5CC5)ccc4[nH]3)CC2)cc1] | 5-Cyclopropyl-2-[1-(3-phenyl-pyrazin-2-yl)-piperidin-4-yl]-1H-benzoimidazole | 396 | 0.277 |
| 14 | 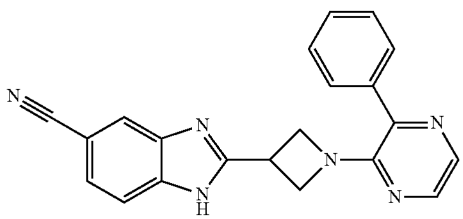 [SMILES: N#Cc1ccc2[nH]c(C3CN(c4nccnc4-c4ccccc4)C3)nc2c1] | 2-[1-(3-phenyl-pyrazin-2-yl)-azetidin-3-yl]-1H-benzoimidazole-5-carbonitrile | 353 | 0.1611 |
| 15 | 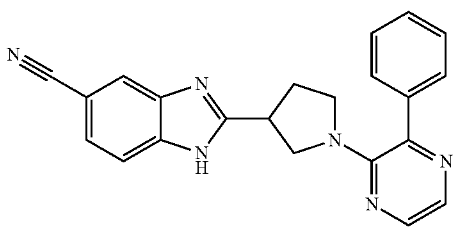 [SMILES: N#Cc1ccc2[nH]c(C3CCN(c4nccnc4-c4ccccc4)C3)nc2c1] | 2-[1-(3-phenyl-pyrazin-2-yl)-pyrrolidin-3-yl]-1H-benzoimidazole-5-carbonitrile | 367 | 0.461 |
| 16 | 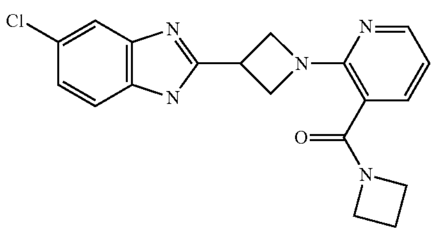 [SMILES: O=C(c1cccnc1N1CC(c2nc3cc(Cl)ccc3[nH]2)C1)N1CCC1] | Azetidin-1-yl-{2-[3-(5-chloro-1H-benzoimidazol-2-yl)-azetidin-1-yl]-pyridin-3-yl}-methanone | 368 | 1.183 |
| 17 | 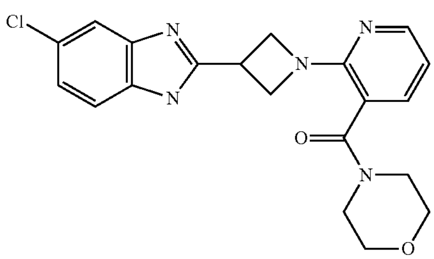 [SMILES: O=C(c1cccnc1N1CC(c2nc3cc(Cl)ccc3[nH]2)C1)N1CCOCC1] | {2-[3-(5-chloro-1H-benzoimidazol-2-yl)-azetidin-1-yl]-pyridin-3-yl}-morpholin-4-yl-methanone | 398 | 32.94 |
| 18 | 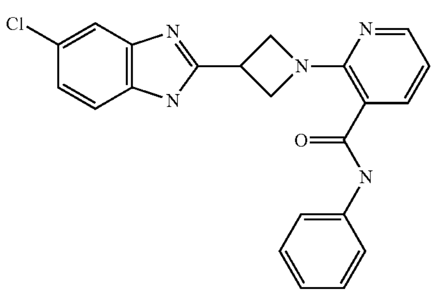 [SMILES: O=C(Nc1ccccc1)c1cccnc1N1CC(c2nc3cc(Cl)ccc3[nH]2)C1] | 2-[3-(5-chloro-1H-benzoimidazol-2-yl)-azetidin-1-yl]-N-phenyl-nicotinamide | 403 | 2.603 |

TABLE 1A-continued

EXAMPLES 11-56 WERE PREPARED ACCORDING TO SCHEMES 1, 3-5, 7, AND 9.

| Example No. | Chemical Structure | Chemical Name | [M + 1] | PDE10 IC$_{50}$ (uM) |
|---|---|---|---|---|
| 19 | 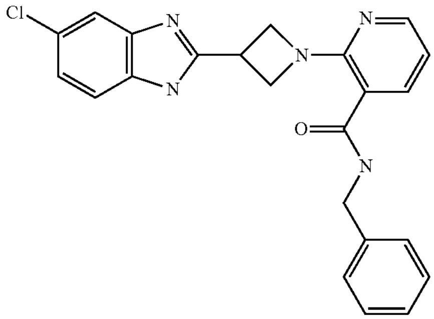 [SMILES: O=C(NCc1ccccc1)c1cccnc1N1CC(c2nc3cc(Cl)ccc3[nH]2)C1] | N-Benzyl-2-[3-(5-chloro-1H-benzoimidazol-2-yl)-azetidin-1-yl]-nicotinamide | 418 | 4.651 |
| 20 | 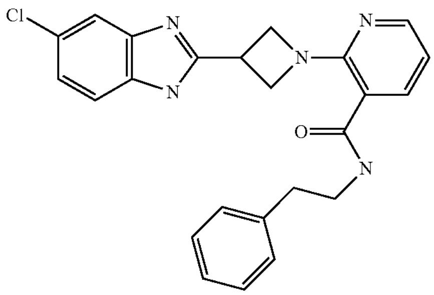 [SMILES: O=C(NCCc1ccccc1)c1cccnc1N1CC(c2nc3cc(Cl)ccc3[nH]2)C1] | 2-[3-(5-chloro-1H-benzoimidazol-2-yl)-azetidin-1-yl]-N-phenethyl-nicotinamide | 432 | 1.678 |
| 21 | 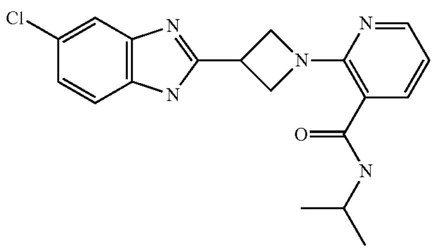 [SMILES: CC(C)NC(=O)c1cccnc1N1CC(c2nc3cc(Cl)ccc3[nH]2)C1] | 2-[3-(5-chloro-1H-benzoimidazol-2-yl)-azetidin-1-yl]-N-isopropyl-nicotinamide | 370 | 4.783 |
| 22 | 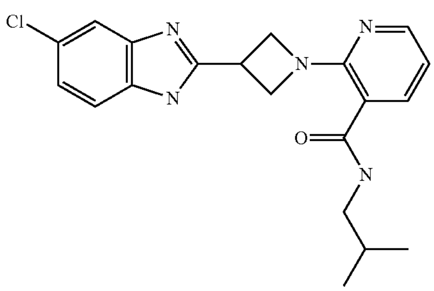 [SMILES: CC(C)CNC(=O)c1cccnc1N1CC(c2nc3cc(Cl)ccc3[nH]2)C1] | 2-[3-(5-chloro-1H-benzoimidazol-2-yl)-azetidin-1-yl]-N-isobutyl-nicotinamide | 384 | 2.226 |
| 23 | 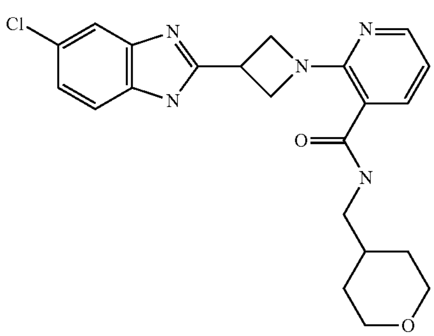 [SMILES: O=C(NCC1CCOCC1)c1cccnc1N1CC(c2nc3cc(Cl)ccc3[nH]2)C1] | 2-[3-(5-chloro-1H-benzoimidazol-2-yl)-azetidin-1-yl]-N-(tetrahydro-pyran-4-ylmethyl)-nicotinamide | 426 | 37.62 |

TABLE 1A-continued

EXAMPLES 11-56 WERE PREPARED ACCORDING TO SCHEMES 1, 3-5, 7, AND 9.

| Example No. | Chemical Structure | Chemical Name | [M + 1] | PDE10 IC$_{50}$ (uM) |
|---|---|---|---|---|
| 24 | 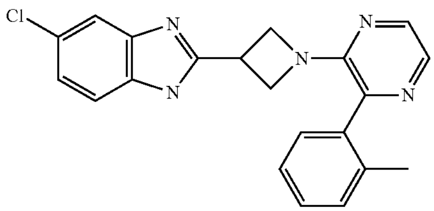 [SMILES: Cc1ccccc1-c1nccnc1N1CC(c2nc3cc(Cl)ccc3[nH]2)C1] | 5-chloro-2-[1-(3-o-tolyl-pyrazin-2-yl)-azetidin-3-yl]-1H-benzoimidazole | 376 | 0.0806 |
| 25 | 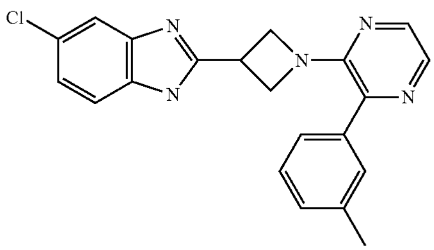 [SMILES: Cc1cccc(-c2nccnc2N2CC(c3nc4cc(Cl)ccc4[nH]3)C2)c1] | 5-chloro-2-[1-(3-m-tolyl-pyrazin-2-yl)-azetidin-3-yl]-1H-benzoimidazole | 376 | 0.015 |
| 26 | 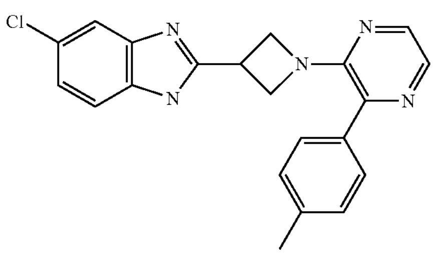 [SMILES: Cc1ccc(-c2nccnc2N2CC(c3nc4cc(Cl)ccc4[nH]3)C2)cc1] | 5-chloro-2-[1-(3-p-tolyl-pyrazin-2-yl)-azetidin-3-yl]-1H-benzoimidazole | 376 | 0.134 |
| 27 | 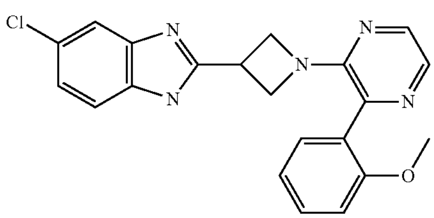 [SMILES: COc1ccccc1-c1nccnc1N1CC(c2nc3cc(Cl)ccc3[nH]2)C1] | 5-chloro-2-{1-[3-(2-methoxy-phenyl)-pyrazin-2-yl]-azetidin-3-yl}-1H-benzoimidazole | 392 | 4.328 |
| 28 | 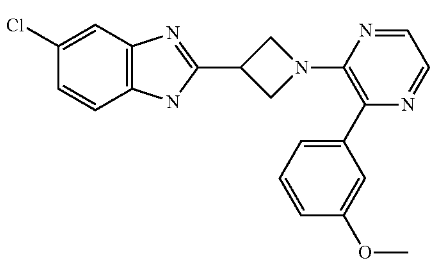 [SMILES: COc1cccc(-c2nccnc2N2CC(c3nc4cc(Cl)ccc4[nH]3)C2)c1] | 5-chloro-2-{1-[3-(3-methoxy-phenyl)-pyrazin-2-yl]-azetidin-3-yl}-1H-benzoimidazole | 392 | 0.026 |
| 29 | 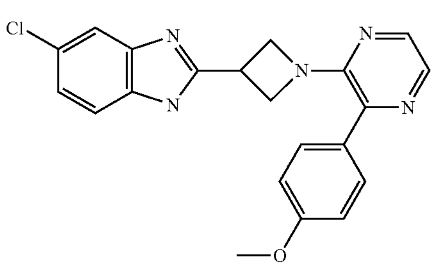 [SMILES: COc1ccc(-c2nccnc2N2CC(c3nc4cc(Cl)ccc4[nH]3)C2)cc1] | 5-chloro-2-{1-[3-(4-methoxy-phenyl)-pyrazin-2-yl]-azetidin-3-yl}-1H-benzoimidazole | 392 | 0.110 |

TABLE 1A-continued

EXAMPLES 11-56 WERE PREPARED ACCORDING TO SCHEMES 1, 3-5, 7, AND 9.

| Example No. | Chemical Structure | Chemical Name | [M + 1] | PDE10 IC$_{50}$ (uM) |
|---|---|---|---|---|
| 30 | 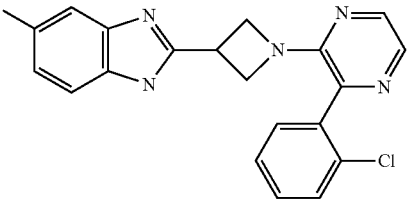 | 5-chloro-2-{1-[3-(2-chloro-phenyl)-pyrazin-2-yl]-azetidin-3-yl}-1H-benzoimidazole | 396 | 0.0586 |
| 31 | 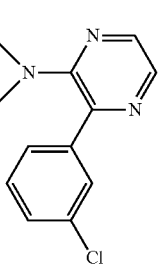 | 5-chloro-2-{1-[3-(3-chloro-phenyl)-pyrazin-2-yl]-azetidin-3-yl}-1H-benzoimidazole | 396 | 0.119 |
| 32 | 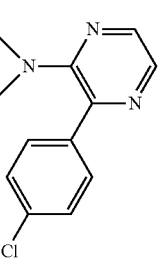 | 5-chloro-2-{1-[3-(4-chloro-phenyl)-pyrazin-2-yl]-azetidin-3-yl}-1H-benzoimidazole | 396 | 0.141 |
| 33 | 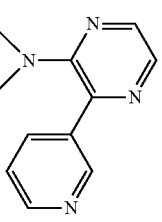 | 5-chloro-2-[1-(3-pyridin-3-yl-pyrazin-2-yl)-azetidin-3-yl]-1H-benzoimidazole | 363 | 0.538 |
| 34 | 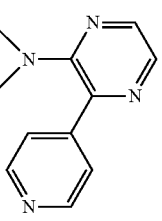 | 5-chloro-2-[1-(3-pyridin-4-yl-pyrazin-2-yl)-azetidin-3-yl]-1H-benzoimidazole | 363 | 0.134 |
| 35 | 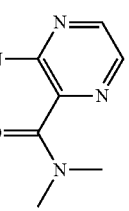 | 3-[3-(5-chloro-1H-benzoimidazol-2-yl)-azetidin-1-yl]-pyrazine-2-carboxylic acid dimethylamide | 357 | 10 |

TABLE 1A-continued

EXAMPLES 11-56 WERE PREPARED ACCORDING TO SCHEMES 1, 3-5, 7, AND 9.

| Example No. | Chemical Structure | Chemical Name | [M + 1] | PDE10 IC$_{50}$ (uM) |
|---|---|---|---|---|
| 36 | 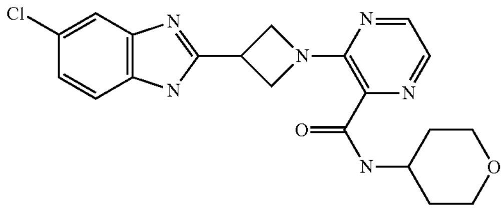 [SMILES: O=C(NC1CCOCC1)c1nccnc1N1CC(c2nc3cc(Cl)ccc3[nH]2)C1] | 3-[3-(5-chloro-1H-benzoimidazol-2-yl)-azetidin-1-yl]-pyrazine-2-carboxylic acid (tetrahydro-pyran-4-yl)-amide | 413 | 3.284 |
| 37 | 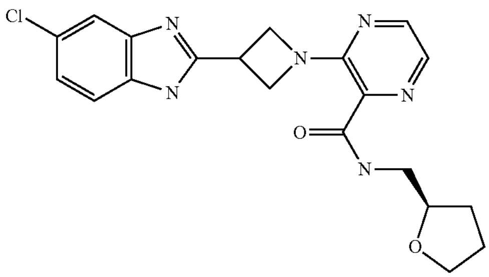 [SMILES: O=C(NC[C@H]1CCCO1)c1nccnc1N1CC(c2nc3cc(Cl)ccc3[nH]2)C1] | 3-[3-(5-chloro-1H-benzoimidazol-2-yl)-azetidin-1-yl]-pyrazine-2-carboxylic acid (tetrahydro-furan-2-ylmethyl)-amide | 413 | 2.53 |
| 38 | 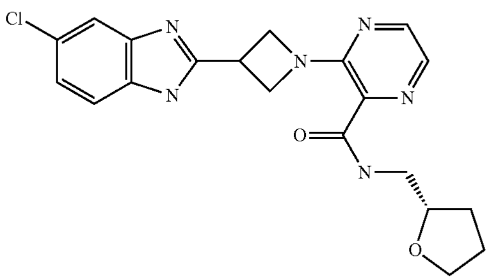 [SMILES: O=C(NC[C@@H]1CCCO1)c1nccnc1N1CC(c2nc3cc(Cl)ccc3[nH]2)C1] | 3-[3-(5-chloro-1H-benzoimidazol-2-yl)-azetidin-1-yl]-pyrazine-2-carboxylic acid (tetrahydro-furan-2-ylmethyl)-amide | 413 | 2.15 |
| 39 | 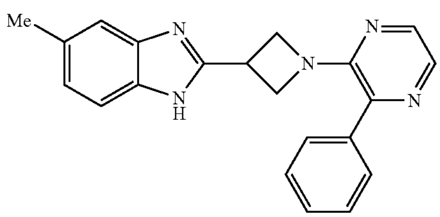 [SMILES: Cc1ccc2[nH]c(C3CN(c4nccnc4-c4ccccc4)C3)nc2c1] | 5-methyl-2-(1-(3-phenylpyrazin-2-yl)azetidin-3-yl)-1H-benzo[d]imidazole | 342 | 0.03978 |
| 40 | 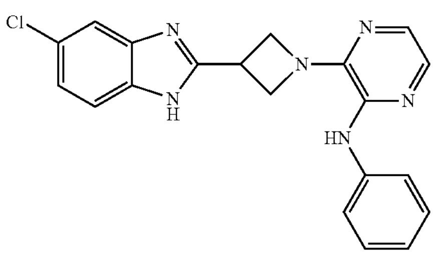 [SMILES: Clc1ccc2[nH]c(C3CN(c4nccnc4Nc4ccccc4)C3)nc2c1] | 3-(3-(5-chloro-1H-benzo[d]imidazol-2-yl)azetidin-1-yl)-N-phenylpyrazin-2-amine | 377 | 0.6299 |
| 41 | 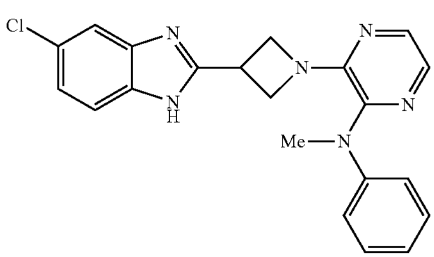 [SMILES: CN(c1ccccc1)c1nccnc1N1CC(c2nc3cc(Cl)ccc3[nH]2)C1] | 3-(3-(5-chloro-1H-benzo[d]imidazol-2-yl)azetidin-1-yl)-N-methyl-N-phenylpyrazin-2-amine | 391 | 0.07401 |

TABLE 1A-continued

EXAMPLES 11-56 WERE PREPARED ACCORDING TO SCHEMES 1, 3-5, 7, AND 9.

| Example No. | Chemical Structure | Chemical Name | [M + 1] | PDE10 IC$_{50}$ (uM) |
|---|---|---|---|---|
| 42 | 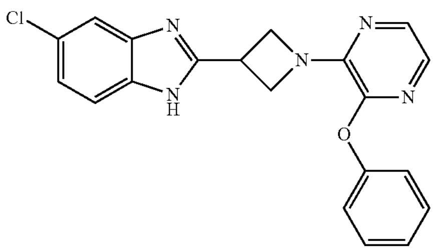 [SMILES: Clc1ccc2[nH]c(C3CN(c4nccnc4Oc4ccccc4)C3)nc2c1] | 5-chloro-2-(1-(3-phenoxypyrazin-2-yl)azetidin-3-yl)-1H-benzo[d]imidazole | 378 | 0.0809 |
| 43 | 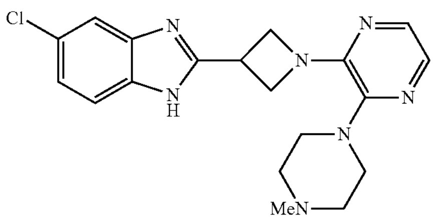 [SMILES: CN1CCN(c2nccnc2N2CC(c3nc4cc(Cl)ccc4[nH]3)C2)CC1] | 5-chloro-2-(1-(3-(4-methylpiperazin-1-yl)pyrazin-2-yl)azetidin-3-yl)-1H-benzo[d]imidazole | 384 | 0.3051 |
| 44 | 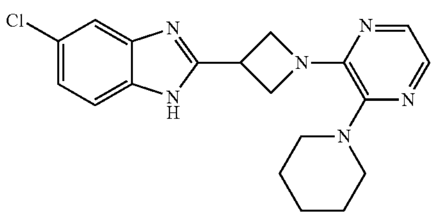 [SMILES: Clc1ccc2[nH]c(C3CN(c4nccnc4N4CCCCC4)C3)nc2c1] | 5-chloro-2-(1-(3-(piperidin-1-yl)pyrazin-2-yl)azetidin-3-yl)-1H-benzo[d]imidazole | 369 | 0.9202 |
| 45 | 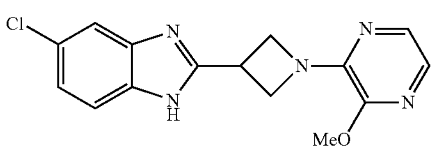 [SMILES: COc1nccnc1N1CC(c2nc3cc(Cl)ccc3[nH]2)C1] | 5-chloro-2-(1-(3-methoxypyrazin-2-yl)azetidin-3-yl)-1H-benzo[d]imidazole | 316 | 0.4992 |
| 46 | 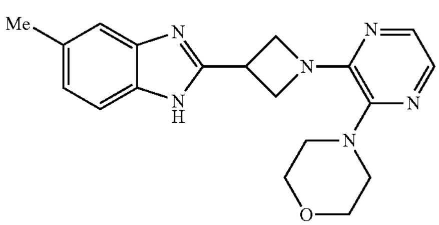 [SMILES: Cc1ccc2[nH]c(C3CN(c4nccnc4N4CCOCC4)C3)nc2c1] | 4-(3-(3-(5-methyl-1H-benzo[d]imidazol-2-yl)azetidin-1-yl)pyrazin-2-yl)morpholine | 351 | 0.6002 |
| 47 | 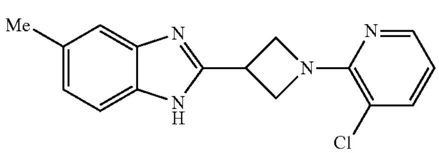 [SMILES: Cc1ccc2[nH]c(C3CN(c4ncccc4Cl)C3)nc2c1] | 2-(1-(3-chloropyridin-2-yl)azetidin-3-yl)-5-methyl-1H-benzo[d]imidazole | 299 | 3.844 |
| 48 | 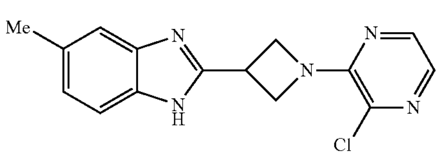 | 2-(1-(3-chloropyrazin-2-yl)azetidin-3-yl)-5-methyl-1H-benzo[d]imidazole | 300 | 0.4563 |

TABLE 1A-continued

EXAMPLES 11-56 WERE PREPARED ACCORDING TO SCHEMES 1, 3-5, 7, AND 9.

| Example No. | Chemical Structure | Chemical Name | [M + 1] | PDE10 IC$_{50}$ (uM) |
|---|---|---|---|---|
| 49 | 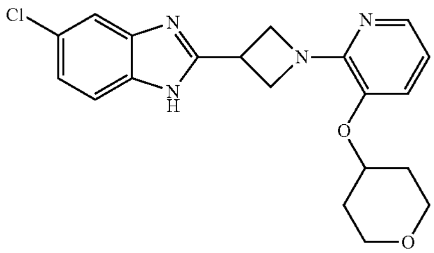 [SMILES: Clc1ccc2[nH]c(C3CN(c4ncccc4OC4CCOCC4)C3)nc2c1] | 5-chloro-2-(1-(3-(tetrahydro-2H-pyran-4-yloxy)pyridin-2-yl)azetidin-3-yl)-1H-benzo[d]imidazole | 385 | 0.1685 |
| 50 | 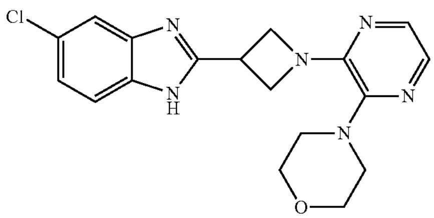 | 4-(3-(3-(5-chloro-1H-benzo[d]imidazol-2-yl)azetidin-1-yl)pyrazin-2-yl)morpholine | 371 | 0.1341 |
| 51 | 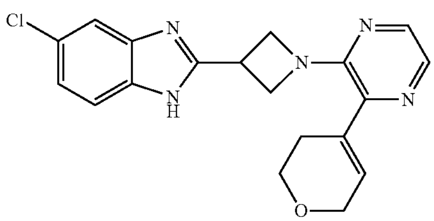 [SMILES: Clc1ccc2[nH]c(C3CN(c4nccnc4C4=CCOCC4)C3)nc2c1] | 5-chloro-2-(1-(3-(3,6-dihydro-2H-pyran-4-yl)pyrazin-2-yl)azetidin-3-yl)-1H-benzo[d]imidazole | 368 | 0.4424 |
| 52 | 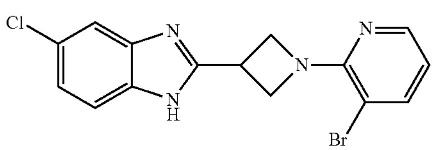 [SMILES: Clc1ccc2[nH]c(C3CN(c4ncccc4Br)C3)nc2c1] | 2-(1-(3-bromopyridin-2-yl)azetidin-3-yl)-5-chloro-1H-benzo[d]imidazole | 363 | 1.824 |
| 53 | 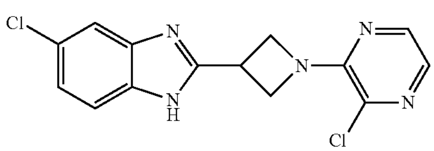 [SMILES: Clc1ccc2[nH]c(C3CN(c4nccnc4Cl)C3)nc2c1] | 5-chloro-2-(1-(3-chloropyrazin-2-yl)azetidin-3-yl)-1H-benzo[d]imidazole | 320 | 1.155 |
| 54 | 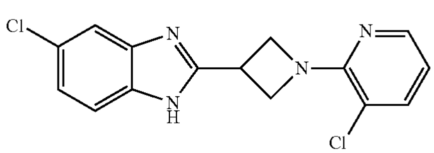 [SMILES: Clc1ccc2[nH]c(C3CN(c4ncccc4Cl)C3)nc2c1] | 5-chloro-2-(1-(3-chloropyridin-2-yl)azetidin-3-yl)-1H-benzo[d]imidazole | 319 | 0.007807 |
| 55 | 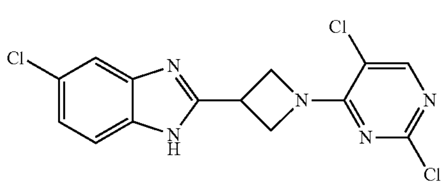 [SMILES: Clc1ccc2[nH]c(C3CN(c4nc(Cl)ncc4Cl)C3)nc2c1] | 5-chloro-2-(1-(2,5-dichloropyrimidin-4-yl)azetidin-3-yl)-1H-benzo[d]imidazole | 354 | 0.5195 |

TABLE 1A-continued

EXAMPLES 11-56 WERE PREPARED ACCORDING TO SCHEMES 1, 3-5, 7, AND 9.

| Example No. | Chemical Structure | Chemical Name | [M + 1] | PDE10 IC$_{50}$ (uM) |
|---|---|---|---|---|
| 56 | 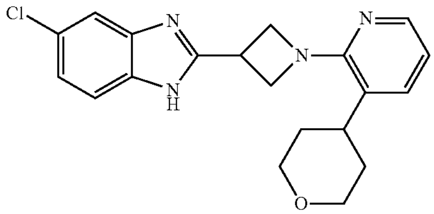 [SMILES: Clc1ccc2[nH]c(C3CN(c4ncccc4C4CCOCC4)C3)nc2c1] | 5-chloro-2-(1-(3-(tetrahydro-2H-pyran-4-yl)pyridin-2-yl)azetidin-3-yl)-1H-benzo[d]imidazole | 369 | 0.9869 |

TABLE 1B

STARTING MATERIALS AND CONDITIONS USED IN PREPARATION OF EXAMPLES 11-56.

| Example No. | Scheme | Starting Material 1 | Starting Material 2 | Principle reagents and solvents |
|---|---|---|---|---|
| 11 | 1 | | | Pyridine, Microwave |
| 12 | 1 | | | Pyridine, Microwave |
| 13 | 1 | | | Pd(dppf)Cl$_2$, K$_2$CO$_3$, dioxane, H$_2$O |
| 14 | 1 | | | Pd(dppf)Cl$_2$, K$_3$PO$_4$, dioxane, H$_2$O |
| 15 | 1 | | | Pd(dppf)Cl$_2$, K$_2$CO$_3$, dioxane, H$_2$O |
| 16 | 3 | | | HATU, ethyl acetate, THF |

TABLE 1B-continued

STARTING MATERIALS AND CONDITIONS USED IN PREPARATION OF EXAMPLES 11-56.

| Example No. | Scheme | Starting Material 1 | Starting Material 2 | Principle reagents and solvents |
|---|---|---|---|---|
| 17 | 3 | (5-chlorobenzimidazol-2-yl-azetidinyl-pyrazine carboxylic acid) | morpholine | HATU, ethyl acetate, THF |
| 18 | 3 | (5-chlorobenzimidazol-2-yl-azetidinyl-pyrazine carboxylic acid) | aniline | HATU, ethyl acetate, THF |
| 19 | 3 | (5-chlorobenzimidazol-2-yl-azetidinyl-pyrazine carboxylic acid) | benzylamine | HATU, ethyl acetate, THF |
| 20 | 3 | (5-chlorobenzimidazol-2-yl-azetidinyl-pyrazine carboxylic acid) | phenethylamine | HATU, ethyl acetate, THF |
| 21 | 3 | (5-chlorobenzimidazol-2-yl-azetidinyl-pyrazine carboxylic acid) | isopropylamine | HATU, ethyl acetate, THF |
| 22 | 3 | (5-chlorobenzimidazol-2-yl-azetidinyl-pyrazine carboxylic acid) | isobutylamine | HATU, ethyl acetate, THF |
| 23 | 3 | (5-chlorobenzimidazol-2-yl-azetidinyl-pyrazine carboxylic acid) | (tetrahydropyran-4-yl)methylamine | HATU, ethyl acetate, THF |
| 24 | 1 | (5-chloro-2-(1-(3-chloropyrazin-2-yl)azetidin-3-yl)benzimidazole) | 2-methylphenylboronic acid pinacol ester | Pd(dppf)Cl$_2$, Na$_2$CO$_3$ Dioxane |

TABLE 1B-continued

STARTING MATERIALS AND CONDITIONS USED IN PREPARATION OF EXAMPLES 11-56.

| Example No. | Scheme | Starting Material 1 | Starting Material 2 | Principle reagents and solvents |
|---|---|---|---|---|
| 25 | 1 | 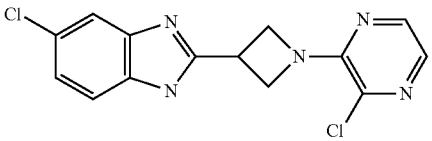 [SMILES: Clc1ccc2[nH]c(C3CN(c4nccnc4Cl)C3)nc2c1] | 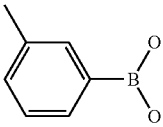 | Pd(dppf)Cl$_2$, Na$_2$CO$_3$ Dioxane |
| 26 | 1 | 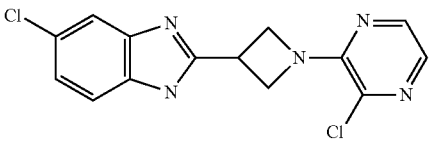 [SMILES: Clc1ccc2[nH]c(C3CN(c4nccnc4Cl)C3)nc2c1] | 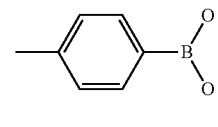 | Pd(dppf)Cl$_2$, Na$_2$CO$_3$ Dioxane |
| 27 | 1 | 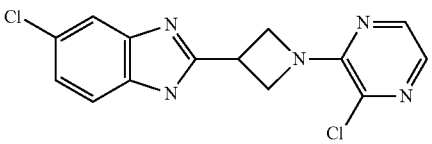 [SMILES: Clc1ccc2[nH]c(C3CN(c4nccnc4Cl)C3)nc2c1] | 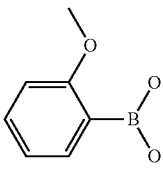 | Pd(dppf)Cl$_2$, Na$_2$CO$_3$ Dioxane |
| 28 | 1 | 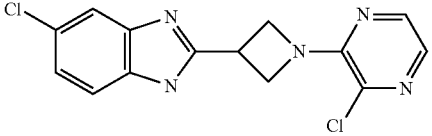 [SMILES: Clc1ccc2[nH]c(C3CN(c4nccnc4Cl)C3)nc2c1] | 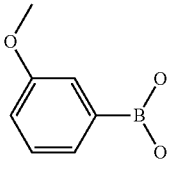 | Pd(dppf)Cl$_2$, Na$_2$CO$_3$ Dioxane |
| 29 | 1 | 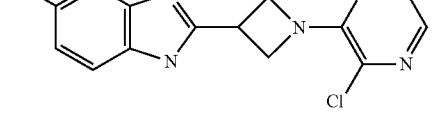 | 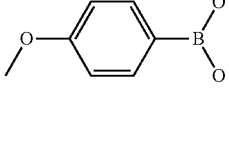 | Pd(dppf)Cl$_2$, Na$_2$CO$_3$ Dioxane |
| 30 | 1 | 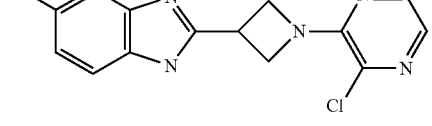 | 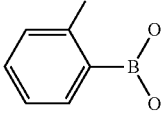 | Pd(dppf)Cl$_2$, Na$_2$CO$_3$ Dioxane |
| 31 | 1 | 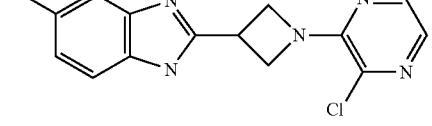 | 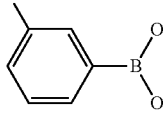 | Pd(dppf)Cl$_2$, Na$_2$CO$_3$ Dioxane |
| 32 | 1 | 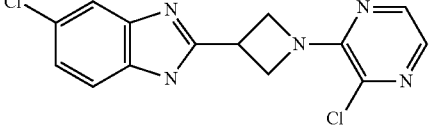 | 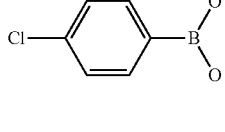 | Pd(dppf)Cl$_2$, Na$_2$CO$_3$ Dioxane |
| 33 | 1 | 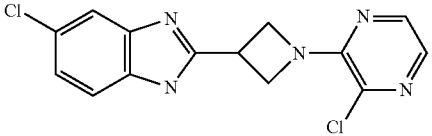 [SMILES: Clc1ccc2[nH]c(C3CN(c4nccnc4Cl)C3)nc2c1] | 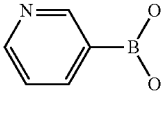 | Pd(dppf)Cl$_2$, Na$_2$CO$_3$ Dioxane |

TABLE 1B-continued

STARTING MATERIALS AND CONDITIONS USED IN PREPARATION OF EXAMPLES 11-56.

| Example No. | Scheme | Starting Material 1 | Starting Material 2 | Principle reagents and solvents |
|---|---|---|---|---|
| 34 | 1 | 5-chloro-benzimidazol-2-yl-azetidinyl-(3-chloropyrazin-2-yl) | pyridin-4-yl boronic acid pinacol ester | Pd(dppf)Cl$_2$, Na$_2$CO$_3$ Dioxane |
| 35 | 4 | 5-chloro-benzimidazol-2-yl-azetidinyl-pyrazine-2-carbonyl chloride | HN(Me)$_2$ | K$_2$CO$_3$, DMF |
| 36 | 4 | 5-chloro-benzimidazol-2-yl-azetidinyl-pyrazine-2-carbonyl chloride | 4-aminotetrahydropyran | K$_2$CO$_3$, DMF |
| 37 | 4 | 5-chloro-benzimidazol-2-yl-azetidinyl-pyrazine-2-carbonyl chloride | (S)-tetrahydrofurfurylamine | K$_2$CO$_3$, DMF |
| 38 | 4 | 5-chloro-benzimidazol-2-yl-azetidinyl-pyrazine-2-carbonyl chloride | (R)-tetrahydrofurfurylamine | K$_2$CO$_3$, DMF |
| 39 | 1 | 5-methyl-benzimidazol-2-yl-azetidinyl-(3-chloropyrazin-2-yl) | phenylboronic acid | S-Phos, Pd(OAc)$_2$, dioxane |
| 40 | 1 | 5-chloro-benzimidazol-2-yl-azetidinyl-(3-chloropyrazin-2-yl) | aniline | NaH, neat |
| 41 | 1 | 5-chloro-benzimidazol-2-yl-azetidinyl-(3-chloropyrazin-2-yl) | N-methylaniline | NaH, neat |
| 42 | 1 | 5-chloro-benzimidazol-2-yl-azetidinyl-(3-chloropyrazin-2-yl) | phenol | phenol, NMP |

TABLE 1B-continued
STARTING MATERIALS AND CONDITIONS USED IN PREPARATION OF EXAMPLES 11-56.
| Example No. | Scheme | Starting Material 1 | Starting Material 2 | Principle reagents and solvents |
|---|---|---|---|---|
| 43 | 1 | 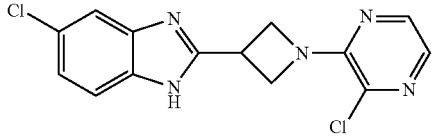 [SMILES: Clc1ccc2[nH]c(C3CN(c4nccnc4Cl)C3)nc2c1] | 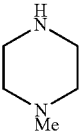 | Cs₂CO₃, neat |
| 44 | 1 | 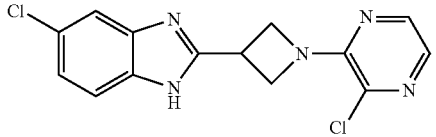 [SMILES: Clc1ccc2[nH]c(C3CN(c4nccnc4Cl)C3)nc2c1] | 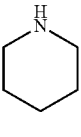 | Cs₂CO₃, neat |
| 45 | 1 | 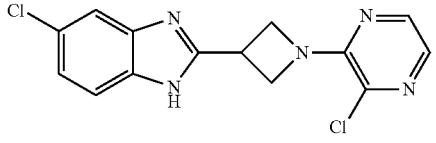 | MeOH | Cs₂CO₃, neat |
| 46 | 1 | 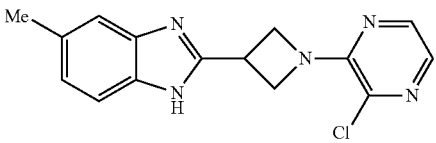 | 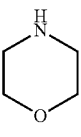 | Neat |
| 47 | 1 | 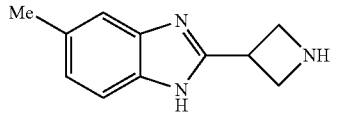 [SMILES: Cc1ccc2[nH]c(C3CNC3)nc2c1] | 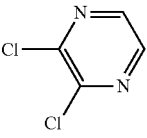 | Cs₂CO₃, NMP |
| 48 | 1 | 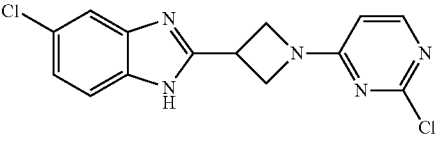 [SMILES: Clc1ccc2[nH]c(C3CN(c4ccnc(Cl)n4)C3)nc2c1] | 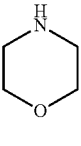 | DMA |
| 49 | 5 | 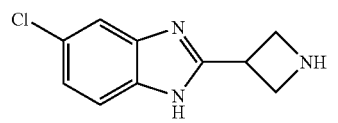 [SMILES: Clc1ccc2[nH]c(C3CNC3)nc2c1] | 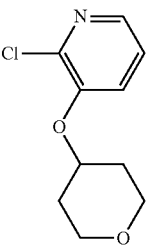 [SMILES: Clc1ncccc1OC1CCOCC1] | Cs₂CO₃, NMP |
| 50 | 1 | 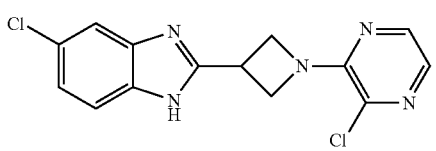 | 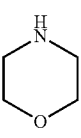 | DMA |

TABLE 1B-continued

STARTING MATERIALS AND CONDITIONS USED IN PREPARATION OF EXAMPLES 11-56.

| Example No. | Scheme | Starting Material 1 | Starting Material 2 | Principle reagents and solvents |
|---|---|---|---|---|
| 51 | 1 | 5-chloro-2-(1-(3-chloropyrazin-2-yl)azetidin-3-yl)-1H-benzo[d]imidazole | 2-(3,6-dihydro-2H-pyran-4-yl)-4,4,5,5-tetramethyl-1,3,2-dioxaborolane | Pd(PPh$_3$)$_4$, Na$_2$CO$_3$ |
| 52 | 1 | 5-chloro-2-(azetidin-3-yl)-1H-benzo[d]imidazole | 3-bromo-2-chloropyridine | Cs$_2$CO$_3$, NMP |
| 53 | 1 | 5-chloro-2-(azetidin-3-yl)-1H-benzo[d]imidazole | 2,3-dichloropyrazine | Cs$_2$CO$_3$, NMP |
| 54 | 1 | 5-chloro-2-(azetidin-3-yl)-1H-benzo[d]imidazole | 2,3-dichloropyridine | NEt$_3$, NMP |
| 55 | 7 | 5-chloro-2-(azetidin-3-yl)-1H-benzo[d]imidazole | 2,4,5-trichloropyrimidine | NEt$_3$, dioxane |
| 56 | 9 | 5-chloro-2-(azetidin-3-yl)-1H-benzo[d]imidazole | 2-fluoro-3-(tetrahydro-2H-pyran-4-yl)pyridine | Cs$_2$CO$_3$, DMA |

TABLE 1C $^1$H NMR: δ (PPM) OF EXAMPLES 11-56

| Example No. | $^1$H NMR |
|---|---|
| 11 | (CDCl$_3$, 400 MHz): 8.09-8.07 (m, 1H); 7.83 (s, 1H); 7.55-7.52 (m, 2H); 7.43-7.41(m, 1H); 6.75-6.72 (m, 1H); 4.19-4.15 (m, 1H); 3.90-3.78 (m, 3H); 3.74-3.68 (m, 1H); 2.52-2.47 (m, 1H); 2.30-2.25(m, 1H). |
| 12 | (CDCl$_3$, 400 MHz): 7.87 (s, 2H); 7.58 (d, J = 8 Hz, 2H); 7.47 (d, J = 8 Hz, 1H); 4.11 (t, J = 6 Hz, 2H); 3.63-3.56 (m, 2H); 3.31 (sz, 4H); 3.14 (sz, 4H); 2.52-2.36 (m, 3H). |
| 13 | (CDCl$_3$, 400 MHz): 8.12 (s, 2H); 8.82 (s, 2H); 7.53-7.44 (m, 3H); 7.34-7.31 (m, 2H); 7.07 (d, J = 8.4 Hz, 1H); 3.68 (s, 2H); 3.30 (s, 1H); 2.69 (s, 2H); 2.07-1.92 (m, 5H); 0.94 (d, J = 7.6 Hz, 2H); 0.61 (d, J = 4.4 Hz, 2H). |
| 14 | (CDCl$_3$, 400 MHz): 7.98 (d, J = 2.4 Hz, 1H); 7.75 (d, J = 2.4 Hz, 1H); 7.49-7.44 (m, 2H); 7.40-7.38 (m, 2H); 7.29-7.27 (m, 3H); 7.19 (s, 1H); 4.07 (t, J = 8.6 Hz, 2H); 3.99 (t, J = 7.4 Hz, 2H); 3.92-3.90 (m, 1H). |
| 15 | (CDCl$_3$, 400 MHz): 7.98 (t, J = 2.4 Hz, 2H); 7.74 (s, 1H); 7.50-7.46 (m, 3H); 7.41 (d, J = 1.2 Hz, 1H); 7.38-7.25 (m, 3H); 3.67 (d, J = 7.2 Hz, 2H); 3.63 (d, J = 6.8 Hz, 1H); 3.23-3.20 (m, 2H); 2.27-2.21 (m, 2H). |
| 16 | (CD$_3$OD, 400 MHz): 8.14-8.12 (m, 1 H); 7.85-7.88 (m, 1H); 7.76-7.75 (m, 1 H); 7.72-7.69(m, 1 H); 7.49-7.47 (m, 1 H); 6.96-6.92 (m, 1 H); 4.75-4.71 (m, 2 H); 4.58-4.52 (m, 3 H); 4.23-4.12 (m, 4 H); 2.38-2.31 (m, 2 H). |

TABLE 1C-continued

| ¹H NMR: δ (PPM) OF EXAMPLES 11-56 |

| Example No. | ¹H NMR |
|---|---|
| 17 | (CD$_3$OD, 400 MHz): 8.13 (d, J = 1.6 Hz, 1 H); 7.87-7.85 (m, 1H); 7.99-7.98 (m, 1 H); 7.75-7.73 (m, 1 H); 7.52-7.50 (m, 1 H); 7.02-6.99 (m, 1 H); 4.84-4.64 (m, 2 H); 4.62-4.55 (m, 3 H); 3.75-3.65 (m, 6 H); 3.51-3.47 (m, 2 H). |
| 18 | (CD$_3$OD, 400 MHz): 8.25-8.20 (m, 1 H); 7.76-7.74 (m, 1 H); 7.66-7.63 (m, 2 H); 7.47-7.41 (m, 2 H); 7.36-7.32 (m, 2 H); 7.27-7.21 (m, 2 H); 7.11-7.01 (m, 1 H); 4.80-4.52 (m, 2 H); 4.50-4.31 (m, 2 H); 4.17-4.01 (m, 1 H). |
| 19 | (CD$_3$OD, 400 MHz): 8.17-8.15 (m, 1 H); 7.67-7.65 (m, 1H); 7.53-7.51 (m, 2 H); 7.33-7.30 (m, 2 H); 7.22-7.20 (m, 4 H); 6.78-6.75 (m, 1 H); 4.89 (s, 2 H); 4.42-4.40 (m, 2 H); 4.19-4.17 (m, 2 H); 4.08-4.05 (m, 1 H). |
| 20 | (CD$_3$OD, 400 MHz): 8.15-8.13 (m, 1 H); 7.55-7.53 (m, 3 H); 7.23-7.20 (m, 3 H); 7.19-7.10 (m, 2 H); 6.95-6.91 (m, 1 H); 6.75-6.72 (m, 1 H); 4.31-4.30 (m, 2 H); 4.09-4.04 (m, 3 H); 3.64-3.60 (m, 2 H); 2.89-2.86 (m, 2 H). |
| 21 | (CD$_3$OD, 400 MHz): 8.10-8.09 (m, 1 H); 7.93-7.90 (m, 1 H); 7.75-7.70 (m, 1 H); 7.69-7.68 (m, 1 H); 7.49-7.47 (m, 1 H); 6.97-6.94 (m, 1 H); 4.79-4.77 (m, 2 H); 4.60-4.53 (m, 2 H); 4.11-4.08 (m, 1 H); 1.23-1.21(m, 7 H). |
| 22 | (CD$_3$OD, 400 MHz): 8.13 (d, J = 2.0 Hz, 1 H); 7.97-7.95 (m, 1 H); 7.77-7.70 (m, 2 H); 7.53-7.50 (m, 1 H); 7.00-6.97 (m, 1 H); 4.79-4.75 (m, 2 H); 4.60-4.54 (m, 3 H); 3.17 (d, J = 6.8 Hz, 2 H); 1.94-1.87 (m, 1 H); 0.97-0.96 (m, 6 H). |
| 23 | (CD$_3$OD, 400 MHz): 8.16-8.14 (m, 1 H); 7.64-7.61 (m, 1 H); 7.49-7.44 (m, 2 H); 7.19-7.16 (m, 1 H); 7.74-6.77 (m, 1 H); 4.48-4.44 (m, 2 H); 4.29-4.26 (m, 2 H); 4.16-4.12 (m, 1 H); 3.88-3.84 (m, 2 H); 3.21-3.20 (m, 2 H); 1.85-1.81 (m, 1 H); 1.79-1.61 (m, 2H); 1.32-1.22 (m, 4 H). |
| 24 | (CD$_3$OD, 400 MHz): 8.21-8.20 (m, 1H); 8.10-8.00 (m, 1 H); 7.72-7.71 (m, 1 H); 7.67-7.65 (m, 1H); 7.51-7.49 (m, 1 H); 7.34-7.26 (m, 4 H); 4.33-4.03 (m, 5H); 2.19 (s, 3 H). |
| 25 | (CD$_3$OD, 400 MHz): 8.17-8.16 (m, 1H); 8.03-8.02 (m, 1 H); 7.71-7.64 (m, 2 H); 7.51-7.50 (m, 1 H); 7.49-7.48 (m, 2 H); 7.45-7.24(m, 2 H); 4.31-4.22 (m, 3 H); 4.08-4.04 (m, 2 H); 2.37 (s, 3 H). |
| 26 | (CD$_3$OD, 400 MHz): 8.18 (d, J = 2.8 Hz, 1 H); 8.04 (d, J = 2.4 Hz, 1 H); 7.74-7.70 (m, 2 H); 7.54-7.51 (m, 3 H); 7.31-7.29 (m, 2 H); 4.34-4.25 (m, 3 H); 4.11-4.07 (m, 2 H); 2.38 (s, 3 H). |
| 27 | (CD$_3$OD, 400 MHz): 8.07-8.06 (m, 1H); 8.00-7.99 (m, 1 H); 7.56-7.53 (m, 2 H); 7.46-7.40 (m, 2 H); 7.16-7.14 (m, 1 H); 7.12-7.04 (m, 2 H); 4.18-4.13 (m, 2 H); 4.03-3.77 (m, 6H). |
| 28 | (CD$_3$OD, 400 MHz): 8.19-8.17 (m, 1 H); 8.04-8.02 (m, 1 H); 7.65-7.63 (m, 2 H); 7.49-7.46 (m, 1 H); 7.39-7.37 (m, 1 H); 7.21-7.18 (m, 2 H); 6.99-6.98 (m, 1 H); 4.29-4.27 (m, 3 H); 4.10-4.09 (m, 2 H); 3.80 (s, 3H). |
| 29 | (CD$_3$OD, 400 MHz): 8.06-8.04 (m, 1 H); 7.95-7.94 (m, 1 H); 7.56-7.53 (m, 2 H); 7.46-7.40 (m, 2 H); 7.16-7.04 (m, 1 H); 6.99-6.98 (m, 2 H); 4.18-4.13 (m, 1 H); 4.03-4.00 (m, 4 H); 3.80 (s, 3H). |
| 30 | (CD$_3$OD, 400 MHz): 8.23 (d, J = 2.8 Hz, 1 H); 8.01(d, J = 2.8 Hz, 1 H); 7.72-7.65 (m, 2 H); 7.52-7.45 (m, 5 H); 4.31-4.29 (m, 2 H); 4.18-4.10 (m, 2 H); 4.06-4.04 (m, 1H). |
| 31 | (CD$_3$OD, 400 MHz): 8.21 (d, J = 2.8 Hz, 1 H); 8.09 (d, J = 2.4 Hz, 1 H); 7.74-7.67 (m, 3 H); 7.60-7.44 (m, 4 H); 4.32-4.28 (m, 3 H); 4.13-4.09 (m, 2 H). |
| 32 | (CD$_3$OD, 400 MHz): 8.12 (d, J = 2.4 Hz, 1 H); 8.08 (d, J = 2.8 Hz, 1 H); 7.67-7.64 (m, 4 H); 7.51-7.49 (m, 3 H); 4.29-4.28 (m, 3 H); 4.11-4.10 (m, 2 H). |
| 33 | (CD$_3$OD, 400 MHz): 9.16-9.15 (m, 1 H); 8.81-8.70 (m, 2 H); 8.30 (d, J = 2.4 Hz, 1 H); 8.23 (d, J = 2.4 Hz, 1 H); 8.05-8.02 (m, 1 H); 7.77-7.51 (m, 3 H); 4.47-4.36 (m, 3 H); 4.24-4.20 (m, 2H). |
| 34 | (CD$_3$OD, 400 MHz): 8.63-8.62 (m, 1 H); 8.19-8.18 (m, 1 H); 8.08-8.07 (m, 2 H); 7.71-7.70 (m, 2 H); 7.46-7.41 (m, 2 H); 7.16-7.13 (m, 1 H); 4.23-4.07 (m, 2 H); 3.30-3.29 (m, 3H). |
| 35 | (CD$_3$OD, 400 MHz): 8.18-8.17 (m, 1H); 7.89-7.88 (m, 1 H); 7.52-7.49 (m, 1 H); 7.40-7.38 (m, 1 H); 7.21-7.18 (m, 1 H); 4.51-4.48 (m, 2 H); 4.35-4.32 (m, 2 H); 4.25-4.23 (m, 1 H); 3.11 (s, 3 H); 3.01 (s, 3 H). |
| 36 | (CD$_3$OD, 400 MHz): 8.09 (br, 1 H); 7.97-7.96 (m, 1 H); 7.80-7.61 (m, 1 H); 7.55-7.54 (br, m, 1 H); 7.28-7.19 (m, 1 H); 4.54-4.44 (m, 3 H); 3.89-3.86 (m, 5H); 3.42-3.36 (m, 2H); 1.84-1.82 (m, 2 H); 1.52-1.50 (m, 2 H). |
| 37 | (CD$_3$OD, 400 MHz): 8.06-8.05 (m, 1 H); 7.85-7.82 (m, 1 H); 7.75-7.61 (m, 1 H); 7.56-7.54 (m, 1 H); 7.28-7.19 (m, 1 H); 4.53-4.50 (m, 5 H); 3.94-3.90 (m, 1 H); 3.67-3.62 (m, 1 H); 3.49-3.44 (m, 1 H); 3.24-3.17 (m, 1 H); 1.93-1.80 (m, 3 H); 1.51-1.46 (m, 1 H). |
| 38 | (CD$_3$OD, 400 MHz): 8.06-8.05 (m, 1 H); 7.85-7.82 (m, 1 H); 7.75-7.61 (m, 1 H); 7.56-7.54 (m, 1 H); 7.28-7.19 (m, 1 H); 4.53-4.50 (m, 5 H); 3.94-3.90 (m, 1 H); 3.67-3.62 (m, 1 H); 3.49-3.44 (m, 1 H); 3.24-3.17 (m, 1 H); 1.93-1.80 (m, 3 H); 1.49-1.46 (m, 1 H). |

TABLE 1C-continued

¹H NMR: δ (PPM) OF EXAMPLES 11-56

| Example No. | ¹H NMR |
|---|---|
| 39 | (DMSO-d6, 400 MHz) 12.16 (s br, 1H), 8.18 (d, J = 2.5 Hz, 1H), 8.10 (d, J = 2.5 Hz, 1H), 7.63 (dm, J = 8.4 Hz, 2H), 7.51-7.18 (m, 5H), 6.94 (t, J = 9.4 Hz, 1H), 4.10-3.94 (m, 5H), 2.37 (d, J = 5.3 Hz, 3H). |
| 40 | (DMSO-d6, 400 MHz) 12.60 (s br, 1H), 7.99 (s, 1H), 7.68 (d, J = 3.0 Hz, 1H), 7.62 (d, J = 2.9 Hz, 1H), 7.64-7.46 (m, 2H), 7.58 (d, J = 7.9 Hz, 2H), 7.24 (t, J = 7.6 Hz, 2H), 7.17 (dd, J = 8.6, 1.6 Hz, 1H), 6.91 (t, J = 7.2 Hz, 1H), 4.52 (t, J = 8.4 Hz, 2H), 4.38 (t, J = 7.3 Hz, 2H), 4.16 (m, 1H). |
| 41 | (CDCl3, 400 MHz) 8.61 (s br, 1H), 7.96 (d, J = 2.8 Hz, 1H), 7.93 (d, J = 2.7 Hz, 1H), 7.57 (s br, 1H), 7.37 (t, J = 7.8 Hz, 2H), 7.32-7.15 (m, 3H), 6.83 (d, J = 7.8 Hz, 2H), 4.26 (t, J = 8.2 Hz, 2H), 3.76 (d br, J = 9.0 Hz, 2H), 3.69 (m, 1H), 3.49 (s, 3H). |
| 42 | (DMSO-d6, 400 MHz) 12.65 (s br, 1H), 7.84 (d, J = 3.0 Hz, 1H), 7.64-7.47 (m, 2H), 7.42 (t, J = 7.8 Hz, 2H), 7.39 (d, J = 2.9 Hz, 1H), 7.24-7.17 (m, 4H), 4.61 (t, J = 8.6 Hz, 2H), 4.50 (t, J = 6.4 Hz, 2H), 4.22 (m, 1H). |
| 43 | (DMSO-d6, 400 MHz) 12.60 (s br, 1H), 7.77 (d, J = 2.7 Hz, 1H), 7.67 (d, J = 2.8 Hz, 1H), 7.64-7.43 (m, 2H), 7.17 (d, J = 8.4 Hz, 1H), 4.40 (t, J = 8.6 Hz, 2H), 4.25 (t, J = 6.8 Hz, 2H), 4.14 (m, 1H), 3.20-3.03 (m, 4H), 2.56-2.41 (m, 4H), 2.21 (s, 3H). |
| 44 | (DMSO-d6, 400 MHz) 12.60 (s br, 1H), 7.74 (d, J = 2.8 Hz, 1H), 7.66 (d, J = 2.8 Hz, 1H), 7.56 (s br, 1H), 7.50 (d br, J = 8.6 Hz, 1H), 7.17 (dd, J = 8.4, 1.9 Hz, 1H), 4.41 (t, J = 8.6 Hz, 2H), 4.26 (t, J = 6.8 Hz, 2H), 4.14 (m, 1H), 3.11-3.05 (m, 4H), 1.69-1.62 (m, 4H), 1.57-1.51 (m, 2H). |
| 45 | (DMSO-d6, 400 MHz) 12.63 (s br, 1H), 7.66 (d, J = 1.3 Hz, 1H), 7.57 (s br, 1H), 7.51 (d br, J = 8.2 Hz, 1H), 7.44 (d, J = 3.1 Hz, 1H), 7.18 (dd, J = 8.7, 2.0 Hz, 1H), 4.50 (t, J = 8.6 Hz, 2H), 4.38 (dd, J = 8.4, 6.3 Hz, 2H), 4.17 (m, 1H), 3.87 (s, 3H). |
| 46 | (DMSO-d6, 400 MHz) 12.26 (s br, 1H), 7.80 (d, J = 2.5 Hz, 1H), 7.69 (d, J = 2.8 Hz, 1H), 7.42-7.22 (m, 2H), 6.95 (t, J = 8.6 Hz, 1H), 4.40 (t, J = 8.4 Hz, 2H), 4.26 (t, J = 6.9 Hz, 2H), 4.11 (m, 1H), 3.76 (t br, J = 4.5 Hz, 4H), 3.11 (t br, J = 4.3 Hz, 4H), 2.39 (d, J = 5.6 Hz, 3H). |
| 47 | (CDCl3, 400 MHz) 9.87 (s br, 1H), 8.08 (dd, J = 4.6, 1.3 Hz, 1H), 7.47 (s br, 1H), 7.46 (dd, J = 7.6, 1.3 Hz, 1H), 7.35 (s br, 1H), 7.07 (dd, J = 8.3, 1.3 Hz, 1H), 6.68 (dd, J = 7.6, 4.7 Hz, 1H), 4.64 (t, J = 8.4 Hz, 2H), 4.48 (dd, J = 8.6, 5.5 Hz, 2H), 4.07 (m, 1H), 2.46 (s, 3H). |
| 48 | (DMSO-d6, 400 MHz) 12.31 (s br, 1H), 8.16 (d, J = 2.6 Hz, 1H), 7.77 (d, J = 2.7 Hz, 1H), 7.40-7.29 (m, 2H), 6.97 (d, J = 7.2 Hz, 1H), 4.64 (t, J = 8.8 Hz, 2H), 4.49 (dd, J = 8.7, 6.5 Hz, 2H), 4.15 (m, 1H), 2.40 (s, 3H). |
| 49 | (400 MHz, CHLOROFORM-d) 1.61-1.74 (m, 2 H) 1.89-2.00 (m, 2 H) 3.53 (ddd, J = 11.64, 8.61, 3.03 Hz, 2 H) 3.84-3.94 (m, 2 H) 4.03-4.15 (m, 1 H) 4.35 (tt, J = 7.92, 3.91 Hz, 1 H) 4.43 (dd, J = 8.22, 5.87 Hz, 2 H) 4.54 (t, J = 8.60 Hz, 2 H) 6.59 (dd, J = 7.82, 5.09 Hz, 1 H) 6.84 (d, J = 8.02 Hz, 1 H) 7.15 (dd, J = 8.61, 1.76 Hz, 1 H) 7.47 (br s., 2 H) 7.69 (d, J = 4.89 Hz, 1 H) 11.77 (br. s., 1H) |
| 50 | (400 MHz, MeOH) 3.18-3.29 (m, 4 H) 3.82-3.92 (m, 4 H) 4.15-4.26 (m, 1 H) 4.38 (dd, J = 8.61, 6.65 Hz, 2 H) 4.56 (t, J = 8.80 Hz, 2 H) 7.24 (dd, J = 8.61, 1.76 Hz, 1 H) 7.55 (br. s., 2 H) 7.70 (d, J = 2.74 Hz, 1 H) 7.78 (d, J = 2.74 Hz, 1 H) |
| 51 | (400 MHz, MeOH) 2.56-2.67 (m, 2 H) 3.95 (t, J = 5.38 Hz, 2 H) 4.15-4.25 (m, 1 H) 4.29-4.40 (m, 4 H) 4.51 (t, J = 8.80 Hz, 2 H) 6.07 (t, J = 1.47 Hz, 1 H) 7.23 (dd, J = 8.61, 1.96 Hz, 1 H) 7.46-7.60 (m, 2 H) 7.94 (d, J = 2.74 Hz, 1 H) 8.07 (d, J = 2.54 Hz, 1 H) |
| 52 | (400 MHz, DMSO-d6) 4.12 (tt, J = 8.61, 6.46 Hz, 1 H) 4.43 (dd, J = 8.22, 6.46 Hz, 2 H) 4.58 (t, J = 8.60 Hz, 2 H) 6.72 (dd, J = 7.73, 4.79 Hz, 1 H) 7.18 (dd, J = 8.61, 1.76 Hz, 1 H) 7.43-7.65 (m, 2 H) 7.83 (dd, J = 7.73, 1.47 Hz, 1 H) 8.16 (dd, J = 4.69, 1.37 Hz, 1 H) 12.65 (br. s., 1 H) |
| 53 | (400 MHz, DMSO-d6) 4.18 (tt, J = 8.71, 6.26 Hz, 1 H) 4.50 (dd, J = 8.61, 6.26 Hz, 2 H) 4.65 (t, J = 8.60 Hz, 2 H) 7.18 (dd, J = 8.51, 2.05 Hz, 1 H) 7.53 (d, J = 8.41 Hz, 1 H) 7.59 (s, 1 H) 7.78 (d, J = 2.74 Hz, 1 H) 8.16 (d, J = 2.54 Hz, 1 H) |
| 54 | (400 MHz, MeOH) 4.15-4.26 (m, 1 H) 4.54 (dd, J = 8.31, 6.36 Hz, 1 H) 4.71 (t, J = 8.60 Hz, 1 H) 6.77 (dd, J = 7.73, 4.79 Hz, 1 H) 7.24 (dd, J = 8.51, 2.05 Hz, 1 H) 7.51 (d, J = 8.41 Hz, 1 H) 7.56 (br. s., 1 H) 7.61 (dd, J = 7.73, 1.47 Hz, 1 H) 8.08 (dd, J = 4.89, 1.57 Hz, 1 H) |
| 55 | (400 MHz, MeOH) 4.26 (tt, J = 9.05, 6.11 Hz, 1 H) 4.72 (br. s., 2 H) 4.85 (s, 2 H) 7.25 (dd, J = 8.61, 1.96 Hz, 1 H) 7.53 (d, J = 8.61 Hz, 1 H) 7.57 (d, J = 1.76 Hz, 1 H) 8.04 (s, 1 H) |
| 56 | (400 MHz, CHLOROFORM-d) 1.71-1.80 (m, 4 H) 2.73-2.86 (m, 1 H) 3.42-3.54 (m, 2 H) 4.04-4.10 (m, 2 H) 4.11-4.18 (m, 1 H) 4.39 (dd, J = 7.73, 5.77 Hz, 2 H) 4.54 (t, J = 8.20 Hz, 2 H) 6.83 (dd, J = 7.63, 4.89 Hz, 1 H) 7.22 (dd, J = 8.61, 1.96 Hz, 1 H) 7.52 (br. s., 2 H) 7.43 (dd, J = 7.63, 1.56 Hz, 1 H) 8.11 (dd, J = 4.89, 1.76 Hz, 1 H) |

SCHEME 11

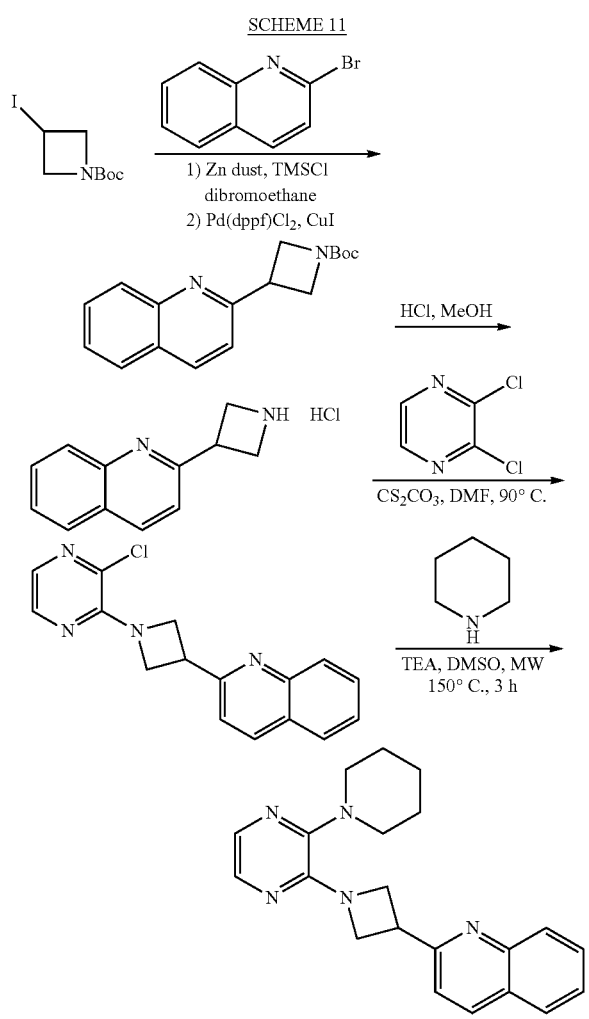

Example 57

2-[1-(3-PIPERIDIN-1-YL-PYRAZIN-7-YL)-AZE-TIDIN-3-YL]-QUINOLINE

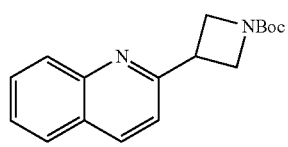 [SMILES: CC(C)(C)OC(=O)N1CC(c2ccc3ccccc3n2)C1]

STEP 1. 3-QUINOLIN-2-YL-AZETIDINE-1-CARBOXYLIC ACID TERT-BUTYL ESTER

Zinc dust was slowly added to a stirring solution of aqueous 2N HCl. The material was allowed to stir for 30 min at which point it was filtered, washed with water, MeOH, and diethyl ether. After drying under vacuum overnight at room temperature, the material was ready for use.

A 100 mL 3-neck round bottom flask fitted with a magnetic stirrer and flushed with nitrogen was charged with zinc dust (300 mg, pre-activated, 4.67 mmol, 2.0 eq.) and DMA (10 mL, anhydrous). 1,2-Dibromoethane (87 mg, 0.47 mmol, 0.2 eq) was added slowly, followed by TMSCl (51 mg, 0.47 mmol, 0.2 eq). The reaction was stirred for 15 min at room temperature. A solution of tert-butyl 3-iodoazetidine-1-carboxylate (1.0 g, 3.5 mmol, 1.5 eq) in DMA (10 mL, anhydrous) was added dropwise. The suspension was stirred for 1 h at room temperature.

A 100 mL 3-neck round bottom flask fitted with a mechanical stirrer was charged with 2-bromo-quinoline (563 mg, 2.4 mmol, 1.0 eq), PdCl2 (dppf) (168 mg, 0.24 mmol, 0.1 eq), CuI (46 mg, 0.24 mmol, 0.1 eq), and DMA (20 mL, anhydrous). The dark solution was degassed for 15 min. The clear zinc reagent solution above the residual solid zinc was transferred to the above 100 mL flask by cannulation. The dark solution was degassed and heated to 80° C. for 16 h. The reaction was diluted with brine and extracted with EtOAc (3×100 mL). The combined organics were washed with water (2×100 mL) and brine (100 mL), followed by drying over sodium sulfate. The solution was concentrated and the residue was purified by flash column chromatography (PE: EtOAc=2:1) provides the title compound (300 mg, 44% yield) as a light yellow solid.

ESI-MS (M+1): 285; calc. for C17H20N2O2 284.

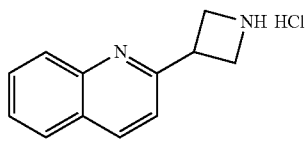 [SMILES: c1ccc2nc(C3CNC3)ccc2c1 ; Cl]

STEP 2. 2-AZETIDIN-3-YL-QUINOLINE HYDROCHLORIDE

A solution of 3-quinolin-2-yl-azetidine-1-carboxylic acid tert-butyl ester (2.2 g, 7.75 mmol) in 4N HCl/MeOH (20 mL) was stirred at room temperature for 30 min. The reaction mixture was concentrated to give the crude product (1.70 g, 7.75 mmol, yield 100%).

ESI-MS (M+1): 185; calc. for $C_{12}H_{12}N_2$ 184.

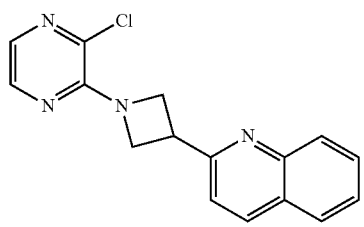 [SMILES: Clc1nccnc1N1CC(c2ccc3ccccc3n2)C1]

STEP 3. 2-[1-(3-CHLORO-PYRAZIN-2-YL)-AZE-TIDIN-3-YL]-QUINOLINE

To a solution of 2-azetidin-3-yl-quinoline hydrochloride (1.70 g, 7.75 mmol) in DMF (30 mL) at room temperature was added Cs₂CO₃ (5.2 g, 16 mmol) and 2,3-dichloro-pyrazine (1.3 g, 9.0 mmol). The reaction mixture was heated to 90° C. overnight and then diluted with water (60 mL) and extracted with EtOAc (2×50 mL). The combined organic extracts were washed with water (60 mL) and brine (60 mL), dried over Na₂SO₄, and filtered. The filtrate was evaporated in vacuo and the residue was purified by flash column chromatography on silica gel (5% to 30% EtOAc in hexanes) to give the title product (1.30 g, 4.4 mmol, 58% yield) as a white solid.

ESI-MS (M+1): 297; calc. for $C_{16}H_{13}ClN_4$ 296.

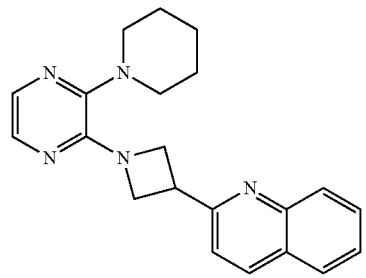 [SMILES: c1ccc2nc(C3CN(c4nccnc4N4CCCCC4)C3)ccc2c1]

STEP 4. 2-[1-(3-PIPERIDIN-1-YL-PYRAZIN-2-YL)-AZETIDIN-3-YL]-QUINOLINE

To a mixture of 2-[1-(3-chloro-pyrazin-2-yl)-azetidin-3-yl]-quinoline (150 mg, 0.51 mmol) and piperidine (43.35 mg, 0.51 mmol) was added DMSO (2 mL) and triethylamine (0.05 g, 0.50 mmol). The solution was heated to 150° C. under microwave for 3 h. Then the mixture was extracted with EtOAc (2×20 mL). The combined organic extracts were washed with water (20 mL) and brine (60 mL), dried over $Na_2SO_4$, and filtered. The filtrate was evaporated in vacuo and the residue was purified by flash column chromatography on silica gel (20% to 60% EtOAc in hexanes) to give the title product (50 mg, 0.15 mmol, 28% yield) as a white solid.

$^1$H NMR (CD$_3$OD, 400 MHz): δ (ppm) 8.94 (d, J=8.8 Hz, 1H); 8.21-8.17 (m, 2H); 8.12 (d, J=8.8 Hz, 1H); 8.07-8.02 (m, 1H); 7.86-7.84 (m, 1H); 7.67-7.64 (m, 2H); 4.75-4.72 (m, 2H); 4.52-4.47 (m, 3H); 3.21-3.18 (m, 4H); 1.75-1.70 (m, 4H); 1.63-1.59 (m, 2H).

ESI-MS (M+1): 346; calc. for $C_{21}H_{23}N_5$ 345. IC$_{50}$ (uM) 0.689.

SCHEME 12

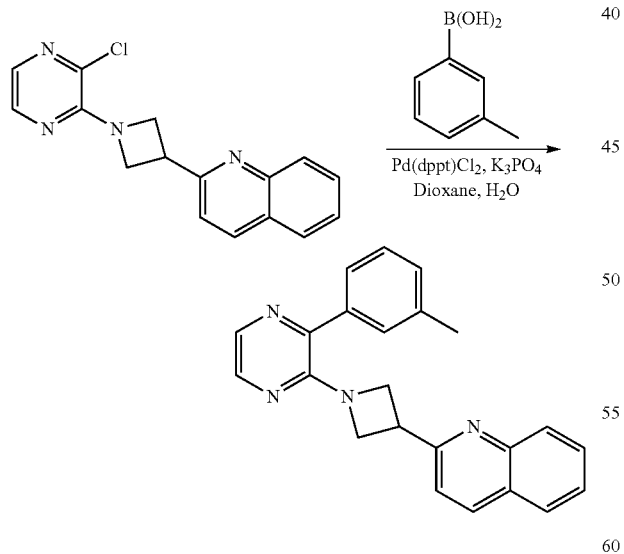

Example 58

2-[1-(3-M-TOLYL-PYRAZIN-2-YL)-AZETIDIN-3-YL]-QUINOLINE

To a solution of 2-[1-(3-chloro-pyrazin-2-yl)-azetidin-3-yl]-quinoline, as prepared in the above Step 3 of Example 57, (150 mg, 0.51 mmol), 3-methyl-phenylboronic acid (75 mg, 0.51 mmol) and K$_3$PO$_4$ (211 mg, 1 mmol) in 1,4-dioxane (12 mL) and H$_2$O (3 mL) was added Pd(dppf)Cl$_2$ (35 mg, 0.05 mmol) then the reaction mixture was stirred at 110° C. under N$_2$ overnight. The reaction mixture was filtered through CELITE™ and washed with CH$_2$Cl$_2$ (50 mL). The organic layer was concentrated and the crude product was purified by silica gel column to give 2-[1-(3-m-tolyl-pyrazin-2-yl)-azetidin-3-yl]-quinoline (50 mg, 0.14 mmol, yield 28%).

$^1$H NMR (CD$_3$OD, 400 MHz): δ (ppm) 9.04 (d, J=8.8 Hz, 1H); 8.25-8.03 (m, 6H); 7.90-7.86 (m, 1H); 7.45 (t, J=11.2 Hz, 2H); 7.36 (t, J=7.6 Hz, 1H); 7.25 (d, J=7.6 Hz, 1H); 4.35-4.33 (m, 3H); 4.06-4.03 (m, 2H); 3.29 (s, 3H)

ESI-MS (M+1): 353; calc. for $C_{23}H_{20}N_4$ 352. IC$_{50}$ (uM) 0.00761.

SCHEME 13

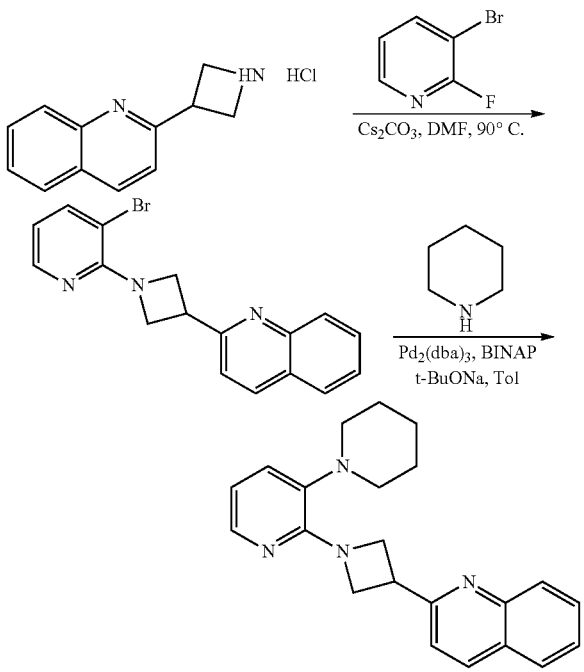

Example 59

2'-(3-QUINOLIN-2-YL-AZETIDIN-1-YL)-3,4,5,6-TETRAHYDRO-2H-[1,3']BIPYRIDINYL

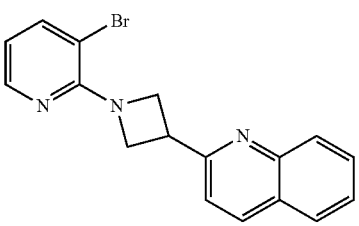 [SMILES: Brc1cccnc1N1CC(c2ccc3ccccc3n2)C1]

STEP 1. 2-[1-(3-BROMO-PYRIDIN-2-YL)-AZETIDIN-3-YL]-QUINOLINE

To a solution of 2-azetidin-3-yl-quinoline hydrochloride (1.70 g, 7.75 mmol) in DMF (30 mL) at room temperature was added Cs$_2$CO$_3$ (5.2 g, 16 mmol) and 3-bromo-2-fluoropyridine (1.5 g, 9.0 mmol). The reaction mixture was heated to 90° C. overnight and then diluted with water (60 mL) and extracted with EtOAc (2×50 mL). The combined organic extracts were washed with water (60 mL) and brine (60 mL), dried over $Na_2SO_4$, and filtered. The filtrate was evaporated in vacuo and the residue was purified by flash column chromatography on silica gel (5% to 30% EtOAc in hexanes) to give the title product (1.50 g, 4.4 mmol, 58% yield) as a white solid.

ESI-MS (M+1): 340; calc. for $C_{17}H_{14}BrN_3$ 339.

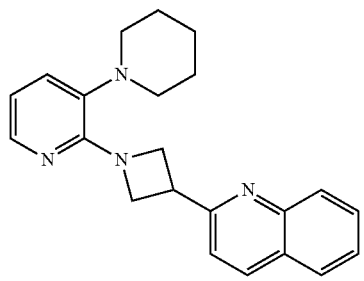 [SMILES: c1cnc(N2CC(c3ccc4ccccc4n3)C2)c(N2CCCCC2)c1]

STEP 2. 2'-(3-QUINOLIN-2-YL-AZETIDIN-1-YL)-3,4,5,6-TETRAHYDRO-2H-[1,3']BIPYRIDINYL

To a solution of 2-[1-(3-bromo-pyridin-2-yl)-azetidin-3-yl]-quinoline (150 mg, 0.51 mmol), piperidine (43.35 mg, 0.51 mmol), BINAP (31.1 mg, 0.05 mmol), t-BuONa (196 mg, 2 mmol) in dioxane (15 mL) was added $Pd_2(dba)_3$ (45.75 mg, 0.05 mmol) then the reaction mixture was stirred at 90° C. under a $N_2$ atmosphere overnight. The reaction mixture was filtered through CELITE™ and washed with EtOAc (50 mL). The filtrate was concentrated and the crude product was purified by silica gel column to give [2'-(3-quinolin-2-yl-azetidin-1-yl)-3,4,5,6-tetrahydro-2H-[1,3']bipyridinyl-4-yl]-methanol (60 mg, 0.17 mmol, yield 34%).

$^1$H NMR ($CD_3OD$, 400 MHz): δ (ppm) 8.71-8.65 (m, 1H); 8.09-8.07 (m, 2H); 7.94-7.84 (m, 2H); 7.87-7.84 (m, 2H); 7.75-7.67 (m, 1H); 6.97-6.95 (m, 1H); 5.09-5.01 (m, 2H); 4.86-4.82 (m, 2H); 4.58-4.54 (m, 1H); 3.04-2.90 (m, 4H); 1.76-1.59 (m, 6H).

ESI-MS (M+1): 345; calc. for $C_{22}H_{24}N_4$ 344. $IC_{50}$ (uM) 0.068.

SCHEME 14

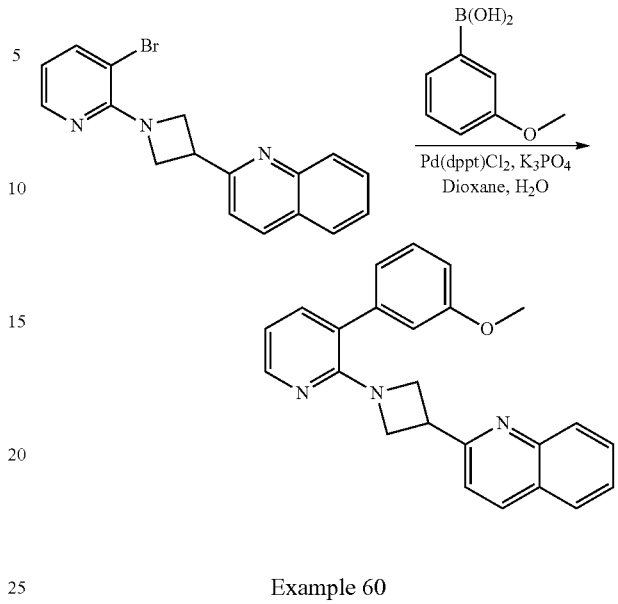

Example 60

2-{1-[3-(3-METHOXY-PHENYL)-PYRIDIN-2-YL]-AZETIDIN-3-YL}-QUINOLINE

To a solution of 2-[1-(3-bromo-pyridin-2-yl)-azetidin-3-yl]-quinoline, as prepared in the above Step 1 of Example 59, (150 mg, 0.44 mmol), 3-methoxyl-phenylboronic acid (80 mg, 0.51 mmol) and $K_3PO_4$ (211 mg, 1 mmol) in 1,4-dioxane (12 mL) and $H_2O$ (3 mL) was added $Pd(dppf)Cl_2$ (35 mg, 0.05 mmol) then the reaction mixture was stirred at 110° C. under $N_2$ overnight. The reaction mixture was filtered through CELITE™ and washed with $CH_2Cl_2$ (50 mL). The organic layer was concentrated and the crude product was purified by silica gel column to give 2-{1-[3-(3-methoxy-phenyl)-pyridin-2-yl]-azetidin-3-yl}-quinoline (70 mg, 0.19 mmol, yield 35%).

$^1$H NMR ($CD_3OD$, 400 MHz): δ (ppm) 8.64 (d, J=8.4 Hz, 1H); 8.09-8.04 (m, 2H); 8.01-7.99 (m, 1H); 7.93-7.89 (m, 1H); 7.87-7.86 (m, 1H); 7.75-7.70 (m, 2H); 7.41-7.37 (m, 1H); 7.08-7.01 (m, 4H); 4.48-4.44 (m, 2H); 4.39-4.31 (m, 3H); 3.81 (s, 3H).

ESI-MS (M+1): 368; calc. for $C_{24}H_{21}N_3O$ 367. $IC_{50}$ (uM) 6.82.

TABLE 2A

EXAMPLES 61-64 WERE PREPARED ACCORDING TO SCHEMES 11 AND 12.

| Example No. | Structure in Chem Draw | Name from Chem Draw | M + 1 | IC50 (uM) |
| --- | --- | --- | --- | --- |
| 61 | | 2-{1-[3-(4-Methyl-piperidin-1-yl)-pyrazin-2-yl]-azetidin-3-yl}-quinoline | 360 | 3.12 |

TABLE 2A-continued

EXAMPLES 61-64 WERE PREPARED ACCORDING TO SCHEMES 11 AND 12.

| Example No. | Structure in Chem Draw | Name from Chem Draw | M + 1 | IC50 (uM) |
|---|---|---|---|---|
| 62 | | {1-[3-(3-Quinolin-2-yl-azetidin-1-yl)-pyrazin-2-yl]-piperidin-4-yl}-methanol | 376 | 0.358 |
| 63 | | 2-{1-[3-(3-Methyl-pyrrolidin-1-yl)-pyrazin-2-yl]-azetidin-3-yl}-quinoline | 346 | 0.641 |
| 64 | | 2-{1-[3-(3-Methoxy-phenyl)-pyrazin-2-yl]-azetidin-3-yl}-quinoline | 369 | 0.0175 |

TABLE 2B

STARTING MATERIALS AND CONDITIONS USED IN PREPARATION OF EXAMPLES 61-64

| Example No. | Scheme | Starting Material 1 | Starting Material 2 | Principle reagents and solvents |
|---|---|---|---|---|
| 61 | 11 | | | TEA, DMSO, MW 150° C., 3 h |
| 62 | 11 | | | TEA, DMSO, MW 150° C., 3 h |

TABLE 2B-continued

STARTING MATERIALS AND CONDITIONS USED IN PREPARATION OF EXAMPLES 61-64

| Example No. | Scheme | Starting Material 1 | Starting Material 2 | Principle reagents and solvents |
|---|---|---|---|---|
| 63 | 11 | (3-chloropyrazin-2-yl azetidine quinoline structure) | 3-methylpyrrolidine (HN) | TEA, DMSO, MW 150° C., 3 h |
| 64 | 12 | (3-chloropyrazin-2-yl azetidine quinoline structure) | 3-methoxyphenylboronic acid | Pd(dppf)Cl$_2$, K$_3$PO$_4$, dioxane, H$_2$O |

TABLE 2C $^1$H NMR: δ (PPM) OF EXAMPLES 61-64

| Example No. | $^1$H NMR |
|---|---|
| 61 | (CD$_3$OD, 400 MHz): 9.01 (d, J = 8.8 Hz, 1H); 8.26-8.17 (m, 3H); 8.11-8.07 (m, 1H); 7.90-7.86 (m, 1H); 7.68-7.66 (m, 2H); 4.78-4.75 (m, 2H); 4.54-4.51 (m, 3H); 3.73-3.70 (m, 2H); 2.80-2.73 (m, 2H); 1.79-1.76 (m, 2H); 1.60-1.54 (m, 1H); 1.42-1.32 (m, 2H); 0.98-0.96 (d, 3H). |
| 62 | (CD$_3$OD, 400 MHz): 8.94 (d, J = 8.8 Hz, 1H); 8.28 (d, J = 8.4 Hz, 1H); 7.99 (d, J = 8.8 Hz, 1H); 7.88-7.86 (m, 2H); 7.59-7.51 (m, 3H); 4.54-4.50 (m, 2H); 4.35-4.32 (m, 2H); 4.20-4.15 (m, 1H); 3.76-3.73 (m, 2H); 3.42 (d, J = 6.4 Hz, 2H); 2.68-2.61 (m, 2H); 1.85-1.81 (m, 2H); 1.61-1.58 (m, 1H); 1.46-1.39 (m, 2H). |
| 63 | (CD$_3$OD, 400 MHz): 8.26 (d, J = 8.4 Hz, 1H); 7.97-7.95 (m, 1H); 7.86-7.84 (m, 1H); 7.71-7.67 (m, 1H); 7.58-7.49 (m, 4H); 4.41-4.33 (m, 1H); 4.31-4.25 (m, 1H); 4.24-4.22 (m, 1H); 4.18-4.13 (m, 2H); 3.56-3.51 (m, 1H); 3.40-3.37 (m, 2H); 2.91-2.87 (m, 1H); 2.31-2.28 (m, 1H); 2.11-2.06 (m, 1H); 1.52-1.46 (m, 1H); 1.08-1.07 (d, 3H). |
| 64 | (CDCl$_3$, 400 MHz): 8.49 (d, J = 8.4 Hz, 1H); 8.33 (d, J = 8.4 Hz, 1H); 8.09-8.06 (dd, J = 2.4 Hz, 2.4 Hz, 2H); 7.9 (d, J = 8 Hz, 2H); 7.85-7.78 (m, 3H); 7.65 (t, J = 7.6 Hz, 1H); 7.28 (t, J = 8 Hz, 1H); 7.19-7.15 (m, 3H); 6.87-6.84 (dd, J = 2.4 Hz, 2.4 Hz, 1H); 4.52-4.46 (m, 1H); 4.30 (t, J = 8.8 Hz, 2H); 3.94 (t, J = 5.2 Hz, 1H); 3.77 (s, 3H) |

It will be appreciated that the following Examples 65 to 86 can be made according to the above schemes and preparations by using commercially available starting materials via known routes and are therefore contemplated to be compounds of the present invention.

TABLE 3

EXAMPLES 65 TO 86

| Ex. # | Structure | Chemical Name |
|---|---|---|
| 65 | (structure) | 2-(1-(3-(tetrahydro-2H-pyran-4-yl)pyrazin-2-yl)-1,2,3,6-tetrahydropyridin-4-yl)quinoline |

TABLE 3-continued
EXAMPLES 65 TO 86
| Ex. # | Structure | Chemical Name |
|---|---|---|
| 66 | 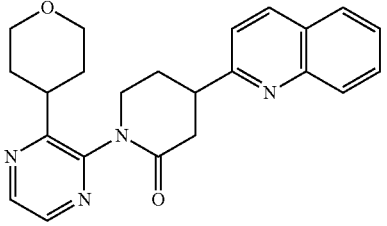 [SMILES: O=C1CC(c2ccc3ccccc3n2)CCN1c1nccnc1C1CCOCC1] | 4-(quinolin-2-yl)-1-(3-(tetrahydro-2H-pyran-4-yl)pyrazin-2-yl)piperidin-2-one |
| 67 | 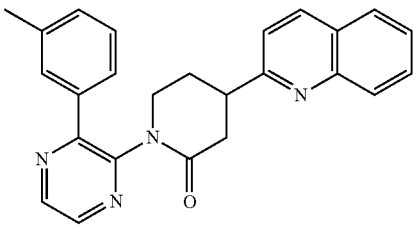 [SMILES: Cc1cccc(-c2nccnc2N2CCC(c3ccc4ccccc4n3)CC2=O)c1] | 4-(quinolin-2-yl)-1-(3-m-tolylpyrazin-2-yl)piperidin-2-one |
| 68 | 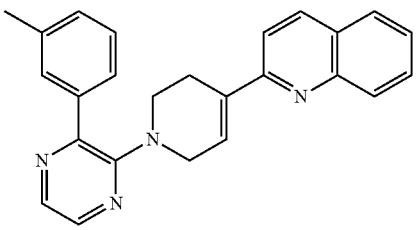 [SMILES: Cc1cccc(-c2nccnc2N2CC=C(c3ccc4ccccc4n3)CC2)c1] | 2-(1-(3-m-tolylpyrazin-2-yl)-1,2,3,6-tetrahydropyridin-4-yl)quinoline |
| 69 | 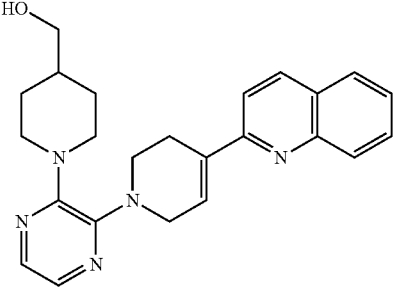 [SMILES: OCC1CCN(c2nccnc2N2CC=C(c3ccc4ccccc4n3)CC2)CC1] | (1-(3-(4-(quinolin-2-yl)-5,6-dihydropyridin-1(2H)-yl)pyrazin-2-yl)piperidin-4-yl)methanol |
| 70 | 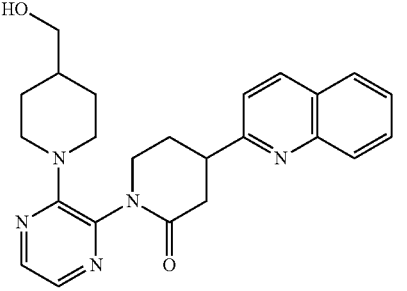 [SMILES: O=C1CC(c2ccc3ccccc3n2)CCN1c1nccnc1N1CCC(CO)CC1] | 1-(3-(4-(hydroxymethyl)piperidin-1-yl)pyrazin-2-yl)-4-(quinolin-2-yl)piperidin-2-one |

TABLE 3-continued

EXAMPLES 65 TO 86

| Ex. # | Structure | Chemical Name |
|---|---|---|
| 71 | 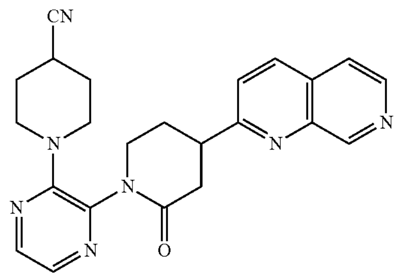 [SMILES: N#CC1CCN(c2nccnc2N2CCC(c3ccc4ccncc4n3)CC2=O)CC1] | 1-(3-(4-(1,7-naphthyridin-2-yl)-2-oxopiperidin-1-yl)pyrazin-2-yl)piperidine-4-carbonitrile |
| 72 | 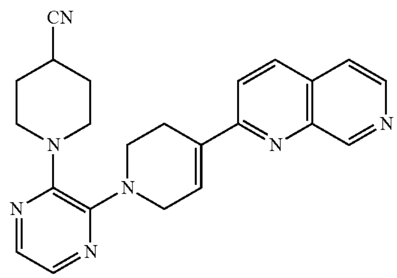 [SMILES: N#CC1CCN(c2nccnc2N2CC=C(c3ccc4ccncc4n3)CC2)CC1] | 1-(3-(4-(1,7-naphthyridin-2-yl)-5,6-dihydropyridin-1(2H)-yl)pyrazin-2-yl)piperidine-4-carbonitrile |
| 73 | 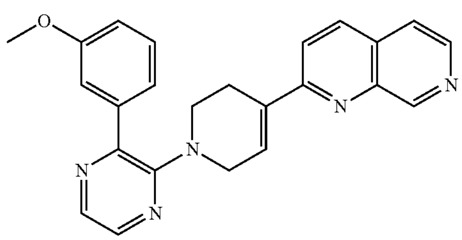 [SMILES: COc1cccc(-c2nccnc2N2CC=C(c3ccc4ccncc4n3)CC2)c1] | 2-(1-(3-(3-methoxyphenyl)pyrazin-2-yl)-1,2,3,6-tetrahydropyridin-4-yl)-1,7-naphthyridine |
| 74 | 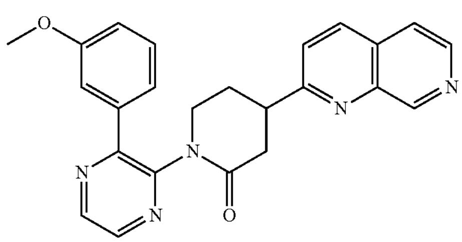 [SMILES: COc1cccc(-c2nccnc2N2CCC(c3ccc4ccncc4n3)CC2=O)c1] | 1-(3-(3-methoxyphenyl)pyrazin-2-yl)-4-(1,7-naphthyridin-2-yl)piperidin-2-one |
| 75 | 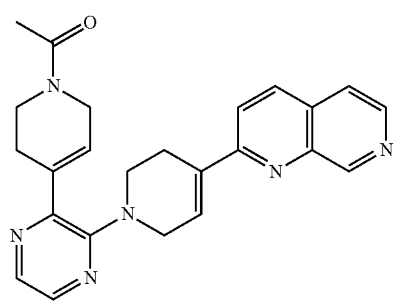 [SMILES: CC(=O)N1CC=C(c2nccnc2N2CC=C(c3ccc4ccncc4n3)CC2)CC1] | 1-(4-(3-(4-(1,7-naphthyridin-2-yl)-5,6-dihydropyridin-1(2H)-yl)pyrazin-2-yl)-5,6-dihydropyridin-1(2H)-yl)ethanone |

TABLE 3-continued

EXAMPLES 65 TO 86

| Ex. # | Structure | Chemical Name |
|---|---|---|
| 76 | 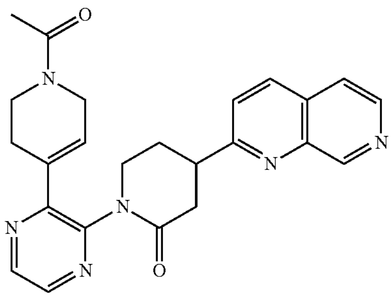 [SMILES: CC(=O)N1CC=C(c2nccnc2N2CCC(c3ccc4ccncc4n3)CC2=O)CC1] | 1-(3-(1-acetyl-1,2,3,6-tetrahydropyridin-4-yl)pyrazin-2-yl)-4-(1,7-naphthyridin-2-yl)piperidin-2-one |
| 77 | 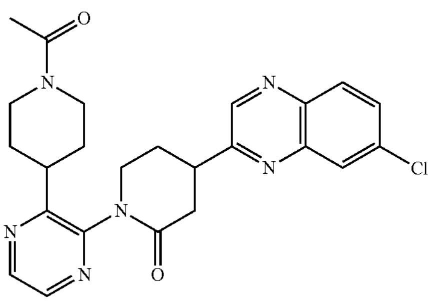 [SMILES: CC(=O)N1CCC(c2nccnc2N2CCC(c3cnc4ccc(Cl)cc4n3)CC2=O)CC1] | 1-(3-(1-acetylpiperidin-4-yl)pyrazin-2-yl)-4-(7-chloroquinoxalin-2-yl)piperidin-2-one |
| 78 | 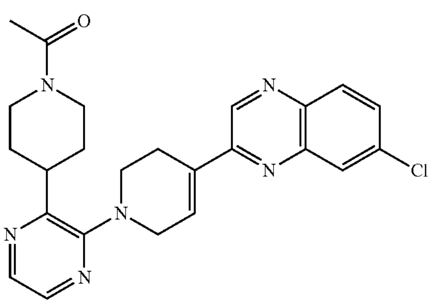 [SMILES: CC(=O)N1CCC(c2nccnc2N2CC=C(c3cnc4ccc(Cl)cc4n3)CC2)CC1] | 1-(4-(3-(4-(7-chloroquinoxalin-2-yl)-5,6-dihydropyridin-1(2H)-yl)pyrazin-2-yl)piperidin-1-yl)ethanone |
| 79 | 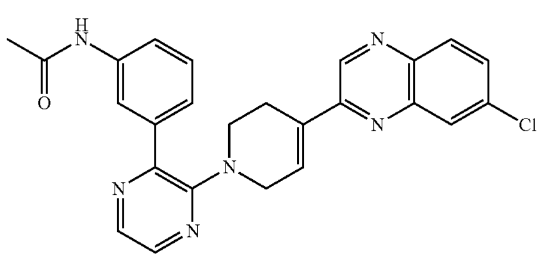 [SMILES: CC(=O)Nc1cccc(-c2nccnc2N2CC=C(c3cnc4ccc(Cl)cc4n3)CC2)c1] | N-(3-(3-(4-(7-chloroquinoxalin-2-yl)-5,6-dihydropyridin-1(2H)-yl)pyrazin-2-yl)phenyl)acetamide |
| 80 | 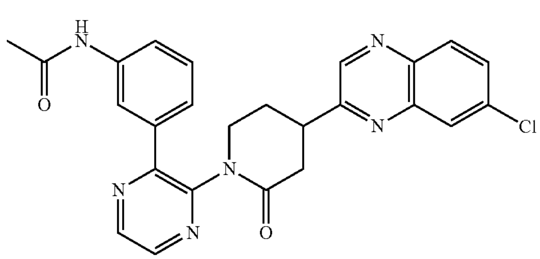 [SMILES: CC(=O)Nc1cccc(-c2nccnc2N2CCC(c3cnc4ccc(Cl)cc4n3)CC2=O)c1] | N-(3-(3-(4-(7-chloroquinoxalin-2-yl)-2-oxopiperidin-1-yl)pyrazin-2-yl)phenyl)acetamide |

TABLE 3-continued

EXAMPLES 65 TO 86

| Ex. # | Structure | Chemical Name |
|---|---|---|
| 81 | 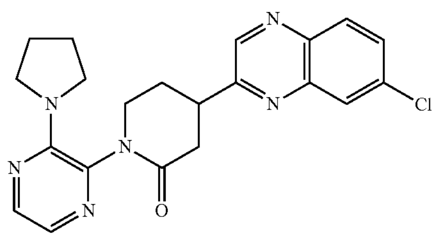 [SMILES: O=C1CC(c2cnc3ccc(Cl)cc3n2)CCN1c1nccnc1N1CCCC1] | 4-(7-chloroquinoxalin-2-yl)-1-(3-(pyrrolidin-1-yl)pyrazin-2-yl)piperidin-2-one |
| 82 | 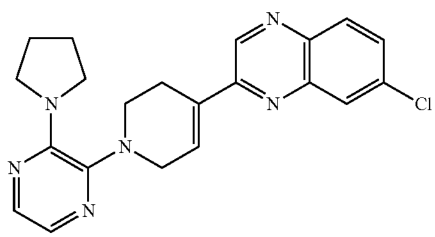 [SMILES: Clc1ccc2ncc(C3=CCN(c4nccnc4N4CCCC4)CC3)nc2c1] | 7-chloro-2-(1-(3-(pyrrolidin-1-yl)pyrazin-2-yl)-1,2,3,6-tetrahydropyridin-4-yl)quinoxaline |
| 83 | 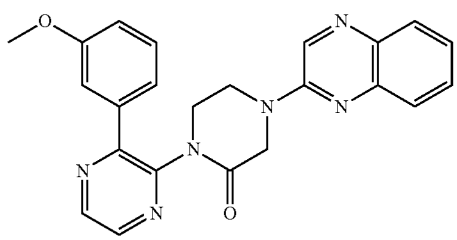 [SMILES: COc1cccc(-c2nccnc2N2CCN(c3cnc4ccccc4n3)CC2=O)c1] | 1-(3-(3-methoxyphenyl)pyrazin-2-yl)-4-(quinoxalin-2-yl)piperazin-2-one |
| 84 | 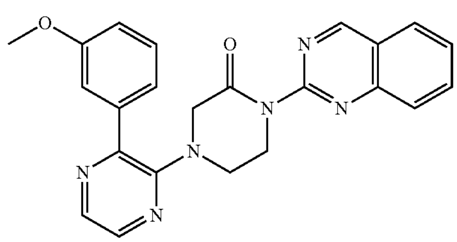 [SMILES: COc1cccc(-c2nccnc2N2CCN(c3ncc4ccccc4n3)C(=O)C2)c1] | 4-(3-(3-methoxyphenyl)pyrazin-2-yl)-1-(quinazolin-2-yl)piperazin-2-one |
| 85 | 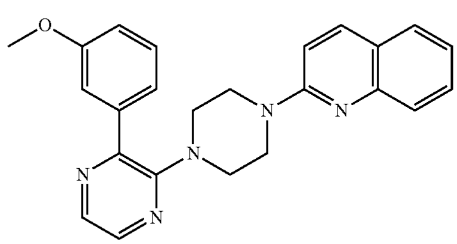 [SMILES: COc1cccc(-c2nccnc2N2CCN(c3ccc4ccccc4n3)CC2)c1] | 2-(4-(3-(3-methoxyphenyl)pyrazin-2-yl)piperazin-1-yl)quinoline |
| 86 | 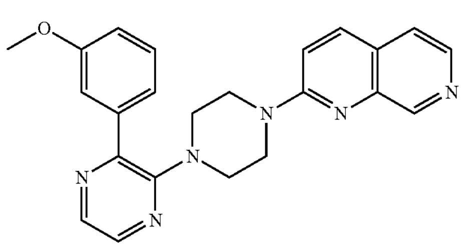 [SMILES: COc1cccc(-c2nccnc2N2CCN(c3ccc4ccncc4n3)CC2)c1] | 2-(4-(3-(3-methoxyphenyl)pyrazin-2-yl)piperazin-1-yl)-1,7-naphthyridine |

BIOLOGICAL EXAMPLES

Example A

MPDE10A7 Enzyme Activity and Inhibition

Enzyme Activity.

An IMAP TR-FRET assay was used to analyze the enzyme activity (Molecular Devices Corp., Sunnyvale Calif.). 5 μL of serial diluted PDE10A (BPS Bioscience, San Diego, Calif.) or tissue homogenate was incubated with equal volumes of diluted fluorescein labeled cAMP or cGMP for 60 min in 384-well polystyrene assay plates (Corning, Corning, N.Y.) at room temperature. After incubation, the reaction was stopped by adding 60 μL of diluted binding reagents and was incubated for 3 hours to overnight at room temperature. The plates were read on an Envision (Perkin Elmer, Waltham, Mass.) for time resolved fluorescence resonance energy transfer. The data were analyzed with GraphPad Prism (La Jolla, Calif.).

Enzyme Inhibition.

To check the inhibition profile, 5 μL of serial diluted compounds were incubated with 5 μL of diluted PDE10 enzyme (BPS Bioscience, San Diego, Calif.) or tissue homogenate in a 384-well polystyrene assay plate (Corning, Corning, N.Y.) for 30 min at room temperature. After incubation, 10 μL of diluted fluorescein labeled cAMP or cGMP substrate were added and incubated for 60 min at room temperature. The reaction was stopped by adding 60 μL of diluted binding reagents and plates were read on an Envision (Perkin Elmer, Waltham, Mass.) for time resolved fluorescence resonance energy transfer. The data were analyzed with GraphPad Prism (La Jolla, Calif.).

Example B

Apomorphine Induced Deficits in Prepulse Inhibition of the Startle Response in Rats, an In Vivo Test for Antipsychotic Activity The thought disorders that are characteristic of schizophrenia may result from an inability to filter, or gate, sensorimotor information. The ability to gate sensorimotor information can be tested in many animals as well as in humans. A test that is commonly used is the reversal of apomorphine-induced deficits in the prepulse inhibition of the startle response. The startle response is a reflex to a sudden intense stimulus such as a burst of noise. In this example, rats can be exposed to a sudden burst of noise, at a level of 120 db for 40 msec, e.g., the reflex activity of the rats can be measured. The reflex of the rats to the burst of noise may be attenuated by preceding the startle stimulus with a stimulus of lower intensity, at 3 db to 12 db above background (65 db), which attenuates the startle reflex by 20% to 80%.

The prepulse inhibition of the startle reflex, described above, may be attenuated by drugs that affect receptor signaling pathways in the CNS. One commonly used drug is the dopamine receptor agonist apomorphine. Administration of apomorphine reduces the inhibition of the startle reflex produced by the prepulse. Antipsychotic drugs such as haloperidol prevents apomorphine from reducing the prepulse inhibition of the startle reflex. This assay can be used to test the antipsychotic efficacy of PDE10 inhibitors, as they reduce the apomorphine-induced deficit in the prepulse inhibition of startle.

Example C

Conditioned Avoidance Responding (Car) in Rats, an In Vivo Test for Antipsychotic Activity Conditioned avoidance responding (CAR) occurs, for instance, when an animal learns that a tone and light predict the onset of a mild foot shock. The subject learns that when the tone and light are on, it must leave the chamber and enter a safe area. All known antipsychotic drugs reduce this avoidance response at doses which do not cause sedation. Examining the ability of test compounds to suppress the conditioned avoidance has been widely used for close to fifty years to screen for drugs with useful antipsychotic properties.

In this example, an animal can be placed in a two-chambered shuttle box and presented with a neutral conditioned stimulus (CS) consisting of a light and tone, followed by an aversive unconditioned stimulus (US) consisting of a mild foot shock through a floor grid in the shuttle box chamber. The animal can be free to escape the US by running from one chamber to the other, where the grid is not electrified. After several presentations of the CS-US pair, the animal typically learns to leave the chamber during the presentation of the CS and avoid the US altogether. Animals treated with clinically-relevant doses of antipsychotic drugs have a suppression of their rate of avoidances in the presence of the CS even though their escape response to the shock itself is unaffected.

Specifically, conditioned avoidance training can be conducted using a shuttle box (Med Associates, St. Albans, Vt.). The shuttle box is typically divided into 2 equal compartments that each contain a light source, a speaker that emits an 85 dB tone when activated and an electrified grid that can deliver a scrambled foot shock. Sessions can consist of 20 trials per day (intertrial interval of 25-40 sec) during which a 10 sec illumination and a concurrent 10 sec tone signals the subsequent delivery of a 0.5 mA shock applied for a maximum of 10 sec. Active avoidance, defined as the crossing into the opposite compartment during the 10 sec conditioning stimuli (light and tone) prevents the delivery of the shock. Crossing over to the other compartment after the delivery of the shock terminates shock delivery and may be recorded as an escape response. If an animal does not leave the conditioning chamber during the delivery of the shock it is recorded as an escape failure. Training can be continued daily until the avoidance of 16 or more shocks out of 20 trials (80% avoidance) on 2 consecutive days is achieved. After this criterion is reached the rats may be given one day of pharmacological testing. On test day, rats can be randomly assigned to experimental groups, weighed and injected intraperitoneally (i.p.) (1 cc tuberculin syringe, 26⅜ gauge needle) or per os (p.o.) (18 gauge feeding needle) with either control or compound solutions. Compounds can be injected at 1.0 ml/kg for i.p. and 10 mL/kg for p.o. administration. Compounds can be administered either acutely or chronically. For testing, each rat may be placed in the shuttle box, and given 20 trials with the same parameters as described above for training trials. The number of avoidances, escapes, and escape failures can be recorded.

Example D

PCP-Induced Hyperactivity (PCP-LMA)

Equipment Used: 4×8 home cage photobeam activity system (PAS) frame from San Diego Instruments. Open PAS program and prepare an experimental session using the following variables:

Multiphase Experiment
300 sec/interval (5 min)
12 intervals (1 h)
Individual on screen switches.
Start recording after first beam break.
End session after end of interval.

Cage Preparation

Techniplast™ rat cage with filter top, but no wire lid. Place ~400 mL bedding and one food pellet in cage and place 250 mL techniplast water bottle in holder on filter top. Place the prepped cage in the PAS frame. Make sure bedding or pellet doesn't block the photobeams.

Animal Preparation

Mark rats and record their weights. Bring rats to testing room.

Phase I

Habituation

Start the experiment session. Place the rat in the enclosure. The computer should start recording when it detects the rat breaking the beam. The computer will record for 1 h. During the habituation phase, prepare risperidone (positive control): Measure out risperidone, calculate final volume at 1 mg/mL concentration and add 1% glacial acetic acid of the final volume to dissolve risperidone. When risperidone is dissolved, add saline to final volume to make a concentration of 1 mg/mL. Fill syringes (3 mL syringes with 23 g½ needle or oral gavage needle) with Amgen compound solution (5 mL/kg) or risperidone (1 mL syringe with 23 g½ needle) control (1 mL/kg) s.c.

Phase II

Compound Pre-Treatment

Make sure Phase I has ended. Remove rat from enclosure, start the next phase using on-screen individual switch, administer compound p.o or i.p. and control s.c. and place rat back in the enclosure. The computer should start recording when it detects the rat breaking the beam. The computer will record for 1 h.

During phase II, prepare pcp: Dissolve pcp in saline to a concentration of 5 mg/mL.

Fill syringes (1 mL syringes with 26 g⅜ needle) with pcp solution (1 mL/kg).

Phase III

PCP Administration

Make sure phase II is ended. Remove rat from enclosure, start the next phase using on-screen individual switch, administer pcp s.c. and place rat back in the enclosure. The computer will record for 1 h.

Clean-Up

End-session to terminate experiment and so that computer will compile data. Export raw data to excel file for data analysis. Euthanize rats and take necessary tissue/sample for PK.

Data Generation

Export raw data to excel file for data analysis. Total time of movement is recorded as the number of photobeam breaks by the computer. Total time of movement (seconds) is combined into 5 minute bins and averaged for each treatment group for an N of 7-10 animals. Data are analyzed for statistical significance using a two-way ANOVA followed by a Bonferroni's post-hoc test for multiple comparisons.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound of formula I:

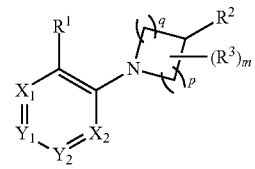

or a pharmaceutically acceptable salt thereof, wherein: the group

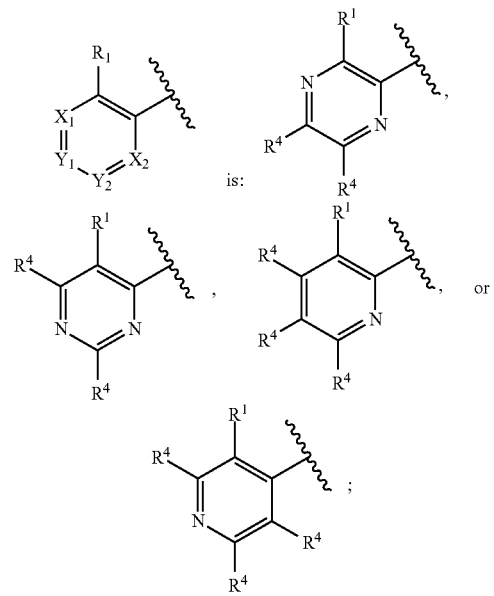

is:

wherein the group

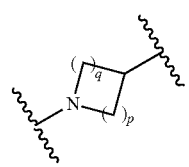

is azetidinyl;

$R^1$ is halo, $OR^a$, —$OR^c$, —$C(=O)R^c$, —$NR^aR^c$, —$C(=O)NR^aR^b$, —$C(=O)NR^a(C_{0-4}alk)R^c$, or $C_{0-4}alk-L^1$;

R² is unsaturated 9- or 10-membered bicyclo-heterocyclic ring; wherein each R² is substituted by 0, 1, 2 or 3 R⁵ groups;

R³ is halo, OH, OC₁₋₄alk, C₁₋₄alk, C₁₋₄haloalk, or oxo;

R⁴ is independently H, halo, OH, OC₁₋₄alk, C₁₋₄alk or C₁₋₄haloalk;

R⁵ is independently halo, CN, or C₁₋₄alk;

m is 0;

each of p and q is independently 1;

the ring containing p and q contains 0 double bonds;

Rᵃ is independently H or Rᵇ;

Rᵇ is independently phenyl, benzyl, or C₁₋₆alk, wherein said phenyl, benzyl, and C₁₋₆alk are being substituted by 0, 1, 2 or 3 substituents which are independently halo, C₁₋₄alk, C₁₋₃haloalk, —OH, —OC₁₋₄alk, —NH₂, —NHC₁₋₄alk, —OC(=O)C₁₋₄alk, or —N(C₁₋₄alk)C₁₋₄alk;

Rᶜ is C₀₋₄alk-L²; and each of L¹ and L² is independently a carbon-linked or nitrogen-linked saturated, partially-saturated or unsaturated 3-, 4-, 5-, 6-, or 7-membered monocyclic ring or a saturated, partially-saturated or unsaturated 8-, 9-, 10-, 11-, or 12-membered bicyclic ring, wherein each said ring contains 0, 1, 2, 3, or 4 N atoms and 0, 1, or 2 atoms which are independently O or S; wherein each L¹ and L² is independently substituted by 0, 1, 2 or 3 R⁶ groups which are independently F, Cl, Br, C₁₋₆alk, C₁₋₄haloalk, —ORᵃ, —OC₁₋₄haloalk, CN, —C(=O)Rᵇ, —C(=O)ORᵃ, or —C(=O)NRᵃRᵃ.

2. The compound according to claim 1, or a pharmaceutically acceptable salt thereof, or a pharmaceutically acceptable salt thereof, wherein the group

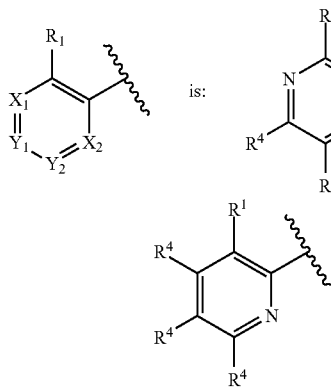

3. The compound according to claim 1, or a pharmaceutically acceptable salt thereof, wherein R¹ is Cl, Br, or C₀₋₄alk-L¹.

4. The compound according to claim 1, or a pharmaceutically acceptable salt thereof, wherein R¹ is a carbon-linked or nitrogen-linked unsaturated 4-, 5-, 6-, or 7-membered monocyclic ring, wherein each said ring contains 0, 1, 2, or 3 N atoms and 0, 1, or 2 O atoms, and wherein each said ring is substituted by 0, 1, or 2 R⁶ groups which are independently F, Cl, Br, or C₁₋₆alk.

5. The compound according to claim 1, or a pharmaceutically acceptable salt thereof, wherein R¹ is a carbon-linked saturated or partially-saturated 5- to 6-membered monocyclic ring, wherein each said ring contains 0, 1, 2, or 3 N atoms and 0, 1, or 2 O atoms, and wherein each said ring is substituted by 0, 1, 2 or 3 R⁶ groups which are independently F, Cl, Br, or C₁₋₆alk.

6. The compound according to claim 1, or a pharmaceutically acceptable salt thereof, wherein R¹ is a carbon-linked or nitrogen-linked saturated, partially-saturated or unsaturated 8-, 9-, 10-, 11-, or 12-membered bicyclic ring, wherein each said ring contains 0, 1, 2, or 3 N atoms and 0, 1, or 2 O atoms, and wherein each said ring is substituted by 0, 1, 2 or 3 R⁶ groups which are independently F, Cl, Br, C₁₋₆alk, C₁₋₄haloalk, —ORᵃ, —OC₁₋₄haloalk, CN, —C(=O)Rᵇ, or —C(=O)ORᵃ.

7. The compound according to claim 1, or a pharmaceutically acceptable salt thereof, wherein Rᵃ is H or C₁₋₆alk substituted by 0 or 1 —OH, —OC₁₋₄alk, —OC(=O)C₁₋₄alk, or —N(C₁₋₄alk)C₁₋₄alk.

8. The compound according to claim 1, or a pharmaceutically acceptable salt thereof, wherein Rᶜ is a C₀₋₄alk-saturated, partially-saturated or unsaturated 3-, 4-, 5-, or 6-membered monocyclic ring containing 0 or 1 N atom and 0 or 1 atom which are independently O or S, which is substituted by 0 or 1 R⁶ groups which are independently F, Cl, C₁₋₆alk, C₁₋₄haloalk, or —ORᵃ.

9. The compound according to claim 1, or a pharmaceutically acceptable salt thereof, wherein Rᶜ is a C₀₋₄alk-saturated, partially-saturated or unsaturated 3-, 4-, 5-, or 6-membered monocyclic ring which is cyclohexyl, cyclopentyl, cyclopentenyl, cyclohexenyl, cycloheptyl, azetidinyl, phenyl, pyridyl, pyrazolyl, morpholinyl, pyrimidyl, piperazinyl, piperidinyl, dihydropyranyl, tetrahydropyranyl, tetrahydrofuranyl, tetrahydropyridinyl, and tetrahydrothiopyranyl, all of which are substituted by 0, 1, 2 or 3 R⁶ groups which are independently F, Cl, Br, C₁₋₆alk, C₁₋₄haloalk, —ORᵃ, CN, —C(=O)Rᵇ, or —C(=O)ORᵃ.

10. The compound according to claim 1, or a pharmaceutically acceptable salt thereof, wherein R¹ is: Cl, Br,

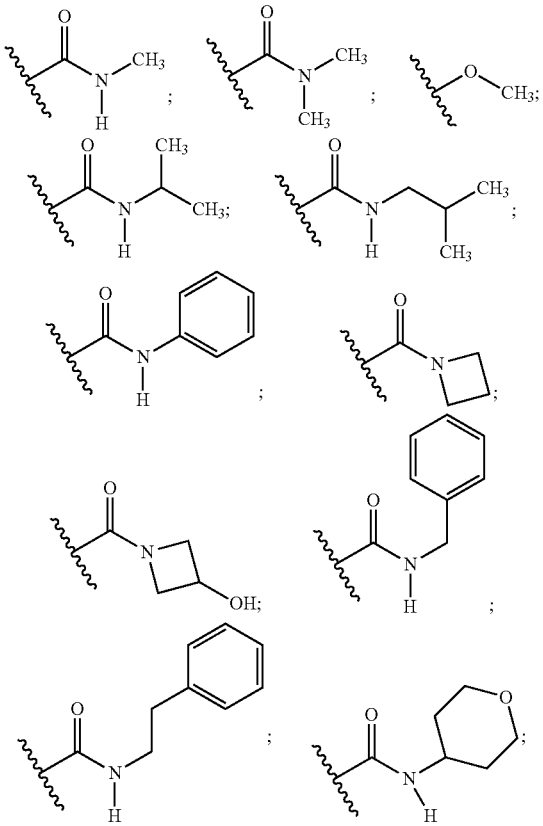

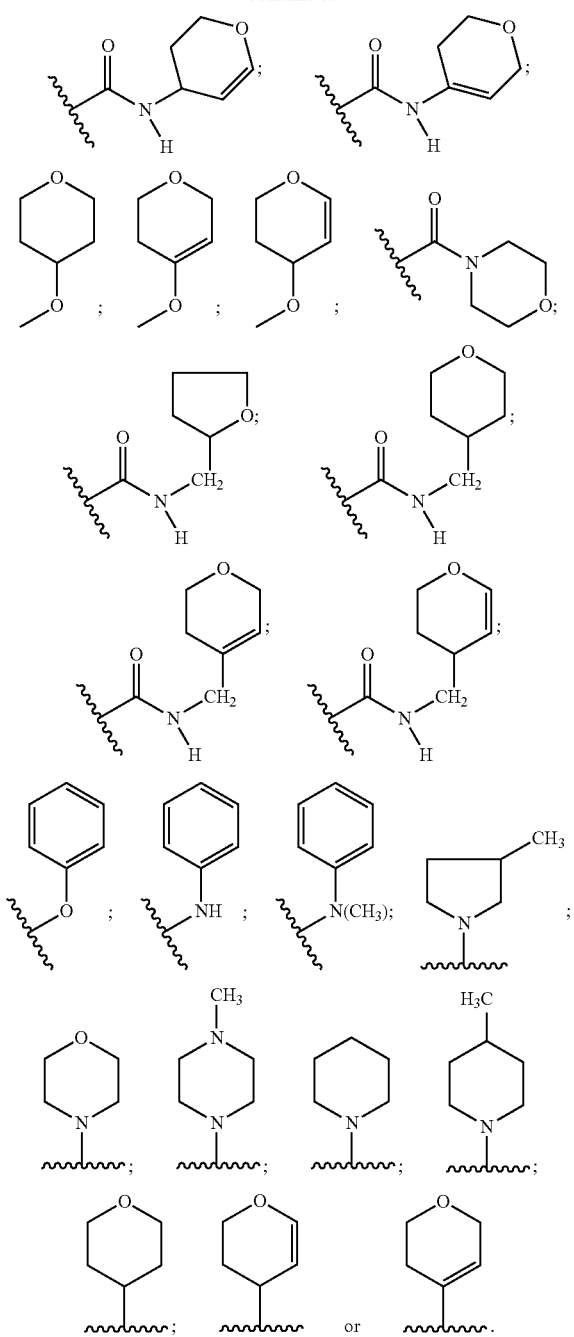
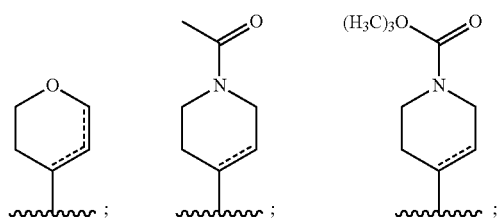
11. The compound according to claim 1, or a pharmaceutically acceptable salt thereof, wherein $R^1$ is:
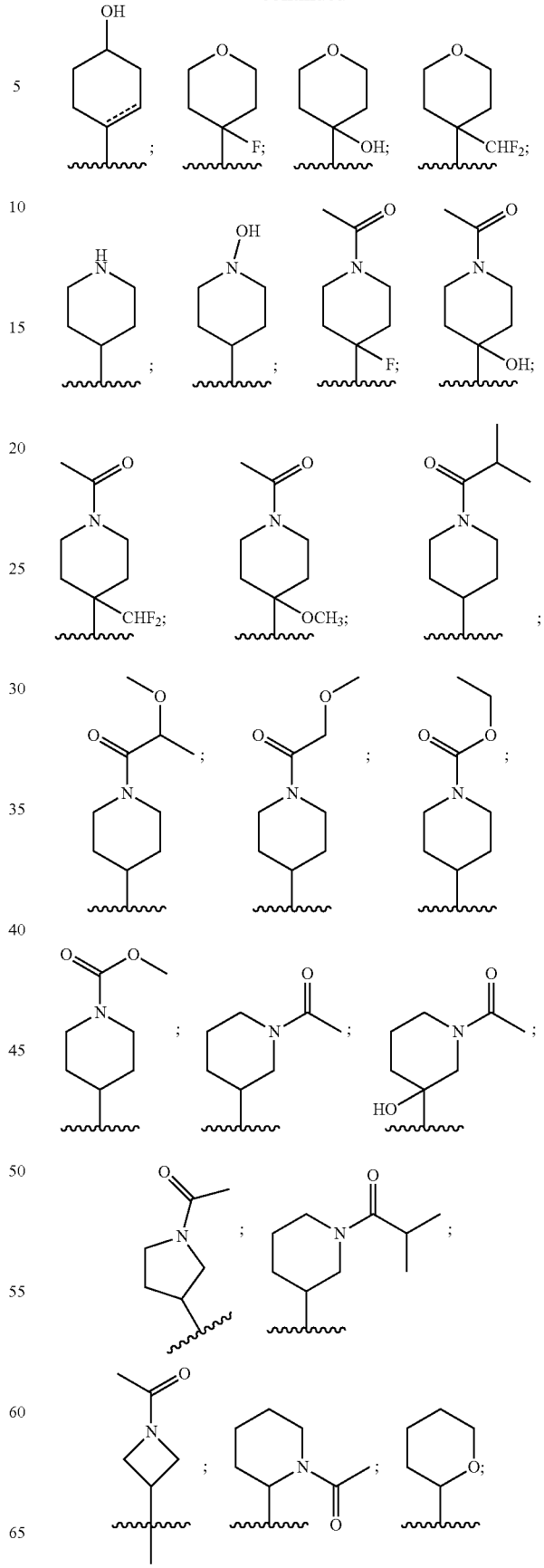

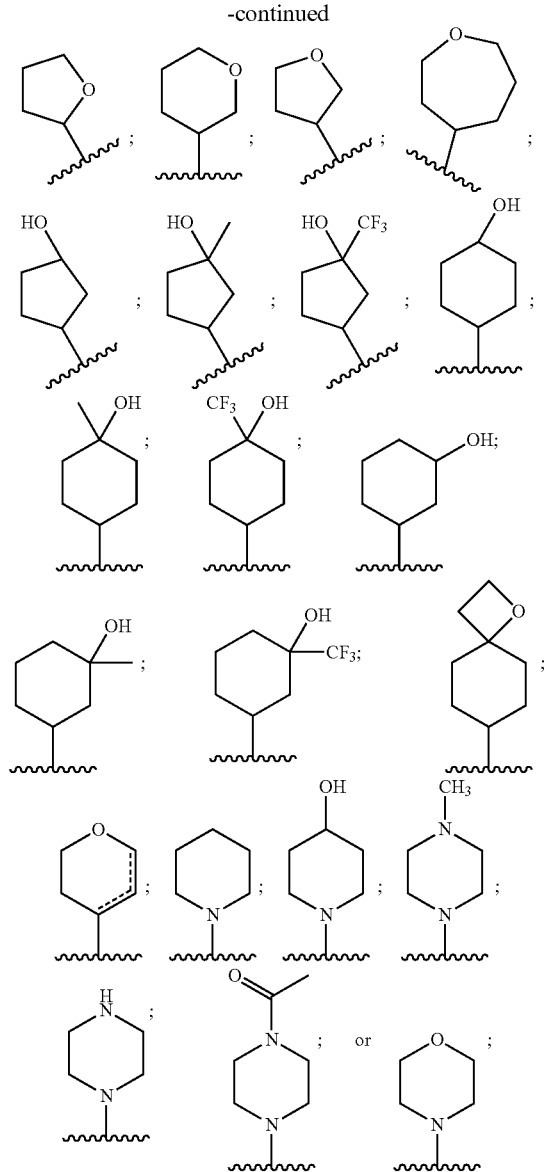

wherein the dotted bond is an optional double bond.

12. The compound according to claim 1, or a pharmaceutically acceptable salt thereof, wherein $R^1$ is:

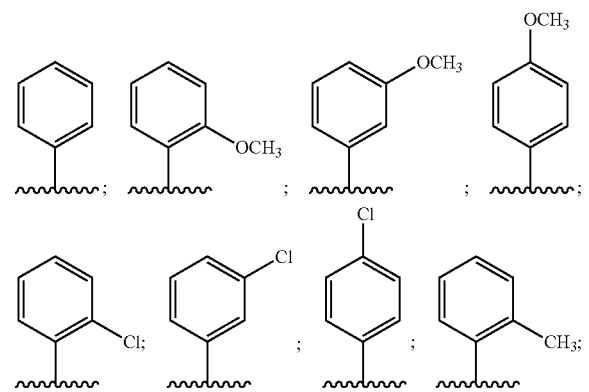

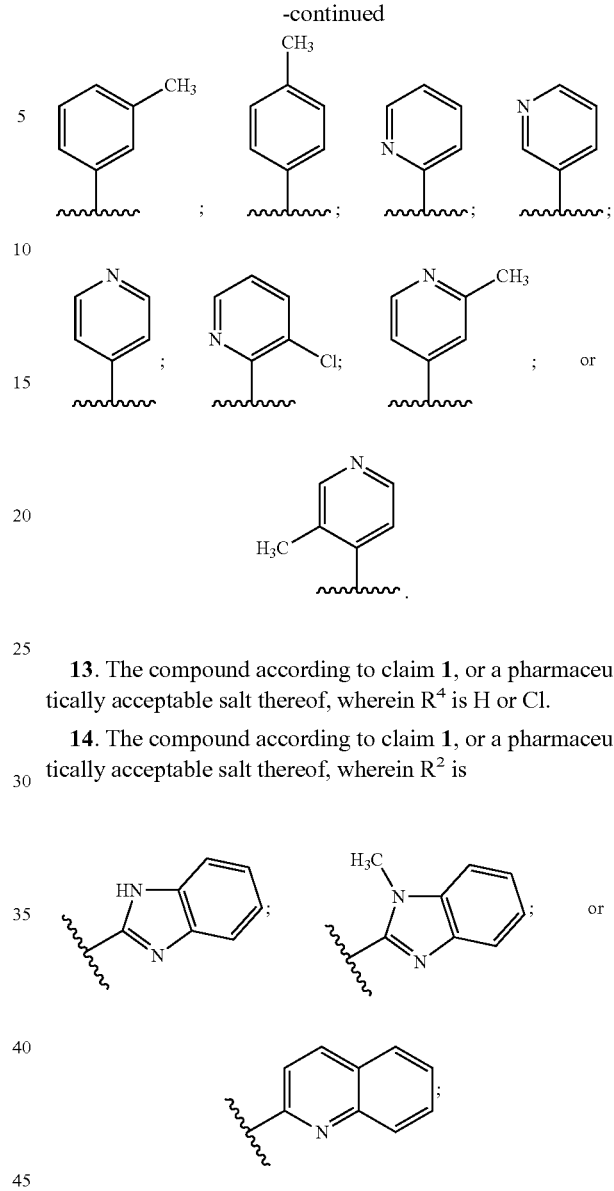

wherein each $R^2$ is substituted by 0, 1 or 2 $R^5$ groups.

13. The compound according to claim 1, or a pharmaceutically acceptable salt thereof, wherein $R^4$ is H or Cl.

14. The compound according to claim 1, or a pharmaceutically acceptable salt thereof, wherein $R^2$ is

15. The compound according to claim 1, or a Pharmaceutically acceptable salt thereof, wherein $R^2$ is

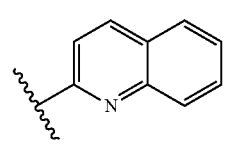 [SMILES: *c1ccc2ccccc2n1]

substituted by 0, 1 or 2 $R^5$ groups.

16. The compound according to claim 14, or a pharmaceutically acceptable salt thereof, wherein $R^5$ is independently Cl, CN, or $C_{1-4}$alk.

17. The compound according to claim 14, or a pharmaceutically acceptable salt thereof, wherein $R^5$ is Cl, CN, or methyl.

18. A compound of formula II:

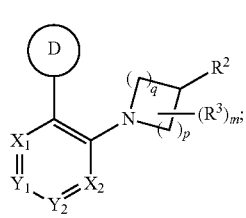

(II)

or a pharmaceutically acceptable salt thereof, having the formula:

ring D is -L$^1$;

each of X$_1$, X$_2$, Y$_1$ and Y$_2$ is independently N or CR$^4$; wherein no more than two of X$_1$, X$_2$, Y$_1$ and Y$_2$ are N;

R$^2$ is of formula:

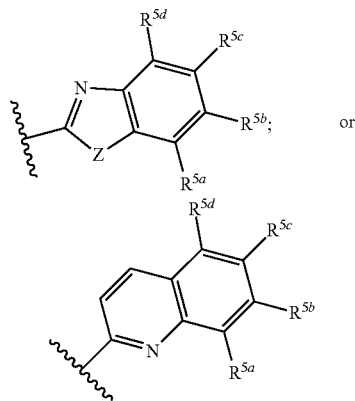

wherein each of R$^{5a}$, R$^{5b}$, R$^{5c}$, and R$^{5d}$ is R$^5$; Z is S, O, or NR$^7$; and R$^7$ is H or C$_{1-6}$alk;

R$^3$ is halo, OH, OC$_{1-4}$alk, C$_{1-4}$alk, C$_{1-4}$haloalk, or oxo;

R$^4$ is independently H, halo, OH, OC$_{1-4}$alk, C$_{1-4}$alk, or C$_{1-4}$haloalk;

R$^5$ is independently halo, CN, or C$_{1-4}$alk;

m is 0;

each of p and q is independently 1;

R$^a$ is independently H or R$^b$;

R$^b$ is independently phenyl, benzyl, or C$_{1-6}$alk, wherein said phenyl, benzyl, and C$_{1-6}$alk are being substituted by 0, 1, 2 or 3 substituents which are independently halo, C$_{1-4}$alk, C$_{1-3}$haloalk, —OH, —OC$_{1-4}$alk, —NH$_2$, —NHC$_{1-4}$alk, —OC(=O)C$_{1-4}$alk, or —N(C$_{1-4}$alk) C$_{1-4}$alk; and each of L$^1$ is independently a carbon-linked or nitrogen-linked saturated, partially-saturated or unsaturated 3-, 4-, 5-, 6-, or 7-membered monocyclic ring or a saturated, partially-saturated or unsaturated 8-, 9-, 10-, 11-, or 12-membered bicyclic ring, wherein each said ring contains 0, 1, 2, 3, or 4 N atoms and 0, 1, or 2 atoms which are independently O or S; wherein each L$^1$ is independently substituted by 0, 1, 2 or 3 R$^6$ groups which are independently F, Cl, Br, C$_{1-6}$alk, C$_{1-4}$haloalk, —OR$^a$, —OC$_{1-4}$haloalk, CN, —C(=O)R$^b$, —C(=O)OR$^a$, or —C(=O)NR$^a$R$^a$;

with the proviso that when R$^2$ is

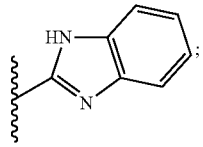 [SMILES: *c1nc2ccccc2[nH]1]

then at least one of X$_1$, X$_2$, Y$_1$ and Y$_2$ must be N.

19. A pharmaceutical composition comprising a compound according to claim 1, or a pharmaceutically acceptable salt thereof, and a pharmaceutically-acceptable excipient.

20. A compound, or a pharmaceutically acceptable salt thereof, which is:

5-methyl-2-(1-(3-(tetrahydro-2H-pyran-4-yloxy)pyrazin-2-yl)azetidin-3-yl)-1H-benzo[d]imidazole;

2-[1-(3,5-dichloro-pyridin-4-yl)-azetidin-3-yl]-5-methyl-1H-benzoimidazole;

2-[1-(3-chloro-5-phenyl-pyridin-4-yl)-azetidin-3-yl]-5-methyl-1H-benzoimidazole;

{2-[3-(5-chloro-1H-benzoimidazol-2-yl)-azetidin-1-yl]-pyridin-3-yl}-(3-hydroxy-azetidin-1-yl)-methanone;

3-[3-(5-chloro-1H-benzoimidazol-2-yl)-azetidin-1-yl]-pyrazine-2-carboxylic acid methylamide;

5-chloro-2-(1-(4-(tetrahydro-2H-pyran-4-yloxy)pyridin-2-yl)azetidin-3-yl)-1H-benzo[d]imidazole;

5-chloro-2-(1-(3-(tetrahydro-2H-pyran-4-yl)pyrazin-2-yl)azetidin-3-yl)-1H-benzo[d]imidazole;

5-chloro-2-(1-(3-(tetrahydro-2H-pyran-4-yloxy)pyrazin-2-yl)azetidin-3-yl)-1H-benzo[d]imidazole;

2-[1-(3-phenyl-pyrazin-2-yl)-azetidin-3-yl]-1H-benzoimidazole-5-carbonitrile;

azetidin-1-yl-{2-[3-(5-chloro-1H-benzoimidazol-2-yl)-azetidin-1-yl]-pyridin-3-yl}-methanone;

{2-[3-(5-chloro-1H-benzoimidazol-2-yl)-azetidin-1-yl]-pyridin-3-yl}-morpholin-4-yl-methanone;

2-[3-(5-chloro-1H-benzoimidazol-2-yl)-azetidin-1-yl]-N-phenyl-nicotinamide;

N-benzyl-2-[3-(5-chloro-1H-benzoimidazol-2-yl)-azetidin-1-yl]-nicotinamide;

2-[3-(5-chloro-1H-benzoimidazol-2-yl)-azetidin-1-yl]-N-phenethyl-nicotinamide;

2-[3-(5-chloro-1H-benzoimidazol-2-yl)-azetidin-1-yl]-N-isopropyl-nicotinamide;

2-[3-(5-chloro-1H-benzoimidazol-2-yl)-azetidin-1-yl]-N-isobutyl-nicotinamide;

2-[3-(5-chloro-1H-benzoimidazol-2-yl)-azetidin-1-yl]-N-(tetrahydro-pyran-4-ylmethyl)-nicotinamide;

5-chloro-2-[1-(3-o-tolyl-pyrazin-2-yl)-azetidin-3-yl]-1H-benzoimidazole;

5-chloro-2-[1-(3-m-tolyl-pyrazin-2-yl)-azetidin-3-yl]-1H-benzoimidazole;

5-chloro-2-[1-(3-p-tolyl-pyrazin-2-yl)-azetidin-3-yl]-1H-benzoimidazole;

5-chloro-2-{1-[3-(2-methoxy-phenyl)-pyrazin-2-yl]-azetidin-3-yl}-1H-benzoimidazole;

5-chloro-2-{1-[3-(3-methoxy-phenyl)-pyrazin-2-yl]-azetidin-3-yl}-1H-benzoimidazole;

5-chloro-2-{1-[3-(4-methoxy-phenyl)-pyrazin-2-yl]-azetidin-3-yl}-1H-benzoimidazole;

5-chloro-2-{1-[3-(2-chloro-phenyl)-pyrazin-2-yl]-azetidin-3-yl}-1H-benzoimidazole;

5-chloro-2-{1-[3-(3-chloro-phenyl)-pyrazin-2-yl]-azetidin-3-yl}-1H-benzoimidazole;

5-chloro-2-{1-[3-(4-chloro-phenyl)-pyrazin-2-yl]-azetidin-3-yl}-1H-benzoimidazole;
5-chloro-2-[1-(3-pyridin-3-yl-pyrazin-2-yl)-azetidin-3-yl]-1H-benzoimidazole;
5-chloro-2-[1-(3-pyridin-4-yl-pyrazin-2-yl)-azetidin-3-yl]-1H-benzoimidazole;
3-[3-(5-chloro-1H-benzoimidazol-2-yl)-azetidin-1-yl]-pyrazine-2-carboxylic acid dimethylamide;
3-[3-(5-chloro-1H-benzoimidazol-2-yl)-azetidin-1-yl]-pyrazine-2-carboxylic acid (tetrahydro-pyran-4-yl)-amide;
3-[3-(5-chloro-1H-benzoimidazol-2-yl)-azetidin-1-yl]-pyrazine-2-carboxylic acid (tetrahydro-furan-2-ylmethyl)-amide;
5-methyl-2-(1-(3-phenylpyrazin-2-yl)azetidin-3-yl)-1H-benzo[d]imidazole;
3-(3-(5-chloro-1H-benzo[d]imidazol-2-yl)azetidin-1-yl)-N-phenylpyrazin-2-amine;
3-(3-(5-chloro-1H-benzo[d]imidazol-2-yl)azetidin-1-yl)-N-methyl-N-phenylpyrazin-2-amine;
5-chloro-2-(1-(3-phenoxypyrazin-2-yl)azetidin-3-yl)-1H-benzo[d]imidazole;
5-chloro-2-(1-(3-(4-methylpiperazin-1-yl)pyrazin-2-yl)azetidin-3-yl)-1H-benzo[d]imidazole;
5-chloro-2-(1-(3-(piperidin-1-yl)pyrazin-2-yl)azetidin-3-yl)-1H-benzo[d]imidazole;
5-chloro-2-(1-(3-methoxypyrazin-2-yl)azetidin-3-yl)-1H-benzo[d]imidazole;
4-(3-(3-(5-methyl-1H-benzo[d]imidazol-2-yl)azetidin-1-yl)pyrazin-2-yl)morpholine;
2-(1-(3-chloropyridin-2-yl)azetidin-3-yl)-5-methyl-1H-benzo[d]imidazole;
2-(1-(3-chloropyrazin-2-yl)azetidin-3-yl)-5-methyl-1H-benzo[d]imidazole;
5-chloro-2-(1-(3-(tetrahydro-2H-pyran-4-yloxy)pyridin-2-yl)azetidin-3-yl)-1H-benzo[d]imidazole;
4-(3-(3-(5-chloro-1H-benzo[d]imidazol-2-yl)azetidin-1-yl)pyrazin-2-yl)morpholine;
5-chloro-2-(1-(3-(3,6-dihydro-2H-pyran-4-yl)pyrazin-2-yl)azetidin-3-yl)-1H-benzo[d]imidazole;
2-(1-(3-bromopyridin-2-yl)azetidin-3-yl)-5-chloro-1H-benzo[d]imidazole;
5-chloro-2-(1-(3-chloropyrazin-2-yl)azetidin-3-yl)-1H-benzo[d]imidazole;
5-chloro-2-(1-(3-chloropyridin-2-yl)azetidin-3-yl)-1H-benzo[d]imidazole;
5-chloro-2-(1-(2,5-dichloropyrimidin-4-yl)azetidin-3-yl)-1H-benzo[d]imidazole; or
5-chloro-2-(1-(3-(tetrahydro-2H-pyran-4-yl)pyridin-2-yl)azetidin-3-yl)-1H-benzo[d]imidazole.

21. A compound, or a pharmaceutically acceptable salt thereof, which is:
2-[1-(3-Piperidin-1-yl-pyrazin-2-yl)-azetidin-3-yl]-quinoline;
2-[1-(3-m-Tolyl-pyrazin-2-yl)-azetidin-3-yl]-quinoline;
2-{1-[3-(3-Methoxy-phenyl)-pyridin-2-yl]-azetidin-3-yl}-quinoline;
2'-(3-Quinolin-2-yl-azetidin-1-yl)-3,4,5,6-tetrahydro-2H-[1,3']bipyridinyl;
2-{1-[3-(4-Methyl-piperidin-1-yl)-pyrazin-2-yl]-azetidin-3-yl}-quinoline;
{1-[3-(3-Quinolin-2-yl-azetidin-1-yl)-pyrazin-2-yl]-piperidin-4-yl}-methanol;
2-{1-[3-(3-Methyl-pyrrolidin-1-yl)-pyrazin-2-yl]-azetidin-3-yl}-quinoline; or
2-{1-[3-(3-Methoxy-phenyl)-pyrazin-2-yl]-azetidin-3-yl}-quinoline.

22. The compound of formula II according to claim 18, wherein ring D is cyclohexyl, cyclopentyl, cyclopentenyl, cyclohexenyl, or cycloheptyl.

23. The compound of formula II according to claim 18, wherein ring D is azetidinyl, phenyl, 2-pyridyl, 3-pyridyl, pyrazolyl, morpholinyl, pyrimidyl, piperazinyl, piperidinyl, dihydropyranyl, tetrahydropyranyl, tetrahydrofuranyl, tetrahydropyridinyl, or tetrahydrothiopyranyl.

24. The compound of formula II according to claim 18, wherein ring D is cyclohexyl, cyclopentyl, cyclopentenyl, cyclohexenyl, cycloheptyl, azetidinyl, phenyl, 2-pyridyl, 3-pyridyl, pyrazolyl, morpholinyl, pyrimidyl, piperazinyl, piperidinyl, dihydropyranyl, tetrahydropyranyl, tetrahydrofuranyl, tetrahydropyridinyl, tetrahydrothiopyranyl, oxaspiro[3.5]nonyl, azepanyl, oxepanyl, or quinolinyl, all of which are substituted by 0, 1, 2 or 3 $R^6$ groups which are independently F, Cl, Br, or $C_{1-6}$alk.

* * * * *